US008569065B2

(12) United States Patent
Polach et al.

(10) Patent No.: US 8,569,065 B2
(45) Date of Patent: Oct. 29, 2013

(54) COMPOSITIONS AND METHODS FOR THE DELIVERY OF BIOLOGICALLY ACTIVE RNAS

(75) Inventors: Kevin Polach, Huntsville, AL (US); Jason Fewell, Huntsville, AL (US); Khursheed Anwer, Huntsville, AL (US)

(73) Assignee: EGEN, Inc., Huntsville, AL (US)

( * ) Notice: Subject to any disclaimer, the term of this patent is extended or adjusted under 35 U.S.C. 154(b) by 56 days.

(21) Appl. No.: 12/724,408

(22) Filed: Mar. 15, 2010

(65) Prior Publication Data

US 2010/0233141 A1   Sep. 16, 2010

Related U.S. Application Data

(60) Provisional application No. 61/160,287, filed on Mar. 13, 2009, provisional application No. 61/160,288, filed on Mar. 13, 2009.

(51) Int. Cl.
| | |
|---|---|
| *C12N 15/00* | (2006.01) |
| *C12N 5/00* | (2006.01) |
| *C12N 5/02* | (2006.01) |
| *A01N 63/00* | (2006.01) |
| *A01N 65/00* | (2009.01) |
| *A61K 48/00* | (2006.01) |

(52) U.S. Cl.
USPC ........ 435/455; 435/320.1; 435/325; 435/440; 424/93.1; 424/93.2; 424/93.21

(58) Field of Classification Search
None
See application file for complete search history.

(56) References Cited

U.S. PATENT DOCUMENTS

| 5,880,276 A | 3/1999 | Hammarskjold et al. |
| 2003/0096243 A1 | 5/2003 | Busa |
| 2003/0232058 A1 | 12/2003 | Dubensky et al. |
| 2004/0005593 A1* | 1/2004 | Lorens .............................. 435/6 |
| 2004/0241845 A1 | 12/2004 | Desgroseillers et al. |
| 2005/0008617 A1 | 1/2005 | Chen et al. |

(Continued)

FOREIGN PATENT DOCUMENTS

| WO | WO 03/060101 | 7/2003 |
| WO | WO 2007/126386 | 8/2007 |

OTHER PUBLICATIONS

Bottger et al., Genetic screen for signal peptides in Hydra reveals novel secreted proteins and evidence for non-classical protein secretion, Eur J Cell Biol. 85(9-10):1107-17, 2006.*

(Continued)

*Primary Examiner* — Anne-Marie Falk
(74) *Attorney, Agent, or Firm* — McDonnell Boehnen Hulbert & Berghoff LLP

(57) ABSTRACT

The present invention provides novel compounds, compositions, and methods for the delivery of biologically active RNA molecules to cells. Specifically, the invention provides novel nucleic acid molecules, polypeptides, and RNA-protein complexes useful for the delivery of biologically active RNAs to cells and polynucleotides encoding the same. The invention also provides vectors for expressing said polynucleotides. In addition, the invention provides cells and compositions comprising the novel compounds and vectors, which can be used as transfection reagents. The invention further provides methods for producing said compounds, vectors, cells, and compositions. Additionally, vectors and methods for delivering biologically active RNA molecules to cells and/or tissues are provided. The novel compounds, vectors, cells, and compositions are useful, for example, in delivering biologically active RNA molecules to cells to modulate target gene expression in the diagnosis, prevention, amelioration, and/or treatment of diseases, disorders, or conditions in a subject or organism.

30 Claims, 26 Drawing Sheets

BioReactor mediated delivery of Sec-shRNAs targeting genes of interest (GOI)

(56) References Cited

U.S. PATENT DOCUMENTS

| | | | |
|---|---|---|---|
| 2005/0074865 | A1 | 4/2005 | Afeyan et al. |
| 2007/0036773 | A1 | 2/2007 | Cooper et al. |
| 2007/0190520 | A1 | 8/2007 | Wolf et al. |
| 2009/0093026 | A1* | 4/2009 | Dowdy et al. ............ 435/69.7 |
| 2011/0207799 | A1 | 8/2011 | Rozema et al. |

OTHER PUBLICATIONS

International Search Report from International Application No. PCT/US2010/27365 mailed on May 27, 2010.
Aagaard & Rossi, "RNAi therapeutics: principles, prospects and challenges," Adv Drug Deliv Rev. 59(2-3):75-86 (2007).
Aigner, "Applications of RNA interference: current state and prospects for siRNA-based strategies in vivo," Appl Microbiol Biotechnol. 76(1):9-21 (2007).
Akhtar & Benter, "Nonviral delivery of synthetic siRNAs in vivo," J Clin Invest. 117(12):3623-32 (2007).
Anesti et al., "Efficient delivery of RNA Interference to peripheral neurons in vivo using herpes simplex virus," Nucleic Acids Res. 36(14):e86 (2008).
Bogdanovich et al., "Functional improvement of dystrophic muscle by myostatin blockade," Nature 420 (6914):418-21 (2002).
Böttger et al., "Genetic screen for signal peptides in Hydra reveals novel secreted proteins and evidence for non-classical protein secretion," Eur J Cell Biol. 85(9-10):1107-17 (2006).
Bourbeau et al., "Improvement of antitumor activity by gene amplification with a replicating but nondisseminating adenovirus," Cancer Res. 67(7):3387-95 (2007).
Bromberg-White et al., "Delivery of short hairpin RNA sequences by using a replication-competent avian retroviral vector," J Virol. 78(9):4914-16 (2004).
Cascante et al., "GCV modulates the antitumoural efficacy of a replicative adenovirus expressing the Tat8-TK as a late gene in a pancreatic tumour model," Gene Ther. 14(20): 1471-80 (2007).
Cerchia et al., "Neutralizing aptamers from whole-cell SELEX inhibit the RET receptor tyrosine kinase," PLoS Biol. 3 (4):e123 (2005).
Chen et al., "Adenovirus-mediated RNA interference against foot-and-mouth disease virus infection both in vitro and in vivo," J Virol. 80(7):3559-66 (2006).
De Fougerolles et al., "Interfering with disease: a progress report on siRNA-based therapeutics," Nat Rev Drug Discov. 6(6):443-53 (2007).
Derré et al., "Expression and Release of HLA-E by Melanoma Cells and Melanocytes: Potential Impact on the Response of Cytotoxic Effector Cells," J Immunol. 177(5):3100-3107 (2006).
Deutscher et al., "A sequence-specific conformational epitope on U1 RNA is recognized by a unique autoantibody," Proc Natl Acad Sci USA 85(10) 3299-3303 (1988).
Di Figlia et al., "Therapeutic silencing of mutant huntingtin with siRNA attenuates striatal and cortical neuropathology and behavioral deficits," Proc Natl Acad Sci USA 104(43):17204-09 (2007).
Evans et al., "Gene transfer to human joints: progress toward a gene therapy of arthritis," Proc Natl Acad Sci USA 102(24):8698-703 (2005).
Falcone et al., "Replication of primate foamy viruses in natural and experimental hosts," Curr Top Microbiol Immunol. 277:161-80 (2003).
Farazi et al., "The growing catalog of small RNAs and their association with distinct Argonaute/Piwi family members," Development 135(7):1201-14 (2008).
Fewell et al., "Synthesis and application of a non-viral gene delivery system for immunogene therapy of cancer," J Control Release 109(1-3):288-98 (2005).
Gary et al., "Polymer-based siRNA delivery: perspectives on the fundamental and phenomenological distinctions from polymer-based DNA delivery," J Control Release 121(1-2):64-73 (2007).

Gorbatyuk et al., "Suppression of mouse rhodopsin expression in vivo by AAV mediated siRNA delivery," Vision Res. 47(9):1202-08 (2007).
Grimm & Kay, "Therapeutic application of RNAi: is mRNA targeting finally ready for prime time?," J Clin Invest. 117 (12):3633-41 (2007).
Gwizdek et al., "Terminal minihelix, a novel RNA motif that directs polymerase III transcripts to the cell cytoplasm. Terminal minihelix and RNA export," J Biol Chem 276(28):25910-18 (2001).
Heinkelein et al., "Experimental therapy of allogeneic solid tumors induced in athymic mice with suicide gene-transducing replication-competent foamy virus vectors," Cancer Gene Ther. 12(12):947-53 (2005).
Hiraoka et al., "Therapeutic efficacy of replication-competent retrovirus vector-mediated suicide gene therapy in a multifocal colorectal cancer metastasis model," Cancer Res. 67(11):5345-53 (2007).
Hiraoka et al., "Tumor-selective gene expression in a hepatic metastasis model after locoregional delivery of a replication-competent retrovirus vector," Clin Cancer Res. 12(23):7108-16 (2006).
Ireson & Kelland, "Discovery and development of anticancer aptamers," Mol Cancer Ther. 5(12):2957-62 (2006).
Juliano et al., "Mechanisms and strategies for effective delivery of antisense and siRNA oligonucleotides," Nucleic Acids Res. 36(12):4158-71 (2008).
Khoury et al., "Efficient suppression of murine arthritis by combined anticytokine small interfering RNA lipoplexes," Arthritis Rheum. 58(8):2356-67 (2008).
Kikuchi et al., "Highly efficient gene delivery for bladder cancers by intravesically administered replication-competent retroviral vectors," Clin Cancer Res. 13(15 Pt1):4511-18 (2007).
Koerber et al., "DNA shuffling of adeno-associated virus yields functionally diverse viral progeny," Mol Ther. 16 (10):1703-09 (2008).
Lee et al., "Replicating adenoviral vector-mediated transfer of a heat-inducible double suicide gene for gene therapy," Cancer Gene Ther. 8(6):397-404 (2001).
Lee et al., "beta-catenin regulates multiple steps of RNA metabolism as revealed by the RNA aptamer in colon cancer cells," Cancer Res. 67(19):9315-21 (2007).
Li et al., "Long-term inhibition of HIV-1 infection in primary hematopoietic cells by lentiviral vector delivery of a triple combination of anti-HIV shRNA, anti-CCR5 ribozyme, and a nucleolar-localizing TAR decoy," Mol Ther. 12(5):900-09 (2005).
Li et al., "A highly functional mini-dystrophin/GFP fusion gene for cell and gene therapy studies of Duchenne muscular dystrophy," Hum Mol Genet. 15(10):1610-22 (2006).
Liu et al., "Phi29 pRNA vector for efficient escort of hammerhead ribozyme targeting survivin in multiple cancer cells," Cancer Biol Ther. 6(5):697-704 (2007).
Lund et al., "Pseudovirions as Vehicles for the Delivery of siRNA," Pharm Res. 27(3):400-20 (2009).
Mi et al., "RNA aptamer-targeted inhibition of NF-kappa B suppresses non-small cell lung cancer resistance to doxorubicin," Mol Ther. 16(1):66-73 (2007).
Michienzi et al., "U1 small nuclear RNA chimeric ribozymes with substrate specificity for the Rev pre-mRNA of human immunodeficiency virus" Proc Natl Acad Sci USA 93(14) 7219-24 (1996).
Nestler et al., "Foamy virus vectors for suicide gene therapy," Gene Ther. 4(11):1270-77 (1997).
Parada et al., "Adenovirus E1a protein enhances the cytotoxic effects of the herpes thymidine kinase-ganciclovir system," Cancer Gene Ther. 10(2):152-60 (2003).
Qiao et al., "VSV-G pseudotyped, MuLV-based, semi-replication-competent retrovirus for cancer treatment," Gene Ther. 13(20):1457-70 (2006).
Rayburn & Zhang, "Antisense, RNAi, and gene silencing strategies for therapy: mission possible or impossible?," Drug Discov Today. 13(11-12):513-21 (2008).
Raoul et al., "Lentiviral-mediated silencing of SOD1 through RNA interference retards disease onset and progression in a mouse model of ALS," Nat Med. 11(4):423-28 (2005).

(56) References Cited

OTHER PUBLICATIONS

Reinblatt et al., Carcinoembryonic antigen directed herpes viral oncolysis improves selectivity and activity in colorectal cancer. Surgery 136(3):579-84 (2004).
Ring, "Cytolytic viruses as potential anti-cancer agents," J Gen Virol. 83(Pt 3):491-502 (2002).
Scherer et al., "Progress and prospects: RNA-based therapies for treatment of HIV infection," Gene Ther., 14 (14):1057-64 (2007).
Scherr et al., "Lentivirus-mediated antagomir expression for specific inhibition of miRNA function," Nucleic Acids Res. 35(22):e149 (2007).
Scherr et al., "Modulation of gene expression by lentiviral-mediated delivery of small interfering RNA," Cell Cycle. 2 (3):251-57 (2003).
Song et al., "Validation of tissue-specific promoter-driven tumor-targeting trans-splicing ribozyme system as a multifunctional cancer gene therapy device in vivoTrans-splicing ribozyme as tumor targeting-device," Cancer Gene Therapy 16:113-25 (2009).
Sontheimer, "Assembly and function of RNA silencing complexes," Nat Rev Mol Cell Biol. 6(2):127-38 (2005).
Tiede et al., "Recombinant factor VIII expression in hematopoietic cells following lentiviral transduction," Gene Ther. 10(22):1917-25 (2003).
Trang et al., "Developing RNase P ribozymes for gene-targeting and antiviral therapy," Cell Microbiol. 6(6):499-508 (2004).
Tseng et al., "Controlled propagation of replication-competent Sindbis viral vector using suicide gene strategy," Gene Ther. 16(2):291-6 (2009).
Tseng et al., "In vivo antitumor activity of Sindbis viral vectors," J Nat'l Cancer Inst. 94:1790-1802 (2002).
Varghese et al., Systemic therapy of spontaneous prostate cancer in transgenic mice with oncolytic herpes simplex viruses. Cancer Res. 67(19):9371-79 (2007).
Varghese et al., "Systemic oncolytic herpes virus therapy of poorly immunogenic prostate cancer metastatic to lung," Clin Cancer Res. 12(9):2919-27 (2006).
Weng et al., "A phase I clinical trial of a ribozyme-based angiogenesis inhibitor targeting vascular endothelial growth factor receptor-1 for patients with refractory solid tumors," Mol Cancer Ther. 4(6):948-55 (2005).
Wolff & Rozema, "Breaking the bonds: non-viral vectors become chemically dynamic," Mol Ther. 16(1):8-15 (2007).
Wood et al., "Modulating the expression of disease genes with RNA-based therapy," PLoS Genet. 3(6):e109 (2007).
Yang & Yu, "Intracerebral transplantation of neural stem cells combined with trehalose ingestion alleviates pathology in a mouse model of Huntington's disease," J Neurosci Res. 87(1):26-33 (2009).
Zamore & Haley, "Ribo-gnome: the big world of small RNAs," Science 309(5740):1519-24 (2005).
Ostersetzer, Oren et al.: "CRS1, a Chloroplast Group II Intron splicing Factor, Promotes Intron Folding through Specific Interactions with Two Intron Domains," The Plant Cell, vol. 17, 251-255 (Jan. 2005).
Seetharaman, Mahadevan et al.: "Structur of a self-splicing group II intron catalytic effector domain 5: Parallels with spliceomal U6 RNA," RNA (2006) vol. 12, pp. 235-247.
Mook, Olaf R. et al.: "Evaluation of locked nucleic acid-modified small interfering RNA in vitro and in vivo," Mol Cancer Ther (2007) vol. 6, pp. 833-843.
Terrazas, Montserrat et al.: "RNA major groove modifications improve siRNA stability and biological activity," Nucleic Acids Research (2009) vol. 37, No. 2, pp. 346-353.
Manoharan, Muthiah et al.: "RNA interference and chemically modified siRNAs," Nucleic Acids Research Supplement No. 3, pp. 115-116, downloaded from http://nass.oxfordjounrals.org by guest on Mar. 14, 2012.
Keren, Ido et al.: "Characterization of the Molecular Basis of Group II Intron RNA Recognition by CRS1-CRM Domains," The American Society for Biochemistry and Molecular Biology, Inc., JBC Papers in Press. Published on Jun. 17, 2008 as Manuscript M710488200.
Amarzguioui, Mohammaed et al.: "Tolerance for mutations and chemical modifications in a siRNA," Nucleic Acids Research (2003) vol. 31, No. 2, pp. 589-595.
Konforti, Boyana B. et al.: "A map of the binding site for catalytic domain 5 in the core of a group II intron ribozyme," The EMBO Journal, vol. 17, No. 23, (1998) pp. 7105-7117.
Clerico, et al., Review Article—Use of Synthetic Signal Sequences to Explore the Protein Export Machinery; Peptide Science, 90:307-319 (2007).
Choo, et al., SPdb—a signal peptide database; BMC Bioinformatics, 6:1-8 (2005).
Nickel, W., The mystery of nonclassical protein secretion—A current view on cargo proteins and potential export routes; Eur. J. Biochem., 270:2109-2119 (2003).
Nickel, W., Unconventional Secretory Routes: Direct protein Export Across the Plasma Membrane of mammalian cells; Traffic, 6:607-614 (2005).
Cleves, Protein transport: The nonclassical ins and outs, Current Biology, 7:R318-R320 (1997).
Prudovsky, et al., Secretion with Golgi, J. Cell Biochem, 103:1327-1343 (2008).
Tai, et al., Single-Shot, Multicycle Suicide Gene Therapy by Replication-Competent Retrovirus Vectors Achieves Long-Term Survival Benefit in Experimental Glimoa, Molecular Therapy, 12:842-851 (2005).
Xiang, et al., Short hairpin RNA-expressing bacteria elicit RNA interference in mammals, Nature Biotechnology, 24:697-702 (2006).
Endoh, et al., Cellular siRNA Delivery Mediated by a Cell-Permeant RNA-Binding Protein and Photoinduced RNA Interference, Bioconjugate Chem. 19:1017-1024 (2008).
Raemdonck, et al., Maintaining the Silence: reflections on long-term RNAi, Drug Discovery Today, 13:917-931 (2008).
Jose, et al., Export of RNA silencing from C. elegans tissues does not require the RNA channel SID-1, PNAS, 106:2283-2288 (2009).
Yoo, et al., A Systemic Small RNA Signaling System in Plants, The Plant Cell, 16:1979-2000 (2004).
Valadi, et al, Exosome-mediated transfer of mRNAs and microRNAs is a novel mechanism of genetic exchange between cells, Nature Cell Biology, 9:654-659 (2007).
Jose, et al., Transport of Sequence-Specific RNA Interference Information Between Cells, Annual Review of Genetics, 41:305-330 (2007).
Dinger, et al., RNAs as extracellular 1-15 signaling molecules, Journal of Molecular Endocrinology, 40:151-159 (2008).
Vlassov, et al., Extracellular nucleic acids, BioEssays, 29:654-667 (2007).
Laufer, et al., Peptide-Mediated Cellular Delivery of Oligonucleotide-Based therapeutics In Vitro: Quantitative Evaluation of Overall efficacy Employing Easy to Handle Reporter Systems, Current Pharmaceutical Design, 24:3637-3655 (2008).
Belting, et al., Nanotubes, exosomes, and nucleic acid-binding peptides provide novel mechanisms of intercellular communication in eukaryotic cells: implications in health and disease, The Journal of Cell Biology, 183:1187-1191 (2008).

\* cited by examiner

Figure 1. BioReactor mediated delivery of Sec-shRNAs targeting genes of interest (GOI)
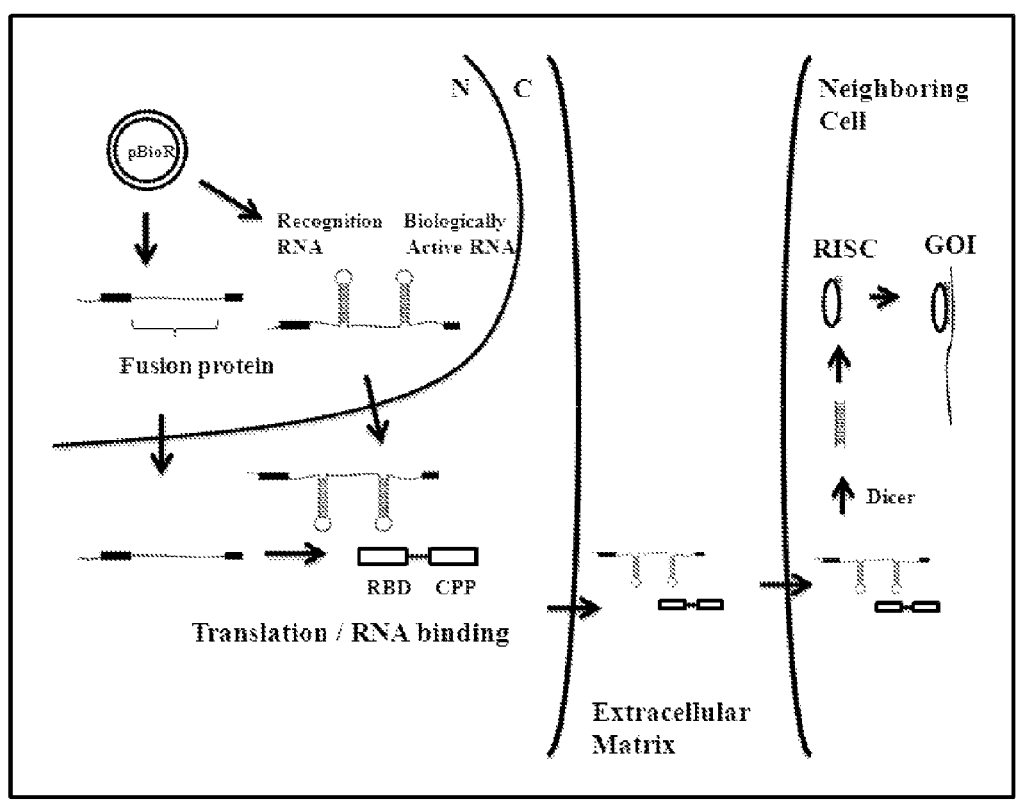

Figure 2. BioReactor mediated delivery of Sec-shRNAs targeting genes of interest (GOI)
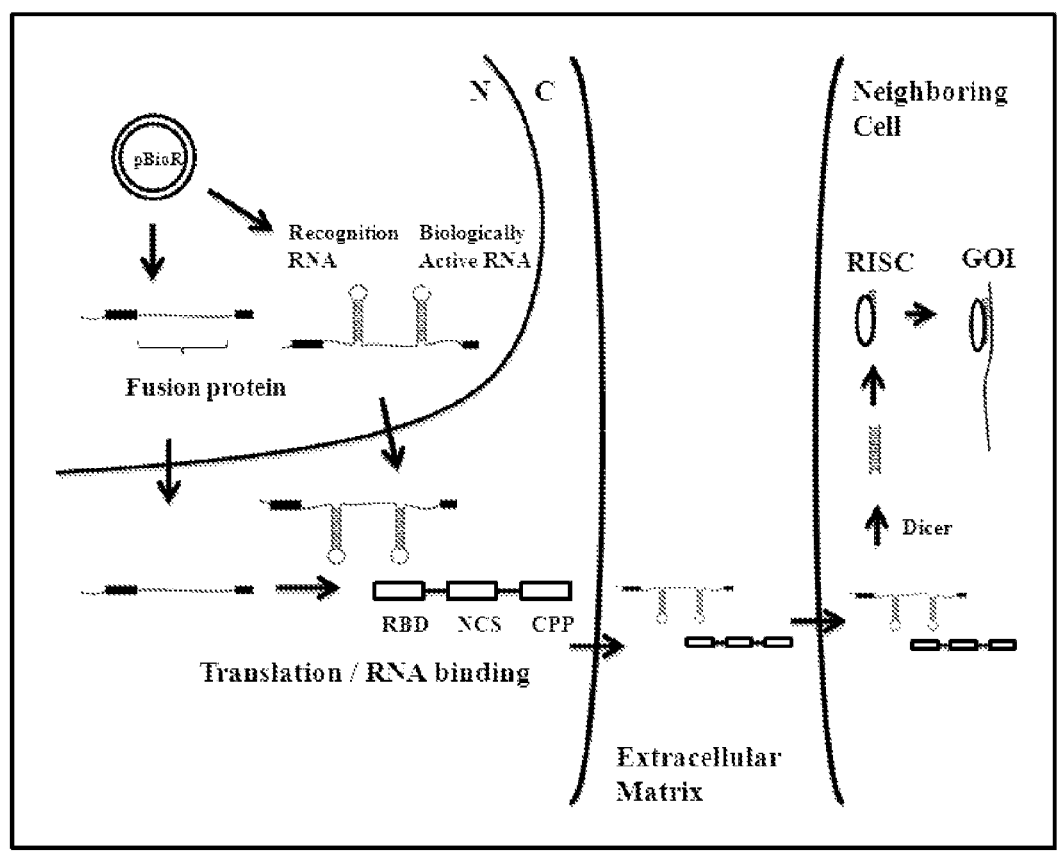

Figure 3. BioReactor mediated delivery of Sec-RNA aptamer targeting cell receptors Figure 4. BioReactor mediated delivery of Sec-RNA aptamer targeting extracellular proteins
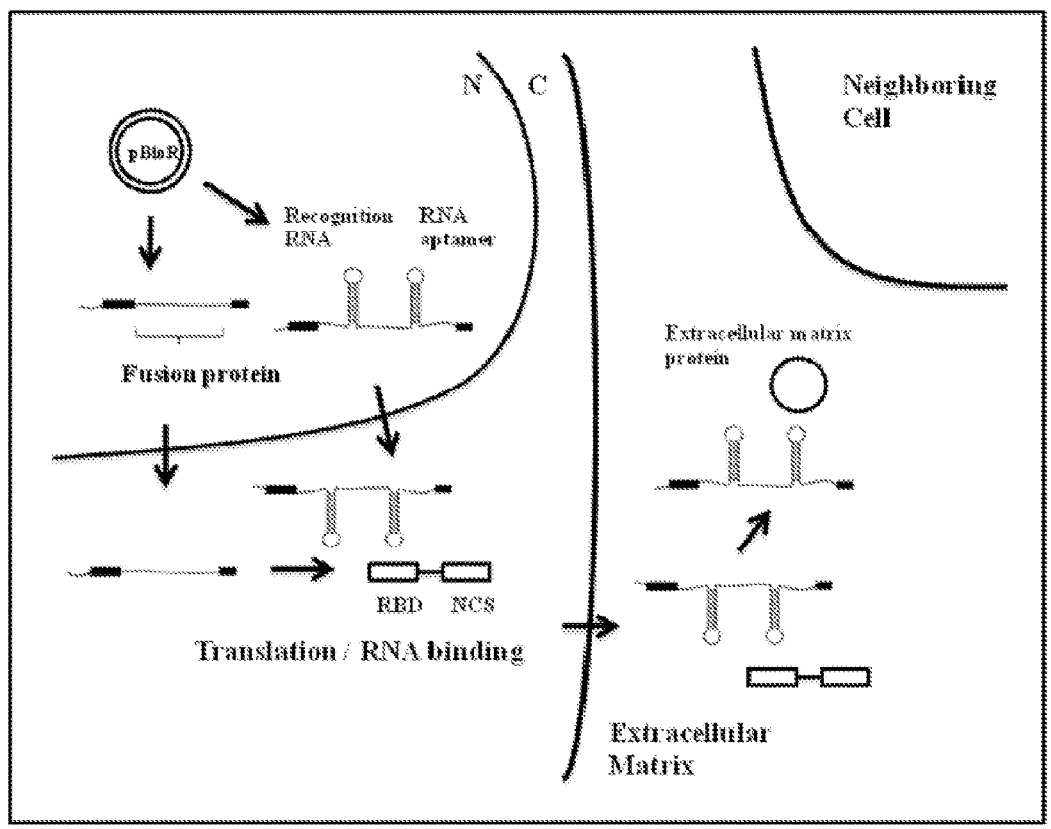

Figure 5. Plasmid map of pEGEN1.1
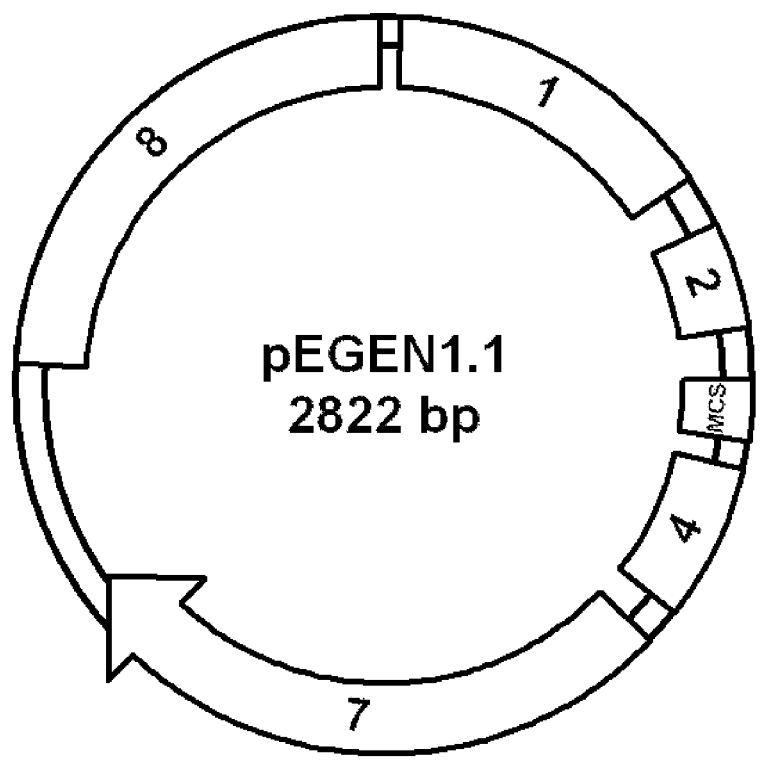

Figure 6. Plasmid map of pEGEN2.1
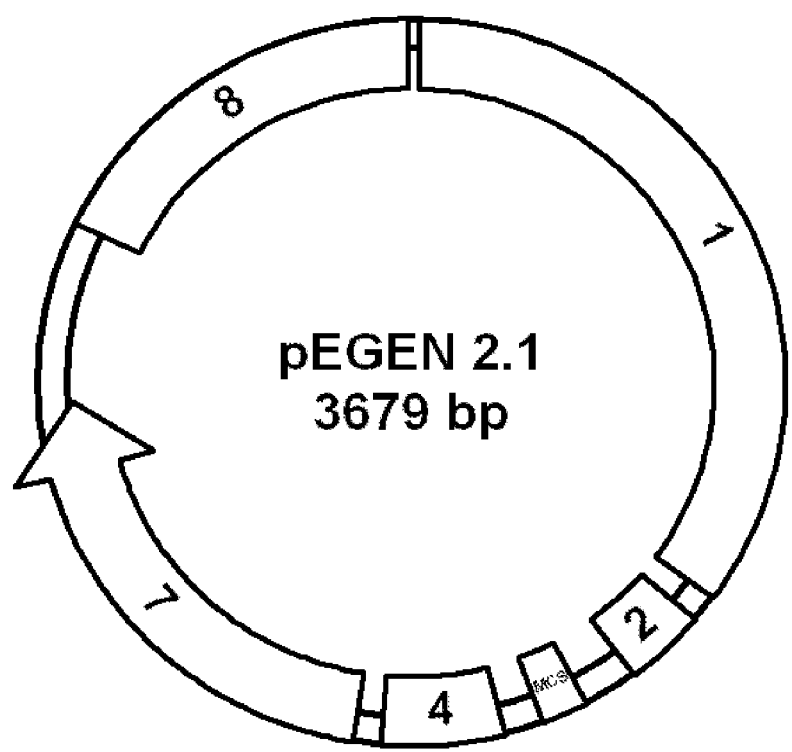

Figure 7. Plasmid map of pEGEN3.1
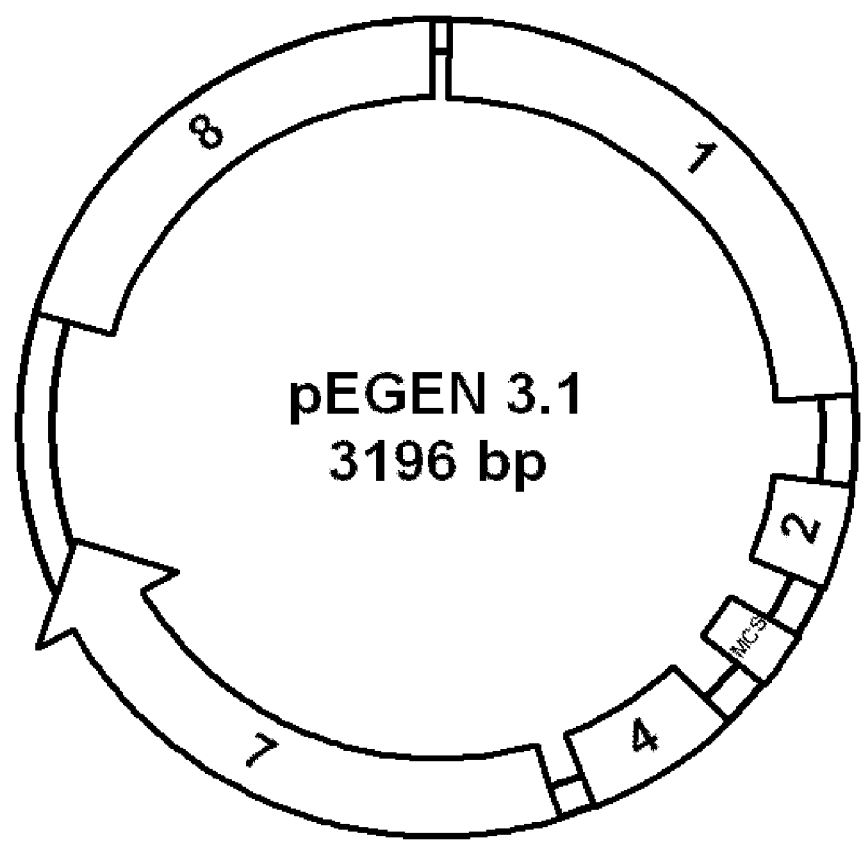

Figure 8. Plasmid map of pEGEN4.1
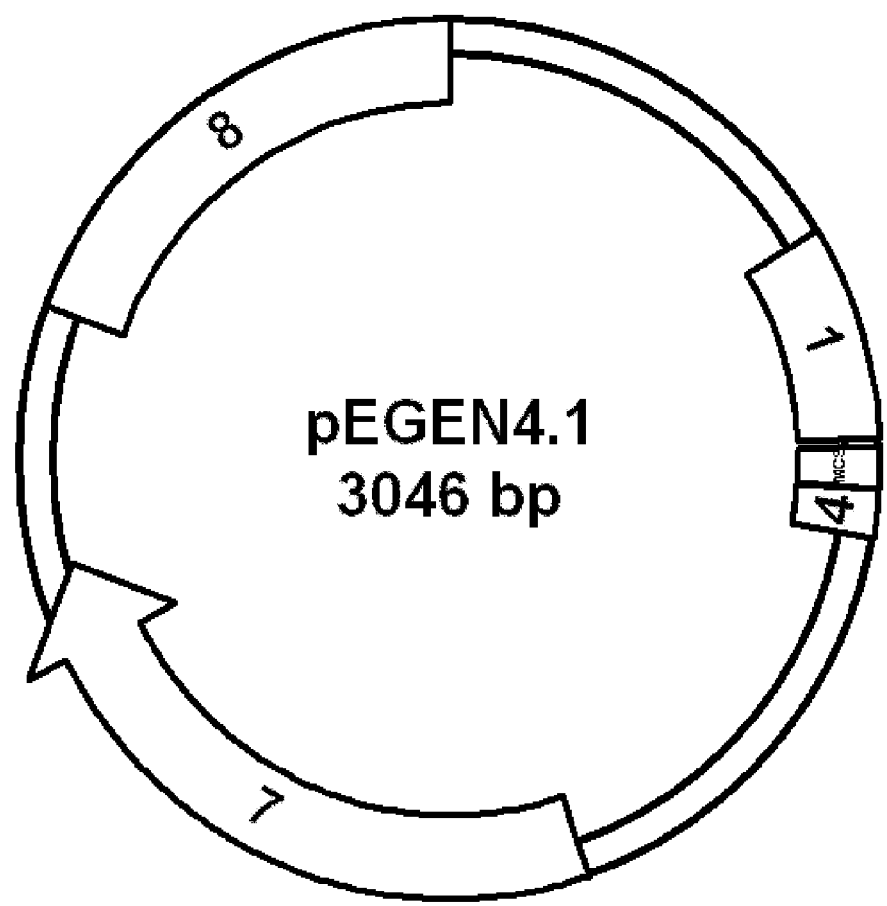

Figure 9. Plasmid map of pBioR Pol II
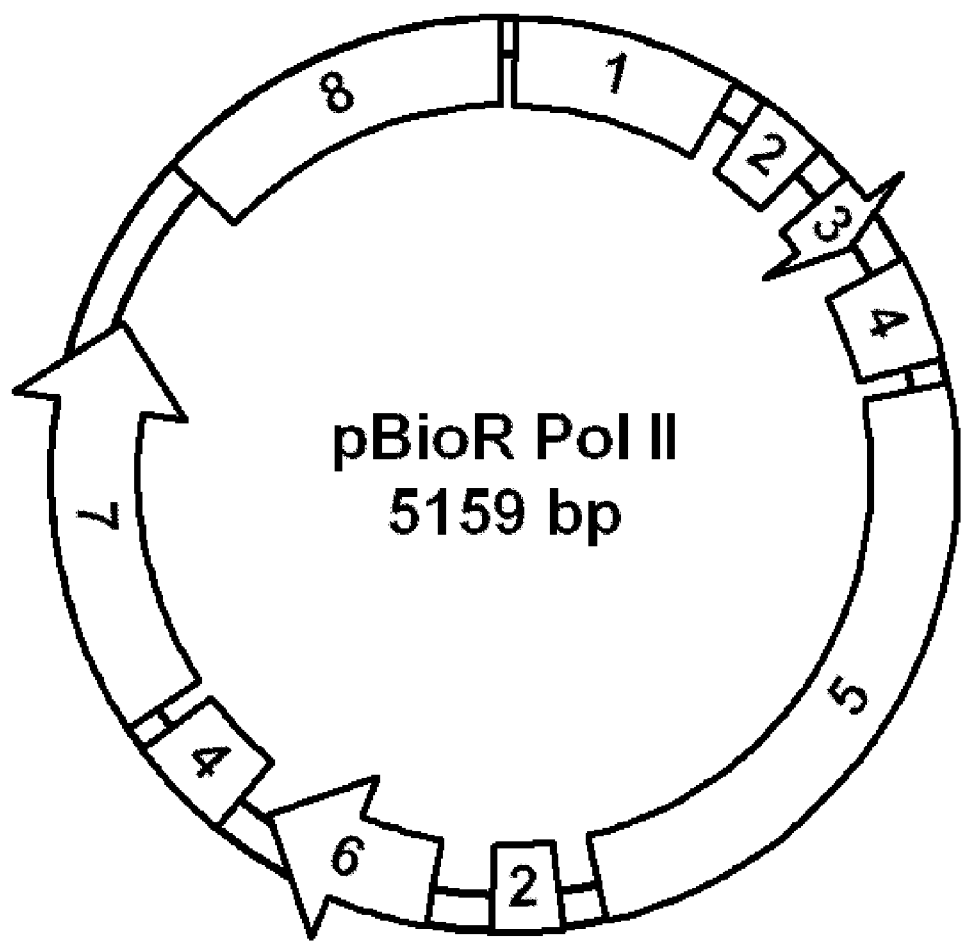

Figure 10. Plasmid map of pBioR Pol III
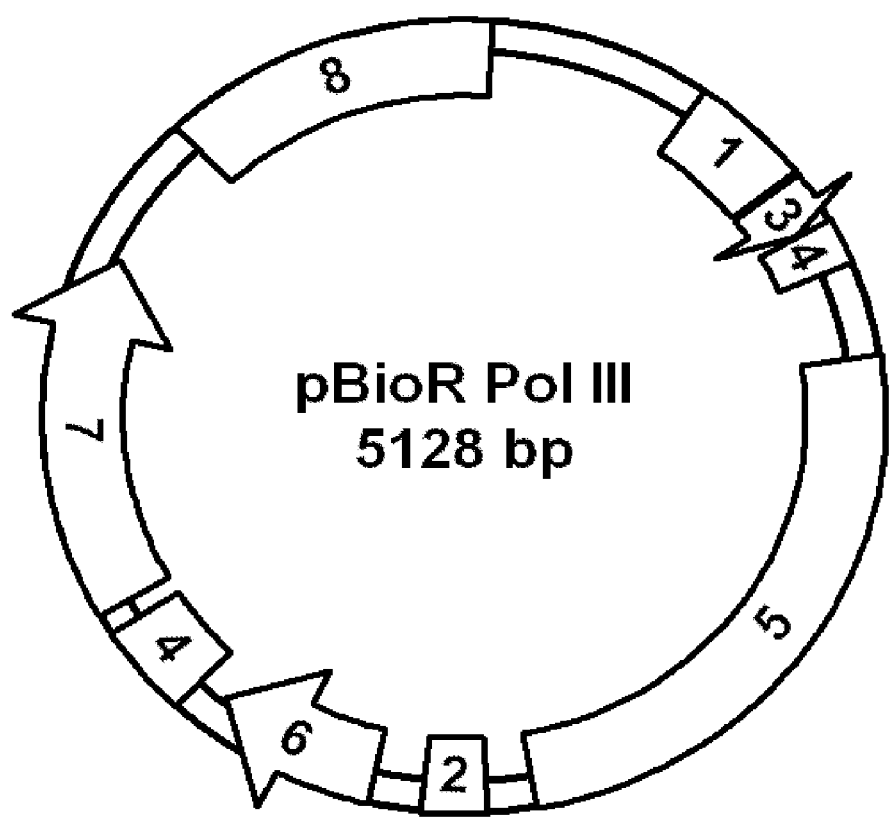

Figure 11. Plasmid map of pBioR combo
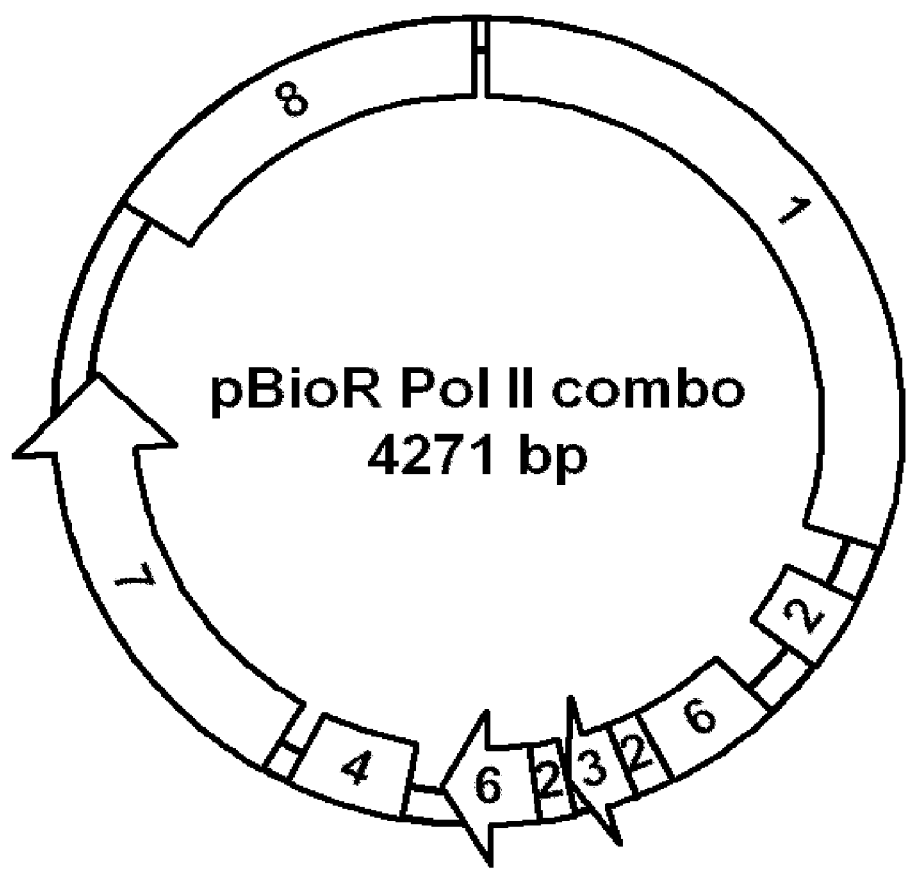

Figure 12. Plasmid map of pBioR Pol II stable
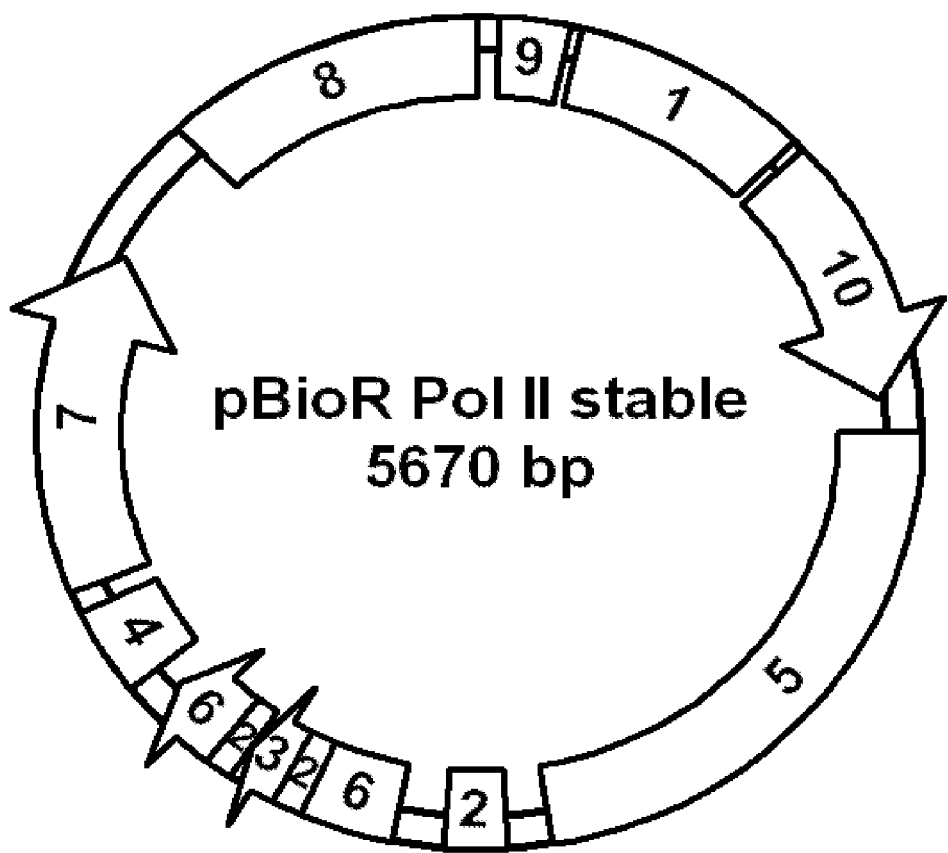

Figure 13. Plasmid map of pBioR Dicer
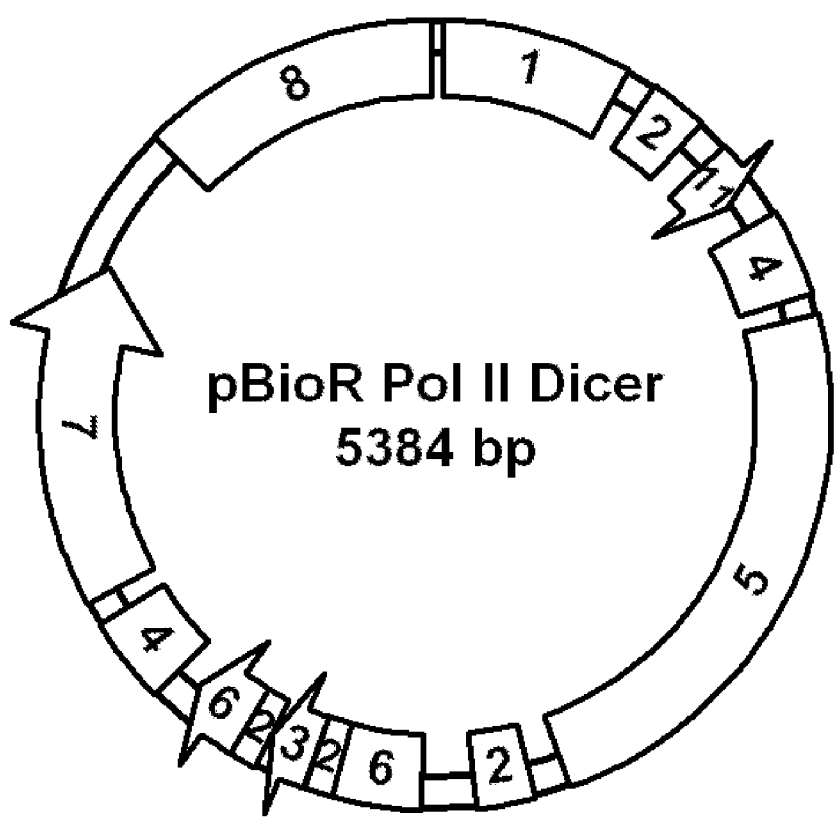

Figure 14A and 14B. Luciferase / Alkaline Phosphatase assay of BioReactor activity
14A.
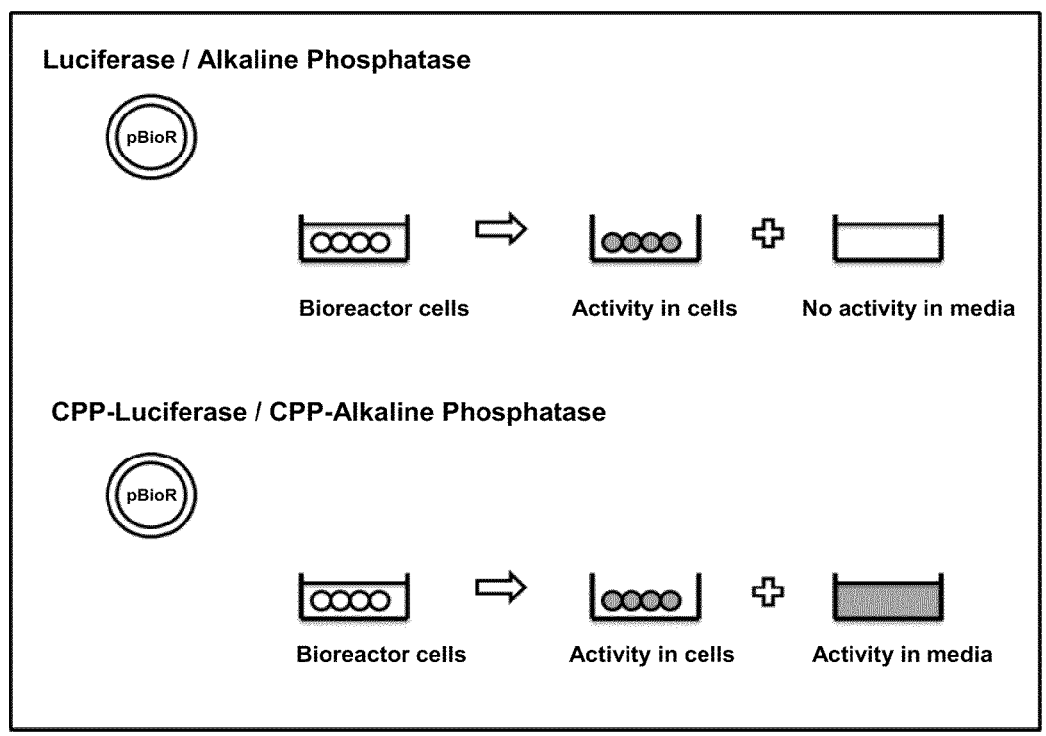
14B.
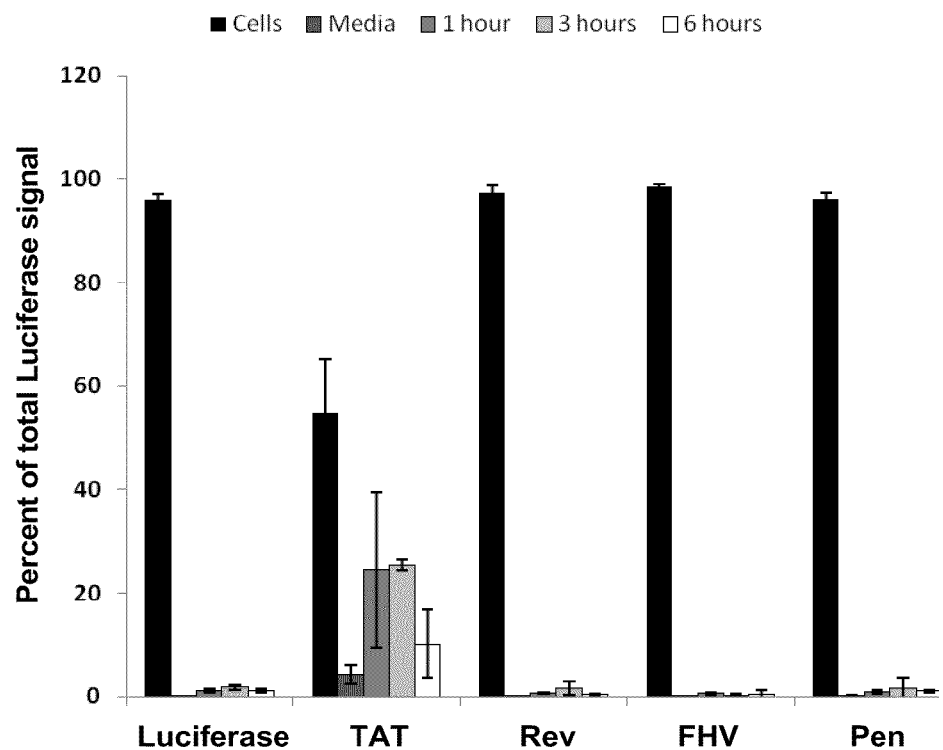

Figure 15A and 15B. Bioreactor component plasmid construction
15A.
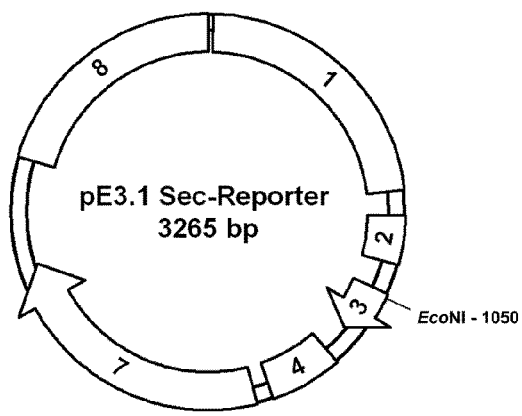
15B.
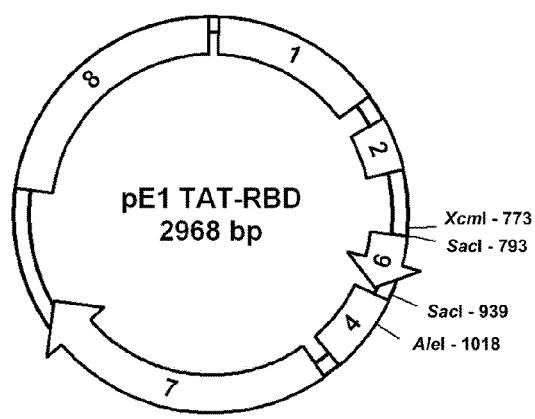
15C.
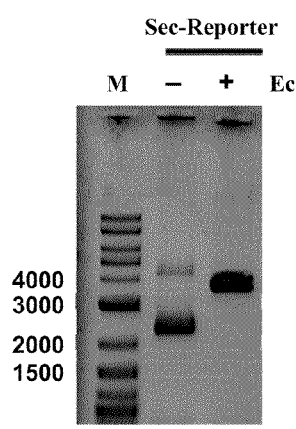
15D.
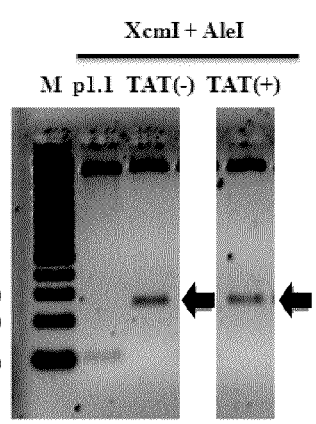
15E.
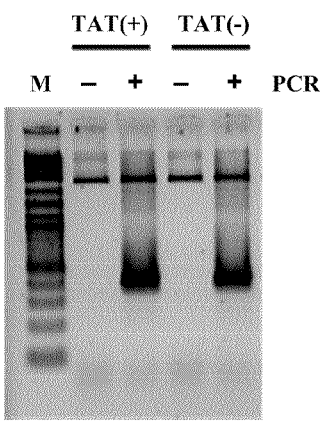

Figure 16. Bioreactor plasmid products
16A. Sec-RNA bioreactor plasmid product
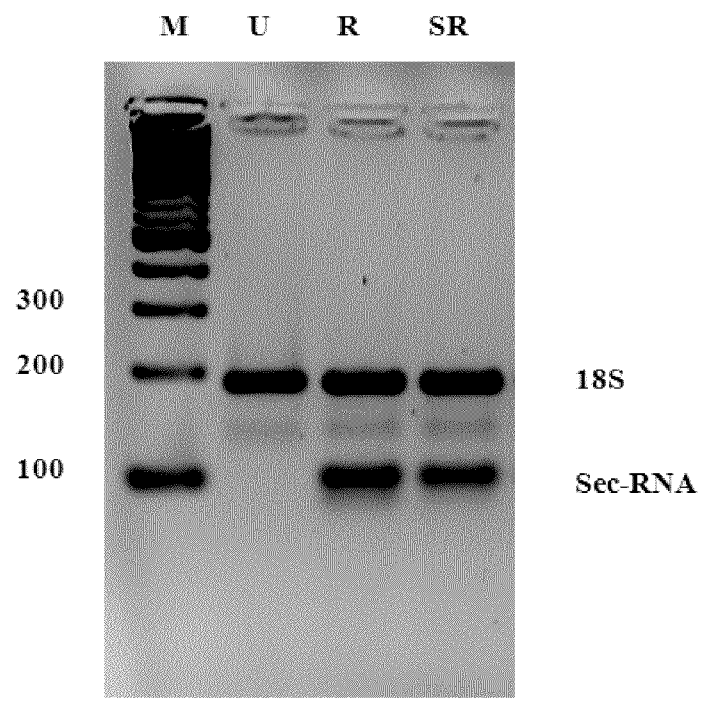
16B. Fusion protein bioreactor plasmid products
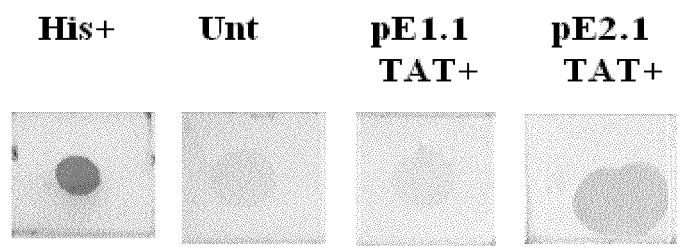

Figure 17. Bioreactor activity
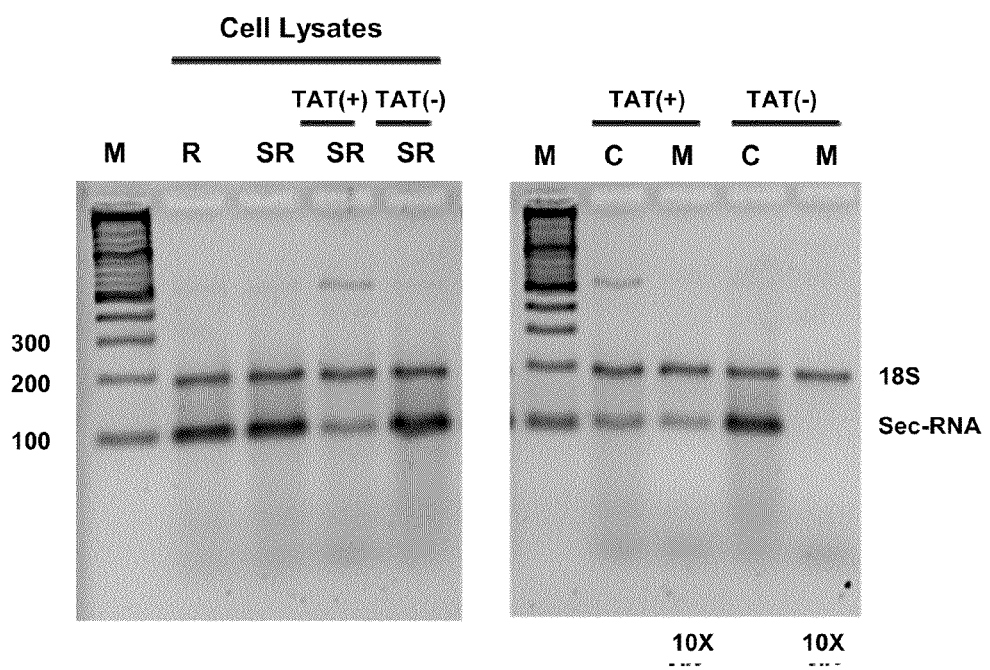
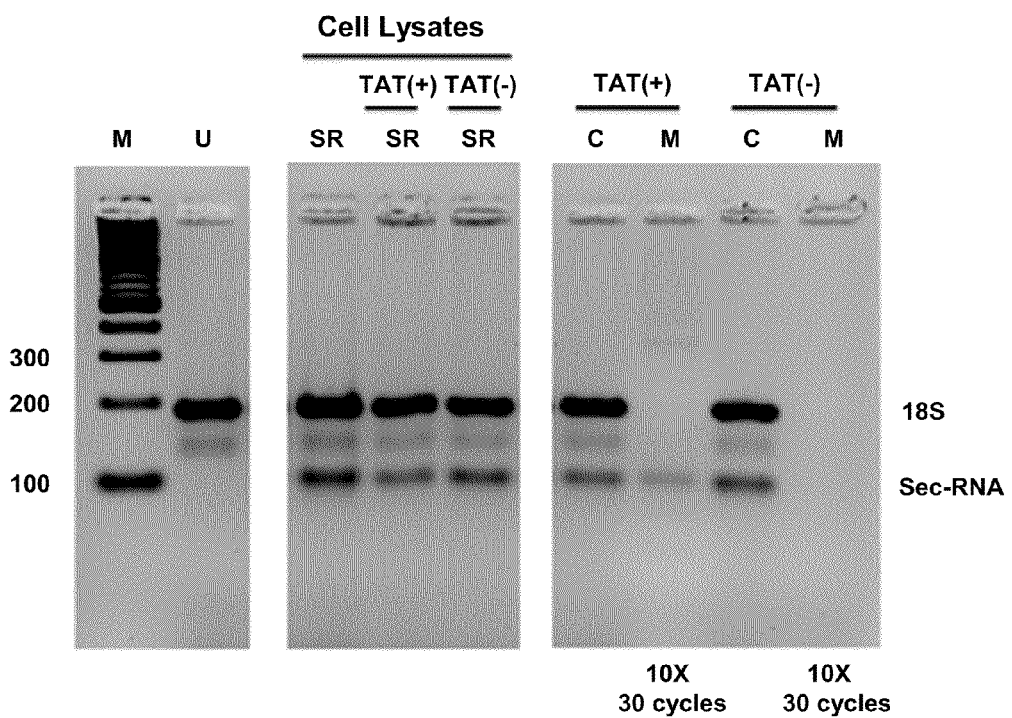

Figure 18. Cell mixing assay of BioReactor activity
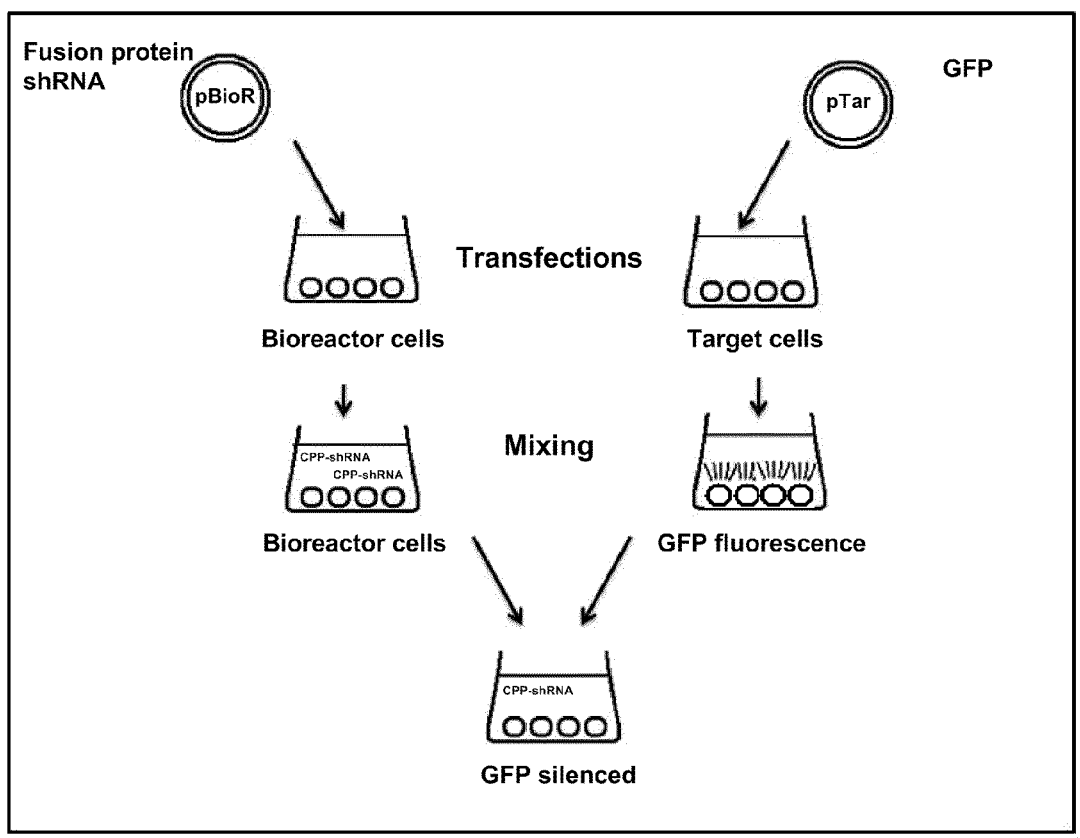

Figure 19A. BioReactor mediated secretion of the Oncostatin M aptamer and reporter assay
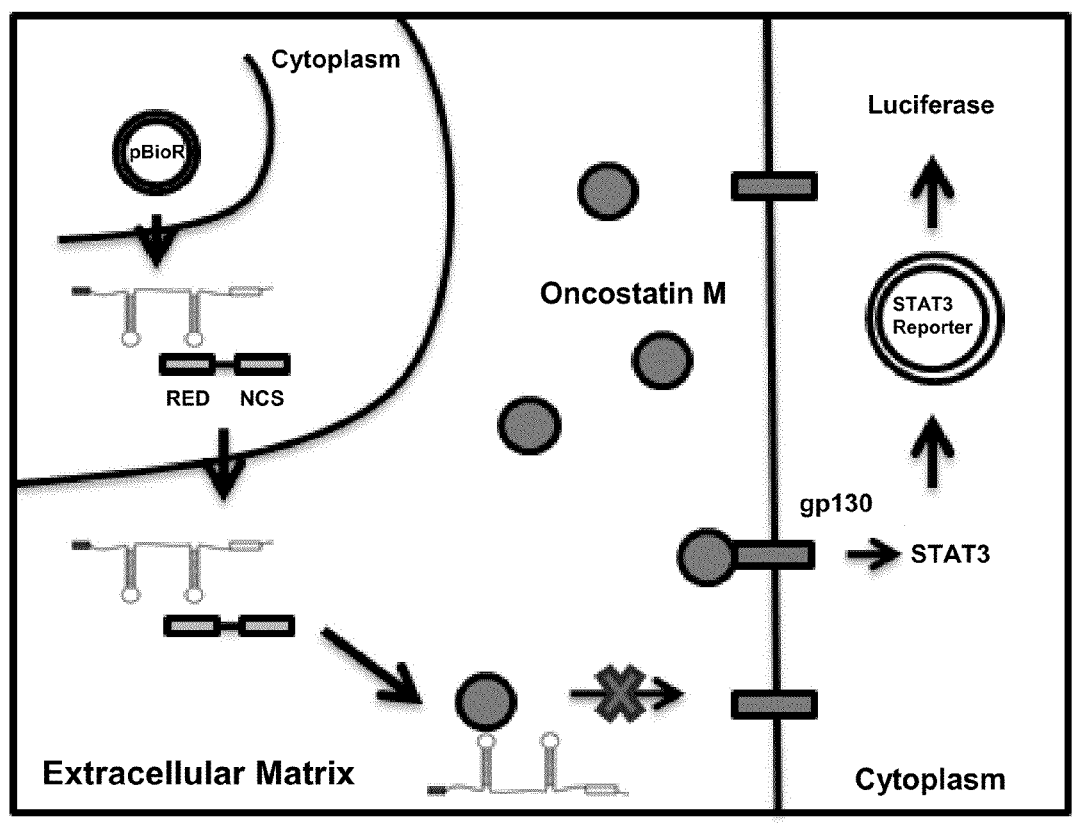

Figure 19B. Cell mixing assay of BioReactor activity secreting an aptamer targted to Onstatin M
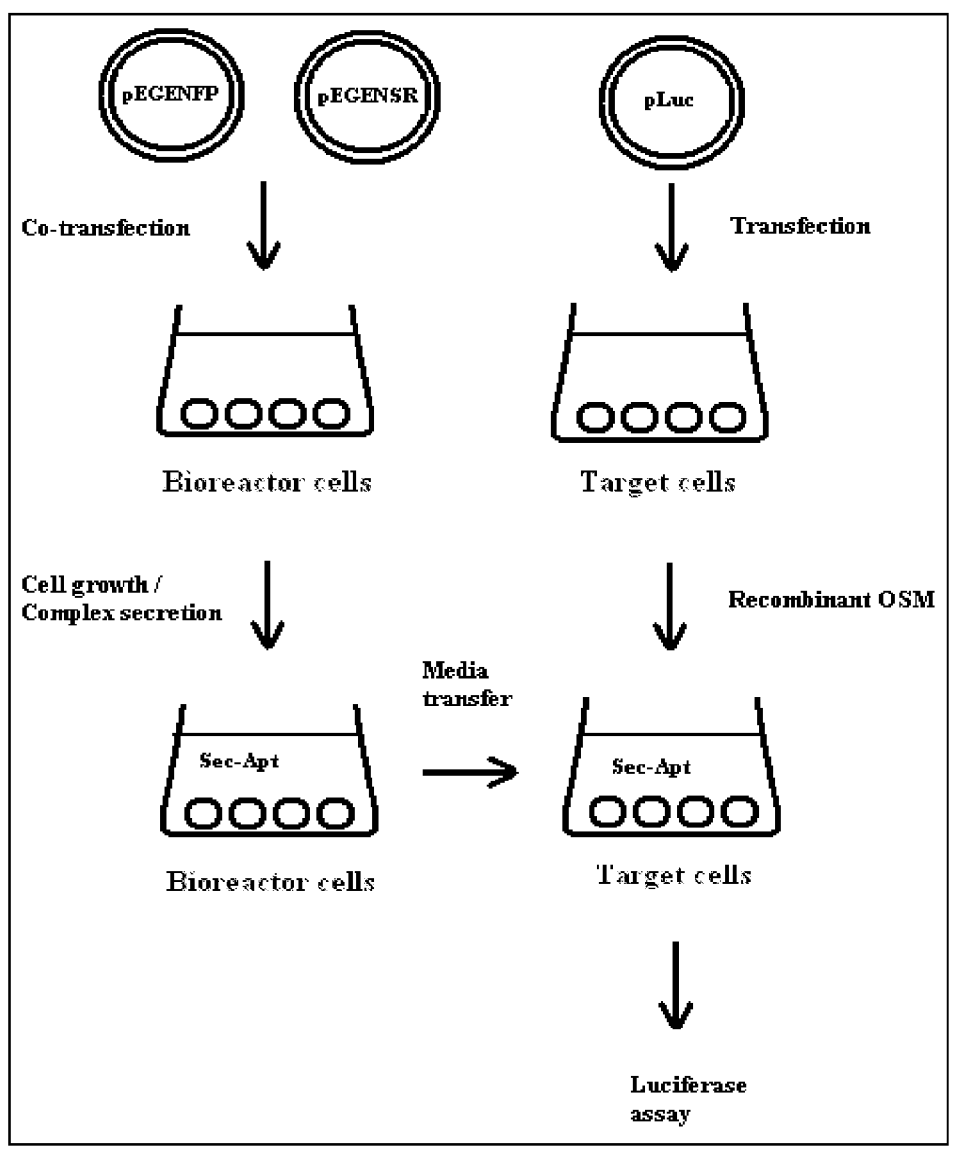

Figure 20A. Bioreactor mediated secretion of the HER3 aptamer and growth assay
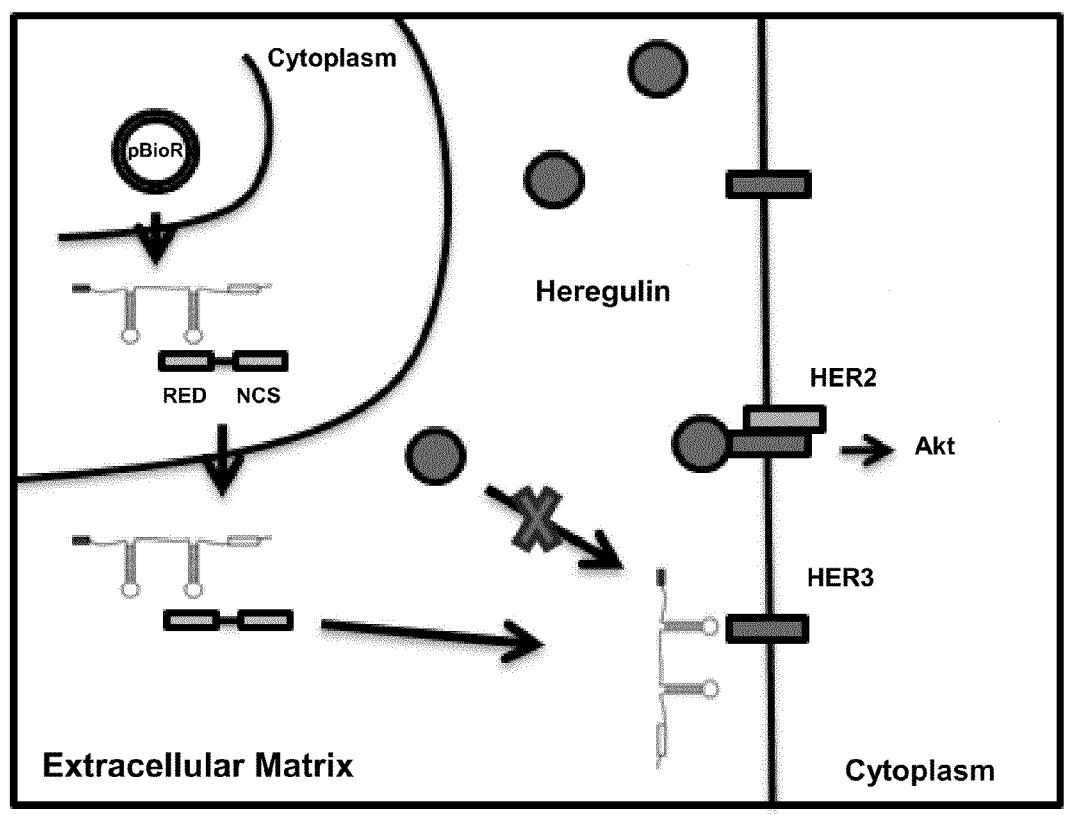

Figure 20B. Cell mixing assay of BioReactor activity secreting an aptamer targeted to HER3
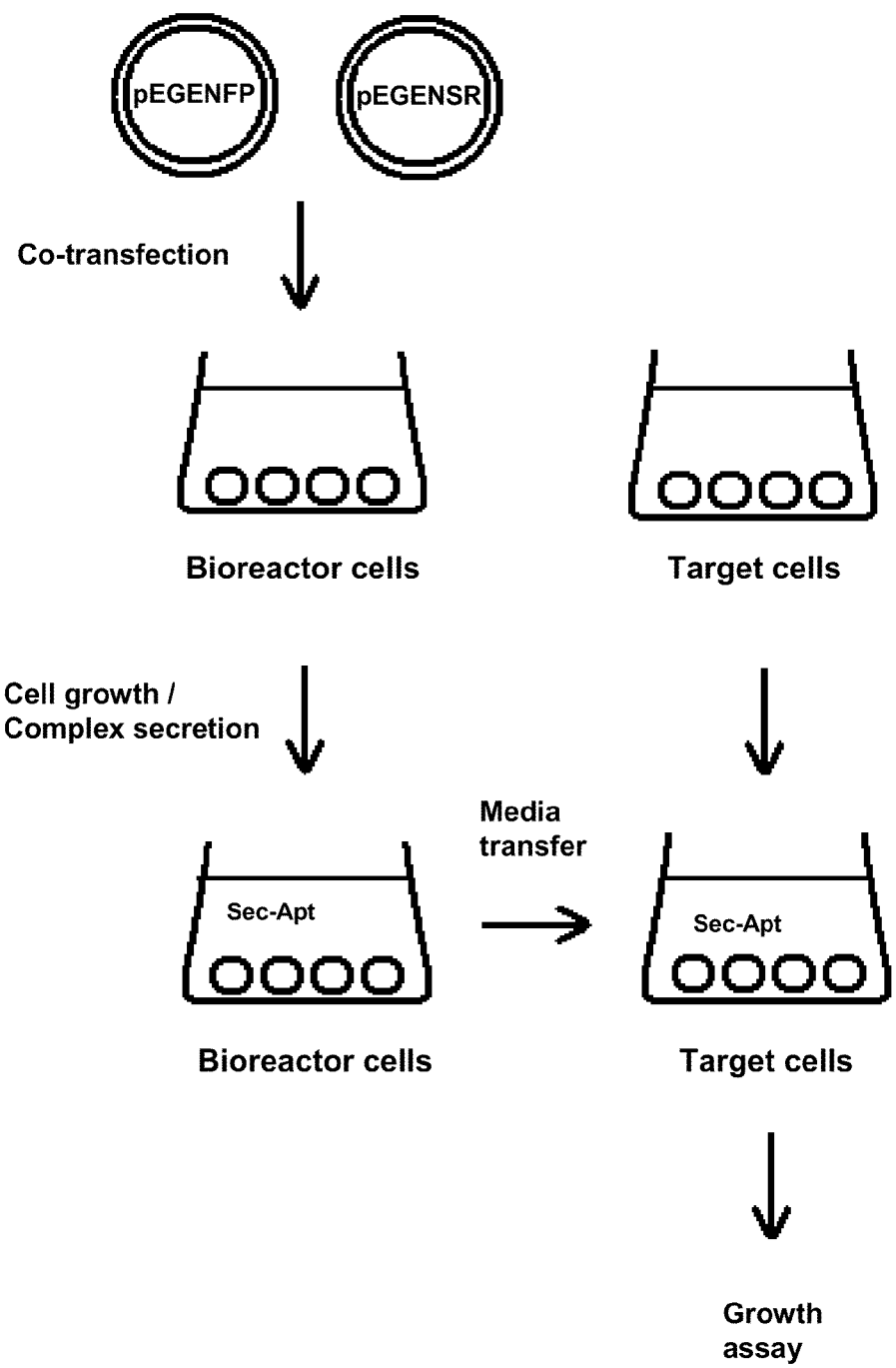

Figure 21. Bioreactor mediated secretion and delivery of an shRNA to target cells
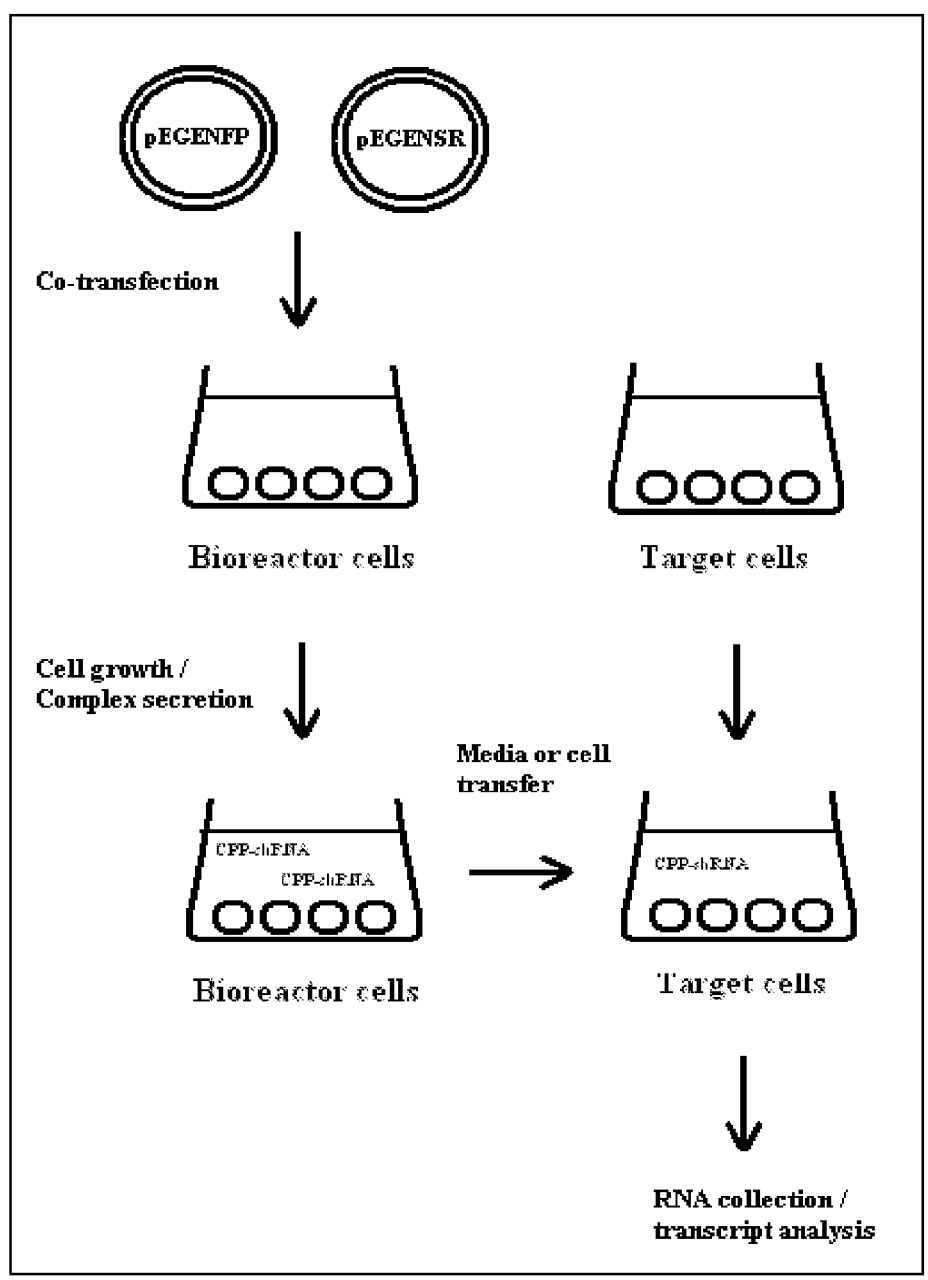

Figure 22. Viral RNAs for viral based delivery system
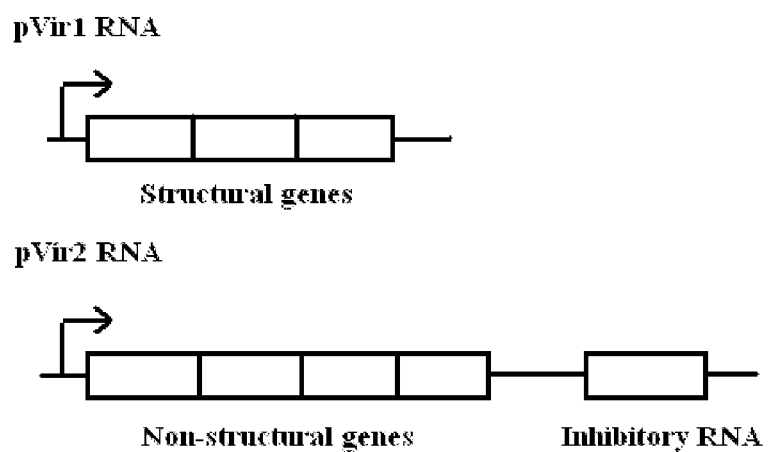

Figure 23. Viral based delivery
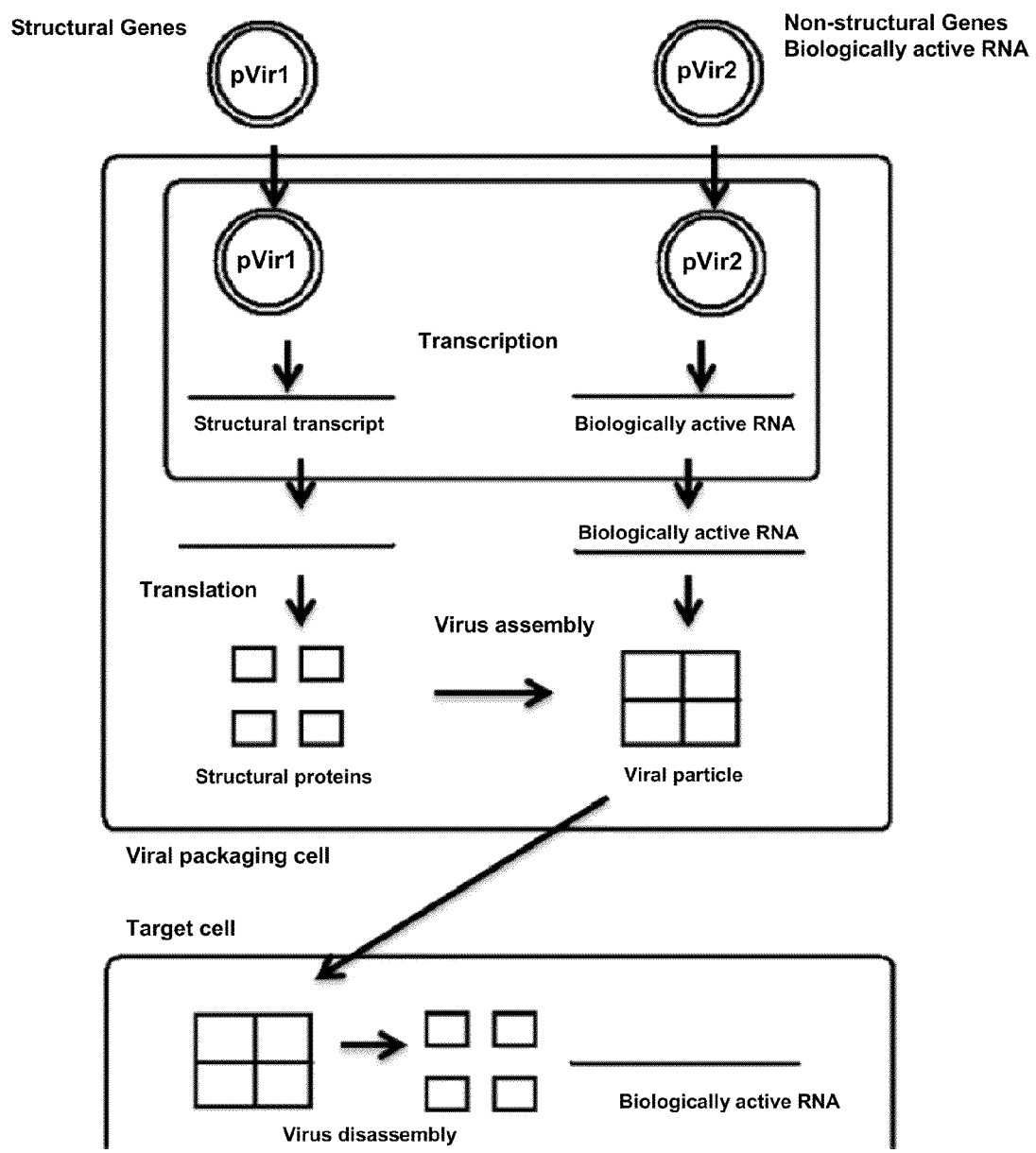

Figure 24. Viral mediated establishment of protein based bioreactor delivery systems
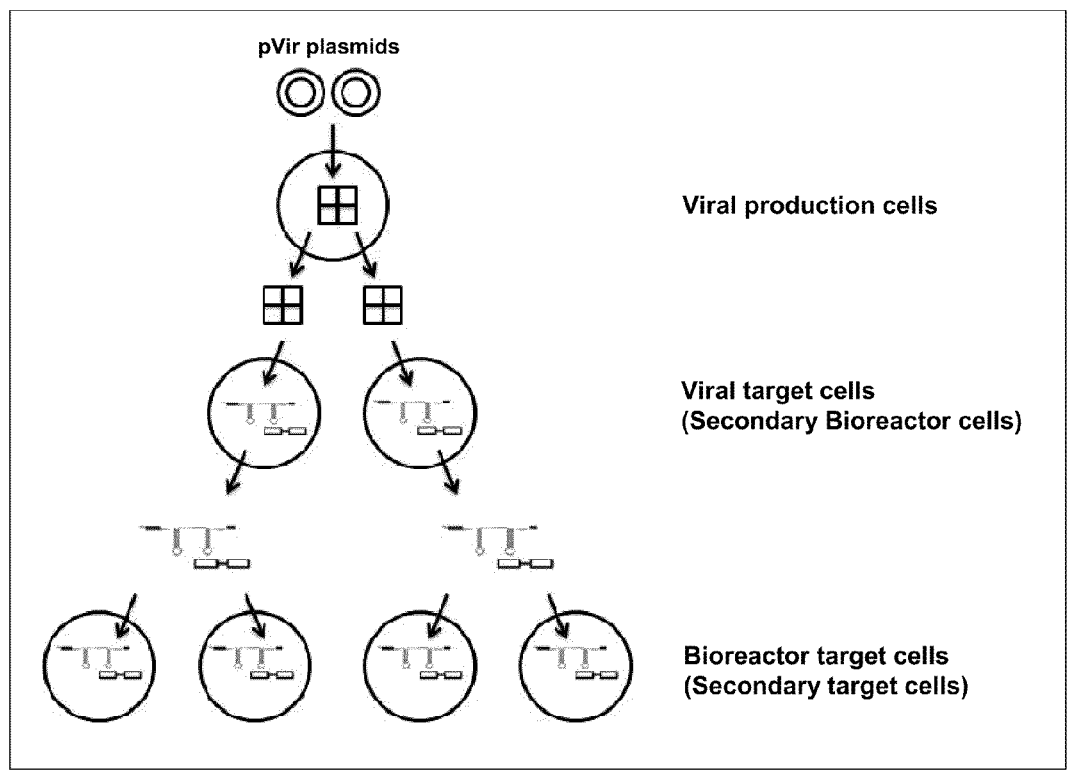

SEQUENCE LISTING

<160> NUMBER OF SEQ ID NOS: 54

<210> SEQ ID NO 1
<211> LENGTH: 48
<212> TYPE: RNA
<213> ORGANISM: Artificial Sequence
<220> FEATURE:
<223> OTHER INFORMATION: Synthetic

<400> SEQUENCE: 1
gcaauaccug aauacuuucu acucgaguag aaaguauuca gguauugc         48

<210> SEQ ID NO 2
<211> LENGTH: 47
<212> TYPE: RNA
<213> ORGANISM: Artificial Sequence
<220> FEATURE:
<223> OTHER INFORMATION: Synthetic

<400> SEQUENCE: 2
gcggaucaaa ccuaccaaa cucgaguuug gugagguuug auccgca         47

<210> SEQ ID NO 3
<211> LENGTH: 47
<212> TYPE: RNA
<213> ORGANISM: Artificial Sequence
<220> FEATURE:
<223> OTHER INFORMATION: Synthetic

<400> SEQUENCE: 3
ccauguacca gccuggcuga ugaguccgug aggacgaaaa ccacuug         47

<210> SEQ ID NO 4
<211> LENGTH: 47
<212> TYPE: RNA
<213> ORGANISM: Artificial Sequence
<220> FEATURE:
<223> OTHER INFORMATION: Synthetic

<400> SEQUENCE: 4
gacccacucu uugaagcugu ucucgagaac agcuucaaag agugggu         47

<210> SEQ ID NO 5
<211> LENGTH: 47
<212> TYPE: RNA
<213> ORGANISM: Artificial Sequence
<220> FEATURE:
<223> OTHER INFORMATION: Synthetic

<400> SEQUENCE: 5
cuccauaaau gcuacgaaua cucgaguauu cguagcauuu auggaga         47

<210> SEQ ID NO 6
<211> LENGTH: 48
<212> TYPE: RNA
<213> ORGANISM: Artificial Sequence
<220> FEATURE:
<223> OTHER INFORMATION: Synthetic

<400> SEQUENCE: 6
ccaggaggag uacagcgcca ucucgagaug gcgcuguacu ccuccugg        48

<210> SEQ ID NO 7
<211> LENGTH: 47
<212> TYPE: RNA
<213> ORGANISM: Artificial Sequence
<220> FEATURE:
<223> OTHER INFORMATION: Synthetic

<400> SEQUENCE: 7
ggaugacuga guaccugaac cucgagguuc agguacucag ucaucca         47

<210> SEQ ID NO 8
<211> LENGTH: 47
<212> TYPE: RNA
<213> ORGANISM: Artificial Sequence
<220> FEATURE:
<223> OTHER INFORMATION: Synthetic

<400> SEQUENCE: 8
ggcuggcuuc auccacugcu ucaagagagc aguggaugaa gccagcc         47

<210> SEQ ID NO 9
<211> LENGTH: 48
<212> TYPE: RNA
<213> ORGANISM: Artificial Sequence
<220> FEATURE:
<223> OTHER INFORMATION: Synthetic

```
<400> SEQUENCE: 9
aaccaccugg gccaguauua ucucgagaua auacuggccc aggugguu                    48

<210> SEQ ID NO 10
<211> LENGTH: 41
<212> TYPE: RNA
<213> ORGANISM: Artificial Sequence
<220> FEATURE:
<223> OTHER INFORMATION: Synthetic

<400> SEQUENCE: 10
gccgaucuag gcagaugcca cacccaucug ccuagaucgg c                          41

<210> SEQ ID NO 11
<211> LENGTH: 67
<212> TYPE: RNA
<213> ORGANISM: Artificial Sequence
<220> FEATURE:
<223> OTHER INFORMATION: Synthetic

<400> SEQUENCE: 11
cgcgugugcc agcgaaaguu gcguaugggu cacaucgcag gcacauguca ucgggcggu       60 ccguucg                                                                67

<210> SEQ ID NO 12
<211> LENGTH: 81
<212> TYPE: RNA
<213> ORGANISM: Artificial Sequence
<220> FEATURE:
<223> OTHER INFORMATION: Synthetic

<400> SEQUENCE: 12
ggacgcgugg uaccaggccg aucuauggac gcuauaggca caccggauac uuuaacgauu      60
ggcuaagcuu ccgcggggau c                                                81

<210> SEQ ID NO 13
<211> LENGTH: 48
<212> TYPE: RNA
<213> ORGANISM: Artificial Sequence
<220> FEATURE:
<223> OTHER INFORMATION: Synthetic

<400> SEQUENCE: 13
ucagagcggu uacugcucaa ucucgagauu gagcaguaac cgcucuga                   48

<210> SEQ ID NO 14
<211> LENGTH: 50
<212> TYPE: RNA
<213> ORGANISM: Artificial Sequence
<220> FEATURE:
<223> OTHER INFORMATION: Synthetic

<400> SEQUENCE: 14
gcgcgggaau aguauggaag gauacguaua ccgugcaauc cagggcaacg                 50

<210> SEQ ID NO 15
<211> LENGTH: 33
<212> TYPE: RNA
<213> ORGANISM: Artificial Sequence
<220> FEATURE:
<223> OTHER INFORMATION: Synthetic

<400> SEQUENCE: 15
gaucuugaaa cuguuuuaag guuggccgau cuu                                   33
```

<210> SEQ ID NO 16
<211> LENGTH: 25
<212> TYPE: RNA
<213> ORGANISM: Artificial Sequence
<220> FEATURE:
<223> OTHER INFORMATION: Synthetic

<400> SEQUENCE: 16
ggguauccau ugcacuccgg augcc                                         25

<210> SEQ ID NO 17
<211> LENGTH: 104
<212> TYPE: RNA
<213> ORGANISM: Artificial Sequence
<220> FEATURE:
<223> OTHER INFORMATION: Synthetic

<400> SEQUENCE: 17
uuugaagaaa aaauaaaagg aauucuauca auuuuuauuu uccauuuauu uaguuaguuu     60
uucuuaauga aauugaaauu auuaacuaac agagcaaaca caaa                    104

<210> SEQ ID NO 18
<211> LENGTH: 22
<212> TYPE: RNA
<213> ORGANISM: Artificial Sequence
<220> FEATURE:
<223> OTHER INFORMATION: Synthetic

<400> SEQUENCE: 18
ggccgaaauc ccgaaguagg cc                                            22

<210> SEQ ID NO 19
<211> LENGTH: 21
<212> TYPE: RNA
<213> ORGANISM: Artificial Sequence
<220> FEATURE:
<223> OTHER INFORMATION: Synthetic

<400> SEQUENCE: 19
ggacugucca caagacaguc c                                             21

<210> SEQ ID NO 20
<211> LENGTH: 13
<212> TYPE: RNA
<213> ORGANISM: Artificial Sequence
<220> FEATURE:
<223> OTHER INFORMATION: Synthetic

<400> SEQUENCE: 20
auuuauuuau uua                                                      13

<210> SEQ ID NO 21
<211> LENGTH: 16
<212> TYPE: RNA
<213> ORGANISM: Artificial Sequence
<220> FEATURE:
<223> OTHER INFORMATION: Synthetic

<400> SEQUENCE: 21
ggcccugaaa aagggc                                                   16

<210> SEQ ID NO 22
<211> LENGTH: 33
<212> TYPE: RNA
<213> ORGANISM: Artificial Sequence

```
<220> FEATURE:
<223> OTHER INFORMATION: Synthetic

<400> SEQUENCE: 22
ggucugggcg cagcgcaagc ugcgguacag gcc                              33

<210> SEQ ID NO 23
<211> LENGTH: 42
<212> TYPE: RNA
<213> ORGANISM: Artificial Sequence
<220> FEATURE:
<223> OTHER INFORMATION: Synthetic

<400> SEQUENCE: 23
ggcaugcuca ugcaaaacug caugaaugcc ccuaagggau gc                    42

<210> SEQ ID NO 24
<211> LENGTH: 98
<212> TYPE: PRT
<213> ORGANISM: Artificial Sequence
<220> FEATURE:
<223> OTHER INFORMATION: Synthetic

<400> SEQUENCE: 24
```

Met Ala Val Pro Glu Thr Arg Pro Asn His Thr Ile Tyr Ile Asn Asn
1               5                   10                  15

Leu Asn Glu Lys Ile Lys Lys Asp Glu Leu Lys Lys Ser Leu Tyr Ala
            20                  25                  30

Ile Phe Ser Gln Phe Gly Gln Ile Leu Asp Ile Leu Val Ser Arg Ser
        35                  40                  45

Leu Lys Met Arg Gly Gln Ala Phe Val Ile Phe Lys Glu Val Ser Ser
    50                  55                  60

Ala Arg Asn Ala Leu Arg Ser Met Gln Gly Phe Pro Phe Tyr Asp Lys
65                  70                  75                  80

Pro Met Arg Ile Gln Tyr Ala Lys Thr Asp Ser Asp Ile Ile Ala Lys
                85                  90                  95

Met Lys

```
<210> SEQ ID NO 25
<211> LENGTH: 86
<212> TYPE: PRT
<213> ORGANISM: Artificial Sequence
<220> FEATURE:
<223> OTHER INFORMATION: Synthetic

<400> SEQUENCE: 25
```

Leu Glu Thr His Glu Leu Arg Arg Leu Arg Arg Leu Ala Arg Gly Ile
1               5                   10                  15

Gly Arg Trp Ala Arg Ala Lys Lys Ala Gly Val Thr Asp Glu Val Val
            20                  25                  30

Lys Glu Val Arg Arg Glu Trp Ala Ser Gly Glu Leu Ala Ala Val
        35                  40                  45

Arg Ile Val Glu Pro Leu Arg Arg Ser Met Asp Arg Ala Arg Glu Ile
    50                  55                  60

Leu Glu Ile Lys Thr Gly Gly Leu Val Val Trp Thr Lys Gly Asp Met
65                  70                  75                  80

His Phe Val Tyr Arg Gly
                85

```
<210> SEQ ID NO 26
<211> LENGTH: 176
```

<212> TYPE: PRT
<213> ORGANISM: Artificial Sequence
<220> FEATURE:
<223> OTHER INFORMATION: Synthetic

<400> SEQUENCE: 26

Met Gly Ser His Met Val Glu Gly Ser Glu Ser Thr Thr Pro Phe Asn
1               5                   10                  15

Leu Phe Ile Gly Asn Leu Asn Pro Asn Lys Ser Val Ala Glu Leu Lys
            20                  25                  30

Val Ala Ile Ser Glu Leu Phe Ala Lys Asn Asp Leu Ala Val Val Asp
        35                  40                  45

Val Arg Thr Gly Thr Asn Arg Lys Phe Gly Tyr Val Asp Phe Glu Ser
    50                  55                  60

Ala Glu Asp Leu Glu Lys Ala Leu Glu Leu Thr Gly Leu Lys Val Phe
65                  70                  75                  80

Gly Asn Glu Ile Lys Leu Glu Lys Pro Lys Gly Arg Asp Ser Lys Lys
                85                  90                  95

Val Arg Ala Ala Arg Thr Leu Leu Ala Lys Asn Leu Ser Phe Asn Ile
            100                 105                 110

Thr Glu Asp Glu Leu Lys Glu Val Phe Glu Asp Ala Leu Glu Ile Arg
        115                 120                 125

Leu Val Ser Gln Asp Gly Lys Ser Lys Cys Ile Ala Tyr Ile Glu Phe
    130                 135                 140

Lys Ser Glu Ala Asp Ala Glu Lys Asn Leu Glu Glu Lys Gln Gly Ala
145                 150                 155                 160

Glu Ile Asp Gly Arg Ser Val Ser Leu Tyr Tyr Thr Gly Glu Lys Gly
                165                 170                 175

<210> SEQ ID NO 27
<211> LENGTH: 98
<212> TYPE: PRT
<213> ORGANISM: Artificial Sequence
<220> FEATURE:
<223> OTHER INFORMATION: Synthetic

<400> SEQUENCE: 27

Met Val Glu Ala Asp His Pro Gly Lys Leu Thr Ile Gly Gly Leu Asn
1               5                   10                  15

Arg Glu Thr Asn Glu Lys Met Leu Lys Ala Val Phe Gly Lys His Gly
            20                  25                  30

Pro Ile Ser Glu Val Leu Leu Ile Lys Asp Arg Thr Ser Lys Ser Arg
        35                  40                  45

Gly Phe Ala Phe Ile Thr Phe Glu Asn Pro Ala Asp Ala Lys Asn Ala
    50                  55                  60

Ala Lys Asp Met Asn Gly Lys Ser Leu His Gly Lys Ala Ile Lys Val
65                  70                  75                  80

Glu Gln Ala Lys Lys Pro Ser Phe Gln Ser Gly Gly Arg Arg Arg Pro
                85                  90                  95

Pro Ala

<210> SEQ ID NO 28
<211> LENGTH: 74
<212> TYPE: PRT
<213> ORGANISM: Artificial Sequence
<220> FEATURE:
<223> OTHER INFORMATION: Synthetic

<400> SEQUENCE: 28

Met Ser Arg Tyr Lys Thr Glu Leu Cys Arg Thr Phe Ser Glu Ser Gly
1               5                   10                  15

Arg Cys Arg Tyr Gly Ala Lys Cys Gln Phe Ala His Gly Leu Gly Glu
            20                  25                  30

Leu Arg Gln Ala Asn Arg His Pro Lys Tyr Lys Thr Glu Leu Cys His
        35                  40                  45

Lys Phe Tyr Leu Gln Gly Arg Cys Pro Tyr Gly Ser Arg Cys His Phe
    50                  55                  60

Ile His Asn Pro Ser Glu Asp Leu Ala Ala
65                  70

<210> SEQ ID NO 29
<211> LENGTH: 22
<212> TYPE: PRT
<213> ORGANISM: Artificial Sequence
<220> FEATURE:
<223> OTHER INFORMATION: Synthetic

<400> SEQUENCE: 29

Met Asp Ala Gln Thr Arg Arg Arg Glu Arg Arg Ala Glu Lys Gln Ala
1               5                   10                  15

Gln Trp Lys Ala Ala Asn
            20

<210> SEQ ID NO 30
<211> LENGTH: 23
<212> TYPE: PRT
<213> ORGANISM: Artificial Sequence
<220> FEATURE:
<223> OTHER INFORMATION: Synthetic

<400> SEQUENCE: 30

Asp Thr Arg Gln Ala Arg Arg Asn Arg Arg Arg Arg Trp Arg Glu Arg
1               5                   10                  15

Gln Arg Ala Ala Ala Ala Arg
            20

<210> SEQ ID NO 31
<211> LENGTH: 26
<212> TYPE: PRT
<213> ORGANISM: Artificial Sequence
<220> FEATURE:
<223> OTHER INFORMATION: Synthetic

<400> SEQUENCE: 31

Ser Ser Ser Gln Lys Lys Ala Gly Gly Lys Ala Gly Lys Pro Thr Lys
1               5                   10                  15

Arg Ser Gln Asn Tyr Ala Ala Leu Arg Lys
            20                  25

<210> SEQ ID NO 32
<211> LENGTH: 16
<212> TYPE: PRT
<213> ORGANISM: Artificial Sequence
<220> FEATURE:
<223> OTHER INFORMATION: Synthetic

<400> SEQUENCE: 32

Arg Gln Ile Lys Ile Trp Phe Gln Asn Arg Arg Met Lys Trp Lys Lys
1               5                   10                  15

<210> SEQ ID NO 33
<211> LENGTH: 26
<212> TYPE: PRT

<210> SEQ ID NO 33
<211> LENGTH: (not shown)
<212> TYPE: PRT
<213> ORGANISM: Artificial Sequence
<220> FEATURE:
<223> OTHER INFORMATION: Synthetic

<400> SEQUENCE: 33

```
Gly Trp Thr Leu Asn Ser Ala Gly Tyr Leu Leu Lys Ile Asn Leu Lys
1               5                   10                  15
Ala Leu Ala Ala Leu Ala Lys Lys Ile Leu
            20                  25
```

<210> SEQ ID NO 34
<211> LENGTH: 21
<212> TYPE: PRT
<213> ORGANISM: Artificial Sequence
<220> FEATURE:
<223> OTHER INFORMATION: Synthetic

<400> SEQUENCE: 34

```
Lys Leu Ala Leu Lys Leu Ala Leu Lys Ala Leu Lys Ala Leu Lys Ala
1               5                   10                  15
Ala Leu Lys Leu Ala
            20
```

<210> SEQ ID NO 35
<211> LENGTH: 13
<212> TYPE: PRT
<213> ORGANISM: Artificial Sequence
<220> FEATURE:
<223> OTHER INFORMATION: Synthetic

<400> SEQUENCE: 35

```
Gly Arg Lys Lys Arg Arg Gln Arg Arg Arg Pro Pro Gln
1               5                   10
```

<210> SEQ ID NO 36
<211> LENGTH: 16
<212> TYPE: PRT
<213> ORGANISM: Artificial Sequence
<220> FEATURE:
<223> OTHER INFORMATION: Synthetic

<400> SEQUENCE: 36

```
Arg Gln Ile Lys Ile Tyr Phe Gln Asn Arg Arg Met Lys Trp Lys Lys
1               5                   10                  15
```

<210> SEQ ID NO 37
<211> LENGTH: 17
<212> TYPE: PRT
<213> ORGANISM: Artificial Sequence
<220> FEATURE:
<223> OTHER INFORMATION: Synthetic

<400> SEQUENCE: 37

```
Thr Arg Gln Ala Arg Arg Asn Arg Arg Arg Trp Arg Glu Arg Gln
1               5                   10                  15
Arg
```

<210> SEQ ID NO 38
<211> LENGTH: 14
<212> TYPE: PRT
<213> ORGANISM: Artificial Sequence
<220> FEATURE:
<223> OTHER INFORMATION: Synthetic

<400> SEQUENCE: 38

```
Arg Arg Arg Asn Arg Thr Arg Arg Asn Arg Arg Arg Val Arg
```

<210> SEQ ID NO 39
<211> LENGTH: 21
<212> TYPE: PRT
<213> ORGANISM: Artificial Sequence
<220> FEATURE:
<223> OTHER INFORMATION: Synthetic

<400> SEQUENCE: 39

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 40
<211> LENGTH: 18
<212> TYPE: PRT
<213> ORGANISM: Artificial Sequence
<220> FEATURE:
<223> OTHER INFORMATION: Synthetic

<400> SEQUENCE: 40

Leu Leu Ile Ile Leu Arg Arg Arg Ile Arg Lys Gln Ala His Ala His
1               5                   10                  15

Ser Lys

<210> SEQ ID NO 41
<211> LENGTH: 155
<212> TYPE: PRT
<213> ORGANISM: Artificial Sequence
<220> FEATURE:
<223> OTHER INFORMATION: Synthetic

<400> SEQUENCE: 41

Met Ala Glu Gly Glu Ile Thr Thr Phe Ala Ala Leu Thr Glu Arg Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Ala Gly Glu Val Tyr Ile Lys Gly Thr Glu Thr Gly Gln Tyr Leu
65                  70                  75                  80

Ala Met Asp Thr Glu Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 42
<211> LENGTH: 155
<212> TYPE: PRT
<213> ORGANISM: Artificial Sequence
<220> FEATURE:
<223> OTHER INFORMATION: Synthetic

```
<400> SEQUENCE: 42

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Arg Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Ala Met Ser Ala Lys Ser
145                 150                 155

<210> SEQ ID NO 43
<211> LENGTH: 105
<212> TYPE: PRT
<213> ORGANISM: Artificial Sequence
<220> FEATURE:
<223> OTHER INFORMATION: Synthetic

<400> SEQUENCE: 43

Met Val Lys Gln Ile Glu Ser Lys Thr Ala Phe Gln Glu Ala Leu Asp
1               5                   10                  15

Ala Ala Gly Asp Lys Leu Val Val Val Asp Phe Ser Ala Thr Trp Cys
            20                  25                  30

Gly Pro Cys Lys Met Ile Lys Pro Phe Phe His Ser Leu Ser Glu Lys
        35                  40                  45

Tyr Ser Asn Val Ile Phe Leu Glu Val Asp Val Asp Asp Cys Gln Asp
50                  55                  60

Val Ala Ser Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val
            100                 105

<210> SEQ ID NO 44
<211> LENGTH: 135
<212> TYPE: PRT
<213> ORGANISM: Artificial Sequence
<220> FEATURE:
<223> OTHER INFORMATION: Synthetic

<400> SEQUENCE: 44

Met Ala Cys Gly Leu Val Ala Ser Asn Leu Asn Leu Lys Pro Gly Glu
1               5                   10                  15

Cys Leu Arg Val Arg Gly Glu Val Ala Pro Asp Ala Lys Ser Phe Val
            20                  25                  30
```

-continued

Leu Asn Leu Gly Lys Asp Ser Asn Asn Leu Cys Leu His Phe Asn Pro
            35                  40                  45

Arg Phe Asn Ala His Gly Asp Ala Asn Thr Ile Val Cys Asn Ser Lys
 50                      55                  60

Asp Gly Gly Ala Trp Gly Thr Glu Gln Arg Glu Ala Val Phe Pro Phe
 65                  70                  75                  80

Gln Pro Gly Ser Val Ala Glu Val Cys Ile Thr Phe Asp Gln Ala Asn
                85                  90                  95

Leu Thr Val Lys Leu Pro Asp Gly Tyr Glu Phe Lys Phe Pro Asn Arg
                100                 105                 110

Leu Asn Leu Glu Ala Ile Asn Tyr Met Ala Ala Asp Gly Asp Phe Lys
            115                 120                 125

Ile Lys Cys Val Ala Phe Asp
            130                 135

<210> SEQ ID NO 45
<211> LENGTH: 250
<212> TYPE: PRT
<213> ORGANISM: Artificial Sequence
<220> FEATURE:
<223> OTHER INFORMATION: Synthetic

<400> SEQUENCE: 45

Met Ala Asp Asn Phe Ser Leu His Asp Ala Leu Ser Gly Ser Gly Asn
 1               5                   10                  15

Pro Asn Pro Gln Gly Trp Pro Gly Ala Trp Gly Asn Gln Pro Ala Gly
                20                  25                  30

Ala Gly Gly Tyr Pro Gly Ala Ser Tyr Pro Gly Ala Tyr Pro Gly Gln
            35                  40                  45

Ala Pro Pro Gly Ala Tyr Pro Gly Gln Ala Pro Pro Gly Ala Tyr Pro
 50                      55                  60

Gly Ala Pro Gly Ala Tyr Pro Gly Ala Pro Ala Pro Gly Val Tyr Pro
 65                  70                  75                  80

Gly Pro Pro Ser Gly Pro Gly Ala Tyr Pro Ser Ser Gly Gln Pro Ser
                85                  90                  95

Ala Thr Gly Ala Tyr Pro Ala Thr Gly Pro Tyr Gly Ala Pro Ala Gly
                100                 105                 110

Pro Leu Ile Val Pro Tyr Asn Leu Pro Leu Pro Gly Gly Val Val Pro
            115                 120                 125

Arg Met Leu Ile Thr Ile Leu Gly Thr Val Lys Pro Asn Ala Asn Arg
 130                     135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Glu Arg Gln Ser Val Phe Pro Phe
            180                 185                 190

Glu Ser Gly Lys Pro Phe Lys Ile Gln Val Leu Val Glu Pro Asp His
            195                 200                 205

Phe Lys Val Ala Val Asn Asp Ala His Leu Leu Gln Tyr Asn His Arg
 210                     215                 220

Val Lys Lys Leu Asn Glu Ile Ser Lys Leu Gly Ile Ser Gly Asp Ile
225                 230                 235                 240

Asp Leu Thr Ser Ala Ser Tyr Thr Met Ile
                245                 250

```
<210> SEQ ID NO 46
<211> LENGTH: 271
<212> TYPE: PRT
<213> ORGANISM: Artificial Sequence
<220> FEATURE:
<223> OTHER INFORMATION: Synthetic

<400> SEQUENCE: 46

Met Ala Lys Val Pro Asp Met Phe Glu Asp Leu Lys Asn Cys Tyr Ser
1               5                   10                  15

Glu Asn Glu Glu Asp Ser Ser Ser Ile Asp His Leu Ser Leu Asn Gln
            20                  25                  30

Lys Ser Phe Tyr His Val Ser Tyr Gly Pro Leu His Glu Gly Cys Met
        35                  40                  45

Asp Gln Ser Val Ser Leu Ser Ile Ser Glu Thr Ser Lys Thr Ser Lys
    50                  55                  60

Leu Thr Phe Lys Glu Ser Met Val Val Ala Thr Asn Gly Lys Val
65                  70                  75                  80

Leu Lys Lys Arg Arg Leu Ser Leu Ser Gln Ser Ile Thr Asp Asp Asp
                85                  90                  95

Leu Glu Ala Ile Ala Asn Asp Ser Glu Glu Ile Ile Lys Pro Arg
            100                 105                 110

Ser Ala Pro Phe Ser Phe Leu Ser Asn Val Lys Tyr Asn Phe Met Arg
        115                 120                 125

Ile Ile Lys Tyr Glu Phe Ile Leu Asn Asp Ala Leu Asn Gln Ser Ile
    130                 135                 140

Ile Arg Ala Asn Asp Gln Tyr Leu Thr Ala Ala Leu His Asn Leu
145                 150                 155                 160

Asp Glu Ala Val Lys Phe Asp Met Gly Ala Tyr Lys Ser Ser Lys Asp
                165                 170                 175

Asp Ala Lys Ile Thr Val Ile Leu Arg Ile Ser Lys Thr Gln Leu Tyr
            180                 185                 190

Val Thr Ala Gln Asp Glu Asp Gln Pro Val Leu Leu Lys Glu Met Pro
        195                 200                 205

Glu Ile Pro Lys Thr Ile Thr Gly Ser Glu Thr Asn Leu Leu Phe Phe
    210                 215                 220

Trp Glu Thr His Gly Thr Lys Asn Tyr Phe Thr Ser Val Ala His Pro
225                 230                 235                 240

Asn Leu Phe Ile Ala Thr Lys Gln Asp Tyr Trp Val Cys Leu Ala Gly
                245                 250                 255

Gly Pro Pro Ser Ile Thr Asp Phe Gln Ile Leu Glu Asn Gln Ala
            260                 265                 270

<210> SEQ ID NO 47
<211> LENGTH: 269
<212> TYPE: PRT
<213> ORGANISM: Artificial Sequence
<220> FEATURE:
<223> OTHER INFORMATION: Synthetic

<400> SEQUENCE: 47

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
```

```
                50                  55                  60
Ala Ser Val Val Ala Met Asp Lys Leu Arg Lys Met Leu Val Pro
 65                  70                  75                  80

Cys Pro Gln Thr Phe Gln Glu Asn Asp Leu Ser Thr Phe Phe Pro Phe
                 85                  90                  95

Ile Phe Glu Glu Pro Ile Phe Phe Asp Thr Trp Asp Asn Glu Ala
                100                 105                 110

Tyr Val His Asp Ala Pro Val Arg Ser Leu Asn Cys Thr Leu Arg Asp
                115                 120                 125

Ser Gln Gln Lys Ser Leu Val Met Ser Gly Pro Tyr Glu Leu Lys Ala
130                 135                 140

Leu His Leu Gln Gly Gln Asp Met Glu Gln Gln Val Val Phe Ser Met
145                 150                 155                 160

Ser Phe Val Gln Gly Glu Ser Asn Asp Lys Ile Pro Val Ala Leu
                165                 170                 175

Gly Leu Lys Glu Lys Asn Leu Tyr Leu Ser Cys Val Leu Lys Asp Asp
                180                 185                 190

Lys Pro Thr Leu Gln Leu Glu Ser Val Asp Pro Lys Asn Tyr Pro Lys
                195                 200                 205

Lys Lys Met Glu Lys Arg Phe Val Phe Asn Lys Ile Glu Ile Asn Asn
210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
                260                 265

<210> SEQ ID NO 48
<211> LENGTH: 297
<212> TYPE: PRT
<213> ORGANISM: Artificial Sequence
<220> FEATURE:
<223> OTHER INFORMATION: Synthetic

<400> SEQUENCE: 48

Met Val His Gln Val Leu Tyr Arg Ala Leu Val Ser Thr Lys Trp Leu
 1               5                  10                  15

Ala Glu Ser Val Arg Ala Gly Lys Val Gly Pro Gly Leu Arg Val Leu
                 20                  25                  30

Asp Ala Ser Trp Tyr Ser Pro Gly Thr Arg Glu Ala Arg Lys Glu Tyr
                 35                  40                  45

Leu Glu Arg His Val Pro Gly Ala Ser Phe Phe Asp Ile Glu Glu Cys
 50                  55                  60

Arg Asp Lys Ala Ser Pro Tyr Glu Val Met Leu Pro Ser Glu Ala Gly
 65                  70                  75                  80

Phe Ala Asp Tyr Val Gly Ser Leu Gly Ile Ser Asn Asp Thr His Val
                 85                  90                  95

Val Val Tyr Asp Gly Asp Asp Leu Gly Ser Phe Tyr Ala Pro Arg Val
                100                 105                 110

Trp Trp Met Phe Arg Val Phe Gly His Arg Thr Val Ser Val Leu Asn
                115                 120                 125

Gly Gly Phe Arg Asn Trp Leu Lys Glu Gly His Pro Val Thr Ser Glu
130                 135                 140

Pro Ser Arg Pro Glu Pro Ala Ile Phe Lys Ala Thr Leu Asn Arg Ser
145                 150                 155                 160
```

```
Leu Leu Lys Thr Tyr Glu Gln Val Leu Glu Asn Leu Glu Ser Lys Arg
            165                 170                 175

Phe Gln Leu Val Asp Ser Arg Ala Gln Gly Arg Tyr Leu Gly Thr Gln
        180                 185                 190

Pro Glu Pro Asp Ala Val Gly Leu Asp Ser Gly His Ile Arg Gly Ser
            195                 200                 205

Val Asn Met Pro Phe Met Asn Phe Leu Thr Glu Asp Gly Phe Glu Lys
        210                 215                 220

Ser Pro Glu Glu Leu Arg Ala Met Phe Glu Ala Lys Lys Val Asp Leu
225                 230                 235                 240

Thr Lys Pro Leu Ile Ala Thr Cys Arg Lys Gly Val Thr Ala Cys His
                245                 250                 255

Ile Ala Leu Ala Ala Tyr Leu Cys Gly Lys Pro Asp Val Ala Ile Tyr
            260                 265                 270

Asp Gly Ser Trp Phe Glu Trp Phe His Arg Ala Pro Pro Glu Thr Trp
        275                 280                 285

Val Ser Gln Gly Lys Gly Gly Lys Ala
    290                 295
```

<210> SEQ ID NO 49
<211> LENGTH: 49
<212> TYPE: DNA
<213> ORGANISM: Artificial Sequence
<220> FEATURE:
<223> OTHER INFORMATION: Synthetic

<400> SEQUENCE: 49
ttggcttcct cctggttatg ttcaagagac ataaccagga ggaagccaa          49

<210> SEQ ID NO 50
<211> LENGTH: 20
<212> TYPE: PRT
<213> ORGANISM: Artificial Sequence
<220> FEATURE:
<223> OTHER INFORMATION: Synthetic

<400> SEQUENCE: 50

```
Gly Leu Phe Gly Ala Ile Ala Gly Phe Ile Glu Gly Gly Trp Thr Gly
1               5                   10                  15

Leu Ile Asp Gly
            20
```

<210> SEQ ID NO 51
<211> LENGTH: 16
<212> TYPE: PRT
<213> ORGANISM: Artificial Sequence
<220> FEATURE:
<223> OTHER INFORMATION: Synthetic

<400> SEQUENCE: 51

```
Ala Val Gly Ile Gly Ala Leu Phe Leu Gly Phe Leu Gly Ala Ala Gly
1               5                   10                  15
```

<210> SEQ ID NO 52
<211> LENGTH: 26
<212> TYPE: PRT
<213> ORGANISM: Artificial Sequence
<220> FEATURE:
<223> OTHER INFORMATION: Synthetic

<400> SEQUENCE: 52

```
Gly Ile Gly Ala Val Leu Lys Val Leu Thr Thr Gly Leu Pro Ala Leu
```

```
                1               5                  10              15
Ile Ser Trp Ile Lys Arg Lys Arg Gln Gln
                20                  25

<210> SEQ ID NO 53
<211> LENGTH: 30
<212> TYPE: PRT
<213> ORGANISM: Artificial Sequence
<220> FEATURE:
<223> OTHER INFORMATION: Synthetic

<400> SEQUENCE: 53

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
                20                  25                  30

<210> SEQ ID NO 54
<211> LENGTH: 30
<212> TYPE: PRT
<213> ORGANISM: Artificial Sequence
<220> FEATURE:
<223> OTHER INFORMATION: Synthetic

<400> SEQUENCE: 54

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
                20                  25                  30
```

COMPOSITIONS AND METHODS FOR THE DELIVERY OF BIOLOGICALLY ACTIVE RNAS

This application claims priority to U.S. application Ser. No. 61/160,287, filed Mar. 13, 2009 and U.S. application Ser. No. 61/160,288, filed Mar. 13, 2009, both of which applications are incorporated by reference herein in their entireties, including the drawings.

FIELD OF THE INVENTION

The present invention provides novel compounds, compositions, and methods for the delivery of biologically active RNA molecules to cells. Specifically, the invention provides novel nucleic acid molecules, polypeptides, and RNA-protein complexes useful for the delivery of biologically active RNAs to cells and polynucleotides encoding the same. The invention also provides vectors for expressing said polynucleotides. In addition, the invention provides cells and compositions comprising the novel compounds and vectors, which can be used as transfection reagents, among other things. The invention further provides methods for producing said compounds, vectors, cells, and compositions. Additionally, vectors and methods for delivering biologically active RNA molecules, such as ribozymes, antisense nucleic acids, allozymes, aptamers, short interfering RNA (siRNA), double-stranded RNA (dsRNA), micro-RNA (miRNA), and short hairpin RNA (shRNA) molecules, to cells and/or tissues are provided. The novel compounds, vectors, cells, and compositions are useful, for example, in delivering biologically active RNA molecules to cells to modulate target gene expression in the diagnosis, prevention, amelioration, and/or treatment of diseases, disorders, or conditions in a subject or organism.

BACKGROUND OF THE INVENTION

RNA molecules have the capacity to act as potent modulators of gene expression in vitro and in vivo. These molecules can function through a number of mechanisms utilizing either specific interactions with cellular proteins or base pairing interactions with other RNA molecules. This modulation can act in opposition to the cellular machinery, as with RNA aptamers that disrupt RNA-protein and protein-protein interactions, or in concert with cellular processes, as with siRNAs that act by redirecting the endogenous RNAi machinery to targets of choice. Modulation of gene expression via RNA effector molecules has great therapeutic potential as the modulatory complexes formed, be they RNA-protein complexes or RNA-RNA complexes, are often highly specific (Aagaard et al., 2007, Adv Drug Deliv Rev., 59:75-86; de Fougerolles et al., 2007, Nat Rev Drug Discov., 6:443-53; Grimm et al., 2007, J Clin Invest., 117:3633-411-4; Rayburn et al., 2008, Drug Discov Today., 13:513-21). When this specificity is determined by the well established rules of base pairing, targeting of this regulatory machinery to particular gene products becomes accessible to direct experimental design.

RNA molecules that modulate gene expression may take a number of different forms. Perhaps the seminal example for all is the antisense RNA molecule. This inhibitory RNA is typically a direct complement of the mRNA transcript it targets and functions by presenting an obstacle to the translational machinery and also by targeting the transcript for degradation by cellular nucleases. Another related and overlapping class is the small inhibitory RNA (siRNA) which acts through the post-transcriptional gene silencing or RNAi pathway. These RNAs are typically about 21-23 nucleotides in length and associate with specific cellular proteins to form RNA-induced silencing complexes (RISCs). These small RNAs are also complementary to sequences within their mRNA targets and binding of these complexes leads to translational silencing or degradation of the transcripts (Farazi et al., 2008, Development., 135:1201-145-7; Sontheimer et al., 2005, Nat Rev Mol Cell Biol., 6:127-38; Zamore et al., 2005, Science., 309:1519-24).

Two additional classes of RNA molecules that can modulate gene expression and activity are the catalytic RNA ribozymes and the competitive RNA aptamers. Ribozymes are RNA based enzymes that catalyze chemical reactions on RNA substrates, most often hydrolysis of the phosphodiester backbone. Formation of the catalytic active site requires base pairing between the ribozyme and the RNA substrate, so ribozyme activity can also be targeted to desired substrates by providing appropriate guide sequences (Wood et al., 2007, PLoS Genet., 3:e109; Scherer et al., 2007, Gene Ther., 14:1057-64; Trang et al., 2004, Cell Microbiol., 6:499-508). When targeted to mRNA transcripts, ribozymes have the potential to cleave those transcripts and lead to downregulation of the associated protein (Liu et al., 2007, Cancer Biol Ther., 6:697-704; Song et al., 2009, Cancer Gene Ther.,; Weng et al., 2005, Mol Cancer Ther., 4:948-55; Li et al., 2005, Mol Ther. 12:900-9). RNA aptamers are typically selected from pools of random RNA sequences by their ability to interact with a target molecule, often a protein molecule. Engineering RNA aptamers is less straightforward as the binding is not defined by base pairing interactions, but once an effective sequence is found the specificity and affinity of the binding often rivals that of antibody-antigen interactions (Mi et al., 2008, Mol Ther., 16:66-73; Lee et al., 2007, Cancer Res., 67:9315-21; Ireson et al., 2006, Mol Cancer Ther., 12:2957-62; Cerchia et al., 2005, PLoS Biol., 3:e1230). RNA aptamers also have a greater range of target molecules and the potential to alter gene activity via a number of different mechanisms.

Two methods for delivering inhibitory RNA molecules to cells have become standard practice. The first method involves production of the RNA molecules in the test tube by using purified polymerases and DNA templates or through direct chemical synthesis. These RNA molecules can then be purified and mixed with a synthetic carrier, typically a polymer, a liposome, or a peptide, and delivered to the target cells (Aigner et al., 2007, Appl Microbiol Biotechnol., 76:9-21; Juliano et al., 2008, Nucleic Acids Res., 36:4158-71; Akhtar et al., 2007, J Clin Invest., 117:3623-32). These molecules are delivered to the cytoplasm where they bind to their mRNA or protein targets directly or through the formation of modulatory complexes. The second method involves transfecting the target cells with a plasmid molecule encoding the biologically active RNA. Once again, the purified plasmid molecule is coupled with a synthetic carrier in the test tube and delivered to the target cell (Fewell et al., 2005, J Control Release., 109:288-98; Wolff et al., 2008, Mol. Ther., 16:8-15; Gary et al., 2007, J Control Release., 121:64-73).

In this case, the plasmid template must be delivered to the cell nucleus where the DNA is transcribed into the biologically active RNA molecule. This RNA is then exported to the cytoplasm, where it finds its way to modulatory complexes and specific mRNA transcript targets. With each of these approaches, the extent of gene regulation within a population of cells is limited by the transfection efficiency of the delivery system. Cells that are not transfected with the biologically active RNA molecules or plasmids encoding biologically active RNAs have no mechanism for receiving the modulatory signal. Although high transfection efficiencies are possible for cells growing in culture, achieving similar extents of transfection is difficult in vivo. This delivery issue is currently the major prohibitive factor for the application of RNA based therapeutics in vivo as it limits the extent to which a particular gene can be regulated in a population of cells. Thus, there remains a need to for an effective delivery system for efficiently delivering biologically active RNAs to cells and tissues.

SUMMARY OF THE INVENTION

The present invention provides novel approaches for circumventing the current problems associated with low transfection efficiencies in the delivery of biologically active RNA molecules to mammalian cells and tissues. One approach involves the use of one or more "bioreactor" cells which produce and subsequently secrete one or more biologically active RNA molecules, such as ribozymes, antisense nucleic acids, allozymes, aptamers, short interfering RNA (siRNA), double-stranded RNA (dsRNA), micro-RNA (miRNA), and short hairpin RNA (shRNA) molecules, as well as RNA transcripts encoding one or more biologically active peptides, thereby delivering said molecule(s) to the extracellular matrix and surrounding cells and tissues. The bioreactor cell is generated by administering to a cell one or more expression vectors designed to produce an RNA-protein complex comprising at least one biologically active RNA molecule targeting one or more genes of interest and a fusion protein capable of delivering the biologically active RNA molecule(s) to the extracellular matrix and/or neighboring cells and tissues.

The RNA portion of the RNA-protein complex comprises at least a recognition RNA sequence and one or more biologically active RNA sequences. The protein portion of the RNA-protein complex is a fusion protein comprising at least an RNA binding domain and a transport peptide. Examples of suitable transport peptides include, but are not limited to, one or more peptides selected from a cell penetrating peptide, a non-classical secretory domain, an endosomal release domain, a receptor binding domain, and a fusogenic peptide. The RNA portion and the protein portion of the RNA-protein complex are expressed from one or more vectors in the nucleus of the transfected bioreactor cell and are transported to the cytoplasm, where the fusion protein is translated and binds to the RNA sequence comprising the biologically active RNA, thereby generating the RNA-protein complex. The RNA-protein complex is secreted from the bioreactor cell and remains intact in the extracellular matrix. The RNA-protein complex can remain in the extracellular matrix where it exerts its modulatory action within the extracellular matrix or at the cell surface of a neighboring target cells. Alternatively, the RNA-protein complex can be designed such that, at the surface of a target cell, the fusion protein facilitates import of the biologically active RNA to the cytoplasm of the target cell.

Thus, in essence, the transfected cells are converted into "bioreactors" that produce and deliver biologically active RNA molecules, secreted as RNA-protein complexes, to the extracellular matrix and/or other neighboring cells. This approach takes advantage of the amplification of the modulatory signal provided by directing the cellular machinery to synthesize the biologically active RNA molecules from the plasmid template. Thus, the modulatory signal is no longer bound by the initial transfection efficiency of a single delivery event but has the potential to reach many cells over a sustained period of time.

Such bioreactor cells can also be generated in cell culture by transfection of appropriate cells with one or more of the expression vectors described herein. In essence, the transfected cells are converted into bioreactors that produce and deliver the biologically active RNA molecules to other cells in culture. Accordingly, the bioreactor cells have in vivo and ex vivo applications as a therapeutic delivery system, as well as in vitro and in vivo applications as a novel transfection agent.

The purpose of the bioreactor cell is to secrete a biologically active RNA molecule to the extracellular matrix in a form that can then function within the extracellular matrix or at the cell surface of a neighboring target cells or can be delivered to neighboring target cells. Viral packaging cells can serve the same purpose: secretion and delivery of biologically active RNA molecules. But in contrast to the bioreactor producing fusion proteins which are assembled from individual domains taken from various sources, the viral particles have evolved for the purpose of transferring nucleic acids from one cell to another (thus, mobile genetic elements). Both RNA and DNA viruses can be utilized as potential carriers for nucleic acid modulators. In the case of RNA viruses, a polynucleotide encoding the biologically active RNA molecule is added to a viral transcript encoding the non-structural genes of the virus. This transcript serves both as template for the viral proteins responsible for viral processes and as the genome which is packaged into the viral particles. The biologically active RNA is coupled with the RNA encoding the non-structural genes so that the biologically active RNA is incorporated into the virus particles. In the case of DNA viruses, a DNA segment encoding the biologically active RNA is added to the viral DNA such that synthesis of the viral transcript produces the biologically active RNA as well. The viral particles are assembled from the structural proteins encoded by transcripts produced from the helper plasmid. Likewise, one or more polynucleotides encoding the biologically active RNA and the fusion protein can be added to a viral transcript encoding the non-structural viral genes (in the case of RNA viruses) or added to the viral DNA (in the case of DNA viruses). Thus, cells transfected with expression vectors comprising sequence for encoding viral non-structural genes and sequence for encoding either a biologically active RNA or a biologically active RNA-protein complex of the invention can be used in the same manner as the bioreactor cells, as described herein.

These approaches directly address the key issue in application of plasmid based RNA-mediated therapeutics, namely the low transfection efficiencies associated with plasmid delivery. Use of the described bioreactor cells circumvents the need for high efficiency transfection, as the RNA-mediated effect is amplified through the in vivo production and delivery of biologically active RNAs to surrounding cells and tissues.

The present invention thus provides novel nucleic acid molecules, polypeptides, RNA-protein complexes, polynucleotides, and vectors useful for the delivery of biologically active RNA molecules to mammalian cells and tissues. In addition, the invention provides compositions comprising said nucleic acid molecules, polypeptides, RNA-protein complexes, polynucleotides and vectors. The invention also provides cells comprising the nucleic acid molecules, polypeptides, RNA-protein complexes, polynucleotides and vectors of the invention. Additionally, the invention provides methods of producing the nucleic acid molecules, polypeptides, RNA-protein complexes, polynucleotides, vectors, compositions, and cells of the invention, as well as therapeutic methods for using the inventive molecules in vitro, ex vivo, and in vivo.

The present invention provides novel expression vectors useful in the production of the nucleic acid molecules, polypeptides, and RNA-protein complexes of the invention. In one embodiment, the invention provides an expression vector that expresses an RNA-protein complex of the invention. Thus, in one embodiment, the invention provides an expression vector comprising a polynucleotide that encodes a nucleic acid comprising one or more biologically active RNA sequences, a recognition RNA sequence, and optionally a terminal minihelix sequence, and a polynucleotide that encodes a polypeptide comprising an RNA binding domain and one or more transport peptides. The RNA portion and the protein portion of the RNA-protein complex expressed from the expression vector are expressed in the nucleus of the transfected bioreactor cell and are transported separately to the cytoplasm, where the fusion protein is translated and binds to the RNA sequence comprising the biologically active RNA, thereby generating the RNA-protein complex. The RNA-protein complex is secreted from the bioreactor cell as discussed herein. The one or more biologically active RNA sequences can be one or more different types of biologically active RNA sequences directed to the same gene target or can be biologically active RNA sequences directed to different gene targets.

In a further embodiment, the expression vector additionally comprises a first promoter sequence, a termination sequence, and optionally one or more primers sequences, a second promoter sequence, a polyA addition sequence, and optionally one or more primers sequences, wherein the polynucleotide encoding the first biologically active RNA sequence, the recognition RNA sequence, and the optional terminal minihelix sequence is operably linked to the first promoter sequence and the termination sequence and wherein the polynucleotide encoding the RNA binding domain sequence and the transport peptide sequence is operably linked to the second promoter sequence and the polyA addition sequence.

In another embodiment, the expression vector further comprises one or more polynucleotide sequences encoding one or more viral polymerases and one or more viral accessory proteins necessary for viral replication. In a further embodiment, the vector additionally comprises one or more promoter sequences, one or more polyA addition sequences, and optionally one or more primers sequences, wherein the polynucleotide sequence(s) encoding the viral polymerase(s) and the viral accessory protein(s) is operably linked to the one or more promoter sequences and the one or more polyA addition sequences. The vectors comprising viral polymerase and accessory protein sequences can be used with expression vectors comprising one or more polynucleotide sequences encoding one or more viral coat proteins and one or more viral fusogenic proteins. In a further embodiment, the expression vectors comprising one or more polynucleotide sequences encoding one or more viral coat proteins and one or more viral fusogenic proteins can further comprise one or more promoter sequences and one or more polyA addition sequences, wherein the polynucleotide sequence(s) encoding the viral coat protein(s) and the viral fusogenic protein(s) is operably linked to the one or more promoter sequences and the one or more polyA addition sequences.

In certain embodiments of the described expression vectors, the biologically active RNA sequence is selected from a ribozyme, antisense nucleic acid, allozyme, aptamer, short interfering RNA (siRNA), double-stranded RNA (dsRNA), micro-RNA (miRNA), short hairpin RNA (shRNA), and a transcript encoding one or more biologically active peptides. In one specific embodiment, the biologically active RNA sequence is a short hairpin RNA (shRNA). In another specific embodiment, the biologically active RNA sequence is an aptamer. In certain embodiments, the recognition RNA sequence is selected from a U1 loop, Group II intron, NRE stem loop, S1A stem loop, Bacteriophage BoxBR, HIV Rev response element, AMVCP recognition sequence, and ARE sequence. In one embodiment, the terminal minihelix sequence is from the adenovirus VA1 RNA molecule. In certain embodiments, the RNA binding domain is selected from a U1A, CRS1, CRM1, Nucleolin RBD12, hRBMY, Bacteriophage Protein N, HIV Rev, alfalfa mosaic virus coat protein (AMVCP), and tristetrapolin amino acid sequence. In certain embodiments, the one or more transport peptides is selected from a cell penetrating peptide, a non-classical secretory domain, a receptor binding domain, a fusogenic peptide, and an endosomal release domain, as well as any combinations thereof. In one specific embodiment, the transport peptide is a cell penetrating peptide. In certain specific embodiments, the cell penetrating peptide is selected from a penetratin, transportan, MAP, HIV TAT, Antp, Rev, FHV coat protein, TP10, and pVEC sequence. In another specific embodiment, the transport peptide is a non-classical secretory domain. In certain specific embodiments, the non-classical secretory domain is selected from a Galcetin-1 peptide, Galectin-3 peptide, IL-1α, IL-1β, HASPB, HMGB1, FGF-1, FGF-2, IL-2 signal, secretory transglutaminase, annexin-1, HIV TAT, Herpes VP22, thioredoxin, Rhodanese, and plasminogen activator signal sequence. In one specific embodiment, the transport peptides are a cell penetrating peptide, and one or more transport peptides selected from a non-classical secretory domain, a receptor binding domain, a fusogenic peptide, and an endosomal release domain. In one specific embodiment, the transport peptides are a cell penetrating peptide, and a non-classical secretory domain. In certain embodiments, the viral non-structural and structural genes (viral polymerases, accessory proteins, coat proteins, and fusogenic proteins) are selected from DNA viruses and RNA viruses, including, but not limited to, Adenovirus, Adeno-Associated Virus, Herpes Simplex Virus Lentivirus, Retrovirus, Sindbis virus, and Foamy virus.

In any of the above-described embodiments, the expression vector can further comprise an additional polynucleotide sequence that encodes a nucleic acid comprising one or more biologically active RNA sequences that target one or more further gene target(s). In one embodiment, the additional polynucleotide sequence encodes a nucleic acid comprising one or more biologically active RNA sequences that target a further gene target and an RNA recognition sequence. In another embodiment, where one of the biologically active RNA sequences in the vector is a short interfering RNA (siRNA), double-stranded RNA (dsRNA), micro-RNA (miRNA), or short hairpin RNA (shRNA), the expression vector additionally comprises a polynucleotide that encodes a nucleic acid comprising one or more biologically active RNA sequences targeted to Dicer and/or Drosha. None of the polynucleotide sequences encoding nucleic acid comprising one or more biologically active RNA sequences targeted to Dicer and/or Drosha comprise a recognition RNA sequence.

In another embodiment, the expression vector comprises a first expression cassette and a second expression cassette, wherein the first expression cassette comprises a promoter sequence, one or biologically active RNA sequences directed to one or more target genes, a recognition RNA sequence, optionally a terminal minihelix sequence, a termination sequence, and optionally one or more primers sequences, wherein the biologically active RNA sequence(s), the recognition RNA sequence, and the optional terminal minihelix sequence are operably linked to the promoter sequence and the termination sequence; and the second expression cassette comprises a promoter sequence, an RNA binding domain sequence, a transport peptide sequence, a poly A addition sequence, and optionally one or more primers sequences, wherein the RNA binding domain sequence and the transport peptide sequence are operably linked to the promoter sequence and the poly A addition sequence. In a further embodiment, the expression vector additionally comprises a third expression cassette, wherein the third expression cassette comprises one or more promoter sequences, one or more polynucleotide sequences encoding one or more viral polymerases and one or more viral accessory proteins necessary for viral replication, one or more polyA addition sequences, and optionally one or more primers sequences, wherein the polynucleotide sequence(s) encoding the viral polymerase(s) and the viral accessory protein(s) is operably linked to the one or more promoter sequences and the one or more polyA addition sequences. The vectors comprising a third expression cassette comprising viral polymerase and accessory protein sequences can be used with expression vectors comprising one or more polynucleotide sequences encoding one or more viral coat proteins and one or more viral fusogenic proteins. In a further embodiment, the expression vectors comprising one or more polynucleotide sequences encoding one or more viral coat proteins and one or more viral fusogenic proteins can further comprise one or more promoter sequences and one or more polyA addition sequences, wherein the polynucleotide sequence(s) encoding the viral coat protein(s) and the viral fusogenic protein(s) is operably linked to the one or more promoter sequences and the one or more polyA addition sequences.

In one embodiment of the above-described expression vectors, the expression cassette comprising the RNA portion of the RNA-protein complex, (i.e., comprising an RNA recognition sequence, one or more biologically active RNAs and optionally a terminal minihelix sequence) is ligated into an artificial intron within the expression cassette for the fusion protein (i.e., RNA binding domain and one or more transport peptides). In this expression vector, the Sec-RNA is encoded within an artificial intron placed within the mRNA sequence encoding the fusion protein. DNA fragments encoding for Sec-RNA molecules or fusion proteins are prepared by PCR. DNA fragments encoding for Sec-RNA molecules are prepared with primers including splice donor and acceptor sites and restriction sites for subcloning into a unique restriction site within the fusion protein sequence. DNA fragments encoding for the fusion protein are prepared with primers including restriction sites for subcloning into the plasmids described above. After transcription, the Sec-RNA is released from the mRNA encoding the fusion protein by the splicing machinery endogenous to the bioreactor cell.

In any of these embodiments, the biologically active RNA sequence is selected from a ribozyme, antisense nucleic acid, allozyme, aptamer, short interfering RNA (siRNA), double-stranded RNA (dsRNA), micro-RNA (miRNA), short hairpin RNA (shRNA), and a transcript encoding one or more biologically active peptides. The recognition RNA sequence is selected from a U1 loop, Group II intron, NRE stem loop, S1A stem loop, Bacteriophage BoxBR, HIV Rev response element, AMVCP recognition sequence, and ARE sequence. The terminal minihelix sequence is selected from the adenovirus VA1 RNA molecule. The RNA binding domain is selected from a U1A, CRS1, CRM1, Nucleolin RBD12, hRBMY, Bacteriophage Protein N, HIV Rev, alfalfa mosaic virus coat protein (AMVCP), and tristetrapolin amino acid sequence. The one or more transport peptides is selected from a cell penetrating peptide, a non-classical secretory domain, a receptor binding domain, a fusogenic peptide, and an endosomal release domain, as well as any combinations thereof.

In any of the above-described embodiments, the expression vector can further comprise an additional expression cassette, wherein the additional expression cassette comprises one or more promoter sequences, one or more polynucleotide sequences encoding nucleic acid comprising one or more biologically active RNA sequences that target a further gene transcript and one or more polyA addition sequences, wherein the polynucleotide sequence encoding nucleic acid comprising one or more biologically active RNA sequences that target a further gene transcript is operably linked to the one or more promoter sequences and the one or more polyA addition sequences. In one embodiment, the additional polynucleotide sequence encodes a nucleic acid comprising one or more biologically active RNA sequences that target a further gene transcript and an RNA recognition sequence. In another embodiment, where one of the biologically active RNA sequences in the vector is a short interfering RNA (siRNA), double-stranded RNA (dsRNA), micro-RNA (miRNA), or short hairpin RNA (shRNA), the additional polynucleotide sequence encodes nucleic acid comprising one or more biologically active RNA sequences targeted to Dicer and/or Drosha. None of the polynucleotide sequences encoding nucleic acid comprising one or more biologically active RNA sequences targeted to Dicer and/or Drosha comprise a recognition RNA sequence.

In one embodiment, the invention provides an expression vector comprising a polynucleotide that encodes a nucleic acid molecule comprising one or more biologically active RNA sequences, a recognition RNA sequence, and an optional terminal minihelix sequence. In one embodiment, the expression vector comprises a polynucleotide that encodes a nucleic acid molecule comprising one or more biologically active RNA sequences and one or more polynucleotide sequences encoding one or more viral polymerases and one or more viral accessory proteins necessary for viral replication. In certain embodiments, the expression vector comprises a polynucleotide encoding a nucleic acid molecule wherein the biologically active RNA sequence is selected from a ribozyme, antisense nucleic acid, allozyme, aptamer, short interfering RNA (siRNA), double-stranded RNA (dsRNA), micro-RNA (miRNA), short hairpin RNA (shRNA), and a transcript encoding one or more biologically active peptides. In one specific embodiment, the expression vector comprises a polynucleotide encoding a nucleic acid molecule wherein the biologically active RNA sequence is a short hairpin RNA (shRNA). In another specific embodiment, the expression vector comprises a polynucleotide encoding a nucleic acid molecule wherein the biologically active RNA sequence is an aptamer. In certain embodiments, the expression vector comprises a polynucleotide encoding a nucleic acid molecule wherein the recognition RNA sequence is selected from a U1 loop, Group II intron, NRE stem loop, S1A stem loop, Bacteriophage BoxBR, HIV Rev response element, AMVCP recognition sequence, and ARE sequence. In one embodiment, the terminal minihelix sequence is from the adenovirus VA1 RNA molecule.

The invention also provides an expression vector comprising a polynucleotide that encodes a polypeptide comprising an RNA binding domain and one or more transport peptides. In certain embodiments, the RNA binding domain is selected from a U1A, CRS1, CRM1, Nucleolin RBD12, hRBMY, Bacteriophage Protein N, HIV Rev, alfalfa mosaic virus coat protein (AMVCP), and tristetrapolin amino acid sequence. In certain embodiments, the one or more transport peptides is selected from a cell penetrating peptide, a non-classical secretory domain, a receptor binding domain, a fusogenic peptide, and an endosomal release domain, as well as any combinations thereof. In one embodiment, the invention provides an expression vector comprising a polynucleotide that encodes a polypeptide comprising an RNA binding domain and a cell penetrating peptide. In certain specific embodiments, the cell penetrating peptide is selected from a penetratin, transportan, MAP, HIV TAT, Antp, Rev, FHV coat protein, TP10, and pVEC sequence. In another embodiment, the invention provides an expression vector comprising a polynucleotide that encodes a polypeptide comprising an RNA binding domain and a non-classical secretory domain. In certain specific embodiments, the non-classical secretory domain is selected from a Galcetin-1 peptide, Galectin-3 peptide, IL-1α, IL-1β, HASPB, HMGB1, FGF-1, FGF-2, IL-2 signal, secretory transglutaminase, annexin-1, HIV TAT, Herpes VP22, thioredoxin, Rhodanese, and plasminogen activator signal sequence. In one embodiment, the invention provides an expression vector comprising a polynucleotide that encodes a polypeptide comprising an RNA binding domain, a cell penetrating peptide, and one or more transport peptides selected from a non-classical secretory domain, a receptor binding domain, a fusogenic peptide, and an endosomal release domain. In one embodiment, the invention provides an expression vector comprising a polynucleotide that encodes a polypeptide comprising an RNA binding domain, a cell penetrating peptide, and a non-classical secretory domain.

Thus, the invention provides a first expression vector comprising a polynucleotide that encodes a nucleic acid molecule comprising one or more biologically active RNA sequences, a recognition RNA sequence and optionally a terminal minihelix sequence and a second expression vector comprising a polynucleotide that encodes a polypeptide comprising an RNA binding domain and one or more transport peptides, for example, a peptide selected from a cell penetrating peptide, a non-classical secretory domain, a receptor binding domain, a fusogenic peptide, and an endosomal release domain. The RNA portion of the RNA-protein complex expressed from the first expression vector and the protein portion of the RNA-protein complex expressed from the second expression vector are expressed in the nucleus of the transfected bioreactor cell and are transported separately to the cytoplasm, where the fusion protein is translated and binds to the RNA sequence comprising the biologically active RNA, thereby generating the RNA-protein complex. The RNA-protein complex is secreted from the bioreactor cell as discussed herein.

In any of the expression vectors of the invention, one or more of the sequences comprising the recognition RNA sequence, the individual biologically active RNA sequences, the optional terminal minihelix sequence, the RNA binding domain, and the transport peptide(s), as well as any other sequences, including viral sequences, promoters, primers, termination sequences, and polyA sequences are joined directly without the addition of one or more intervening or additional sequences. Alternatively, one or more of the sequences comprising the recognition RNA sequence, the individual biologically active RNA sequences, the optional terminal minihelix sequence, the RNA binding domain, and the transport peptide(s), as well as any other sequences, including viral sequences, promoters, primers, termination sequences, and polyA sequences are joined with the addition of one or more intervening or additional sequences. In any of the above-described embodiments, the individual biologically active RNA sequences themselves are joined directly without any intervening or additional sequences or are joined with the addition of one or more intervening or additional sequences. In any of the above-described embodiments, the recognition RNA sequence and any of the biologically active RNAs are joined directly without the addition of one or more linker, spacer, or other sequences or are joined with the addition of one or more linker, spacer, and/or other sequences. In any of the above-described embodiments, the RNA binding domain and any of the individual transport peptides are joined directly without the addition of one or more linker, spacer, or other sequences or are joined with the addition of one or more linker, spacer, and/or other sequences.

In any of the expression vectors of the invention, the vector is selected from a suitable backbone vector. Examples of suitable vectors include those derived from pCI, pET, pSI, pcDNA, pCMV, etc. In certain embodiments, the vector is selected from pEGEN 1.1, pEGEN 2.1, pEGEN3.1, and pEGEN 4.1. The pEGEN vectors are derived from pSI (Promega, product #E1721), pCI (Promega, product #E1731), pVAX (Invitrogen, product #12727-010) and other in house constructs. In one embodiment, the vector comprises a pUC origin of replication. In one embodiment, the expression vector comprises a drug resistance gene. Non-limiting examples of suitable drug resistance genes include those selected from puromycin, ampicillin, tetracycline, and chloramphenicol resistant genes, as well as any other drug resistant genes known and described in the art.

The invention also provides compositions comprising one or more expression vectors of the invention and a pharmaceutically acceptable carrier. The expression vector of the composition can be any of the expression vectors described herein. In one embodiment, the composition comprises an expression vector comprising a polynucleotide encoding a nucleic acid comprising one or more biologically active RNA sequences, a recognition RNA sequence, optionally a terminal minihelix sequence, and a polynucleotide encoding a polypeptide comprising an RNA binding domain, and one or more transport peptide sequences (for example, a cell penetrating peptide, non-classical secretory domain, endosomal release domain, receptor binding domain, fusogenic peptide) and a pharmaceutically acceptable carrier. In one embodiment, the composition further comprises a second expression vector comprising a polynucleotide sequence that encodes a nucleic acid comprising one or more biologically active RNA sequences that target one or more further gene target(s). In one embodiment, the additional polynucleotide sequence encodes a nucleic acid comprising one or more biologically active RNA sequences that target one or more further gene targets and an RNA recognition sequence. In another embodiment, where one of the biologically active RNA sequences in the vector is a short interfering RNA (siRNA), double-stranded RNA (dsRNA), micro-RNA (miRNA), or short hairpin RNA (shRNA), the expression vector additionally comprises a polynucleotide that encodes a nucleic acid comprising one or more biologically active RNA sequences targeted to Dicer and/or Drosha.

In one embodiment, the composition comprises an expression vector comprising a polynucleotide sequence encoding a nucleic acid comprising one or more biologically active RNA sequences, a recognition RNA sequence, optionally a terminal minihelix sequence, and a polynucleotide sequence encoding a polypeptide comprising an RNA binding domain, and one or more transport peptide sequences (for example, a cell penetrating peptide, non-classical secretory domain, endosomal release domain, receptor binding domain, fusogenic peptide) and a polynucleotide sequence encoding a nucleic acid comprising one or more biologically active RNA sequences that target Dicer and/or Drosha and a pharmaceutically acceptable carrier.

In one embodiment, the composition comprises an expression vector comprising a polynucleotide encoding a nucleic acid comprising one or more biologically active RNA sequences, a recognition RNA sequence, optionally a terminal minihelix sequence, and a polynucleotide encoding a polypeptide comprising an RNA binding domain, and one or more transport peptide sequences, as well as a first promoter sequence, a termination sequence, and optionally one or more primers sequences, a second promoter sequence, a polyA addition sequence, and optionally one or more primers sequences and a pharmaceutically acceptable carrier. In this embodiment, the polynucleotide encoding the first biologically active RNA sequence, the recognition RNA sequence, and the optional terminal minihelix sequence is operably linked to the first promoter sequence and the termination sequence and the polynucleotide encoding the RNA binding domain sequence and the transport peptide sequence is operably linked to the second promoter sequence and the polyA addition sequence.

In one embodiment, the composition comprises an expression vector comprising a polynucleotide encoding a nucleic acid comprising one or more biologically active RNA sequences, a recognition RNA sequence, optionally a terminal minihelix sequence, a polynucleotide encoding a polypeptide comprising an RNA binding domain, and one or more transport peptide sequences, and a polynucleotide encoding a nucleic acid comprising one or more biologically active RNA sequences targeted to Dicer and/or Drosha, as well as a first promoter sequence, a first termination sequence, and optionally one or more primers sequences, a second promoter sequence, a polyA addition sequence, and optionally one or more primer sequences, and a one or more further promoter sequences, one or more further termination sequences, and one or more primer sequences and a pharmaceutically acceptable carrier. In this embodiment, the polynucleotide encoding the first biologically active RNA sequence, the recognition RNA sequence, and the optional terminal minihelix sequence is operably linked to the first promoter sequence and the first termination sequence and the polynucleotide encoding the RNA binding domain sequence and the transport peptide sequence is operably linked to the second promoter sequence and the polyA addition sequence and the polynucleotide encoding the one or more biologically active RNA sequences targeted to Dicer and/or Drosha is operably linked to the one or more further promoter sequence and the one or more further termination sequences.

In one embodiment, the composition comprises a first expression vector comprising a polynucleotide encoding a nucleic acid comprising one or more biologically active RNA sequences, a recognition RNA sequence, optionally a terminal minihelix sequence, and a polynucleotide encoding a polypeptide comprising an RNA binding domain, and one or more transport peptide sequences, and one or more polynucleotide sequences encoding one or more viral polymerases and one or more viral accessory proteins necessary for viral replication and a second expression vector comprising one or more polynucleotide sequences encoding one or more viral coat proteins and one or more viral fusogenic proteins in a pharmaceutically acceptable carrier. In certain embodiments, the expression vectors of these compositions additionally comprise a first promoter sequence, a termination sequence, and optionally one or more primer sequences, a second promoter sequence, a polyA addition sequence, and optionally one or more primer sequences, and a one or more further promoter sequences, one or more further polyA addition sequences, and optionally one or more further primers sequences, wherein the polynucleotide encoding the first biologically active RNA sequence, the recognition RNA sequence, and the optional terminal minihelix sequence is operably linked to the first promoter sequence and the termination sequence and wherein the polynucleotide encoding the RNA binding domain sequence and the transport peptide sequence is operably linked to the second promoter sequence and the polyA addition sequence, and wherein the one or more polynucleotides encoding one or more viral polymerases and one or more viral accessory proteins are operably linked to the one or more promoter sequences and one or more polyA addition sequences, and wherein the one or more polynucleotide sequences encoding the viral coat protein(s) and the viral fusogenic protein(s) are operably linked to the one or more promoter sequences and the one or more polyA addition sequences.

In one embodiment, the composition comprises an expression vector comprising a polynucleotide that encodes a nucleic acid molecule comprising one or more biologically active RNA sequences, a recognition RNA sequence, and optionally a terminal minihelix sequence and a pharmaceutically acceptable carrier.

In one embodiment, the composition comprises an expression vector comprising a polynucleotide that encodes a polypeptide comprising an RNA binding domain and one or more transport peptide sequences (for example, a cell penetrating peptide, non-classical secretory domain, endosomal release domain, receptor binding domain, fusogenic peptide) and a pharmaceutically acceptable carrier.

In one embodiment, the composition comprises a first expression vector comprising a polynucleotide that encodes a nucleic acid molecule comprising one or more biologically active RNA sequences, a recognition RNA sequence, and optionally a terminal minihelix sequence and a second expression vector comprising a polynucleotide that encodes a polypeptide comprising an RNA binding domain and one or more transport peptide sequences (for example, a cell penetrating peptide, non-classical secretory domain, endosomal release domain, receptor binding domain, fusogenic peptide) and a pharmaceutically acceptable carrier. In one embodiment, the composition further comprises a third expression vector comprising a polynucleotide sequence that encodes a nucleic acid comprising one or more biologically active RNA sequences that target one or more further gene target(s). In one embodiment, the additional polynucleotide sequence encodes a nucleic acid comprising one or more biologically active RNA sequences that target a further gene target and an RNA recognition sequence. In another embodiment, where one of the biologically active RNA sequences in the vector is a short interfering RNA (siRNA), double-stranded RNA (dsRNA), micro-RNA (miRNA), or short hairpin RNA (shRNA), the expression vector additionally comprises a polynucleotide that encodes a nucleic acid comprising one or more biologically active RNA sequences targeted to Dicer and/or Drosha.

In one embodiment, the composition comprises a first expression vector comprising a polynucleotide encoding a nucleic acid comprising one or more biologically active RNA sequences and one or more polynucleotide sequences encoding one or more viral polymerases and one or more viral accessory proteins necessary for viral replication and a second expression vector comprising one or more polynucleotide sequences encoding one or more viral coat proteins and one or more viral fusogenic proteins in a pharmaceutically acceptable carrier.

In one embodiment, the composition comprises an expression vector comprising a first expression cassette and a second expression cassette, wherein the first expression cassette comprises a first promoter sequence, one or more biologically active RNA sequences directed to one or more target genes, a recognition RNA sequence, optionally a terminal minihelix sequence, a termination sequence, and optionally one or more primer sequences, and the second expression cassette comprises a second promoter sequence, an RNA binding domain sequence, a transport peptide sequence, a poly A addition sequence, and optionally one or more primer sequences and a pharmaceutically acceptable carrier. In these embodiments, the biologically active RNA sequence(s), the recognition RNA sequence, and the optional terminal minihelix sequence are operably linked to the first promoter sequence and the termination sequence and the RNA binding domain sequence and the transport peptide sequence are operably linked to the second promoter sequence and the poly A addition sequence.

In another embodiment, the composition comprises a first expression vector comprising a first expression cassette, a second expression cassette, and a third expression cassette, wherein the first expression cassette comprises a first promoter sequence, one or more biologically active RNA sequences directed to one or more target genes, a recognition RNA sequence, optionally a terminal minihelix sequence, a termination sequence, and optionally one or more primer sequences, and the second expression cassette comprises a second promoter sequence, an RNA binding domain sequence, a transport peptide sequence, a poly A addition sequence, and optionally one or more primer sequences, and the third expression cassette comprises one or more promoter sequences, one or more polynucleotide sequences encoding one or more viral polymerases and one or more viral accessory proteins necessary for viral replication, one or more polyA addition sequences, and optionally one or more primers sequences, and a second expression vector comprising a fourth expression cassette comprising one or more promoter sequences, one or more polynucleotide sequences encoding one or more viral coat proteins and one or more viral fusogenic proteins, one or more polyA addition sequences, and optionally one or more primers sequences, and a pharmaceutically acceptable carrier. In these embodiments, the biologically active RNA sequence(s), the recognition RNA sequence, and the optional terminal minihelix sequence are operably linked to the first promoter sequence and the termination sequence, the RNA binding domain sequence and the transport peptide sequence are operably linked to the second promoter sequence and the poly A addition sequence, the polynucleotide sequence(s) encoding the viral polymerase(s) and the viral accessory protein(s) is operably linked to the one or more promoter sequences and the one or more polyA addition sequences and the polynucleotide sequence(s) encoding the viral coat proteins and the viral fusogenic proteins is operably linked to the one or more promoter sequences and the one or more polyA addition sequences.

The expression vectors and compositions of the invention can be used to generate "bioreactor" cells which produce an RNA-protein complex of the invention. The RNA portion of the RNA-protein complex comprises one or more biologically active RNA sequences, a recognition RNA sequence, and optionally a terminal minihelix sequence. The protein portion of the RNA-complex comprises an RNA binding domain and one or more transport peptide sequences. The transcripts are exported from the cell nucleus to the cell cytoplasm, where the transcript comprising the RNA binding domain and the transport peptide sequence(s) is translated. The RNA binding domain of the translated peptide interacts with the recognition RNA sequence of the RNA portion, forming the RNA-protein complex. The protein-RNA complex is subsequently secreted from the cell and imported into the extracellular matrix and/or neighboring cells where the biologically active RNA acts to modulate gene expression.

In one embodiment, the invention provides a cell comprising any of the expression vectors and compositions thereof provided herein. In one embodiment, the invention provides a cell comprising an expression vector comprising a polynucleotide sequence encoding a nucleic acid comprising a biologically active RNA sequence, a recognition RNA sequence, and optionally a terminal minihelix sequence and a polynucleotide sequence encoding a polypeptide comprising an RNA binding domain sequence and a transport peptide.

In one embodiment, the invention provides a cell comprising an expression vector comprising a polynucleotide sequence encoding a nucleic acid comprising a biologically active RNA sequence, a recognition RNA sequence, and optionally a terminal minihelix sequence, a polynucleotide sequence encoding a polypeptide comprising an RNA binding domain sequence and a transport peptide, and one or more polynucleotide sequences encoding one or more viral polymerases and one or more viral accessory proteins necessary for viral replication and an expression vector comprising one or more polynucleotide sequences encoding one or more viral coat proteins and one or more viral fusogenic proteins.

In one embodiment, the invention provides a cell comprising an expression vector comprising a polynucleotide sequence encoding a nucleic acid comprising a biologically active RNA sequence, a recognition RNA sequence, and optionally a terminal minihelix sequence, a polynucleotide sequence encoding a polypeptide comprising an RNA binding domain sequence and a transport peptide, and an additional polynucleotide sequence encoding a nucleic acid comprising one or more biologically active RNA sequences that target one or more further gene target(s). In one embodiment, the additional polynucleotide sequence encodes a nucleic acid comprising one or more biologically active RNA sequences that target a further gene target and an RNA recognition sequence. In another embodiment, where one of the biologically active RNA sequences in the vector is a short interfering RNA (siRNA), double-stranded RNA (dsRNA), micro-RNA (miRNA), or short hairpin RNA (shRNA), the additional polynucleotide sequence encodes a nucleic acid comprising one or more biologically active RNA sequences targeted to Dicer and/or Drosha.

In one embodiment, the invention provides a cell comprising an expression vector comprising a polynucleotide sequence encoding a nucleic acid comprising a biologically active RNA sequence, a recognition RNA sequence, and optionally a terminal minihelix sequence, a polynucleotide sequence encoding a polypeptide comprising an RNA binding domain sequence and a transport peptide, one or more polynucleotide sequences encoding one or more viral polymerases and one or more viral accessory proteins necessary for viral replication, and an additional polynucleotide sequence encoding a nucleic acid comprising one or more biologically active RNA sequences that target one or more further gene target(s) (for example, Dicer and/or Drosha gene targets) and an expression vector comprising one or more polynucleotide sequences encoding one or more viral coat proteins and one or more viral fusogenic proteins.

In one embodiment, the invention provides a cell comprising an expression vector comprising a polynucleotide sequence encoding a nucleic acid comprising a biologically active RNA sequence and one or more polynucleotide sequences encoding one or more viral polymerases and one or more viral accessory proteins necessary for viral replication, and an expression vector comprising one or more polynucleotide sequences encoding one or more viral coat proteins and one or more viral fusogenic proteins.

In one embodiment, the invention provides a cell comprising an expression vector comprising a polynucleotide sequence encoding a nucleic acid comprising a biologically active RNA sequence, a recognition RNA sequence, and optionally a terminal minihelix sequence and an expression vector comprising a polynucleotide sequence encoding a polypeptide comprising an RNA binding domain sequence and one or more transport peptides. In one embodiment, the cell further comprises a third expression vector comprising a polynucleotide sequence encoding a nucleic acid comprising one or more biologically active RNA sequences that target one or more gene target(s) that differ from the gene target(s) of the biologically active RNA in the first expression vector. In one embodiment, the third expression vector comprises a polynucleotide sequence encoding a nucleic acid comprising one or more biologically active RNA sequences that target one or more gene targets and an RNA recognition sequence. In another embodiment, where one of the biologically active RNA sequences in the first expression vector is a short interfering RNA (siRNA), double-stranded RNA (dsRNA), micro-RNA (miRNA), or short hairpin RNA (shRNA), the third expression vector comprises a polynucleotide sequence encoding a nucleic acid comprising one or more biologically active RNA sequences targeted to Dicer and/or Drosha.

The invention also provides a composition comprising a bioreactor cell of the invention and a pharmaceutically acceptable carrier. The composition can comprise any of the bioreactor cells described herein and a pharmaceutically acceptable carrier. In one embodiment, the composition comprises one or more cells comprising an expression vector of the invention and a pharmaceutically acceptable carrier. The cell can comprise one or more of any of the expression vectors described herein. In one embodiment, the invention provides a composition comprising one or more bioreactor cells that express an RNA-complex of the invention and a pharmaceutically acceptable carrier. In one embodiment, the composition comprises one or more cells that express an RNA-protein complex comprising one or more biologically active RNA sequences, a recognition RNA sequence, optionally a terminal minihelix sequence, an RNA binding domain, and one or more transport peptide sequences. In one embodiment, the composition comprises one or more cells that express an RNA-protein complex comprising one or more biologically active RNA sequences, a recognition RNA sequence, optionally a terminal minihelix sequence, an RNA binding domain, and a cell-penetrating peptide sequence, and a pharmaceutically acceptable carrier. In one embodiment, the composition comprises one or more cells that express an RNA-protein complex comprising one or more biologically active RNA sequences, a recognition RNA sequence, optionally a terminal minihelix sequence, an RNA binding domain, and a non-classical secretory domain and a pharmaceutically acceptable carrier. In one embodiment, the composition comprises one or more cells that express an RNA-protein complex comprising one or more biologically active RNA sequences, a recognition RNA sequence, optionally a terminal minihelix sequence, an RNA binding domain, a cell-penetrating peptide sequence, and a non-classical secretory domain and a pharmaceutically acceptable carrier.

Bioreactor cells comprising one or more expression vectors of the invention are able to produce and secrete an RNA-protein complex of the invention. The bioreactor cells are then useful in vitro, ex vivo, and in vivo as novel transfection reagents for the delivery of one or more biologically active RNA(s) to other target cells and tissues. Accordingly, the invention provides a method for producing a transfection reagent comprising one or more bioreactor cells comprising the steps of: (a) preparing an expression vector that encodes an RNA-protein complex comprising one or more biologically active RNAs, a recognition RNA sequence, optionally a terminal minihelix sequence, an RNA binding domain sequence, and one or more transport peptide sequences (for example, selected from a cell penetrating peptide, non-classical secretory domain, endosomal release domain, receptor binding domain, and fusogenic peptide sequence); (b) administering the expression vector of step (a) to cells in culture to produce one or more bioreactor cells expressing the RNA-protein complex; and (c) collecting the cultured cells of step (b) as the transfection reagent. In one embodiment, the method further comprises (d) testing the cells of (c) to determine the bioreactor cells expressing the RNA-protein complex; and (e) isolating the bioreactor cells from the other cells in culture for use as the transfection reagent. The expression vector can be any of the expression vectors described herein. The RNA-protein complex can be any of the RNA-protein complexes described herein. In one embodiment, the biologically active RNA of the RNA-protein complex is an shRNA. In another embodiment, the biologically active RNA of the RNA-protein complex is an aptamer. In one embodiment, the cells of step (b) are stably transfected with the expression vector.

In another embodiment, the invention provides a method for producing a transfection reagent comprising one or more bioreactor cells comprising the steps of: (a) preparing an expression vector comprising a polynucleotide sequence that encodes a nucleic acid comprising one or more biologically active RNAs, a recognition RNA sequence, optionally a terminal minihelix sequence, a polynucleotide sequence that encodes a polypeptide comprising an RNA binding domain and one or more transport peptide sequences, and an additional polynucleotide sequences that encodes a nucleic acid comprising one or more biologically active RNA sequences that target one or more further gene target(s); (b) administering the expression vector of step (a) to cells in culture to produce one or more bioreactor cells expressing the RNA-protein complex; and (c) collecting the cultured cells of step (b) as the transfection reagent. In one embodiment, the method further comprises (d) testing the cells of (d) to determine the bioreactor cells expressing the RNA-protein complex; and (e) isolating the bioreactor cells from the other cells in culture for use as the transfection reagent. In one embodiment, the additional polynucleotide sequence encodes a nucleic acid comprising one or more biologically active RNA sequences that target a further gene target and an RNA recognition sequence. In another embodiment, where one of the biologically active RNA sequences in the vector is a short interfering RNA (siRNA), double-stranded RNA (dsRNA), micro-RNA (miRNA), or short hairpin RNA (shRNA), the additional polynucleotide sequence encodes a nucleic acid comprising one or more biologically active RNA sequences targeted to Dicer and/or Drosha.

In another embodiment, the invention provides a method for producing a transfection reagent comprising one or more bioreactor cells comprising the steps of: (a) preparing an expression vector comprising a polynucleotide sequence that encodes a nucleic acid comprising one or more biologically active RNAs, a recognition RNA sequence, optionally a terminal minihelix sequence, a polynucleotide sequence that encodes a polypeptide comprising an RNA binding domain and one or more transport peptide sequences, and one or more polynucleotide sequences encoding one or more viral polymerases and one or more viral accessory proteins necessary for viral replication; (b) preparing an expression vector comprising one or more polynucleotide sequences encoding encoding one or more viral coat proteins and one or more viral fusogenic proteins; (c) administering the expression vector of step (a) and the expression vector of step (b) to cells in culture to produce one or more bioreactor cells (in this case, viral production cells) expressing the RNA-protein complex; and (d) collecting the cultured cells of step (c) as the transfection reagent. In one embodiment, the method further comprises (e) testing the cells of (d) to determine the bioreactor cells expressing the RNA-protein complex; and (f) isolating the bioreactor cells from the other cells in culture for use as the transfection reagent.

In another embodiment, the invention provides a method for producing a transfection reagent comprising one or more bioreactor cells comprising the steps of: (a) preparing an expression vector comprising a polynucleotide sequence that encodes a nucleic acid comprising one or more biologically active RNAs, a recognition RNA sequence, optionally a terminal minihelix sequence, a polynucleotide sequence that encodes a polypeptide comprising an RNA binding domain and one or more transport peptide sequences, an additional polynucleotide sequences that encodes a nucleic acid comprising one or more biologically active RNA sequences that target one or more further gene target(s), and one or more polynucleotide sequences encoding one or more viral polymerases and one or more viral accessory proteins necessary for viral replication; (b) preparing an expression vector comprising one or more polynucleotide sequences encoding encoding one or more viral coat proteins and one or more viral fusogenic proteins; (c) administering the expression vector of step (a) and the expression vector of step (b) to cells in culture to produce one or more bioreactor cells (in this case, viral production cells) expressing the RNA-protein complex; and (d) collecting the cultured cells of step (c) as the transfection reagent. In one embodiment, the method further comprises (e) testing the cells of (d) to determine the bioreactor cells expressing the RNA-protein complex; and (f) isolating the bioreactor cells from the other cells in culture for use as the transfection reagent. In one embodiment, the additional polynucleotide sequence encodes a nucleic acid comprising one or more biologically active RNA sequences that target a further gene target and an RNA recognition sequence. In another embodiment, where one of the biologically active RNA sequences in the vector is a short interfering RNA (siRNA), double-stranded RNA (dsRNA), micro-RNA (miRNA), or short hairpin RNA (shRNA), the additional polynucleotide sequence encodes a nucleic acid comprising one or more biologically active RNA sequences targeted to Dicer and/or Drosha.

In another embodiment, the invention provides a method for producing a transfection reagent comprising one or more bioreactor cells comprising the steps of: (a) preparing an expression vector comprising a polynucleotide sequence that encodes a nucleic acid comprising one or more biologically active RNAs and one or more polynucleotide sequences encoding one or more viral polymerases and one or more viral accessory proteins necessary for viral replication; (b) preparing an expression vector comprising one or more polynucleotide sequences encoding encoding one or more viral coat proteins and one or more viral fusogenic proteins; (c) administering the expression vector of step (a) and the expression vector of step (b) to cells in culture to produce one or more bioreactor cells (in this case, viral production cells) expressing the biologically active RNA; and (d) collecting the cultured cells of step (c) as the transfection reagent. In one embodiment, the method further comprises (e) testing the cells of (d) to determine the bioreactor cells expressing the RNA-protein complex; and (f) isolating the bioreactor cells from the other cells in culture for use as the transfection reagent.

In another embodiment, the invention provides a method for producing a transfection reagent comprising one or more bioreactor cells comprising the steps of: (a) preparing an expression vector comprising a polynucleotide sequence that encodes a nucleic acid comprising one or more biologically active RNAs, a recognition RNA sequence, and optionally a terminal minihelix sequence; (b) preparing an expression vector comprising a polynucleotide sequence that encodes a polypeptide comprising an RNA binding domain and one or more transport peptide sequences; (c) administering the expression vector of step (a) and the expression vector of step (b) to cells in culture to produce one or more bioreactor cells expressing the RNA-protein complex; and (d) collecting the cultured cells of step (c) as the transfection reagent. In one embodiment, the method further comprises (e) testing the cells of (d) to determine the bioreactor cells expressing the RNA-protein complex; and (f) isolating the bioreactor cells from the other cells in culture for use as the transfection reagent.

The invention also provides methods of using the bioreactor cells for the delivery of a biologically active RNA to target cells, including target cells in vitro, ex vivo, and in vivo. In one embodiment, the method of delivering a biologically active RNA to target cells comprises the steps of: (a) preparing an expression vector that encodes an RNA-protein complex comprising a biologically active RNA, a recognition RNA sequence, optionally a terminal minihelix sequence, an RNA binding domain, and one or more transport peptide sequences selected from a cell penetrating domain, non-classical secretory domain, endosomal release domain, fusogenic peptide and a receptor binding domain; (b) administrating the expression vector of step (a) to cells in culture to produce bioreactor cells expressing the RNA-protein complex; (c) collecting the cultured cells of step (b); and (d) mixing one or more target cells with the cultured cell(s) collected in step (c) to deliver a biologically active RNA to the target cells. In one embodiment, the target cells are cells in culture. In another embodiment, the target cells are cells in culture which have been obtained from a subject, for example, a mammalian subject, including a human subject. In one embodiment, the expression vector of step (a) further comprises an additional polynucleotide sequences that encodes a nucleic acid comprising one or more biologically active RNA sequences that target one or more further gene target(s). In one embodiment, the additional polynucleotide sequence encodes a nucleic acid comprising one or more biologically active RNA sequences that target a further gene target and an RNA recognition sequence. In another embodiment, where one of the biologically active RNA sequences in the vector is a short interfering RNA (siRNA), double-stranded RNA (dsRNA), micro-RNA (miRNA), or short hairpin RNA (shRNA), the additional polynucleotide sequence encodes a nucleic acid comprising one or more biologically active RNA sequences targeted to Dicer and/or Drosha.

In another embodiment, the method of delivering a biologically active RNA to target cells comprises the steps of: (a) preparing an expression vector comprising a polynucleotide sequence that encodes a nucleic acid comprising one or more biologically active RNAs, a recognition RNA sequence, optionally a terminal minihelix sequence, a polynucleotide sequence that encodes a polypeptide comprising an RNA binding domain and one or more transport peptide sequences, and one or more polynucleotide sequences encoding one or more viral polymerases and one or more viral accessory proteins necessary for viral replication; (b) preparing an expression vector comprising one or more polynucleotide sequences encoding encoding one or more viral coat proteins and one or more viral fusogenic proteins; (c) administering the expression vector of step (a) and the expression vector of step (b) to cells in culture to produce one or more bioreactor cells (in this case, viral production cells) expressing the RNA-protein complex; (d) collecting the cultured cells of step (c); and (e) mixing one or more target cells with the cultured cell(s) collected in step (d) to deliver a biologically active RNA to the target cells. In one embodiment, the target cells are cells in culture. In another embodiment, the target cells are cells in culture which have been obtained from a subject, for example, a mammalian subject, including a human subject. In one embodiment, the expression vector of step (a) further comprises an additional polynucleotide sequences that encodes a nucleic acid comprising one or more biologically active RNA sequences that target one or more further gene target(s). In one embodiment, the additional polynucleotide sequence encodes a nucleic acid comprising one or more biologically active RNA sequences that target a further gene target and an RNA recognition sequence. In another embodiment, where one of the biologically active RNA sequences in the vector is a short interfering RNA (siRNA), double-stranded RNA (dsRNA), micro-RNA (miRNA), or short hairpin RNA (shRNA), the additional polynucleotide sequence encodes a nucleic acid comprising one or more biologically active RNA sequences targeted to Dicer and/or Drosha.

In another embodiment, the method for delivering a biologically active RNA to target cells comprises the steps of: (a) preparing an expression vector comprising a polynucleotide sequence that encodes a nucleic acid comprising one or more biologically active RNAs and one or more polynucleotide sequences encoding one or more viral polymerases and one or more viral accessory proteins necessary for viral replication; (b) preparing an expression vector comprising one or more polynucleotide sequences encoding encoding one or more viral coat proteins and one or more viral fusogenic proteins; (c) administering the expression vector of step (a) and the expression vector of step (b) to cells in culture to produce one or more bioreactor cells (in this case, viral production cells) expressing the biologically active RNA; (d) collecting the cultured cells of step (c); and (e) mixing one or more target cells with the cultured cell(s) collected in step (d) to deliver a biologically active RNA to the target cells. In one embodiment, the target cells are cells in culture. In another embodiment, the target cells are cells in culture which have been obtained from a subject, for example, a mammalian subject, including a human subject.

In another embodiment, the method for delivering a biologically active RNA to target cells comprises the steps of: (a) preparing an expression vector comprising a polynucleotide sequence that encodes a nucleic acid comprising one or more biologically active RNAs, a recognition RNA sequence, and optionally a terminal minihelix sequence; (b) preparing an expression vector comprising a polynucleotide sequence that encodes a polypeptide comprising an RNA binding domain and one or more transport peptide sequences; (c) administering the expression vector of step (a) and the expression vector of step (b) to cells in culture to produce one or more bioreactor cells expressing the RNA-protein complex; (d) collecting the cultured cells of step (c); (e) mixing one or more target cells with the cultured cell(s) collected in step (d) to deliver a biologically active RNA to the target cells. In one embodiment, the target cells are cells in culture. In another embodiment, the target cells are cells in culture which have been obtained from a subject, for example, a mammalian subject, including a human subject.

In one embodiment, the target cells are cells which have been removed from a subject, for example, a mammalian subject, including a human subject. Thus, in one embodiment, the method of delivering a biologically active RNA to target cells comprises the steps of: (a) preparing an expression vector that encodes an RNA-protein complex comprising a biologically active RNA, a recognition RNA sequence, optionally a terminal minihelix sequence, an RNA binding domain, and one or more transport peptide sequences selected from a cell penetrating domain, non-classical secretory domain, endosomal release domain, fusogenic peptide and a receptor binding domain; (b) administrating the expression vector of step (a) to cells in culture to produce bioreactor cells expressing the RNA-protein complex; (c) collecting the cultured cells of step (b); and (d) mixing one or more target cells removed from a subject with the cultured cell(s) collected in step (c) to deliver a biologically active RNA to the target cells. In one embodiment, the method further comprises the step of administering the cells of step (d) to a subject, for example, a mammalian subject, including a human subject. In another embodiment, the method further comprisies the step of separating the bioreactor cells from the target cells in step (d) before administering the target cells to the subject. In one embodiment, the expression vector of step (a) further comprises an additional polynucleotide sequences that encodes a nucleic acid comprising one or more biologically active RNA sequences that target one or more further gene target(s). In one embodiment, the additional polynucleotide sequence encodes a nucleic acid comprising one or more biologically active RNA sequences that target a further gene target and an RNA recognition sequence. In another embodiment, where one of the biologically active RNA sequences in the vector is a short interfering RNA (siRNA), double-stranded RNA (dsRNA), micro-RNA (miRNA), or short hairpin RNA (shRNA), the additional polynucleotide sequence encodes a nucleic acid comprising one or more biologically active RNA sequences targeted to Dicer and/or Drosha.

In one embodiment, the method of delivering a biologically active RNA to target cells comprises the steps of: (a) preparing an expression vector comprising a polynucleotide sequence that encodes a nucleic acid comprising one or more biologically active RNAs, a recognition RNA sequence, optionally a terminal minihelix sequence, a polynucleotide sequence that encodes a polypeptide comprising an RNA binding domain and one or more transport peptide sequences, and one or more polynucleotide sequences encoding one or more viral polymerases and one or more viral accessory proteins necessary for viral replication; (b) preparing an expression vector comprising one or more polynucleotide sequences encoding encoding one or more viral coat proteins and one or more viral fusogenic proteins; (c) administering the expression vector of step (a) and the expression vector of step (b) to cells in culture to produce one or more bioreactor cells (in this case, viral production cells) expressing the RNA-protein complex; (d) collecting the cultured cells of step (c); and (e) mixing one or more target cells removed from a subject with the cultured cell(s) collected in step (c) to deliver a biologically active RNA to the target cells. In one embodiment, the method further comprises the step of administering the cells of step (e) to a subject, for example, a mammalian subject, including a human subject. In another embodiment, the method further comprises the step of separating the bioreactor cells from the target cells in step (e) before administering the target cells to the subject. In one embodiment, the expression vector of step (a) further comprises an additional polynucleotide sequences that encodes a nucleic acid comprising one or more biologically active RNA sequences that target one or more further gene target(s). In one embodiment, the additional polynucleotide sequence encodes a nucleic acid comprising one or more biologically active RNA sequences that target a further gene target and an RNA recognition sequence. In another embodiment, where one of the biologically active RNA sequences in the vector is a short interfering RNA (siRNA), double-stranded RNA (dsRNA), micro-RNA (miRNA), or short hairpin RNA (shRNA), the additional polynucleotide sequence encodes a nucleic acid comprising one or more biologically active RNA sequences targeted to Dicer and/or Drosha.

In another embodiment, the method for delivering a biologically active RNA to target cells comprises the steps of: (a) preparing an expression vector comprising a polynucleotide sequence that encodes a nucleic acid comprising one or more biologically active RNAs and one or more polynucleotide sequences encoding one or more viral polymerases and one or more viral accessory proteins necessary for viral replication; (b) preparing an expression vector comprising one or more polynucleotide sequences encoding encoding one or more viral coat proteins and one or more viral fusogenic proteins; (c) administering the expression vector of step (a) and the expression vector of step (b) to cells in culture to produce one or more bioreactor cells (in this case, viral production cells) expressing the biologically active RNA; (d) collecting the cultured cells of step (c); and (e) mixing one or more target cells removed from a subject with the cultured cell(s) collected in step (c) to deliver a biologically active RNA to the target cells. In one embodiment, the method further comprises the step of administering the cells of step (e) to a subject, for example, a mammalian subject, including a human subject. In another embodiment, the method further comprises the step of separating the bioreactor cells from the target cells in step (e) before administering the target cells to the subject.

In another embodiment, the method for delivering a biologically active RNA to target cells comprises the steps of: (a) preparing an expression vector comprising a polynucleotide sequence that encodes a nucleic acid comprising one or more biologically active RNAs, a recognition RNA sequence, and optionally a terminal minihelix sequence; (b) preparing an expression vector comprising a polynucleotide sequence that encodes a polypeptide comprising an RNA binding domain and one or more transport peptide sequences; (c) administering the expression vector of step (a) and the expression vector of step (b) to cells in culture to produce one or more bioreactor cells expressing the RNA-protein complex; (d) collecting the cultured cells of step (c); and (e) mixing one or more target cells removed from a subject with the cultured cell(s) collected in step (c) to deliver a biologically active RNA to the target cells. In one embodiment, the method further comprises the step of administering the cells of step (e) to a subject, for example, a mammalian subject, including a human subject. In another embodiment, the method further comprises the step of separating the bioreactor cells from the target cells in step (e) before administering the target cells to the subject.

The invention provides methods for secreting one or more biologically active RNA molecules from a bioreactor cell and methods for modulating target gene expression in vivo, ex vivo, and in vitro. The invention provides an expression vector designed to produce an RNA-protein complex comprising at least one biologically active RNA molecule targeting one or more genes of interest and a fusion protein capable of delivering the biologically active RNA molecule(s) to the extracellular matrix and/or neighboring cells and tissues. The administration of the expression vector to cells in vivo, ex vivo, and in vitro converts the cells into "bioreactors" that produce and deliver biologically active RNA molecules, secreted as RNA-protein complexes, to the extracellular matrix and/or other neighboring cells. Thus, the RNA-mediated effect is amplified through the production and delivery of biologically active RNAs to surrounding cells and tissues.

In one embodiment, the invention provides a method for modulating the expression of one or more target gene(s) in a subject comprising administering to the subject one or more expression vectors of the invention. In another embodiment, the invention provides a method for modulating the expression of one or more target gene(s) in a subject comprising administering to the subject a composition comprising one or more expression vectors of the invention and a pharmaceutically acceptable carrier. In another embodiment, the invention provides a method for modulating the expression of one or more target gene(s) in a subject comprising administering to the subject a cell comprising one or more expression vectors of the invention and a pharmaceutically acceptable carrier. The expression vector can be any of the expression vectors of the invention described herein.

In one embodiment, the invention provides a method for modulating the expression of one or more target gene(s) in a subject comprising administering to the subject one or more bioreactor cells of the invention. In another embodiment, the invention provides a method for modulating the expression of one or more target gene(s) in a subject comprising administering to the subject a composition comprising one or more bioreactor cells of the invention and a pharmaceutically acceptable carrier, including but not limited to phosphate buffered saline (PBS), saline, or 5% dextrose. The bioreactor cell(s) can be any of the bioreactor cells(s) of the invention described herein. In one embodiment, the bioreactor cell(s) produces and secretes an RNA-protein complex comprising one or more biologically active RNA sequences directed to a target gene(s), a recognition RNA sequence, optionally a terminal minihelix sequence, an RNA binding domain sequence, and one or more transport peptide sequences, for example, selected from a cell penetrating peptide sequence, non-classical secretory domain, endosomal release domain, receptor binding domain, and fusogenic peptide.

In any of the methods of modulating gene expression in a subject described herein, the subject can be a mammalian subject, including, for example, a human, rodent, murine, bovine, canine, feline, sheep, equine, and simian subject.

The invention additionally provides a method of preventing, ameliorating, and/or treating a disease or condition associated with defective gene expression and/or activity in a subject comprising administering to the subject one or more expression vectors of the invention. In one embodiment, the invention provides a method of preventing, ameliorating, and/or treating a disease or condition associated with defective gene expression and/or activity in a subject comprising administering to the subject a composition comprising one or more expression vectors of the invention and a pharmaceutically acceptable carrier. In one embodiment, the invention provides a method of preventing, ameliorating, and/or treating a disease or condition associated with defective gene expression and/or activity in a subject comprising administering to the subject a cell comprising one or more expression vectors of the invention and a pharmaceutically acceptable carrier. The expression vector can be any of the expression vectors of the invention described herein.

In one specific embodiment, the invention provides a method for modulating the expression of a target gene in a target cell comprising administering to the target cell an expression vector of the invention, wherein the target cell produces and secretes an RNA-protein complex of the invention and wherein the RNA-protein complex is subsequently delivered to the extracellular matrix or to other target cells. In another embodiment, the invention provides a method for modulating the expression of a target gene in a target cell comprising administering to the target cell a composition comprising an expression vector of the invention, wherein the target cell produces and secretes an RNA-protein complex of the invention and wherein the RNA-protein complex is subsequently delivered to the extracellular matrix or to other target cells. In another embodiment, the invention provides a method for modulating the expression of a target gene in a target cell comprising administering to the target cell a cell comprising an expression vector of the invention, wherein the target cell produces and secretes an RNA-protein complex of the invention and wherein the RNA-protein complex is subsequently delivered to the extracellular matrix or to other target cells. The expression vector can be any expression vector of the invention described herein.

The invention also provides methods for modulating the expression of a target gene in a target cell ex vivo. In one embodiment, the invention provides a method for modulating the expression of a target gene in a target cell ex vivo comprising administering to the target cell ex vivo one or more expression vectors of the invention. In another embodiment, the invention provides a method for modulating the expression of a target gene in a target cell ex vivo comprising administering to the target cell ex vivo a composition comprising one or more expression vectors of the invention and a pharmaceutically acceptable carrier. In another embodiment, the invention provides a method for modulating the expression of a target gene in a target cell ex vivo comprising administering to the target cell ex vivo a bioreactor cell comprising one or more expression vectors of the invention and a pharmaceutically acceptable carrier. The expression vector can be any of the expression vectors of the invention described herein.

The invention also provides methods for modulating gene expression in a cell in culture. In one embodiment, the invention provides a method for modulating the expression of one or more target gene(s) in a cell in culture comprising administering to the cell one or more expression vectors of the invention. In another embodiment, the invention provides a method for modulating the expression of one or more target gene(s) in a cell in culture comprising administering to the cell a composition comprising one or more expression vectors of the invention and a pharmaceutically acceptable carrier. In another embodiment, the invention provides a method for modulating the expression of one or more target gene(s) in a cell in culture comprising administering to the cell a a bioreactor cells comprising one or more expression vectors of the invention and a pharmaceutically acceptable carrier. The expression vector can be any of the expression vectors of the invention described herein.

In one embodiment, the invention provides a method for modulating the expression of one or more target gene(s) in a cell in culture comprising administering to the cell a first expression vector encoding a nucleic acid comprising one or more biologically active RNA sequences directed to a target gene, a recognition RNA sequence, and optionally a terminal minihelix sequence and a second expression vector encoding a polypeptide comprising an RNA binding domain and one or more transport peptide sequences, for example, selected from a cell penetrating peptide sequence, non-classical secretory domain, endosomal release domain, and a receptor binding domain.

In addition the present invention provides expression vectors constructed from a replication defective or replication incompetent viral particles which carry and distribute one or more biologically active RNA molecules from a transformed packaging cell. In one embodiment, the invention provides a viral vector comprising a polynucleotide that encodes any of the nucleic acid molecules described herein. In one embodiment, the invention provides a viral vector comprising a polynucleotide that encodes a nucleic acid molecule comprising one or more biologically active RNA sequences and a recognition RNA sequence. In another embodiment, the invention provides a viral vector comprising a polynucleotide that encodes a nucleic acid molecule comprising one or more biologically active RNA sequences, a recognition RNA sequence, and a terminal minihelix sequence. The biologically active RNA sequence can be any of the biologically active RNA sequences described herein and otherwise known in the art. In one embodiment, the viral vector comprises a polynucleotide encoding a nucleic acid molecule wherein the biologically active RNA sequence is selected from a ribozyme, antisense nucleic acid, allozyme, aptamer, short interfering RNA (siRNA), double-stranded RNA (dsRNA), micro-RNA (miRNA), short hairpin RNA (shRNA), and a transcript encoding one or more biologically active peptides. In one specific embodiment, the viral vector comprises a polynucleotide encoding a nucleic acid molecule wherein the biologically active RNA sequence is a short hairpin RNA (shRNA). In one specific embodiment, the viral vector comprises a polynucleotide encoding a nucleic acid molecule wherein the biologically active RNA sequence is an aptamer. The recognition RNA sequence can be any of the recognition RNA sequences described herein and otherwise known in the art. In one embodiment, viral vector vector comprises a polynucleotide encoding a nucleic acid molecule wherein the recognition RNA sequence is selected from a U1 loop, Group II intron, NRE stem loop, S1A stem loop, Bacteriophage BoxBR, HIV Rev response element, AMVCP recognition sequence, and ARE sequence. The terminal minihelix sequence can be any of the terminal minihelix sequences described herein and otherwise known in the art. In one embodiment, the terminal minihelix sequence is selected from the adenovirus VA1 RNA molecule.

In another embodiment, the viral vector additionally comprises a polynucleotide that encodes a nucleic acid molecule comprising one or more biologically active RNA sequences targeted to Dicer and/or Drosha. None of these polynucleotides encode an RNA binding domain. In one embodiment, the polynucleotide encodes a nucleic acid molecule comprising a single biologically active RNA sequence. In another embodiment, the polynucleotide encodes a nucleic acid molecule comprising two or more biologically active RNA sequences. In certain embodiments, the biologically active RNA sequence is selected from a ribozyme, antisense nucleic acid, allozyme, aptamer, short interfering RNA (siRNA), double-stranded RNA (dsRNA), micro-RNA (miRNA), short hairpin RNA (shRNA), and a transcript encoding one or more biologically active peptides.

In any of the above-described embodiments of the viral vector comprising a polynucleotide encoding a nucleic acid molecule of the invention, the polynucleotide can comprise a sequence wherein the recognition RNA sequence, the individual biologically active RNA sequences, the optional terminal minihelix sequence, and any other included sequences are joined with the addition of one or more intervening or additional sequences or are joined directly without the addition of intervening sequences.

In another embodiment, the viral vector comprises a polynucleotide encoding a polypeptide comprising an RNA binding domain, and one or more transport peptide sequences selected from a cell penetrating peptide, a non-classical secretory domain, a receptor binding domain, an endosomal release domain, and a fusogenic peptide. In one embodiment, the polynucleotide encoding the polypeptide further comprises a promoter sequence, a termination sequence, and optionally one or more primers sequences. In another embodiment, the viral vector additionally comprises a polynucleotide that encodes a nucleic acid molecule comprising one or more biologically active RNA sequences, a recognition RNA sequence, and optionally a terminal minihelix sequence. In yet a further embodiment the polynucleotide encoding the nucleic acid molecule additionally comprises a promoter sequence, a termination sequence, and optionally one or more primer sequences. In yet another embodiment, the viral vector additionally comprises a polynucleotide that encodes a nucleic acid molecule comprising one or more biologically active RNA sequences targeted to Dicer and/or Drosha, and optionally a promoter sequence, a termination sequence, and one or more primer sequences. Thus, in one embodiment, the viral vector comprises a polynucleotide encoding a polypeptide comprising an RNA binding domain, and one or more transport peptides selected from a cell penetrating peptide, a non-classical secretory domain, a receptor binding domain, an endosomal release domain, and a fusogenic peptide, and further comprises a polynucleotide that encodes a nucleic acid molecule comprising one or more biologically active RNA sequences, a recognition RNA sequence, optionally a terminal minihelix sequence. In one embodiment, this viral vector can further comprise a polynucleotide that encodes a nucleic acid molecule comprising one or more biologically active RNA sequences targeted to Dicer and/or Drosha. In any of these embodiments, the viral vector can optionally comprise one or more promoter sequences, one or more termination sequences, and one or more primer sequences.

In any of the above-described embodiments of the viral vector, the polynucleotide can comprise a sequence wherein any of the RNA binding domain, cell penetrating peptide, non-classical secretory domain, receptor binding domain, endosomal release domain, fusogenic peptide, and any other included sequences (i.e., promoter, termination, primer, biologically active RNA, recognition RNA, terminal minihelix sequences, etc.) are joined with the addition of one or more intervening or additional sequences or are joined directly without the addition of intervening sequences. In any of the above-described embodiments, the vector can comprise a polynucleotide that encodes a polypeptide wherein the sequence or sequences of the individual domains and peptides are joined without or with the addition of one or more linker, spacer, or other sequences.

The present invention also provides engineered, replication defective virus to deliver biologically active RNAs from transformed packaging cells to target cells. In one embodiment the invention provides packaging cells generated by transfection of recipient cells with plasmids encoding for the two independent viral RNAs, one encoding the virus structural genes, the other encoding the non-structural genes and a biologically active RNA sequence. In one embodiment the viral non-structural and structural genes are selected from DNA viruses and RNA viruses with non-limiting examples of suitable viruses being Adenovirus, Adeno-Associated Virus, Herpes Simplex Virus Lentivirus, Retrovirus, Sindbis virus, Foamy virus. The biologically active RNA sequence can be any of the biologically active RNA sequences described herein and otherwise known in the art. In one embodiment, the biologically active RNA sequence is selected from a ribozyme, antisense nucleic acid, allozyme, aptamer, short interfering RNA (siRNA), double-stranded RNA (dsRNA), micro-RNA (miRNA), short hairpin RNA (shRNA), and a transcript encoding one or more biologically active peptides. In one specific embodiment, the biologically active RNA sequence is a short hairpin RNA (shRNA). In another specific embodiment, the biologically active RNA sequence is micro-RNA (miRNA).

Successful co-transfection of both plasmids yield packaging cells capable of producing replication defective viral particles. In one embodiment the invention provides packaging cells produced by transfection of cells in vitro, ex vivo or in vivo. In a further embodiment packaging cells are collected and mixed with target cells in vitro. In another embodiment packaging cells are collected and administered in target cells in vivo. In a further embodiment packaging cells are collected and transferred to target cell ex vivo.

BRIEF DESCRIPTION OF THE DRAWINGS

FIG. 1 is a non-limiting schematic exemplifying the in vivo mechanism of action for the vector-based delivery of a biologically active RNA molecule, which exemplary biologically active RNA molecule is a shRNA. As shown, the expression vector (pBioR) expresses a nucleic acid molecule comprising a recognition RNA sequence and an shRNA and a fusion protein comprising an RNA binding domain (RBD) and a cell penetrating peptide (CPP). The fusion protein is translated in the cytoplasm where the RNA binding domain of the translated fusion protein binds to the recognition RNA sequence of the nucleic acid, forming an RNA-protein complex. The RNA-protein complex is secreted into the extracellular matrix and taken up by neighboring cells where the shRNA acts to modulate the target gene of interest (GOI).

FIG. 2 is a non-limiting schematic exemplifying the in vivo mechanism of action for the vector-based delivery of a biologically active RNA molecule, which exemplary biologically active RNA molecule is a shRNA. As shown, the expression vector (pBioR) expresses a nucleic acid molecule comprising a recognition RNA sequence and an shRNA and a fusion protein comprising an RNA binding domain (RBD), a non-classical secretory domain (NCS), and a cell penetrating peptide (CPP). The fusion protein is translated in the cytoplasm where the RNA binding domain of the translated fusion protein binds to the recognition RNA sequence of the nucleic acid, forming an RNA-protein complex. The RNA-protein complex is secreted into the extracellular matrix and taken up by neighboring cells where the shRNA acts to modulate the target gene of interest (GOI).

FIG. 3 is a non-limiting schematic exemplifying the in vivo mechanism of action for the vector-based delivery of a biologically active RNA molecule, which exemplary biologically active RNA molecule is an aptamer targeting a specific cell-surface receptor. As shown, the expression vector (pBioR) expresses a nucleic acid molecule comprising a recognition RNA sequence and an aptamer targeting a specific cell-surface receptor and a fusion protein comprising an RNA binding domain (RBD) and a non-classical secretory domain (NCS). The fusion protein is translated in the cytoplasm where the RNA binding domain of the translated fusion protein binds to the recognition RNA sequence of the nucleic acid, forming an RNA-protein complex. The RNA-protein complex is secreted into the extracellular matrix. The aptamer binds to the target cell-surface receptor, preventing the receptor ligand from binding the receptor.

FIG. 4 is a non-limiting schematic exemplifying the in vivo mechanism of action for the vector-based delivery of a biologically active RNA molecule, which exemplary biologically active RNA molecule is an aptamer targeting a specific extracellular matrix protein. As shown, the expression vector (pBioR) expresses a nucleic acid molecule comprising a recognition RNA sequence and an aptamer targeting a specific extracellular matrix protein and a fusion protein comprising an RNA binding domain (RBD) and a non-classical secretory domain (NCS). The fusion protein is translated in the cytoplasm where the RNA binding domain of the translated fusion protein binds to the recognition RNA sequence of the nucleic acid, forming an RNA-protein complex. The RNA-protein complex is secreted into the extracellular matrix. The aptamer binds to the extracellular matrix protein, preventing the extracellular matrix protein from entering a target cell. The extracellular matrix protein can be, among other things, a cell-surface receptor ligand, whereby the aptamer binds the ligand and prevents it from binding to its receptor (not shown).

FIG. 5 shows a schematic diagram of the backbone plasmid pEGEN 1.1. pEGEN 1.1 includes an SV40 promoter sequence (1), an intronic sequence (2), a multiple cloning sequence (MCS), a human growth hormone poly-A tail sequence (4), a kanamycin resistance gene (7) and a pUC origin of replication (8).

FIG. 6 shows a schematic diagram of the backbone plasmid pEGEN 2.1. pEGEN 2.1 includes a chicken-actin promoter sequence (1), an intronic sequence (2), a multiple cloning sequence (MCS), a human growth hormone poly-A tail sequence (4), a kanamycin resistance gene (7) and a pUC origin of replication (8).

FIG. 7 shows a schematic diagram of the backbone plasmid pEGEN 3.1. pEGEN 3.1 includes a CMV promoter sequence (1), an intronic sequence (2), a multiple cloning sequence (MCS), a human growth hormone poly-A tail sequence (4), a kanamycin resistance gene (7) and a pUC origin of replication (8).

FIG. 8 shows a schematic diagram of the backbone plasmid pEGEN 4.1. pEGEN 4.1 includes a human U6 promoter sequence (1), a multiple cloning sequence (MCS), a polyT terminator sequence (4), a kanamycin resistance gene (7) and a pUC origin of replication (8).

FIG. 9 shows a schematic diagram of the expression vector pBioR Pol II which encodes an exemplary RNA-protein complex of the invention. The vector includes an SV40 promoter (1) and an intronic sequence (2) upstream of an Sec-RNA sequence (3) and a downstream hGH polyA sequence (4). The vector also comprises a β-actin promoter (5) upstream of a fusion protein sequence (6) and a downstream hGH polyA sequence (4). The vector also comprises a kanamycin resistance gene (7) and a pUC origin of replication (8).

FIG. 10 shows a schematic diagram of expression vector pBioR Pol III which encodes an exemplary RNA-protein complex of the invention. The vector includes an hU6 promoter upstream (1) and an intronic sequence (2) upstream of an Sec-RNA sequence (3) and a downstream Pol-III poly-T terminator sequence (4). The vector also comprises a β-actin promoter (5) upstream of a fusion protein sequence (6) and a downstream hGH polyA sequence (4). The vector also comprises a kanamycin resistance gene (7) and a pUC origin of replication (8).

FIG. 11 shows a schematic diagram of expression vector pBioR Pol II combo which encodes an exemplary RNA-protein complex of the invention. The vector includes a β-actin promoter (1), an intronic sequence (2), a fusion protein cassette (6), a Sec-RNA cassette (3) with flanking introns (2) internal to the fusion protein, a human growth hormone poly-A tail sequence (4), a kanamycin resistance gene (7) and a pUC origin of replication (8).

FIG. 12 shows a schematic diagram of expression vector pBioR Pol II stable which encodes an exemplary RNA-protein complex of the invention. The vector includes a CTS regulator (9), a PGK promoter (1), a puromycin resistance gene (10), a chicken-actin promoter (5), a fusion protein cassette (6), a Sec-RNA cassette (3) with flanking introns (2) internal to the fusion protein, a human growth hormone poly-A tail sequence (4), a kanamycin resistance gene (7) and a pUC origin of replication (8).

FIG. 13 shows a schematic diagram of expression vector pBioR Pol II Dicer which encodes an exemplary RNA-protein complex of the invention. The vector includes a SV40 promoter (1), an intronic sequence (2), an shRNA sequence (3), a hGH poly-A tail sequence (4), a chicken β-actin promoter (5), a fusion protein cassette (6), a Sec-RNA cassette (11) with flanking introns (2) internal to the fusion protein, a human growth hormone poly-A tail sequence (4), a kanamycin resistance gene (7) and a pUC origin of replication (8).

FIG. 14A is a non-limiting schematic showing an exemplary transfection assay to generate bioreactor cells and test their secretory activity using the CPP-Luciferase/CPP-Alkaline Phosphatase reporter system. FIG. 14B presents results for TAT mediated secretion of the luciferase reporter protein from CT26 cells. CT26 cells were transfected with plasmids expressing luciferase or a CPP-Luciferase fusion protein. CPP domains assayed include TAT, REV, FHV, and Penetratin (Pen). After 48 hours, cell media was replaced with PBS and cells were incubated at 37° C. for an additional 1 hour, 3 hours, or 6 hours. The PBS supernatant was collected and the cells were lysed in TENT buffer. Luciferase activity was measured for equivalent amounts of solubilized cellular protein and PBS supernatant using standard methods. The relative luciferase activity present in cellular and supernatant fractions is presented as a percentage of the total luciferase activity observed in both fractions.

FIGS. 15A and 15B show schematic diagrams for the construction of plasmids for expression of secreted RNAs and bioreactor fusion proteins. As shown in FIG. 15A, pE3.1 Sec-Reporter includes a CMV promoter sequence (1), an intronic sequence (2), a secreted RNA reporter coding sequence (Box B sequence and glucagon-like peptide 1) (3), a human growth hormone poly-A tail sequence (4), a kanamycin resistance gene (7) and a pUC origin of replication (8). As shown in FIG. 15B, pE1 TAT-RBD includes an SV40 promoter sequence (1), an intronic sequence (2), a fusion protein coding sequence (i.e., an RNA binding domain (RBD) and cell penetrating peptide (TAT)) (6), a human growth hormone poly-A tail sequence (4), a kanamycin resistance gene (7) and a pUC origin of replication (8). FIGS. 15C-E show the restriction enzyme analyses of the pE3.1 Sec-Reporter and pE1 TAT-RBD plasmids. FIG. 15C shows the restriction enzyme analysis of the pE3.1 Sec-Reporter, in which a novel EcoNI restriction site is introduced with the RNA expressing insert. FIGS. 15D and 15E show the restriction enzyme and PCR analyses, respectfully, of two pE1 TAT-RBD plasmids: one expressing a fusion protein with the TAT cell penetrating peptide fused to a Protein N RNA binding domain (TAT+), the other expressing a fusion protein with the TAT cell penetrating peptide fused to a Rev RNA binding domain (TAT−). In these figures, (M) denotes a size marker lane. In FIG. 15C, Sec-Reporter (−) refers to the pE3.1 Sec-Reporter plasmid only and Sec-Reporter (+) refers to the pE3.1 Sec-Reporter plasmid with the RNA expressing insert. In FIGS. 15D and 15E, p1.1 refers to the pE1.1 plasmid only, TAT(−) refers to the pE1.1 plasmid with the fusion protein insert comprising a TAT cell penetrating peptide fused to a Rev RNA binding domain, and TAT(+) refers to the pE1.1 plasmid with the fusion protein insert comprising a TAT cell penetrating peptide fused to a Protein N RNA binding domain.

FIGS. 16A and 16B show the expression products for the secreted RNAs and the bioreactor fusion proteins. For the secreted RNA reporter transcript analyses shown in FIG. 16A, CT26 cells were transfected with pE3.1 Sec-Reporter (FIG. 15A). After 48 hours, total cellular RNA was collected from untreated control cells and transfected cells, and purified RNA was amplified using RT-PCR and separated on 3% low melt agarose gels (1×TAE). Untransfected control cells ("U") show only the 18S rRNA internal control (18S) whereas the transfected cells show both the 18S rRNA product and the parent reporter RNA product ("R"), which corresponds to the plasmid only, or the secreted reporter RNA product ("SR"), which corresponds to the plasmid and the Sec-RNA sequence insert. FIG. 16B shows the fusion protein expression analyses, in which CT26 cells were transfected with plasmids expressing the bioreactor fusion protein. After 48 hours, cell lysates from untreated cells and cells transfected with pE3.1 Sec-Reporter and either pE1.1 TAT+ (TAT fused to a Protein N RNA binding domain and 6× Histidine epitope tage) or pE2.1TAT+ (TAT fused to a Protein N RNA binding domain and 6× Histidine epitope tag) were spotted to PVDF membranes along with a positive control protein for the blotting antibody. The blots were developed with chromogenic substrates and recorded with an image documentation center. "His+" shows the results of the positive control and "Unt" shows the results of untransfected CT26 cells. The blots were developed with chromogenic substrates and recorded with an image documentation center. "His+" shows the chromogenic signal obtained with a purified His-tagged protein (positive control); "Unt" shows the background signal obtained with protein lysates collected from untransfected CHO cells; pE1.1 TAT+ shows the signal obtained with protein lysates collected from CHO cells transfected with pE1.1 TAT-Protein N-6×His; and pE2.1 TAT+ shows the signal obtained with protein lysates collected from CHO cells transfected with pE2.1 TAT-Protein N-6×His.

FIGS. 17A and 17B show bioreactor activity using the two component plasmids described in FIGS. 15A and 15B. RNA from untreated control CT26 cells and CT26 cells transfected with the pE3.1 Sec-Reporter and pE1TAT-RBD plasmids expressing the secreted RNAs and the bioreactor fusion proteins was collected and used as template for RT-PCR amplification reactions. RNA was also collected from the cell culture media, purified and amplified. The amplified products were separated on 3% low melt agarose gels (1×TAE) along with DNA size standards. FIGS. 17A and 17B show the results of a transfection assay with pE3.1 Sec-Reporter and either pE1.1 TAT(+) (TAT fused to the proper RBD) or pE1.1 TAT(−) (TAT fused to a negative control RBD). The left hand panel of FIG. 17A shows RT-PCR products for cell lysates collected from cells transfected with the parent reporter plasmid ("R"), the reporter plasmid containing the sec-RNA sequence insert ("SR"), the sec-RNA reporter plasmid co-transfected with pE1.1 TAT(+) ("TAT(+)"; TAT fused to a Protein N RNA binding domain) or with pE1.1 TAT(−) ("TAT(−)"; TAT fused to a Rev RNA binding domain, serving as a negative control RBD). The right hand panel of FIG. 17A shows both cell lysates ("C") and extracellular media samples ("M") from cells cotransfected with the sec-RNA reporter plasmid and pE1.1 TAT(+) ("TAT(+)"; TAT fused to a Protein N RNA binding domain) or pE1.1 TAT(−) ("TAT(−)"; fused to a Rev RNA binding domain). FIG. 17B shows the results of a second assay, identical to the first, where steps have been taken to eliminate the 18S rRNA contamination of the media observed in the first experiment.

FIG. 18 is a non-limiting schematic showing an exemplary transfection assay to generate and test the import activity of bioreactor cells using the GFP reporter system.

FIG. 19A is a schematic showing the secretion and activity of aptamers targeted to Oncostatin M produced by bioreactor cells of the invention. FIG. 19B is a non-limiting schematic showing an exemplary transfection assay to determine the secretion activity of bioreactor cells using a reporter system and a secreted RNA aptamer targeting the Oncostatin M protein, an activator of the gp130 receptor mediated signaling pathway.

FIG. 20A is a schematic showing the secretion and activity of aptamers targeted to HER3 produced by bioreactor cells of the invention. FIG. 20B is a non-limiting schematic showing an exemplary transfection assay to determine the secretion activity of bioreactor cells using a reporter system and a secreted RNA aptamer targeting the HER3.

FIG. 21 is a non-limiting schematic showing an exemplary transfection assay to determine the secretion activity of bioreactor cells and subsequent delivery of an inhibitory shRNA to the cytoplasm of a target cell.

FIG. 22 is a non-limiting schematic showing the two constructs required for producing the viral packaging cells containing a biologically active inhibitory RNA molecule.

FIG. 23 is a non-limiting schematic showing the production of viral packaging cells containing virus particles and a biologically active RNA molecule. The schematic further exemplifies the transfer of the biologically active RNA molecule into a target cell.

FIG. 24 is a non-limiting schematic showing the production of viral packaging cells containing virus particles, the bioreactor fusion protein and a biologically active RNA molecule. The schematic further exemplifies the transfer of the bioreactor expression cassettes via the virus particle to primary target cells (secondary bioreactor cells) and subsequent transfer of the biologically active RNA molecule into secondary target cells.

DETAILED DESCRIPTION OF THE INVENTION

Definitions

As used herein the term "biologically active RNA" is meant to refer to any RNA sequence that modulates gene expression or gene activity of targeted gene products.

As used herein, the term "recognition RNA sequence" is meant to refer to any RNA sequence that is specifically bound by a peptide comprising an RNA binding domain.

As used herein, the term "RNA binding domain" is meant to refer to any protein or peptide sequence that specifically binds to a corresponding recognition RNA sequence.

As used herein, the term "transport peptide" is meant to refer to any peptide sequence that facilitates movement of any attached cargo within a cell or cells, including facilitating cargo movement across a cell membrane of a cell, secretion of cargo from a cell, and release of cargo from an endosome, as well as other means of cellular movement. In specific, but non-limiting examples, the transport peptide can be a sequence derived from a cell penetrating peptide, a non-classical secretory sequence, an endosomal release domain, a receptor binding domain, and a fusogenic peptide.

As used herein, the term "cell penetrating peptide" is meant to refer to any peptide sequence that facilitates movement of any attached cargo across a lipid bilayer, such as the membrane of a cell.

As used herein, the term "non-classical secretory sequence" is meant to refer to any protein or peptide sequence that provides for secretion of any attached cargo from a cell via an ER-Golgi independent pathway.

As used herein, the term "endosomal release domain" is meant to refer to any peptide sequence that facilitates release of any attached cargo from the endosome of a cell.

As used herein, the term "receptor binding domain" is meant to refer to any RNA or protein domain capable of interacting with a surface bound cellular receptor.

As used herein, the term "fusogenic peptide" is meant to refer to any peptide sequence that facilitates cargo exit from the endosome of a cell.

As used herein, the term "sec-RNA" refers to the RNA portion of the RNA-protein complex of the invention. Typically, the "sec-RNA" comprises one or more biologically active RNAs, a recognition RNA sequence, and optionally a terminal minihelix sequence. When complexed with a fusion protein of the invention, the sec-RNA is secreted from the cell.

As used herein, the term "sec-shRNA" refers to the shRNA portion of the RNA-protein complex of the invention. Typically, the "sec-shRNA" comprises one or more short hairpin RNAs, a recognition RNA sequence, and optionally a terminal minihelix sequence. When complexed with a fusion protein of the invention, the sec-shRNA is secreted from the cell.

As used herein, the term "fusion protein" is meant to refer to at least two polypeptides, typically from different sources, which are operably linked. With regard to polypeptides, the term operably linked is intended to mean that the two polypeptides are connected in a manner such that each polypeptide can serve its intended function. Typically, the two polypeptides are covalently attached through peptide bonds. The fusion protein can be produced by standard recombinant DNA techniques. For example, a DNA molecule encoding the first polypeptide is ligated to another DNA molecule encoding the second polypeptide, and the resultant hybrid DNA molecule is expressed in a host cell to produce the fusion protein. The DNA molecules are ligated to each other in a 5' to 3' orientation such that, after ligation, the translational frame of the encoded polypeptides is not altered (i.e., the DNA molecules are ligated to each other in-frame). In a specific example, a fusion protein refers to a peptide comprising an RNA binding domain sequence and one or more transport peptide sequences.

As used herein, the term "bioreactor cell" or "bioreactor" is meant to refer to any cell that produces and secretes a Sec-RNA molecule.

As used herein, the term "pBioR plasmid" is meant to refer to any plasmid comprising a polynucleotide encoding at least an RNA binding domain sequence, a transport peptide sequence, and a polynucleotide encoding a biologically active RNA and a recognition RNA sequence.

As used herein, the term "expression cassette" is meant to refer to a nucleic acid sequence capable of directing expression of a particular nucleotide sequence, which may include a promoter operably linked to a nucleotide sequence of interest that may be operably linked to termination signals. It also may include sequences required for proper translation of the nucleotide sequence. The coding region can code for a peptide of interest but may also code for a biologically active RNA of interest. The expression cassette including the nucleotide sequence of interest may be chimeric. The expression cassette may also be one that is naturally occurring but has been obtained in a recombinant form useful for heterologous expression. In a specific example, an expression cassette comprises a nucleic acid sequence comprising a promoter sequence, a polynucleotide encoding a peptide sequence or a polynucleotide encoding an RNA sequence, and a terminator sequence.

The term "operatively linked" is used herein to refer to an arrangement of flanking sequences wherein the flanking sequences so described are configured or assembled so as to perform their usual function. A flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

Mechanism of Action for the Vector Based Delivery System

The invention provides a vector based RNA delivery system in which a plasmid converts a transfected cell into an RNA bioreactor capable of producing and secreting biologically active RNA molecules. The plasmid accomplishes this by encoding both the biologically active RNA molecule and a fusion protein capable of facilitating its secretion from the bioreactor and delivery to the extracellular matrix and/or surrounding target cells. Once delivered to the target cells, the biologically active RNA molecule functions as it would in any cell. This approach directly addresses the key issue in application of plasmid based RNAi mediated therapeutics, namely the low transfection efficiencies associated with plasmid delivery. Although the initial transfection of the bioreactor cells may be limited do to the technical difficulties associated with standard gene delivery methods, the subsequent expression of the plasmid based delivery system of the present invention will mitigate the traditional limitations as they permit sustained and continued delivery of active RNAs and associated proteins from bioreactor cells. RNA-mediated knockdown is amplified through bioreactor cell cellular production and delivery of biologically active RNAs to surrounding cells and tissues.

The central component of the plasmid based delivery system is the fusion protein that facilitates secretion and/or delivery. Classical export of protein molecules through the ER-Golgi is co-translational, meaning the proteins are translocated across the ER membrane as they are being made. This prevents the use of classical transport mechanisms in the bioreactor cell, as the RNA binding domain would only briefly exist in the cytoplasm with the Sec-RNA molecule and transport across the membrane would likely disrupt the RNA-protein interaction. Instead, a fully translated and folded protein in the cytoplasm can be subsequently secreted via a non-classical mechanism with the biologically active RNA cargo in tow. A growing number of proteins are now known to be secreted via non-classical pathways which are independent of the ER-Golgi apparatus. Although the precise mechanism of export for these systems is not fully characterized, the proteins are known to be translated in the cytoplasm and therefore contain sequence motifs that allow them to be secreted and are suitable for use in the bioreactor.

An early step in bioreactor cell function is synthesis of the RNA and protein components of the RNA-protein complex and localization of those components to the cell cytoplasm. Promoter driven transcription of the RNA molecules occurs via well established mechanisms and can be optimized for the cell type being used as the bioreactor. Export of the transcript encoding the fusion protein follows typical Pol-II mRNA pathway via the nuclear pore complex. Alternatively, the Sec-RNA molecule can be constructed in such a way that it is exported via the exportin-5 pathway utilized by microRNAs and shRNAs. Still alternatively, the RNA molecule can contain an adenovirus VA1 minihelix domain to facilitate export of the Sec-RNA from the nucleus. It is also possible to express the Sec-RNA construct from a Pol-II promoter and terminate with an hGH poly-adenylation signal, such that the Sec-RNA can be capped and exported from the nucleus via the nuclear pore complex.

Once co-localized in the cytoplasm, the biologically active RNA and fusion protein must come together to form the RNA-protein complex. This binding event involves a specific, high affinity interaction that provides a homogenous population of stable complexes which is achieved by including a high affinity RNA binding domain in the fusion protein and a corresponding sequence specific recognition site in the nucleic acid comprising the biologically active RNA molecule. The RNA binding domain and the RNA recognition sequence interact in the cytoplasm of the bioreactor cell and couple the biologically active RNA sequence to the protein machinery required for secretion and delivery to target cells. The specificity of the interaction minimizes the secretion of other RNAs endogenous to the bioreactor cell and the high affinity helps maintain the complexes in the extracellular space.

RNA-Protein Complexes

As discussed, the invention provides a vector based RNA delivery system in which a plasmid converts a transfected cell into an RNA bioreactor capable of producing and secreting biologically active RNA molecules. The bioreactor plasmid has the capacity to encode and distribute any biologically active RNA molecule linked to the recognition sequence for the delivery fusion protein. Thus, the expression vectors of the invention comprise polynucleotide sequences encoding nucleic acid comprising one or more biologically active RNA sequences, an RNA recognition sequence, and optionally a terminal mini-helix sequence and/or polynucleotide sequences encoding a polypeptide comprising an RNA binding domain and one or more transport peptide sequences. The biologically active RNA molecules can exert a biological effect through a number of different mechanisms depending on the cellular components with which they interact. Most of the biologically active RNAs function through base pairing interactions with specific mRNA transcripts that lead to translational silencing or degradation of the mRNA molecule. Two related classes of inhibitory RNAs are antisense RNA molecules and small inhibitory RNA molecules. The antisense RNA is typically a direct complement of the mRNA transcript it targets and functions by presenting an obstacle to the translational machinery and also by targeting the transcript for degradation by cellular nucleases. The small inhibitory RNA (siRNA) molecules act through the post-transcriptional gene silencing (PTGS) pathway or through the RNA interference (RNAi) pathway. These RNAs are about 22 nucleotides in length and associate with specific cellular proteins to form RNA-induced silencing complexes (RISCs). These small RNAs are also complementary to sequences within their mRNA targets and binding of these complexes leads to translational silencing or degradation of the transcripts.

Two additional classes of RNA molecules that can modulate gene expression are the catalytic RNA ribozymes and the RNA aptamers. Ribozymes are RNA based enzymes that catalyze chemical reactions on RNA substrates, most often hydrolysis of the phosphodiester backbone. Formation of the catalytic active site requires base pairing between the ribozyme and the RNA substrate, so ribozyme activity can also be targeted to desired substrates by providing appropriate guide sequences. When targeted to mRNA transcripts, ribozymes have the potential to degrade those transcripts and lead to downregulation of the associated protein. RNA aptamers are typically selected from pools of random RNA sequences by their ability to interact with a target molecule, often a protein molecule. Engineering RNA aptamers is less straightforward as the binding is not defined by base pairing interactions, but once an effective sequence is found the specificity and affinity of the binding often rivals that of antibody-antigen interactions. RNA aptamers also have a greater range of target molecules and the potential to alter gene activity via a number of different mechanisms. This includes direct inhibition of the biological activity of the target molecule with no requirement for degradation of the protein or the mRNA transcript which produces it.

In certain embodiments of the invention, the one or more biologically active RNA sequences of the RNA-protein complex is selected from a ribozyme, antisense nucleic acid, allozyme, aptamer, short interfering RNA (siRNA), double-stranded RNA (dsRNA), micro-RNA (miRNA), short hairpin RNA (shRNA), and a transcript encoding one or more biologically active peptides, and any combination thereof. In one embodiment, one or more of the biologically active RNA sequences is a short hairpin RNA (shRNA). In another embodiment, one or more of the biologically active RNA sequences is an aptamer. With respect to biologically active RNAs that are a transcript encoding one or more biologically active peptides, exemplary peptides include those selected from a peptide encoded by a tumor suppressor gene, a pro-apoptotic factor, and an intrabody for a cancer system or a protein that restores gene function in a disease system resulting from loss of function or deletion mutations. The biologically active RNA sequence of the nucleic acid molecule can be directed to any target gene of interest. For example, the biologically active RNA can be directed to any gene found in any publicly available gene sequence database, including, for example, any of the databases found in the National Center for Biotech Information (NCBI). In one specific embodiment, the biologically active RNA sequence is a short hairpin RNA (shRNA). In another specific embodiment, the biologically active RNA is an aptamer. Non-limiting examples of suitable shRNA sequences include Mmp2, Vascular Endothelial Growth Factor (VEGF), Vascular Endothelial Growth Factor Receptor (VEGFR), Caveolin-1 (Cav-1), Epidermal Growth Factor Receptor (EGFR), Harvey—retrovirus associated DNA sequences (H-Ras), B-cell CCL/lymphoma 2 (Bc1-2), Survivin, Focal adhesion kinase (FAK), Signal transducer and activator of transcription 3 (STAT-3), Human epidermal growth-factor receptor 3 (HER-3), Beta-Catenin, and Src shRNA sequences, among others described herein and known in the art. Table I provides the nucleotide sequences of non-limiting exemplary biologically active RNA sequences. In certain embodiments, the biologically active RNA sequence comprises one or more sequences selected from any of SEQ ID NOs: 1-15.

The nucleic acid comprising a biologically active RNA sequence additionally comprises a recognition RNA sequence, which sequence is recognized by and specifically binds to an RNA binding domain located in a fusion protein of the invention. Numerous examples of specific, high affinity interactions between recognition RNA sequences (in RNA sequences) and RNA binding domains (in protein sequences) are known and described in the art. The recognition RNA sequence of the invention can be any RNA sequence described in the art known to bind an RNA binding domain of a polypeptide. In one embodiment, the recognition RNA sequence is at least about 10 nucleotides in length. In one embodiment, the recognition RNA sequence is from about 10 nucleotides to about 250 nucleotides. In certain specific embodiments, the recognition RNA sequence is, for example, about 10-15 nucleotides, about 16-20 nucleotides, about 21-25 nucleotides, about 26-30 nucleotides, about 31-35 nucleotides, about 36-40 nucleotides, about 41-45 nucleotides, about 46-50 nucleotides, about 51-75 nucleotides, about 76-100 nucleotides, about 101-125 nucleotides, about 126-150 nucleotides, about 151-175 nucleotides, about 176-200 nucleotides, or about 201-250 nucleotides. In one embodiment, the recognition RNA sequence has a dissociation constant ($K_d$) of at least about 100 nM. In a specific embodiment, the dissociation constant is from about 100 nM to about 1 pM, Non-limiting examples of specific, high affinity interactions between recognition RNA sequences (in RNA sequences) and RNA binding domains (in protein sequences) include U1 loop sequence with U1A sequence, Domain I or Domain IV of Group II intron sequence with CRS1 sequence, NRE stem loop sequence with nucleolin sequence, S1A stem loop sequence with hRBMY sequence, Bacteriophage BoxBR sequence with Bacteriophage Protein N, HIV Rev response element with HIV Rev protein, alfalfa mosaic virus coat protein recognition sequence (AMVCP) with AMVCP protein, and ARE stem loop sequence with tristetrapolin sequence, among others. In certain specific embodiments, the recognition RNA sequence of the nucleic acid comprises a sequence selected from a U1 loop, Group II intron, NRE stem loop, S1A stem loop, Bacteriophage BoxBR, HIV Rev response element, alfalfa mosaic virus coat protein recognition sequence (AMVCP), and ARE sequence. Table II provides the nucleotide sequences of non-limiting exemplary recognition RNA sequences. In certain specific embodiments, the recognition RNA sequence comprises the sequence of any of SEQ ID NOs: 16-23.

In certain embodiments, the nucleic acid molecule comprises one or more biologically active RNA sequences, a recognition RNA sequence, and a terminal minihelix sequence. Terminal minihelix sequences are short sequences of about 17 nucleotides that anneal the 5' and 3' ends of the RNA molecule. This sequence has been shown to facilitate nuclear export of RNA molecules derived from Pol-III promoters and may help drive formation of the RNA—fusion protein complexes in the BioReactor cells. Examples of suitable terminal minihelix sequences are described herein and otherwise known in the art. In one embodiment, the terminal minihelix sequence is at least about 17 nucleotides in length. In a specific embodiment, the terminal minihelix sequence is from about 10 nucleotides to about 100 nucleotides in length. In one embodiment, the terminal minihelix sequence is from the adenovirus VA1 RNA molecule.

In addition, the expression vectors of the invention can comprise one or more polynucleotide sequences encoding polypeptides comprising one or more biologically active RNA sequences targeted to Dicer and/or Drosha. None of the sequences of these embodiments contain an RNA recognition sequence. Such polypeptides are useful when one or more of the biologically active RNA sequences is a short interfering RNA (siRNA), double-stranded RNA (dsRNA), micro-RNA (miRNA), and short hairpin RNA (shRNA).

In any of the above-described nucleic acid molecules, the nucleic acid molecule can comprise a sequence wherein the recognition RNA sequence, the individual biologically active RNA sequences, and the optional terminal minihelix sequence are joined directly without the addition of intervening or additional sequences. Alternatively, in any of the above-described nucleic acid molecules, the nucleic acid molecule can comprise a sequence wherein one or more of the sequences comprising the recognition RNA sequence, the individual biologically active RNA sequences, and the optional terminal minihelix sequence are joined with the addition of one or more intervening or additional sequences. Likewise, in any of the above-described nucleic acid molecules, the nucleic acid molecule can comprise a sequence wherein the individual biologically active RNA sequences themselves are joined directly without the addition of one or more intervening or additional sequences or are joined with the addition of one or more intervening or additional sequences.

The ability of the BioReactor cell to secrete and deliver biologically active RNA molecules to neighboring cells derives from the properties of the RNA-protein complex produced from the pBioR plasmid or plasmids. First, the fusion proteins (comprising an RNA binding domain and optionally other sequences) bind to the biologically active RNAs (via the RNA recognition sequence) and are secreted from the bioreactor cell. In the extracellular matrix, the RNA-protein complex remains intact long enough to reach the target cells. Once at the surface of the target cell, the fusion protein facilitates import of the biologically active RNA to the cytoplasm of the target cell.

The secretion of the RNA-protein complex is optimized by efficient binding of the Sec-RNA by the RNA binding domain of the fusion protein. To drive formation of fusion protein—Sec-RNA complexes, the fusion proteins contain high affinity RNA binding domains of viral or bacterial origin. The utilization of non-native high affinity interaction improves the chances of obtaining a homogenous population of stable complexes with minimal competition from non-specific binding of RNA molecules endogenous to the bioreactor cell.

Thus, in one embodiment, the fusion protein comprises an RNA binding domain and one or more transport peptides. The RNA binding domain of the novel fusion protein can be any amino acid sequence capable of recognizing a corresponding RNA recognition motif. In one embodiment, the RNA binding domain is from about 25 amino acids to about 300 amino acids. In certain specific embodiments, the RNA binding domain is, for example, about 25-49 amino acids, about 50-75 amino acids, about 76-100 amino acids, about 101-125 amino acids, about 126-150 amino acids, about 151-175 amino acids, about 176-200 amino acids, about 201-225 amino acids, about 226-250 amino acids, about 251-275 amino acids, or about 276-300 amino acids. The RNA binding domain of the fusion polypeptide can be any RNA binding domain known and described in the art. In certain specific embodiments, the RNA binding domain of the fusion polypeptide comprises an amino acid sequence selected from a U1A, CRS1, CRM1, Nucleolin RBD12, hRBMY, Bacteriophage Protein N, HIV Rev, alfalfa mosaic virus coat protein (AMVCP), and tristetrapolin amino acid sequence. The amino acid sequences of non-limiting examples of RNA binding domain sequences are shown in Table III. In certain specific embodiments, the RNA binding domain comprises a sequence selected from any of SEQ ID NOs: 24-31.

Another component of the fusion protein is the domain that facilitates secretion of the RNA-protein complex. Proteins that follow the non-classical secretory pathway lack the typical secretory signal that directs the classical export mechanism, are excluded from the ER-Golgi network and can be secreted in the presence of drugs that inhibit ER-Golgi transport. Several mechanisms have been proposed for the non-classical secretion pathway, including membrane blebbing, vesicular and non-vesicular non-classical transport, active and passive membrane transporters and membrane flip-flop. Peptide sequences from proteins that access secretion pathways independent from those of the ER-Golgi network are useful in the secretion of the biologically active RNA molecules of the invention. Another group of sequences useful for facilitating secretion of the RNA-protein complexes are the cell penetrating peptides. The precise mechanism of entry for these peptides is not fully known, but may involve the endosomal pathway, although some data suggests non-endosomal mechanisms.

The transport peptide of the fusion polypeptide can be any amino acid sequence that facilitates the delivery of nucleic acids, peptides, fusion proteins, RNA-protein complexes, and/or other biological molecules to the extracellular matrix and/or to neighboring cells and tissues. One example of a transport peptide is a cell penetrating peptide which facilitates import of the Sec-RNA into the target cell. There are numerous cell penetrating peptides known in the art which peptide sequences are able to cross the plasma membrane. Such peptides are often present in transcription factors, such as the homeodomain proteins and viral proteins, such as TAT of HIV-1. Delivery of RNA-protein complexes to the cytoplasm of cells via cell penetrating peptides has been established experimentally. For example, delivery of siRNAs to CHO cells with a purified fusion protein consisting of the U1A RNA binding domain and the TAT cell penetrating peptide has been reported. Additional reports utilizing a biotin-streptavidin linkage also show successful delivery of various cargo molecules via the TAT peptide. Although TAT mediated delivery of cargo molecules to the cytoplasm of target cells does not appear to require an additional fusogenic peptide to facilitate endosomal release, the addition of such a peptide to TAT can improve the efficiency of delivery. The necessity of fusogenic peptides as part of the delivery system may depend on the identity of the cell penetrating peptide used in the fusion protein.

Thus, in one embodiment, the transport protein is a cell penetrating peptide. Typically such sequences are polycationic or amphiphilic sequences rich in amino acids with positively charged side groups, i.e., basic amino acids such as histidine, lysine, and arginine. Numerous examples of cell penetrating peptides are known and described in the art. Non-limiting examples of suitable cell penetrating peptides include those derived from protein membrane transduction domains which are present in transcription factors, such as the homeodomain proteins, and viral proteins, such as TAT of HIV-1. In one embodiment, the cell penetrating peptide is from about 10 amino acids to about 50 amino acids, including for example, about 10-15 amino acids, about 16-20 amino acids, about 21-25 amino acids, about 26-30 amino acids, about 31-35 amino acids, about 36-40 amino acids, about 41-45 amino acids, and about 46-50 amino acids. In certain specific embodiments, the cell penetrating peptide of the polypeptide comprises an amino acid sequence selected from a penetratin, transportan, MAP, HIV TAT, Antp, Rev, FHV coat protein, TP10, and pVEC amino acid sequence. The amino acid sequences of non-limiting examples of cell penetrating peptide sequences are shown in Table IV. In certain specific embodiments, the cell penetrating peptide comprises a sequence selected from any of SEQ ID NOs: 32-40.

Another example of a transport peptide is a non-classical secretory domain. The non-classical secretory domain can be any amino acid sequence that directs a peptide and/or other biological molecule to be secreted from a cell via a pathway other than the classical pathway(s) of protein secretion. The biological molecule can be secreted into the extracellular matrix and/or can be delivered to surrounding cells and tissues. Numerous examples of non-classical secretory domains are known and described in the art. In one embodiment, the non-classical secretory domain is from about 50 amino acids to about 250 amino acids. In certain specific embodiments, the non-classical secretory domain is, for example, about 50-75 amino acids, about 76-100 amino acids, about 101-125 amino acids, about 126-150 amino acids, about 151-175 amino acids, about 176-200 amino acids, about 201-225 amino acids, or about 226-250 amino acids. In certain specific embodiments, the non-classical secretory domain comprises an amino acid sequence selected from Galcetin-1 peptide, Galectin-3 peptide, IL-1α, IL-1β, HASPB, HMGB1, FGF-1, FGF-2, IL-2 signal, secretory transglutaminase, annexin-1, HIV TAT, Herpes VP22, thioredoxin, Rhodanese, and plasminogen activator signal amino acid sequences. Non-limiting examples of non-classical secretory domain sequences are shown in Table V. In certain specific embodiments, the non-classical secretory domain comprises a sequence selected from any of SEQ ID NOs: 41-48.

Other examples of suitable transport peptides include, but are not limited to sequences derived from a receptor binding domain, a fusogenic peptide, and an endosomal release domain. In one embodiment, the transport peptide comprises a sequence derived from a receptor binding domain. The receptor binding domain can be any amino acid sequence that specifically binds to a surface receptor complex on the extracellular side the target cell membrane. In certain specific embodiments, the receptor binding domain comprises an amino acid sequence selected from the EGF protein, the VEGF protein, the vascular homing peptide, the gp30 protein (or other Erb B-2 binding protein), or the galectin-1 protein (or other CA125 binding protein).

In another embodiment, the transport peptide comprises a sequence derived from an endosomal release domain. The endosomal release domain can be any amino acid sequence that faciliatates release of the RNA—protein complex from the endosomal compartment of the target cell. In certain specific embodiments, the endosomal release domain comprises an amino acid sequence selected from the Hemagglutanin protein from influenza, the E1 protein from Semliki Forrest Virus, or a polyhistidine motif.

In another embodiment, the transport peptide comprises a sequence derived from fusogenic peptide. Table VI provides non-limiting examples of suitable fusogenic peptides. Thus, in certain specific embodiments, the fusogenic peptide comprises a sequence selected from any of SEQ ID NOs: 50-54.

In any of the above-described embodiments of the fusion protein polypeptide, the polypeptide can comprise a sequence or sequences wherein the individual domains and peptides are joined directly without the addition of one or more linker, spacer, or other sequences. In another embodiment, the polypeptide can comprise a sequence or sequences wherein the individual domains and peptides are joined with the addition of one or more linker, spacer, and/or other sequences.

Thus, in certain specific embodiments of the expression vectors of the invention, the biologically active RNA sequence(s) is selected from a ribozyme, antisense nucleic acid, allozyme, aptamer, short interfering RNA (siRNA), double-stranded RNA (dsRNA), micro-RNA (miRNA), short hairpin RNA (shRNA), and a transcript encoding one or more biologically active peptides. The recognition RNA sequence is selected from a U1 loop, Group II intron, NRE stem loop, S1A stem loop, Bacteriophage BoxBR, HIV Rev response element, AMVCP recognition sequence, and ARE sequence. The RNA binding domain comprises an amino acid sequence derived from a U1A, CRS1, CRM1, Nucleolin RBD12, hRBMY, Bacteriopage Protein N, HIV Rev, AMVCP, and tristetrapolin amino acid sequence. The transport peptide is selected from a cell penetrating peptide, a non-classical secretory domain, a receptor binding domain, a fusogenic peptide, and an endosomal release domain. Suitable cell penetrating peptide sequences include, but are not limited to, those peptides having amino acid sequences derived from a penetratin, transportan, MAP, HIV TAT, Antp, Rev, FHV coat protein, TP10, and pVEC amino acid sequence. Suitable non-classical secretory domain sequences include, but are not limited to, peptides having amino acid sequence derived from Galcetin-1 peptide, Galectin-3 peptide, IL-1α, IL-1β, HASPB, HMGB1, FGF-1, FGF-2, IL-2 signal, secretory transglutaminase, annexin-1, HIV TAT, Herpes VP22, thioredoxin, Rhodanese, and plasminogen activator signal amino acid sequences. Suitable fusogenic peptide sequences include, but are not limited to, peptides having amino acid sequence derived from HA from influenza, Gp41 from HIV, Melittin, GALA, and KALA.

In any of the embodiments described herein of the RNA-protein complex, the nucleic acid molecule can comprise a sequence wherein the recognition RNA sequence, the individual biologically active RNA sequences, and the optional terminal minihelix sequence are joined directly without the addition of one or more intervening or additional sequences. Alternatively, in any of the above-described embodiments of the RNA-protein complex, the nucleic acid molecule can comprise a sequence wherein the recognition RNA sequence, the individual biologically active RNA sequences, and the optional terminal minihelix sequence are joined with the addition of one or more intervening or additional sequences. In any of the above-described embodiments of the RNA-protein complex, the nucleic acid molecule can comprise a sequence wherein the individual biologically active RNA sequences themselves are joined with or without the addition of one or more intervening or additional sequences. In any of the above-described embodiments of the RNA-protein complex, the polypeptide portion of the RNA-protein complex can comprise a sequence or sequences wherein any of the individual domains and peptides are joined with or without the addition of linker, spacer, and/or other sequences.

Expression Vectors

In one embodiment, the expression vector comprises a first expression cassette comprising polynucleotide sequence that encodes an RNA molecule comprising one or more biologically active RNA sequences, a recognition RNA site for an RNA binding domain (Sec-RNA), and optionally a mini-terminal helix sequence. The expression vector further comprises a second expression cassette comprising polynucleotide sequence that encodes a fusion protein comprising an RNA binding domain and one or more transport peptides that facilitate secretion of the RNA-protein complex and delivery of the biologically active RNA to the extracellular matrix or to target cells. In a further embodiment, the expression vector additionally comprises a third expression cassette, wherein the third expression cassette comprises one or more polynucleotide sequences encoding one or more viral polymerases and one or more viral accessory proteins necessary for viral replication. Optionally, the expression vector can additionally comprise a fourth expression cassette, or a separate expression vector can comprise an expression cassette, which comprises polynucleotide sequence encoding one or more biologically active RNAs, optionally a recognition RNA sequence, and optionally a terminal minihelix sequence. In one embodiment, the one or more biologically active RNA sequences of the fourth expression cassette are directed to a target gene, which may or may not be the same target gene targeted by the biologically active RNA sequence(s) of the first expression cassette. In another embodiment, the one or more biologically active RNA sequences of the fourth expression cassette are directed to the Dicer protein and/or the Drosha protein within the bioreactor cell. This cassette does not contain a recognition RNA sequence for the RNA binding domain and therefore is not secreted from the bioreactor cell.

In one embodiment, the first and second expression cassettes are combined by placing the Sec-RNA sequence into artificial introns within the RNA encoding the fusion protein. This vector offers the advantages of reducing the overall plasmid size and places the transcription of all BioReactor components under the control of a single promoter. Upon administration of the expression vector to a cell, the RNA-protein complex can be expressed from the vector as a single RNA transcript or as one or more RNA transcripts. For example, the RNA-protein complex can be expressed from the vector as a single transcript comprising the RNA portion of the RNA-protein complex (comprising one or more biologically active RNA sequences, a recognition RNA sequence, and optionally a terminal minihelix sequence) and the protein portion of the RNA-complex (comprising an RNA binding domain and one or more transport peptide sequences selected from, for example, a cell-penetrating peptide, a non-classical secretory domain, an endosomal release domain, fusogenic peptide and a receptor binding domain). The Sec-RNA is encoded within an artificial intron placed in either the 5' untranslated region (UTR) or within the coding sequence for the fusion protein. The Sec-RNA sequence is subcloned between the splice donor and splice acceptor sites of the artificial intron using appropriate restriction sites. After transcription, the Sec-RNA is released from the mRNA encoding the fusion protein by the splicing machinery endogenous to the bioreactor cell. The separate transcripts are exported from the cell nucleus to the cell cytoplasm, where the transcript comprising the RNA binding domain sequence and optional other sequence(s) are translated. The RNA binding domain of the translated peptide interacts with the recognition RNA sequence of the RNA, forming the RNA-protein complex.

In other embodiments, the first and second expression cassettes, and optional third and fourth expression cassettes additionally comprise one or more sequences selected from a promoter sequence, a sequence comprising on or more restriction enzyme sites, a primer sequence, GC base pair sequence, initiation codon, translational start site, and a termination sequence. Suitable promoters include Pol II promoters, including but not limited to, Simian Virus 40 (SV40), Cytomegalovirus (CMV), β-actin, human albumin, human HIF-α, human gelsolin, human CA-125, ubiquitin, and PSA promoters. In another embodiment, the promoter is a Pol III promoter. Non-limiting examples of suitable Pol III promoters include, but are not limited to, human H1 and human U6 promoters. In another embodiment, the cassette additionally comprises one or more termination sequences. Non-limiting examples of suitable termination sequences include, but are not limited to, a human growth hormone (hGH) polyadenylation sequence, a bovine growth hormone (BGH) polyadenylation sequence, a Simian Virus 40 (SV40) large T polyadenylation sequence, and a Herpes Simplex Virus Thymidine Kinase (HSV-tk) polyadenylation sequence. In one embodiment, the expression cassettes additionally comprises one or more primer sequences, which may contain restriction enzyme sites, one or more promoter sequences, and one or more termination sequences.

In any of the above-described embodiments of the expression vector, the polynucleotide can comprise sequence wherein any of the biologically active RNA sequences, recognition RNA sequence, RNA binding domain sequence, transport peptide sequence, viral polypeptides, and any other included sequences (i.e., promoter, termination sequence, primer, etc.) are joined with the addition of one or more intervening or additional sequences or are joined directly without the addition of intervening sequences. In any of the above-described embodiments, the expression vector can comprise a polynucleotide that encodes a polypeptide wherein the sequence or sequences of the individual domains and peptides are joined without or with the addition of one or more linker, spacer, or other sequences.

In a further embodiments, the expression vector additionally comprises one or more multiple cloning site sequences. Also, the expression vector can additionally comprise one or more drug resistance gene sequences. Examples of suitable drug resistant genes include, but are not limited to, kanamycin, ampicillin, puromycin, tetracycline, and chloramphenicol resistant genes, as well as any other drug resistant genes known and described in the art. The expression vector can additionally comprise a pUC origin of replication.

Expression cassettes for the protein or RNA components of the bioreactor plasmid are prepared by PCR amplification of the relevant sequences from cDNA clones or RNA expressing plasmids, respectively, using the appropriate forward and reverse primers. Primers include sequences complementary to the domain of interest or biologically active RNA sequence, sites for restriction enzymes used in subcloning and about six GC base pairs at the 5' end of each primer to facilitate digestion with restriction enzymes. The recognition RNA sequence is added to the primer corresponding to the 5' end of the biologically active RNA sequence in order to generate the Sec-RNA expression construct. This expression construct is digested with appropriate restriction enzymes for subcloning into the pEGEN4.1 construct, which places the Sec-RNA expression cassette downstream from a human U6 promoter sequence and upstream of a Pol III poly-T termination sequence. Alternatively, the Sec-RNA expression cassette can be subcloned into pEGEN3.1, which places RNA expression under the control of the CMV Pol-II promoter and terminates with a human GH poly-adenylation signal.

Several exemplary expression vectors are shown in FIGS. 5-13. One exemplary expression vector is pEGEN 1.1 shown in FIG. 5. As shown, pEGEN 1.1 comprises an SV40 promoter sequence (1), an intronic sequence (2), a multiple cloning sequence (MCS), a human growth hormone poly-A tail sequence (4), a kanamycin resistance gene (7) and a pUC origin of replication (8). DNA fragments encoding for Sec-RNA molecules or fusion proteins are prepared by PCR with primers including restriction sites for subcloning into the multiple cloning sequence. PCR products and the pEGEN1.1 plasmid are digested with the appropriate restriction enzymes and purified prior to ligation. Sec-RNA molecules or mRNAs encoding fusion proteins are transcribed from the SV40 promoter sequence with an artificial intron and polyA tail sequence.

Another exemplary expression vector is pEGEN 2.1 shown in FIG. 6. As shown, pEGEN 2.1 comprises a chicken β-actin promoter sequence (1), an intronic sequence (2), a multiple cloning sequence (MCS), a human growth hormone poly-A tail sequence (4), a kanamycin resistance gene (7) and a pUC origin of replication (8). DNA fragments encoding for Sec-RNA molecules or fusion proteins are prepared by PCR with primers including restriction sites for subcloning into the multiple cloning sequence. PCR products and the pEGEN2.1 plasmid are digested with the appropriate restriction enzymes and purified prior to ligation. Sec-RNA molecules or mRNAs encoding fusion proteins are transcribed from the chicken-actin promoter sequence with an artificial intron and polyA tail sequence.

Another exemplary expression vector is pEGEN 3.1 shown in FIG. 7. As shown, pEGEN 3.1 comprises a CMV promoter sequence (1), an intronic sequence (2), a multiple cloning sequence (MCS), a human growth hormone poly-A tail sequence (4), a kanamycin resistance gene (7) and a pUC origin of replication (8). DNA fragments encoding for Sec-RNA molecules or fusion proteins are prepared by PCR with primers including restriction sites for subcloning into the multiple cloning sequence. PCR products and the pEGEN3.1 plasmid are digested with the appropriate restriction enzymes and purified prior to ligation. Sec-RNA molecules or mRNAs encoding fusion proteins are transcribed from the CMV promoter sequence with an artificial intron and polyA tail sequence.

Another exemplary expression vector is pEGEN 4.1 shown in FIG. 8. As shown, pEGEN 4.1 comprises a human U6 promoter sequence (1), a multiple cloning sequence (MCS), a polyT terminator sequence (4), a kanamycin resistance gene (7) and a pUC origin of replication (8). DNA fragments encoding for Sec-RNA molecules are prepared by PCR with primers including restriction sites for subcloning into the multiple cloning sequence. PCR products and the pEGEN4.1 plasmid are digested with the appropriate restriction enzymes and purified prior to ligation. Sec-RNA molecules are transcribed from the U6 promoter sequence and terminate with the polyT terminator sequence.

Another exemplary expression vector is pBioR Pol II (shown in FIG. 9) which encodes an exemplary RNA-protein complex of the invention. The vector comprises an SV40 promoter (1) upstream of an Sec-RNA sequence (3) and a downstream hGH polyA sequence (4). The vector also comprises a β-actin promoter (5) upstream of a fusion protein sequence (6) and a downstream hGH polyA sequence (4). The vector also comprises a kanamycin resistance gene (7) and a pUC origin of replication (8).

Another exemplary expression vector is pBioR Pol III shown in FIG. 10 which encodes an exemplary RNA-protein complex of the invention. The vector comprises an hU6 promoter upstream (1) of an Sec-RNA sequence (3) and a downstream Pol-III poly-T terminator sequence (4). The vector also comprises a β-actin promoter (5) upstream of a fusion protein sequence (6) and a downstream hGH polyA sequence (4). The vector also comprises a kanamycin resistance gene (7) and a pUC origin of replication (8).

Another exemplary expression vector is pBioR Pol II combo shown in FIG. 11 which encodes an exemplary RNA-protein complex of the invention. The vector comprises a β-actin promoter (1), an intronic sequence (2), a fusion protein (6), a Sec-RNA (3) with flanking introns (2) internal to the fusion protein, a human growth hormone poly-A tail sequence (4), a kanamycin resistance gene (7) and a pUC origin of replication (8). In this expression vector, the Sec-RNA is encoded within an artificial intron placed within the mRNA sequence encoding the fusion protein. DNA fragments encoding for Sec-RNA molecules or fusion proteins are prepared by PCR. DNA fragments encoding for Sec-RNA molecules are prepared with primers including splice donor and acceptor sites and restriction sites for subcloning into a unique restriction site within the fusion protein sequence. DNA fragments encoding for the fusion protein are prepared with primers including restriction sites for subcloning into the plasmids described above. After transcription, the Sec-RNA is released from the mRNA encoding the fusion protein by the splicing machinery endogenous to the bioreactor cell.

Another exemplary expression vector is pBioR Pol II stable shown in FIG. 12 which encodes an exemplary RNA-protein complex of the invention. The vector comprises a CTS regulator (9), a PGK promoter (1), a puromycin resistance gene (10), a chicken β-actin promoter (5), a fusion protein (6), a Sec-RNA (3) with flanking introns (2) internal to the fusion protein, a human growth hormone poly-A tail sequence (4), a kanamycin resistance gene (7) and a pUC origin of replication (8). Sec-RNA sequences can be selected from Tables I and II; fusion protein sequences can be selected from Tables III, IV and V.

Another exemplary expression vector is pBioR Pol II dicer shown in FIG. 13 which encodes an exemplary RNA-protein complex of the invention. The vector comprises a SV40 promoter (1), an intronic sequence (2), a biologically active RNA sequence and a recognition RNA sequence (3), a hGH poly-A tail sequence (4), a chicken-actin promoter (5), a fusion protein (6), a Sec-RNA (3) with flanking introns (2) internal to the fusion protein, a human growth hormone poly-A tail sequence (4), a kanamycin resistance gene (7) and a pUC origin of replication (8). Sec-RNA sequences can be selected from Tables I and II; fusion protein sequences can be selected from Tables III, IV and V.

In other embodiments, the expression vector comprises a first polynucleotide sequence that encodes a nucleic acid molecule comprising one or more biologically active RNA sequences, a recognition RNA sequence, and optionally a terminal minihelix sequence and a second polynucleotide sequence that encodes a polypeptide comprising an RNA binding domain, and one or more transport peptide sequences. In another embodiment, the expression vector further comprises a third polynucleotide that encodes a nucleic acid molecule comprising one or more biologically active RNA sequences, optionally a recognition RNA sequence, and optionally a terminal minihelix sequence. In one embodiment, the biologically active RNAs of the first polynucleotide and the third polynucleotide are targeted to one or more target genes of interest. In another embodiment, the biologically active RNA of the first polynucleotide is selected from a short interfering RNA (siRNA), double-stranded RNA (dsRNA), micro-RNA (miRNA), and short hairpin RNA (shRNA) targeted to one or more target genes of interest and the biologically active RNA of the third polynucleotide is targeted to Dicer and/or Drosha.

In a further embodiment, the expression vector additionally comprises a first promoter sequence, a termination sequence, and optionally one or more primers sequences, a second promoter sequence, a polyA addition sequence, and optionally one or more primers sequences, wherein the first polynucleotide encoding the one or more biologically active RNA sequences, the recognition RNA sequence, and the optional terminal minihelix sequence is operably linked to the first promoter sequence and the termination sequence and wherein the second polynucleotide encoding the RNA binding domain sequence and the transport peptide sequence is operably linked to the second promoter sequence and the polyA addition sequence. In addition, the vector can additionally comprises one or more promoter sequences, one or more termination sequences, and optionally one or more primers sequences, wherein the third polynucleotide sequence(s) encoding the nucleic acid comprising one or more biologically active RNA sequences, optionally a recognition RNA sequence, and optionally a terminal minihelix sequence is operably linked to the one or more promoter sequences and the one or more termination sequences.

In another embodiment, the expression vector further comprises one or more polynucleotide sequences encoding one or more viral polymerases and one or more viral accessory proteins necessary for viral replication. In a further embodiment, the vector additionally comprises one or more promoter sequences, one or more polyA addition sequences, and optionally one or more primers sequences, wherein the polynucleotide sequence(s) encoding the viral polymerase(s) and the viral accessory protein(s) is operably linked to the one or more promoter sequences and the one or more polyA addition sequences.

In one embodiment, the invention provides an expression vector comprising a polynucleotide that encodes a nucleic acid molecule comprising one or more biologically active RNA sequences, a recognition RNA sequence, and an optional terminal minihelix sequence. In one embodiment, the expression vector comprises a polynucleotide that encodes a nucleic acid molecule comprising one or more biologically active RNA sequences and one or more polynucleotide sequences encoding one or more viral polymerases and one or more viral accessory proteins necessary for viral replication.

The invention also provides an expression vector comprising a polynucleotide that encodes a polypeptide comprising an RNA binding domain and one or more transport peptides.

Thus, the invention provides a first expression vector comprising a polynucleotide that encodes a nucleic acid molecule comprising one or more biologically active RNA sequences, a recognition RNA sequence and optionally a terminal minihelix sequence and a second expression vector comprising a polynucleotide that encodes a polypeptide comprising an RNA binding domain and one or more transport peptides, for example, a peptide selected from a cell penetrating peptide, a non-classical secretory domain, a receptor binding domain, a fusogenic peptide, and an endosomal release domain.

In any of the expression vectors of the invention, one or more of the sequences comprising the recognition RNA sequence, the individual biologically active RNA sequences, the optional terminal minihelix sequence, the RNA binding domain, and the transport peptide(s), as well as any other sequences, including viral sequences, promoters, primers, termination sequences, and polyA sequences are joined directly without the addition of one or more intervening or additional sequences. Alternatively, one or more of the sequences comprising the recognition RNA sequence, the individual biologically active RNA sequences, the optional terminal minihelix sequence, the RNA binding domain, and the transport peptide(s), as well as any other sequences, including viral sequences, promoters, primers, termination sequences, and polyA sequences are joined with the addition of one or more intervening or additional sequences. In any of the above-described embodiments, the individual biologically active RNA sequences themselves are joined directly without any intervening or additional sequences or are joined with the addition of one or more intervening or additional sequences. In any of the above-described embodiments, the recognition RNA sequence and any of the biologically active RNAs are joined directly without the addition of one or more linker, spacer, or other sequences or are joined with the addition of one or more linker, spacer, and/or other sequences. In any of the above-described embodiments, the RNA binding domain and any of the individual transport peptides are joined directly without the addition of one or more linker, spacer, or other sequences or are joined with the addition of one or more linker, spacer, and/or other sequences.

In certain embodiments of the described expression vectors, the biologically active RNA sequence is selected from a ribozyme, antisense nucleic acid, allozyme, aptamer, short interfering RNA (siRNA), double-stranded RNA (dsRNA), micro-RNA (miRNA), short hairpin RNA (shRNA), and a transcript encoding one or more biologically active peptides. In one specific embodiment, the biologically active RNA sequence is a short hairpin RNA (shRNA). In another specific embodiment, the biologically active RNA sequence is an aptamer. In certain embodiments, the recognition RNA sequence is selected from a U1 loop, Group II intron, NRE stem loop, S1A stem loop, Bacteriophage BoxBR, HIV Rev response element, AMVCP recognition sequence, and ARE sequence. In one embodiment, the terminal minihelix sequence is from the adenovirus VA1 RNA molecule. In certain embodiments, the RNA binding domain is selected from a U1A, CRS1, CRM1, Nucleolin RBD12, hRBMY, Bacteriophage Protein N, HIV Rev, alfalfa mosaic virus coat protein (AMVCP), and tristetrapolin amino acid sequence. In certain embodiments, the one or more transport peptides is selected from a cell penetrating peptide, a non-classical secretory domain, a receptor binding domain, a fusogenic peptide, and an endosomal release domain, as well as any combinations thereof. In one specific embodiment, the transport peptide is a cell penetrating peptide. In certain specific embodiments, the cell penetrating peptide is selected from a penetratin, transportan, MAP, HIV TAT, Antp, Rev, FHV coat protein, TP10, and pVEC sequence. In another specific embodiment, the transport peptide is a non-classical secretory domain. In certain specific embodiments, the non-classical secretory domain is selected from a Galcetin-1 peptide, Galectin-3 peptide, IL-1α, IL-1β, HASPB, HMGB1, FGF-1, FGF-2, IL-2 signal, secretory transglutaminase, annexin-1, HIV TAT, Herpes VP22, thioredoxin, Rhodanese, and plasminogen activator signal sequence. In one specific embodiment, the transport peptides are a cell penetrating peptide, and one or more transport peptides selected from a non-classical secretory domain, a receptor binding domain, a fusogenic peptide, and an endosomal release domain. In one specific embodiment, the transport peptides are a cell penetrating peptide, and a non-classical secretory domain. In certain embodiments, the viral non-structural and structural genes (viral polymerases, accessory proteins, coat proteins, and fusogenic proteins) are selected from DNA viruses and RNA viruses, including, but not limited to, Adenovirus, Adeno-Associated Virus, Herpes Simplex Virus Lentivirus, Retrovirus, Sindbis virus, and Foamy virus.

In addition the present invention provides expression vectors constructed from a replication competent or replication incompetent viral particles which carry and distribute one or more biologically active RNA molecules from a transformed packaging cell. In one embodiment, the invention provides a viral vector comprising a partial viral genome and a second viral vector comprising a partial viral genome and a polynucleotide that encodes any of the nucleic acid molecules described herein. In one embodiment, the invention provides a viral vector comprising a polynucleotide that encodes a nucleic acid molecule comprising one or more biologically active RNA sequences, a recognition RNA sequence, and optionally a terminal minihelix sequence and a polynucleotide that encodes a polypeptide comprising one or more fusion proteins, ie. RNA binding domain and one or more transport peptides. The biologically active RNA sequence can be any of the biologically active RNA sequences described herein and otherwise known in the art. In one embodiment, the viral vector comprises a polynucleotide encoding a nucleic acid molecule wherein the biologically active RNA sequence is selected from a ribozyme, antisense nucleic acid, allozyme, aptamer, short interfering RNA (siRNA), double-stranded RNA (dsRNA), micro-RNA (miRNA), short hairpin RNA (shRNA), and a transcript encoding one or more biologically active peptides. In one specific embodiment, the viral vector comprises a polynucleotide encoding a nucleic acid molecule wherein the biologically active RNA sequence is a short hairpin RNA (shRNA). In one specific embodiment, the viral vector comprises a polynucleotide encoding a nucleic acid molecule wherein the biologically active RNA sequence is an aptamer. The recognition RNA sequence can be any of the recognition RNA sequences described herein and otherwise known in the art. In one embodiment, viral vector vector comprises a polynucleotide encoding a nucleic acid molecule wherein the recognition RNA sequence is selected from a U1 loop, Group II intron, NRE stem loop, S1A stem loop, Bacteriophage BoxBR, HIV Rev response element, AMVCP recognition sequence, and ARE sequence. The terminal minihelix sequence can be any of the terminal minimhelix sequences described herein and otherwise known in the art. The invention also provides an expression vector comprising a polynucleotide that encodes a polypeptide comprising an RNA binding domain and one or more transport peptides. In certain embodiments, the RNA binding domain is selected from a U1A, CRS1, CRM1, Nucleolin RBD12, hRBMY, Bacteriophage Protein N, HIV Rev, alfalfa mosaic virus coat protein (AMVCP), and tristetrapolin amino acid sequence. In certain embodiments, the one or more transport peptides is selected from a cell penetrating peptide, a non-classical secretory domain, a receptor binding domain, a fusogenic peptide, and an endosomal release domain, as well as any combinations thereof. In one embodiment, the invention provides an expression vector comprising a polynucleotide that encodes a polypeptide comprising an RNA binding domain and a cell penetrating peptide. In certain specific embodiments, the cell penetrating peptide is selected from a penetratin, transportan, MAP, HIV TAT, Antp, Rev, FHV coat protein, TP10, and pVEC sequence. In another embodiment, the invention provides an expression vector comprising a polynucleotide that encodes a polypeptide comprising an RNA binding domain and a non-classical secretory domain. In certain specific embodiments, the non-classical secretory domain is selected from a Galcetin-1 peptide, Galectin-3 peptide, IL-1α, IL-1β, HASPB, HMGB1, FGF-1, FGF-2, IL-2 signal, secretory transglutaminase, annexin-1, HIV TAT, Herpes VP22, thioredoxin, Rhodanese, and plasminogen activator signal sequence. In one embodiment, the invention provides an expression vector comprising a polynucleotide that encodes a polypeptide comprising an RNA binding domain, a cell penetrating peptide, and one or more transport peptides selected from a non-classical secretory domain, a receptor binding domain, a fusogenic peptide, and an endosomal release domain. In one embodiment, the invention provides an expression vector comprising a polynucleotide that encodes a polypeptide comprising an RNA binding domain, a cell penetrating peptide, and a non-classical secretory domain.

In another embodiment, the viral vector additionally comprises a polynucleotide that encodes a partial viral genome and a nucleic acid molecule comprising one or more biologically active RNA sequences targeted to Dicer and/or Drosha. None of these polynucleotides encode an RNA binding domain. In one embodiment, the polynucleotide encodes a nucleic acid molecule comprising a single biologically active RNA sequence. In another embodiment, the polynucleotide encodes a nucleic acid molecule comprising two or more biologically active RNA sequences. In certain embodiments, the biologically active RNA sequence is selected from a ribozyme, antisense nucleic acid, allozyme, aptamer, short interfering RNA (siRNA), double-stranded RNA (dsRNA), micro-RNA (miRNA), short hairpin RNA (shRNA), and a transcript encoding one or more biologically active peptides.

Bioreactor Cells

BioReactor cells are generated by transfecting an expression vector of the invention, for example a pBioR plasmid or plasmids, into a recipient cell line in vitro. Any cell type can serve as a recipient cell for the expression vector(s), including any of the pBioR plasmids. The source of the potential BioReactor cell can vary depending on the identity of domains used in the fusion protein and the identity of the cells being targeted for gene knockdown. BioReactors are capable of producing the fusion protein, producing the Sec-RNA, binding of the Sec-RNA by the fusion protein and secretion of the RNA-protein complex. Production of the fusion protein can be verified through RT-PCR based assays that detect the plasmid derived mRNA transcript encoding the protein and antibody based assays that detect the protein itself. Successful production of the Sec-RNA includes both transcription of the RNA (biologically active RNA and recognition RNA sequence) and export of that transcript from the nucleus. RT-PCR assays can be used to show production of the plasmid derived Sec-RNA molecule and cellular fractionation can be used to demonstrate accumulation of the RNA in the cytoplasm. Binding of the Sec-RNA molecule by the fusion protein can be demonstrated by immunoprecipitation of the RNA-protein complex using an antibody to one of the domains of the fusion protein or, alternatively, via the addition of an epitope tag (FLAG, HA, etc.) to the fusion protein sequence. Secretion of the RNA-protein complex can be verified by detection of the Sec-RNA in the extracellular matrix, or media in the case of cells in culture. Intact RNA-protein complexes can be isolated from the media via immunoprecipitation, as described above, or total RNA may be prepped using Tri-Reagent (Sigma-Aldrich, product #T9424). The Sec-RNA is detected by northern blotting or by RT-PCR as described above.

The BioReactor cells can be produced by transient transfection of a suitable cell with an expression vector of the invention or by the development of stably transfected cells, where the plasmid is integrated into the genome of the BioReactor cell. Cells can be transiently transfected with an expression vector of the invention via liposomal or polymeric delivery agents or via electroporation using methods described herein and otherwise known in the art. The efficiency of these types of transfection precludes the need for purification of BioReactor cells (i.e., transfected cells) from non-transfected cells, which behaves as inert starting material in subsequent delivery steps. In contrast, the development of cell lines stably transfected with an expression vector of the invention and expressing the fusion protein and Sec-RNA from the genome of the recipient cell requires isolation of individual colonies of transfected cells, each representing a single integration event and giving rise to a homogeneous population of BioReactor cells. These cells produce secretion complexes continuously and are useful in both in vitro and in vivo applications.

Bioreactor cells can be used as transfection agents to facilitate the delivery of the Sec-RNA molecule to cells. Bioreactor cells can also be applied to target cells in vitro, ex vivo, or in vivo for the purpose of knocking down the gene product targeted by the Sec-RNA molecule. The particular expression vector and recipient cells used in the transfection are determined by the gene target of interest and the target cell identity. Likewise, the optimal ratio of BioReactor cells to target cells is determined empirically for each system of cells and gene targets. RNA and/or protein samples are collected from the target cells about 24-72 hours after addition of the BioReactor cells in order to assay knockdown of the mRNA transcript or protein, respectively. The mRNA levels of the target gene can be measured via RT-PCR, Northern blot and other methods known in the art. The protein levels of the target gene can be measured using known methods such as Western blot and immunoprecipitation.

Bioreactor cells can be generated by administering one or more of the expression vectors of the invention. In one embodiment, the invention provides a bioreactor cell comprising any of the expression vectors and compositions thereof provided herein. In one embodiment, the invention provides a cell comprising an expression vector comprising a polynucleotide sequence encoding a nucleic acid comprising a biologically active RNA sequence, a recognition RNA sequence, and optionally a terminal minihelix sequence and a polynucleotide sequence encoding a polypeptide comprising an RNA binding domain sequence and a transport peptide.

In one embodiment, the invention provides a cell comprising an expression vector comprising a polynucleotide sequence encoding a nucleic acid comprising a biologically active RNA sequence, a recognition RNA sequence, and optionally a terminal minihelix sequence, a polynucleotide sequence encoding a polypeptide comprising an RNA binding domain sequence and a transport peptide, and one or more polynucleotide sequences encoding one or more viral polymerases and one or more viral accessory proteins necessary for viral replication and an expression vector comprising one or more polynucleotide sequences encoding one or more viral coat proteins and one or more viral fusogenic proteins.

In one embodiment, the invention provides a cell comprising an expression vector comprising a polynucleotide sequence encoding a nucleic acid comprising a biologically active RNA sequence, a recognition RNA sequence, and optionally a terminal minihelix sequence, a polynucleotide sequence encoding a polypeptide comprising an RNA binding domain sequence and a transport peptide, and an additional polynucleotide sequence encoding a nucleic acid comprising one or more biologically active RNA sequences that target one or more further gene target(s). In one embodiment, the additional polynucleotide sequence encodes a nucleic acid comprising one or more biologically active RNA sequences that target a further gene target and an RNA recognition sequence. In another embodiment, where one of the biologically active RNA sequences in the vector is a short interfering RNA (siRNA), double-stranded RNA (dsRNA), micro-RNA (miRNA), or short hairpin RNA (shRNA), the additional polynucleotide sequence encodes a nucleic acid comprising one or more biologically active RNA sequences targeted to Dicer and/or Drosha.

In one embodiment, the invention provides a cell comprising an expression vector comprising a polynucleotide sequence encoding a nucleic acid comprising a biologically active RNA sequence, a recognition RNA sequence, and optionally a terminal minihelix sequence, a polynucleotide sequence encoding a polypeptide comprising an RNA binding domain sequence and a transport peptide, one or more polynucleotide sequences encoding one or more viral polymerases and one or more viral accessory proteins necessary for viral replication, and an additional polynucleotide sequence encoding a nucleic acid comprising one or more biologically active RNA sequences that target one or more further gene target(s) (for example, Dicer and/or Drosha gene targets) and an expression vector comprising one or more polynucleotide sequences encoding one or more viral coat proteins and one or more viral fusogenic proteins.

In one embodiment, the invention provides a cell comprising an expression vector comprising a polynucleotide sequence encoding a nucleic acid comprising a biologically active RNA sequence and one or more polynucleotide sequences encoding one or more viral polymerases and one or more viral accessory proteins necessary for viral replication, and an expression vector comprising one or more polynucleotide sequences encoding one or more viral coat proteins and one or more viral fusogenic proteins.

In one embodiment, the invention provides a cell comprising an expression vector comprising a polynucleotide sequence encoding a nucleic acid comprising a biologically active RNA sequence, a recognition RNA sequence, and optionally a terminal minihelix sequence and an expression vector comprising a polynucleotide sequence encoding a polypeptide comprising an RNA binding domain sequence and one or more transport peptides. In one embodiment, the cell further comprises a third expression vector comprising a polynucleotide sequence encoding a nucleic acid comprising one or more biologically active RNA sequences that target one or more gene target(s) that differ from the gene target(s) of the biologically active RNA in the first expression vector. In one embodiment, the third expression vector comprises a polynucleotide sequence encoding a nucleic acid comprising one or more biologically active RNA sequences that target one or more gene targets and an RNA recognition sequence. In another embodiment, where one of the biologically active RNA sequences in the first expression vector is a short interfering RNA (siRNA), double-stranded RNA (dsRNA), micro-RNA (miRNA), or short hairpin RNA (shRNA), the third expression vector comprises a polynucleotide sequence encoding a nucleic acid comprising one or more biologically active RNA sequences targeted to Dicer and/or Drosha.

The bioreactor cells described herein can be used, among other things, to deliver biologically active RNA to target cells. In one embodiment, the method of delivering a biologically active RNA to target cells comprises the steps of: (a) preparing an expression vector that encodes an RNA-protein complex comprising one or more biologically active RNAs, a recognition RNA sequence, optionally a terminal minihelix sequence, an RNA binding domain, and one or more transport peptide sequences selected from a cell penetrating domain, non-classical secretory domain, endosomal release domain, fusogenic peptide and a receptor binding domain; (b) administering the expression vector of step (a) to cells in culture to produce bioreactor cells expressing the RNA-protein complex; (c) collecting the cultured cells of step (b); (d) testing the cells of (c) to determine the bioreactor cells expressing the RNA-protein complex; and (e) isolating the bioreactor cells from the other cells in culture; and (f) mixing one or more target cells with the isolated bioreactor cells in step (e) to deliver a biologically active RNA to the target cells. In one embodiment, the target cells of (f) are target cells in cell culture. In one embodiment, the target cells of (f) are target cells extracted from an organism, including a mammalian animal. In one embodiment, the mammalian animal is a human. The expression vector can be any expression vector described herein. The RNA-protein complex can be any RNA-protein complex described herein. In one embodiment, the biologically active RNA of the RNA-protein complex is an shRNA. In another embodiment, the biologically active RNA of the RNA-protein complex is an aptamer. In one embodiment, the cells of step (b) are stably transfected with the expression vector. In certain embodiments of the method, the expression vector of step (a) further comprises a polynucleotide sequence encoding a nucleic acid comprising one or more biologically active RNA sequences that target one or more further gene target(s). In one embodiment, the additional polynucleotide sequence encodes a nucleic acid comprising one or more biologically active RNA sequences that target a further gene target and an RNA recognition sequence. In another embodiment, where one of the biologically active RNA sequences in the vector is a short interfering RNA (siRNA), double-stranded RNA (dsRNA), micro-RNA (miRNA), or short hairpin RNA (shRNA), the additional polynucleotide sequence encodes a nucleic acid comprising one or more biologically active RNA sequences targeted to Dicer and/or Drosha.

In another embodiment, the method of delivering a biologically active RNA to target cells comprises the steps of: (a) preparing an expression vector comprising a polynucleotide sequence encoding nucleic acid comprising one or more biologically active RNAs, a recognition RNA sequence, and optionally a terminal minihelix sequence, a polynucleotide sequence encoding a polypeptide comprising an RNA binding domain, and one or more transport peptide sequences, and one or more polynucleotide sequences encoding one or more viral polymerases and one or more viral accessory proteins necessary for viral replication; (b) preparing an expression vector comprising one or more polynucleotide sequences encoding one or more viral coat proteins and one or more viral fusogenic proteins; (c) administering the expression vector of step (a) and the expression vector of (b) to cells in culture to produce bioreactor cells expressing the RNA-protein complex; (d) collecting the cultured cells of step (c); (e) testing the cells of (d) to determine the bioreactor cells expressing the RNA-protein complex; and (f) isolating the bioreactor cells from the other cells in culture; and (g) mixing one or more target cells with the isolated bioreactor cells in step (f) to deliver a biologically active RNA to the target cells. In one embodiment, the target cells of (g) are target cells in cell culture. In one embodiment, the target cells of (g) are target cells extracted from an organism, including a mammalian animal. In one embodiment, the mammalian animal is a human. In one embodiment, the cells of step (c) are stably transfected with the expression vector.

In certain embodiments of the method, the expression vector of step (a) further comprises a polynucleotide sequence encoding a nucleic acid comprising one or more biologically active RNA sequences that target one or more further gene target(s). In one embodiment, the additional polynucleotide sequence encodes a nucleic acid comprising one or more biologically active RNA sequences that target a further gene target and an RNA recognition sequence. In another embodiment, where one of the biologically active RNA sequences in the vector is a short interfering RNA (siRNA), double-stranded RNA (dsRNA), micro-RNA (miRNA), or short hairpin RNA (shRNA), the additional polynucleotide sequence encodes a nucleic acid comprising one or more biologically active RNA sequences targeted to Dicer and/or Drosha.

In another embodiment, the method of delivering a biologically active RNA to target cells comprises the steps of: (a) preparing an expression vector comprising a polynucleotide sequence encoding nucleic acid comprising one or more biologically active RNAs and one or more polynucleotide sequences encoding one or more viral polymerases and one or more viral accessory proteins necessary for viral replication; (b) preparing an expression vector comprising one or more polynucleotide sequences encoding one or more viral coat proteins and one or more viral fusogenic proteins; (c) administering the expression vector of step (a) and the expression vector of (b) to cells in culture to produce bioreactor cells expressing the RNA-protein complex; (d) collecting the cultured cells of step (c); (e) testing the cells of (d) to determine the bioreactor cells expressing the RNA-protein complex; and (f) isolating the bioreactor cells from the other cells in culture; and (g) mixing one or more target cells with the isolated bioreactor cells in step (f) to deliver a biologically active RNA to the target cells. In one embodiment, the target cells of (g) are target cells in cell culture. In one embodiment, the target cells of (g) are target cells extracted from an organism, including a mammalian animal. In one embodiment, the mammalian animal is a human. In one embodiment, the cells of step (c) are stably transfected with the expression vector.

In another embodiment, the method of delivering a biologically active RNA to target cells comprises the steps of: (a) preparing an expression vector comprising a polynucleotide sequence encoding nucleic acid comprising one or more biologically active RNAs, a recognition RNA sequence, and optionally a terminal minihelix sequence; (b) preparing an expression vector comprising a polynucleotide sequence encoding a polyprptide comprising an RNAs binding domain and one or more transport peptides; (c) administering the expression vector of step (a) and the expression vector of (b) to cells in culture to produce bioreactor cells expressing the RNA-protein complex; (d) collecting the cultured cells of step (c); (e) testing the cells of (d) to determine the bioreactor cells expressing the RNA-protein complex; and (f) isolating the bioreactor cells from the other cells in culture; and (g) mixing one or more target cells with the isolated bioreactor cells in step (f) to deliver a biologically active RNA to the target cells. In one embodiment, the target cells of (g) are target cells in cell culture. In one embodiment, the target cells of (g) are target cells extracted from an organism, including a mammalian animal. In one embodiment, the mammalian animal is a human. In one embodiment, the cells of step (c) are stably transfected with the expression vector.

In another embodiment, the methods comprises preparing and administering a third expression vector comprising a polynucleotide sequence encoding a nucleic acid comprising one or more biologically active RNA sequences that target one or more further gene target(s). In one embodiment, the additional polynucleotide sequence encodes a nucleic acid comprising one or more biologically active RNA sequences that target a further gene target and an RNA recognition sequence. In another embodiment, where one of the biologically active RNA sequences in the first vector is a short interfering RNA (siRNA), double-stranded RNA (dsRNA), micro-RNA (miRNA), or short hairpin RNA (shRNA), the additional polynucleotide sequence encodes a nucleic acid comprising one or more biologically active RNA sequences targeted to Dicer and/or Drosha.

The invention also provides methods of using the bioreactor cells ex vivo for the delivery of a biologically active RNA to target cells. In one embodiment, the method of delivering a biologically active RNA to target cells ex vivo comprises the steps of: (a) preparing an expression vector that encodes an RNA-protein complex comprising one or more biologically active RNAs, a recognition RNA sequence, optionally a terminal minihelix sequence, an RNA binding domain, and one or more target peptide sequences; (b) administering the expression vector of step (a) to cells in culture to produce bioreactor cells expressing the RNA-protein complex; (c) collecting the cultured cells of step (b); (d) obtaining target cells from a subject; (e) mixing one or more target cells obtained in step (d) with the cultured cell(s) collected in step (c) to deliver a biologically active RNA to the target cells. In one embodiment, the method further comprises the step of: (f) administering the cells in step (e) to a subject. In one embodiment, the method further comprises the step of separating the bioreactor cells from the target cells before administering the target cells to the subject. In one embodiment, the subject of step (f) is the same subject as the subject in step (d) from which the target cells were obtained. In another embodiment, the subject of step (f) is a different subject from the subject in step (d) from which the target cells were obtained. In certain embodiments of the method, the expression vector of step (a) further comprises a polynucleotide sequence encoding a nucleic acid comprising one or more biologically active RNA sequences that target one or more further gene target(s). In one embodiment, the additional polynucleotide sequence encodes a nucleic acid comprising one or more biologically active RNA sequences that target a further gene target and an RNA recognition sequence. In another embodiment, where one of the biologically active RNA sequences in the vector is a short interfering RNA (siRNA), double-stranded RNA (dsRNA), micro-RNA (miRNA), or short hairpin RNA (shRNA), the additional polynucleotide sequence encodes a nucleic acid comprising one or more biologically active RNA sequences targeted to Dicer and/or Drosha.

In another embodiment, the method of delivering a biologically active RNA to target cells comprises the steps of: (a) preparing an expression vector comprising a polynucleotide sequence encoding nucleic acid comprising one or more biologically active RNAs, a recognition RNA sequence, and optionally a terminal minihelix sequence, a polynucleotide sequence encoding a polypeptide comprising an RNA binding domain, and one or more transport peptide sequences, and one or more polynucleotide sequences encoding one or more viral polymerases and one or more viral accessory proteins necessary for viral replication; (b) preparing an expression vector comprising one or more polynucleotide sequences encoding one or more viral coat proteins and one or more viral fusogenic proteins; (c) administering the expression vector of step (a) and the expression vector of (b) to cells in culture to produce bioreactor cells expressing the RNA-protein complex; (d) collecting the cultured cells of step (c); (e) obtaining target cells from a subject; (f) mixing one or more target cells obtained in step (e) with the cultured cell(s) collected in step (d) to deliver a biologically active RNA to the target cells. In one embodiment, the method further comprises the step of: (g) administering the cells in step (d) to a subject. In one embodiment, the method further comprises the step of separating the bioreactor cells from the target cells before administering the target cells to the subject. In one embodiment, the subject of step (g) is the same subject as the subject in step (e) from which the target cells were obtained. In another embodiment, the subject of step (g) is a different subject from the subject in step (e) from which the target cells were obtained.

In certain embodiments of the method, the expression vector of step (a) further comprises a polynucleotide sequence encoding a nucleic acid comprising one or more biologically active RNA sequences that target one or more further gene target(s). In one embodiment, the additional polynucleotide sequence encodes a nucleic acid comprising one or more biologically active RNA sequences that target a further gene target and an RNA recognition sequence. In another embodiment, where one of the biologically active RNA sequences in the vector is a short interfering RNA (siRNA), double-stranded RNA (dsRNA), micro-RNA (miRNA), or short hairpin RNA (shRNA), the additional polynucleotide sequence encodes a nucleic acid comprising one or more biologically active RNA sequences targeted to Dicer and/or Drosha.

In another embodiment, the method of delivering a biologically active RNA to target cells comprises the steps of: (a) preparing an expression vector comprising a polynucleotide sequence encoding nucleic acid comprising one or more biologically active RNAs and one or more polynucleotide sequences encoding one or more viral polymerases and one or more viral accessory proteins necessary for viral replication; (b) preparing an expression vector comprising one or more polynucleotide sequences encoding one or more viral coat proteins and one or more viral fusogenic proteins; (c) administering the expression vector of step (a) and the expression vector of (b) to cells in culture to produce bioreactor cells expressing the RNA-protein complex; (d) collecting the cultured cells of step (c); (e) obtaining target cells from a subject; (f) mixing one or more target cells obtained in step (e) with the cultured cell(s) collected in step (d) to deliver a biologically active RNA to the target cells. In one embodiment, the method further comprises the step of: (g) administering the cells in step (d) to a subject. In one embodiment, the method further comprises the step of separating the bioreactor cells from the target cells before administering the target cells to the subject. In one embodiment, the subject of step (g) is the same subject as the subject in step (e) from which the target cells were obtained. In another embodiment, the subject of step (g) is a different subject from the subject in step (e) from which the target cells were obtained.

In another embodiment, the method of delivering a biologically active RNA to target cells comprises the steps of: (a) preparing an expression vector comprising a polynucleotide sequence encoding nucleic acid comprising one or more biologically active RNAs, a recognition RNA sequence, and optionally a terminal minihelix sequence; (b) preparing an expression vector comprising a polynucleotide sequence encoding a polyprptide comprising an RNAs binding domain and one or more transport peptides; (c) administering the expression vector of step (a) and the expression vector of (b) to cells in culture to produce bioreactor cells expressing the RNA-protein complex; (d) collecting the cultured cells of step (c); (e) obtaining target cells from a subject; (f) mixing one or more target cells obtained in step (e) with the cultured cell(s) collected in step (d) to deliver a biologically active RNA to the target cells. In one embodiment, the method further comprises the step of: (g) administering the cells in step (d) to a subject. In one embodiment, the method further comprises the step of separating the bioreactor cells from the target cells before administering the target cells to the subject. In one embodiment, the subject of step (g) is the same subject as the subject in step (e) from which the target cells were obtained. In another embodiment, the subject of step (g) is a different subject from the subject in step (e) from which the target cells were obtained.

In any of the above described methods, the method can further comprise the steps of: testing the cells of (c) or (d) to determine the bioreactor cells expressing the RNA-protein complex and isolating the bioreactor cells from the other cells in culture before obtaining target cells from a subject.

In any of these methods, the subjects of the steps are a mammalian animal, including a human. In any of the ex vivo methods described herein, the subject from which the target cells are obtained and the subject to which the cells are administered is a mammalian animal subject, including, for example a human subject. The expression vector can be any of the expression vectors described herein. The RNA-protein complex can be any of the RNA-protein complexes described herein. In one embodiment, the biologically active RNA of the RNA-protein complex is an shRNA. In another embodiment, the biologically active RNA of the RNA-protein complex is an aptamer. In one embodiment, the RNA-protein complex encoded by the expression vector comprises a non-classical secretory domain sequence. In another embodiment, the RNA-protein complex encoded by the expression vector comprises a cell penetrating peptide. In another embodiment, the RNA-protein complex encoded by the expression vector comprises a cell penetrating peptide and a non-classical secretory domain. In one embodiment, the cells of step (b) or step(c) are stably transfected with the expression vector.

The invention also provides methods of using the bioreactor cells in vivo for the delivery of a biologically active RNA to target cells and/or tissues. In one embodiment, the method of delivering a biologically active RNA to target cells in vivo comprises the steps of: (a) preparing an expression vector that encodes an RNA-protein complex comprising one or more biologically active RNAs, a recognition RNA sequence, optionally a terminal minihelix sequence, an RNA binding domain, and one or more transport peptide sequences (i.e., selected from a cell penetrating domain, non-classical secretory domain, endosomal release domain, fusogenic peptide, and a receptor binding domain); (b) administering the expression vector of step (a) to cells in culture to produce bioreactor cells expressing the RNA-protein complex; (c) collecting the cultured cells of step (b); (d) administering the cells in step (c) to a subject. In one embodiment, the subject of step (d) is a mammalian animal. In one embodiment, the mammalian animal is a human subject.

In certain embodiments of the method, the expression vector of step (a) further comprises a polynucleotide sequence encoding a nucleic acid comprising one or more biologically active RNA sequences that target one or more further gene target(s). In one embodiment, the additional polynucleotide sequence encodes a nucleic acid comprising one or more biologically active RNA sequences that target a further gene target and an RNA recognition sequence. In another embodiment, where one of the biologically active RNA sequences in the vector is a short interfering RNA (siRNA), double-stranded RNA (dsRNA), micro-RNA (miRNA), or short hairpin RNA (shRNA), the additional polynucleotide sequence encodes a nucleic acid comprising one or more biologically active RNA sequences targeted to Dicer and/or Drosha.

The invention also provides methods of using the bioreactor cells in vivo for the delivery of a biologically active RNA to target cells and/or tissues. In one embodiment, the method of delivering a biologically active RNA to target cells in vivo comprises the steps of: (a) preparing an expression vector that encodes an RNA-protein complex comprising one or more biologically active RNAs, a recognition RNA sequence, optionally a terminal minihelix sequence, an RNA binding domain, and one or more transport peptide sequences and one or more polynucleotide sequences encoding one or more viral polymerases and one or more viral accessory proteins necessary for viral replication; (b) preparing an expression vector comprising one or more polynucleotide sequences encoding one or more viral coat proteins and one or more viral fusogenic proteins; (c) administering the expression vector of step (a) and the expression vector of step (b) to cells in culture to produce bioreactor cells expressing the RNA-protein complex; (d) collecting the cultured cells of step (c); (e) administering the cells in step (d) to a subject. In one embodiment, the subject of step (e) is a mammalian animal. In one embodiment, the mammalian animal is a human subject.

In certain embodiments of the method, the expression vector of step (a) further comprises a polynucleotide sequence encoding a nucleic acid comprising one or more biologically active RNA sequences that target one or more further gene target(s). In one embodiment, the additional polynucleotide sequence encodes a nucleic acid comprising one or more biologically active RNA sequences that target a further gene target and an RNA recognition sequence. In another embodiment, where one of the biologically active RNA sequences in the vector is a short interfering RNA (siRNA), double-stranded RNA (dsRNA), micro-RNA (miRNA), or short hairpin RNA (shRNA), the additional polynucleotide sequence encodes a nucleic acid comprising one or more biologically active RNA sequences targeted to Dicer and/or Drosha.

The invention also provides methods of using the bioreactor cells in vivo for the delivery of a biologically active RNA to target cells and/or tissues. In one embodiment, the method of delivering a biologically active RNA to target cells in vivo comprises the steps of: (a) preparing an expression vector comprising a polynucleotide sequence encoding nucleic acid comprising one or more biologically active RNAs and one or more polynucleotide sequences encoding one or more viral polymerases and one or more viral accessory proteins necessary for viral replication; (b) preparing an expression vector comprising one or more polynucleotide sequences encoding one or more viral coat proteins and one or more viral fusogenic proteins; (c) administering the expression vector of step (a) and the expression vector of (b) to cells in culture to produce bioreactor cells expressing the RNA-protein complex; (d) collecting the cultured cells of step (c); (e) administering the cells in step (d) to a subject. In one embodiment, the subject of step (e) is a mammalian animal. In one embodiment, the mammalian animal is a human subject.

The invention also provides methods of using the bioreactor cells in vivo for the delivery of a biologically active RNA to target cells and/or tissues. In one embodiment, the method of delivering a biologically active RNA to target cells in vivo comprises the steps of: (a) preparing an expression vector comprising a polynucleotide sequence encoding nucleic acid comprising one or more biologically active RNAs, a recognition RNA sequence, and optionally a terminal minihelix sequence; (b) preparing an expression vector comprising a polynucleotide sequence encoding a polypeptide comprising an RNAs binding domain and one or more transport peptides; (c) administering the expression vector of step (a) and the expression vector of (b) to cells in culture to produce bioreactor cells expressing the RNA-protein complex; (d) collecting the cultured cells of step (c); (e) administering the cells in step (d) to a subject. In one embodiment, the subject of step (e) is a mammalian animal. In one embodiment, the mammalian animal is a human subject.

In any of the above described methods, the method can further comprise the steps of: testing the cells of (c) or (d) to determine the bioreactor cells expressing the RNA-protein complex and isolating the bioreactor cells from the other cells in culture before administering the cells to a subject. In one embodiment, the subject is a mammalian animal. In one embodiment, the mammalian animal is a human subject.

Methods of Treatment

In one embodiment, the invention provides a method of preventing, ameliorating, and/or treating a disease or condition associated with defective gene expression and/or activity in a subject comprising administering to the subject an expression vector of the invention. Any of the expression vector described herein can be used in the methods for preventing, ameliorating, and/or treating a disease or condition associated with defective gene expression and/or activity in a subject.

In one embodiment, the invention provides a method of preventing, ameliorating, and/or treating a disease or condition associated with defective gene expression and/or activity in a subject comprising administering to the subject an expression vector comprising a polynucleotide encoding a nucleic acid comprising one or more biologically active RNA sequences directed to a target gene, a recognition RNA sequence, and optionally a terminal minihelix sequence and a polynucleotide encoding a polypeptide comprising an RNA binding domain and one or more transport peptide sequences (i.e., selected from a cell penetrating peptide sequence, non-classical secretory domain, endosomal release domain, and a receptor binding domain). In one embodiment, the expression vector further comprises a polynucleotide encoding a further nucleic acid comprising one or more biologically active RNA sequences directed to a target gene(s), optionally a recognition RNA binding domain, and optionally a terminal minihelix sequence. In one embodiment, the target gene(s) of the further nucleic acid is selected from Dicer and/or Drosha.

In one embodiment, the invention provides a method of preventing, ameliorating, and/or treating a disease or condition associated with defective gene expression and/or activity in a subject comprising administering to the subject an expression vector comprising a polynucleotide encoding a nucleic acid comprising one or more biologically active RNA sequences directed to a target gene, a recognition RNA sequence, and optionally a terminal minihelix sequence and a polynucleotide encoding a polypeptide comprising an RNA binding domain and one or more transport peptide sequences and one or more polynucleotide sequences encoding one or more viral polymerases and one or more viral accessory proteins necessary for viral replication and an expression vector comprising one or more polynucleotide sequences encoding one or more viral coat proteins and one or more viral fusogenic proteins. In one embodiment, the expression vector further comprises a polynucleotide encoding a further nucleic acid comprising one or more biologically active RNA sequences directed to a target gene(s), optionally a recognition RNA binding domain, and optionally a terminal minihelix sequence. In one embodiment, the target gene(s) of the further nucleic acid is selected from Dicer and/or Drosha.

In one embodiment, the invention provides a method of preventing, ameliorating, and/or treating a disease or condition associated with defective gene expression and/or activity in a subject comprising administering to the subject an expression vector comprising a polynucleotide encoding a nucleic acid comprising one or more biologically active RNA sequences directed to a target gene and one or more polynucleotide sequences encoding one or more viral polymerases and one or more viral accessory proteins necessary for viral replication and an expression vector comprising one or more polynucleotide sequences encoding one or more viral coat proteins and one or more viral fusogenic proteins;

In one embodiment, the invention provides a method of preventing, ameliorating, and/or treating a disease or condition associated with defective gene expression and/or activity in a subject comprising administering to the subject a first expression vector encoding a nucleic acid comprising one or more biologically active RNA sequences directed to a target gene, a recognition RNA sequence, and optionally a terminal minihelix sequence and a second expression vector encoding a polypeptide comprising an RNA binding domain and one or more transport peptide sequences (i.e, selected from a cell penetrating peptide sequence, non-classical secretory domain, endosomal release domain, and a receptor binding domain). In one embodiment, the method further comprises administering to the subject a third expression vector encoding a nucleic acid comprising one or more biologically active RNA sequences directed to a target gene(s), optionally a recognition RNA binding domain, and optionally a terminal minihelix sequence. In one embodiment, the target gene(s) of the second nucleic acid is selected from Dicer and/or Drosha.

In any of the above-described methods, the expression vectors can be administered as a composition comprising the expression vectors and a pharmaceutically acceptable carrier.

The invention additionally provides a method of preventing, ameliorating, and/or treating a disease or condition associated with defective gene expression and/or activity in a subject comprising administering to the subject one or more bioreactor cells of the invention. In one embodiment, the invention provides a method of preventing, ameliorating, and/or treating a disease or condition associated with defective gene expression and/or activity in a subject comprising administering to the subject a composition comprising one or more bioreactor cells of the invention and a pharmaceutically acceptable carrier including but not limited to phosphate buffered saline, saline or 5% dextrose. The bioreactor cell(s) can be any of the bioreactor cell(s) of the invention described herein. In one embodiment, the bioreactor cell encodes an RNA-protein complex comprising one or more biologically active RNA sequences directed to a target gene, a recognition RNA sequence, optionally a terminal minihelix sequence, an RNA binding domain sequence, and one or more transport peptide sequences selected from a cell penetrating peptide sequence, non-classical secretory domain, endosomal release domain, receptor binding domain, and fusogenic peptide.

In another embodiment, the invention provides a method of preventing, ameliorating, and/or treating a disease or condition associated with defective gene expression and/or activity in a subject comprising administering to the subject a composition comprising one or more bioreactor cells and a pharmaceutically acceptable carrier including but not limited to phosphate buffered saline, saline or 5% dextrose, wherein the bioreactor cell(s) produces and secretes an RNA-protein complex comprising one or more biologically active RNA sequences directed to a target gene(s), a recognition RNA sequence, and optionally a terminal minihelix sequence, an RNA binding domain sequence, one or more transport peptide sequences selected from a cell penetrating peptide sequence, non-classical secretory domain, endosomal release domain, receptor binding domain, and further produces an RNA comprising one or more biologically active RNA sequences directed to Dicer and/or Drosha.

In any of the above described methods of preventing, ameliorating, and/or treating a disease or condition associated with defective gene expression and/or activity, suitable gene targets include Mmp2, Vascular Endothelial Growth Factor (VEGF), Vascular Endothelial Growth Factor Receptor (VEGFR), Cav-1, Epidermal Growth Factor Receptor (EGFR), H-Ras, Bcl-2, Survivin, FAK, STAT-3, HER-3, Beta-Catenin, and Src.

Thus, in one embodiment, the present invention provides a method of preventing, ameliorating, and/or treating a disease or condition associated with defective target gene expression and/or activity in a subject comprising administering to the subject a composition comprising one or more expression vectors and a pharmaceutically acceptable carrier, wherein the expression vector(s) encodes an RNA-protein complex comprising one or more biologically active RNA sequences directed to the target gene, a recognition RNA sequence, optionally a terminal minihelix sequence, an RNA binding domain sequence, and one or more sequences selected from a cell penetrating peptide sequence, non-classical secretory domain, endosomal release domain, receptor binding domain, and fusogenic peptide. Exemplary target genes include Mmp2, Vascular Endothelial Growth Factor (VEGF), Vascular Endothelial Growth Factor Receptor (VEGFR), Cav-1, Epidermal Growth Factor Receptor (EGFR), H-Ras, Bcl-2, Survivin, FAK, STAT-3, HER-3, Beta-Catenin, and Src.

In another embodiment, the present invention provides a method of preventing, ameliorating, and/or treating a disease or condition associated with defective gene expression and/or activity in a subject comprising administering to the subject a composition comprising one or more bioreactor cells and a pharmaceutically acceptable carrier, wherein the defective gene expression and/or activity is selected from defective Mmp2, Vascular Endothelial Growth Factor (VEGF), Vascular Endothelial Growth Factor Receptor (VEGFR), Cav-1, Epidermal Growth Factor Receptor (EGFR), H-Ras, Bcl-2, Survivin, FAK, STAT-3, HER-3, Beta-Catenin, and Src expression and/or activity and wherein the bioreactor cell(s) produces and secretes an RNA-protein complex comprising one or more biologically active RNA sequences, a recognition RNA sequence, optionally a terminal minihelix sequence, an RNA binding domain sequence, and one or more sequences selected from a cell penetrating peptide sequence, non-classical secretory domain, endosomal release domain, receptor binding domain, wherein the biologically active RNA(s) is directed to a gene(s) selected from Mmp2, Vascular Endothelial Growth Factor (VEGF), Vascular Endothelial Growth Factor Receptor (VEGFR), Cav-1, Epidermal Growth Factor Receptor (EGFR), H-Ras, Bcl-2, Survivin, FAK, STAT-3, HER-3, Beta-Catenin, and Src and wherein the biologically active RNA(s) targets the gene(s) having defective expression and/or activity.

Polynucleotides and Polypeptides of the Invention

The present invention provides novel polynucleotides useful in the production of nucleic acid molecules, polypeptides, RNA-protein complexes, and expression vectors comprising the same, for the delivery of biologically active RNAs to cells. In one embodiment, the invention provides an isolated polynucleotide that encodes a nucleic acid molecule comprising one or more biologically active RNA sequences, a recognition RNA sequence, and optionally a terminal minihelix sequence. In one specific embodiment, the isolated polynucleotide encodes a nucleic acid molecule comprising one or more short hairpin RNAs, a recognition RNA sequence, and optionally a terminal minihelix sequence. In another embodiment, the isolated polynucleotide encodes a nucleic acid molecule comprising one or more aptamers, a recognition RNA sequence, and optionally a terminal minihelix sequence. In another embodiment, the isolated polynucleotide encodes a nucleic acid molecule comprising one or more ribozymes, a recognition RNA sequence, and optionally a terminal minihelix sequence. In another embodiment, the isolated polynucleotide encodes a nucleic acid molecule comprising one or more antisense nucleic acids, a recognition RNA sequence, and optionally a terminal minihelix sequence. In addition, the invention provides an isolated polynucleotide that encodes a nucleic acid molecule comprising one or more biologically active RNA sequences targeted to Dicer, for example, a polynucleotide comprising SEQ ID NO: 49.

In addition, the invention provides a novel fusion protein comprising an amino acid sequence (RNA binding domain) that binds to the recognition RNA sequence of the above-described nucleic acid sequence and an amino acid sequence that facilitates the transport and secretion of the above-described biologically active RNA from a cell (transport peptide). Thus, in one embodiment, the fusion protein comprises an RNA binding domain and one or more transport peptides. The transport peptide of the fusion polypeptide can be any amino acid sequence that facilitates the delivery of nucleic acids, peptides, fusion proteins, RNA-protein complexes, and/or other biological molecules to the extracellular matrix and/or to neighboring cells and tissues.

The invention also provides an isolated polynucleotide that encodes any of the polypeptide molecules described herein.

In one embodiment, the invention provides an isolated polynucleotide that encodes a polypeptide comprising an amino acid sequence of an RNA binding domain and a polypeptide comprising an amino acid sequence of one or more transport peptide sequences, for example, selected from a non-classical secretory domain, a cell penetrating peptide, a receptor binding domain, an endosomal release domain, and a fusogenic peptide.

In any of the above-described embodiments of the isolated polynucleotide encoding a nucleic acid or polypeptide of the invention, the isolated polynucleotide can comprise a sequence wherein the individual sequences, domains and peptides are joined directly without the addition of one or more linker, spacer, or other sequences or are joined with the addition of one or more linker, spacer, and/or other sequences.

The invention also provides the complementary sequence of any of the polynucleotides described in this section and elsewhere in the application. As used herein, the term "complementary" refers to the hybridization or base pairing between nucleotides, such as, for example, between the two strands of a double-stranded polynucleotide or between an oligonucleotide primer and a primer binding site on a single-stranded polynucleotide to be amplified or sequenced. Two single-stranded nucleotide molecules are said to be complementary when the nucleotides of one strand, optimally aligned with appropriate nucleotide insertions, deletions or substitutions, pair with at least about 80% of the nucleotides of the other strand.

A "polynucleotide" of the invention also includes those polynucleotides capable of hybridizing, under stringent hybridization conditions, to any of the polynucleotides described herein or the complements thereof "Stringent hybridization conditions" are generally selected to be about 5° C. lower than the thermal melting point ($T_M$) for the specific sequence at a defined ionic strength and pH. One example of stringent hybridization conditions refers to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

The invention also relates to polynucleotides comprising nucleotide sequences having at least 80% identity over their entire length with any of the polynucleotides of the invention, for example, at least 85%, at least 90% identity, at least 95% identity, at least 98% identity, and at least 99% identity. Thus, in certain specific embodiments, the invention provides an isolated polynucleotide comprising nucleotide sequence having at least 80% identity (i.e., at least 85%, 90%, 95%, 98%, or 99% identity) over its entire length to a polynucleotide encoding a nucleic acid molecule comprising one or more sequences selected from SEQ ID NOs: 1-15 and a sequence selected from SEQ ID NOs: 16-23.

In one embodiment, the invention provides an isolated polynucleotide comprising a nucleotide sequence having at least 80% (i.e., at least 85%, 90%, 95%, 98%, or 99% identity) identity over its entire length to a polynucleotide encoding a polypeptide comprising an amino acid sequence selected from SEQ ID NOs: 24-31. In another embodiment, the invention provides an isolated polynucleotide comprising a nucleotide sequence having at least 80% identity over its entire length to a polynucleotide encoding a polypeptide comprising an amino acid sequence selected from SEQ ID NOs: 24-31 and a sequence selected from SEQ ID NOs: 32-40. In another embodiment, the invention provides an isolated polynucleotide comprising a nucleotide sequence having at least 80% identity over its entire length to a polynucleotide encoding a polypeptide comprising an amino acid sequence selected from SEQ ID NOs: 50-54. In another embodiment, the invention provides an isolated polynucleotide comprising a nucleotide sequence having at least 80% identity over its entire length to a polynucleotide encoding a polypeptide comprising an amino acid sequence selected from SEQ ID NOs: 24-31 and a sequence selected from SEQ ID NOs: 41-48. In another embodiment, the invention provides an isolated polynucleotide comprising a nucleotide sequence having at least 80% identity over its entire length to a polynucleotide encoding a polypeptide comprising an amino acid sequence selected from SEQ ID NOs: 24-31, a sequence selected from SEQ ID NOs: 32-40, and a sequence selected from SEQ ID NOs: 41-48.

The invention also relates to polynucleotide and polypeptide variants. "Polynucleotide variant" refers to a polynucleotide differing from the polynucleotide of the invention, but retaining essential properties thereof. Likewise, "polypeptide variant" refers to a polypeptide differing from the polypeptide of the present invention, but retaining essential properties thereof. In certain embodiments, the invention provides a polynucleotide variant of a sequence selected from SEQ ID NOs: 1-23. In certain embodiments, the invention provides a polynucleotide encoding a polypeptide variant of a sequence selected from SEQ ID NOs: 24-54.

Variants include, but are not limited to, splice variants and allelic variants, as well as addition, deletion, truncation, and substitution variants. "Allelic variants" are naturally-occurring variants that refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level. Alternatively, non-naturally occurring variants may be produced by mutagenesis techniques or by direct synthesis.

Variants can include sequences having "conservative amino acid substitution", which term refers to a substitution of a native amino acid residue with a normative residue such that there is little or no effect on the polarity or charge of the amino acid residue at that position. For example, a conservative substitution results from the replacement of a non-polar residue in a polypeptide with any other non-polar residue. Another example of a conservative substitution is the replacement of an acidic residue with another acidic residue. Variants can also include "orthologs", which term refers to a polypeptide that corresponds to a polypeptide identified from a different species.

In a particular embodiment, the transport polypeptide comprises one or more substitutions, deletions, truncations, additions and/or insertions, such that the bioactivity of the native transport polypeptide is not substantially diminished. In other words, the bioactivity of a transport polypeptide variant may be diminished by, less than 50%, and preferably less than 20%, relative to the native protein.

Preferably, a transport polypeptide variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. A variant may also, or alternatively, contain nonconservative changes. In a particular embodiment, variant polypeptides differ from a native sequence by substitution, deletion or addition of amino acids. Variants may also (or alternatively) be modified by, for example, the deletion or addition of amino acids that have minimal influence on the bioactivity, secondary structure and hydropathic nature of the polypeptide.

The invention provides methods for isolating or recovering a nucleic acid encoding a polypeptide having a transport polypeptide activity from a biological sample comprising the steps of: (a) providing an amplification primer sequence pair for amplifying a nucleic acid encoding a polypeptide of interest, wherein the primer pair is capable of amplifying a nucleic acid of the invention; (b) isolating a nucleic acid from the biological sample or treating the biological sample such that nucleic acid in the sample is accessible for hybridization to the amplification primer pair; and, (c) combining the nucleic acid of step (b) with the amplification primer pair of step (a) and amplifying nucleic acid from the biological sample, thereby isolating or recovering a nucleic acid encoding a polypeptide having a transport polypeptide activity from a biological sample. One or each member of the amplification primer sequence pair can comprise an oligonucleotide comprising at least about 10 to 50 consecutive bases of a sequence of the invention. In one aspect, the biological sample can be derived from a bacterial cell, a protozoan cell, an insect cell, a yeast cell, a plant cell, a fungal cell or a mammalian cell.

The invention provides methods of generating a variant of a nucleic acid encoding a transport polypeptide having a transport polypeptide activity comprising the steps of: (a) providing a template nucleic acid comprising a nucleic acid of the invention; and (b) modifying, deleting or adding one or more nucleotides in the template sequence, or a combination thereof, to generate a variant of the template nucleic acid. In one aspect, the method can further comprise expressing the variant nucleic acid to generate a variant transport polypeptide polypeptide. The modifications, additions or deletions can be introduced by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis (GSSM), synthetic ligation reassembly (SLR) or a combination thereof. In another aspect, the modifications, additions or deletions are introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

In one aspect, the method can be iteratively repeated until a transport polypeptide having an altered or different activity or an altered or different stability from that of a polypeptide encoded by the template nucleic acid is produced. In one aspect, the method can be iteratively repeated until a transport protein coding sequence having an altered codon usage from that of the template nucleic acid is produced. In another aspect, the method can be iteratively repeated until a transport protein having higher or lower level of message expression or stability from that of the template nucleic acid is produced.

The invention provides methods for modifying codons in a nucleic acid encoding a polypeptide having transport protein activity to increase its expression in a host cell, the method comprising the following steps: (a) providing a nucleic acid of the invention encoding a polypeptide having transport protein activity; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying codons in a nucleic acid encoding a polypeptide having transport protein activity; the method comprising the following steps: (a) providing a nucleic acid of the invention; and, (b) identifying a codon in the nucleic acid of step (a) and replacing it with a different codon encoding the same amino acid as the replaced codon, thereby modifying codons in a nucleic acid encoding a transport protein.

The invention provides methods for modifying codons in a nucleic acid encoding a polypeptide having transport protein activity to increase its expression in a host cell, the method comprising the following steps: (a) providing a nucleic acid of the invention encoding a transport protein polypeptide; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying a codon in a nucleic acid encoding a polypeptide having a transport protein activity to decrease its expression in a host cell, the method comprising the following steps: (a) providing a nucleic acid of the invention; and (b) identifying at least one preferred codon in the nucleic acid of step (a) and replacing it with a non-preferred or less preferred codon encoding the same amino acid as the replaced codon, wherein a preferred codon is a codon over-represented in coding sequences in genes in a host cell and a non-preferred or less preferred codon is a codon under-represented in coding sequences in genes in the host cell, thereby modifying the nucleic acid to decrease its expression in a host cell. In one aspect, the host cell can be a bacterial cell, a fungal cell, an insect cell, a yeast cell, a plant cell or a mammalian cell.

The invention provides methods for producing a library of nucleic acids encoding a plurality of modified transport protein active sites or substrate binding sites, wherein the modified active sites or substrate binding sites are derived from a first nucleic acid comprising a sequence encoding a first active site or a first substrate binding site the method comprising the following steps: (a) providing a first nucleic acid encoding a first active site or first substrate binding site, wherein the first nucleic acid sequence comprises a sequence that hybridizes under stringent conditions to a nucleic acid of the invention, and the nucleic acid encodes a transport protein active site or a transport protein substrate binding site; (b) providing a set of mutagenic oligonucleotides that encode naturally-occurring amino acid variants at a plurality of targeted codons in the first nucleic acid; and, (c) using the set of mutagenic oligonucleotides to generate a set of active site-encoding or substrate binding site-encoding variant nucleic acids encoding a range of amino acid variations at each amino acid codon that was mutagenized, thereby producing a library of nucleic acids encoding a plurality of modified transport protein active sites or substrate binding sites. In one aspect, the method comprises mutagenizing the first nucleic acid of step (a) by a method comprising an optimized directed evolution system, gene site-saturation mutagenesis (GSSM), synthetic ligation reassembly (SLR), error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis (GSSM), synthetic ligation reassembly (SLR) and a combination thereof. In another aspect, the method comprises mutagenizing the first nucleic acid of step (a) or variants by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

Thus, the invention includes those polynucleotides that encode a nucleic acid or polypeptide of the invention, including the described substitution, deletion, truncation, and insertion variants, as well as allelic variants, splice variants, fragments, derivatives, and orthologs. Accordingly, the polynucleotide sequences of the invention include both the naturally occurring sequences as well as variant forms. Likewise, the polypeptides of the invention encompass both naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Administration of Expression Vectors

The expression vectors of the invention are administered to cells and/or mammalian subjects so as to modulate target gene expression, for example, in the treatment, prevention, and/or amelioration of a disorder associated with defective target gene expression and/or activity.

The expression vectors of the invention and formulations thereof can be delivered by local or systemic administration and can be administered by a variety of routes including orally, topically, rectally or via parenteral, intranasal, intradermal, intra-arterial, intravenous and intramuscular routes, as well as by direct injection into diseased tissue. The term parenteral is meant to include percutaneous, subcutaneous, intravascular, intramuscular, as well as intrathecal injection or infusion techniques and the like. The expression vector can be directly injected into the brain. Alternatively, the vector can be introduced intrathecally for brain and spinal cord conditions. In another example, the vector can be introduced intramuscularly. Direct injection of the vectors of the invention, whether subcutaneous, intramuscular, or intradermal, can take place using standard needle and syringe methodologies, or by known needle-free technologies. Traditional approaches to CNS delivery are known and include, for example, intrathecal and intracerebroventricular administration, implantation of catheters and pumps, direct injection or perfusion at the site of injury or lesion, injection into the brain arterial system, or by chemical or osmotic opening of the blood-brain barrier. The vectors of the invention and formulations thereof can be administered via pulmonary delivery, such as by inhalation of an aerosol or spray dried formulation administered by an inhalation device or nebulizer, providing rapid local uptake of the vectors into relevant pulmonary tissues. The compositions of the invention can also be formulated and used as creams, gels, sprays, oils and other suitable compositions for topical, dermal, or transdermal administration as is known in the art.

Dosing frequency will depend upon the pharmacokinetic parameters of the expression vector in the formulation used. Typically, a clinician administers the composition until a dosage is reached that achieves the desired effect. The composition can therefore be administered as a single dose, or as two or more doses (which may or may not contain the same amount of the desired vector) over time, or as a continuous infusion via an implantation device or catheter. Further refinement of the appropriate dosage is routinely made by those of ordinary skill in the art and is within the ambit of tasks routinely performed by them. Thus, administration of the expression vectors in accordance with the present invention is effected in one dose or can be administered continuously or intermittently throughout the course of treatment, depending, for example, upon the recipient's physiological condition, whether the purpose of the administration is therapeutic or prophylactic, and other factors known to skilled practitioners. The administration of the expression vectors of the invention can be essentially continuous over a preselected period of time or can be in a series of spaced doses.

An effective amount of vector to be added can be empirically determined. Methods of determining the most effective means and dosages of administration are well known to those of skill in the art and will vary with the vector, the target cells, and the subject being treated. For example, the amount to be administered depends on several factors including, but not limited to, the RNA-protein complex, the disorder, the weight, physical condition, and the age of the mammal, and whether prevention or treatment is to be achieved. Such factors can be readily determined by the clinician employing animal models or other test systems which are well known in the art. For example, appropriate dosages may be ascertained through use of appropriate dose-response data. Thus, single and multiple administrations can be carried out with the dose level and pattern being selected by the treating physician. A pharmaceutically effective dose is that dose required to prevent, inhibit the occurrence, or treat (alleviate a symptom) of a disease state. In general, as mentioned, a pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered.

It also may be desirable to use pharmaceutical compositions of the vectors according to the invention ex vivo. In such instances, cells, tissues or organs that have been removed from the subject are exposed to vectors pharmaceutical compositions after which the cells, tissues and/or organs are subsequently implanted back into the subject.

Pharmaceutical Compositions

The invention provides a pharmaceutical composition comprising one or more expression vectors of the invention in an acceptable carrier, such as a stabilizer, buffer, solubilizer, emulsifier, preservative and/or adjuvant. Preferably, acceptable formulation materials are nontoxic to recipients at the dosages and concentrations employed. The vectors of the invention can be administered to a subject by any standard means, with or without stabilizers, buffers, and the like, to form a pharmaceutical composition. A pharmacological composition or formulation refers to a composition or formulation that allows for the effective distribution of the vectors of the instant invention in a form suitable for administration, e.g., systemic or local administration, into a cell or subject, including for example a human. Suitable forms, in part, depend upon the use or the route of entry, for example oral, transdermal, or by injection. Such forms should be administered in the physical location most suitable for the desired activity and should not prevent the composition or formulation from reaching a target cell. In one embodiment, the pharmaceutical composition comprises sufficient vector to produce a therapeutically effective amount of the RNA-protein complex, i.e., an amount sufficient to reduce or ameliorate symptoms of the disease state in question or an amount sufficient to confer the desired benefit. The pharmaceutical compositions can also contain a pharmaceutically acceptable excipient, for example, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, tris-hcl, citrates, phosphates or other organic acids); bulking agents (such as mannitol or glycine); chelating agents (such as ethylenediamine tetraacetic acid (edta)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, peg, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See REMINGTON'S PHARMACEUTICAL SCIENCES, 18$^{th}$ edition, (A. R. Gennaro, ed.), 1990, Mack Publishing Company.

The expression vectors of the invention and formulations thereof can be administered orally, topically, parenterally, by inhalation or spray, or rectally in dosage unit formulations containing conventional non-toxic pharmaceutically acceptable carriers, adjuvants and/or vehicles. Compositions intended for oral use can be prepared according to any method known to the art for the manufacture of pharmaceutical compositions and such compositions can contain one or more such sweetening agents, flavoring agents, coloring agents or preservative agents in order to provide palatable preparations.

Aqueous suspensions contain the active materials in a mixture with excipients suitable for the manufacture of aqueous suspensions. Such excipients include, for example, suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

Methods of Modulating Gene Expression

The expression vectors of the invention and the Bioreactors of the invention can be used in vitro, ex vivo, and in vivo to modulate the expression of a target gene of interest. The invention provides an expression vector designed to produce an RNA-protein complex comprising at least one biologically active RNA molecule targeting one or more genes of interest and a fusion protein capable of delivering the biologically active RNA molecule(s) to the extracellular matrix and/or neighboring cells and tissues. The administration of the expression vector to cells in vivo, ex vivo, and in vitro converts the cells into "bioreactors" that produce and deliver biologically active RNA molecules, secreted as RNA-protein complexes, to the extracellular matrix and/or other neighboring cells.

The invention provides methods for modulating the expression of one or more target gene(s) in a subject comprising administering to the subject one or more expression vectors of the invention or a composition(s) thereof. In one embodiment, the method for modulating the expression of one or more target gene(s) in a subject comprises administering to the subject an expression vector comprising a polynucleotide encoding a nucleic acid comprising a biologically active RNA sequence, recognition RNA sequence, optionally a terminal minihelix sequence, and a polynucleotide encoding a polypeptide comprising an RNA binding domain and one or more transport peptide (i.e., sequences selected from a cell penetrating peptide sequence, non-classical secretory domain, endosomal release domain, receptor binding domain, and fusogenic peptide). In one embodiment, the expression vector comprises a further nucleic acid comprising one or more biologically active RNA sequences directed to a target gene(s), optionally a recognition RNA binding domain, and optionally a terminal minihelix sequence, wherein the target gene(s) of the further nucleic acid is different from the target gene of the first nucleic acid. In one embodiment, the target gene is selected from Dicer and/or Drosha.

In one embodiment, the method for modulating the expression of one or more target gene(s) in a subject comprises administering to the subject an expression vector comprising a polynucleotide sequence encoding a nucleic acid comprising one or more biologically active RNA sequences, a recognition RNA sequence, and optionally a terminal minihelix sequence, a polynucleotide encoding a polypeptide comprising an RNA binding domain and one or more transport peptide and one or more polynucleotide sequences encoding one or more viral polymerases and one or more viral accessory proteins necessary for viral replication and an expression vector comprising one or more polynucleotide sequences encoding one or more viral coat proteins and one or more viral fusogenic proteins. In one embodiment, the expression vector comprises a further nucleic acid comprising one or more biologically active RNA sequences directed to a target gene(s), optionally a recognition RNA binding domain, and optionally a terminal minihelix sequence, wherein the target gene(s) of the further nucleic acid is different from the target gene of the first nucleic acid. In one embodiment, the target gene is selected from Dicer and/or Drosha.

In one embodiment, the method for modulating the expression of one or more target gene(s) in a subject comprises administering to the subject an expression vector comprising a polynucleotide sequence encoding a nucleic acid comprising one or more biologically active RNA sequences and one or more polynucleotide sequences encoding one or more viral polymerases and one or more viral accessory proteins necessary for viral replication and an expression vector comprising one or more polynucleotide sequences encoding one or more viral coat proteins and one or more viral fusogenic proteins.

In another embodiment, the method for modulating the expression of one or more target gene(s) in a subject comprises administering to the subject a first expression vector encoding a nucleic acid comprising one or more biologically active RNA sequences directed to a target gene, a recognition RNA sequence, and optionally a terminal minihelix sequence and a second expression vector encoding a polypeptide comprising an RNA binding domain and one or more transport peptide sequences (i.e., selected from a cell penetrating peptide sequence, non-classical secretory domain, endosomal release domain, receptor binding domain, and fusogenic peptide) or a composition(s) comprising both expression vectors. The method can further comprise administering to the subject a further expression vector encoding a nucleic acid comprising one or more biologically active RNA sequences directed to a target gene(s), optionally a recognition RNA binding domain, and optionally a terminal minihelix sequence, wherein the target gene(s) is selected from Dicer and/or Drosha.

The invention also provides a method for modulating the expression of one or more target gene(s) in a subject comprising administering to the subject one or more bioreactor cells of the invention, or a composition thereof, wherein the bioreactor cell(s) produces and secretes an RNA-protein complex comprising one or more biologically active RNA sequences directed to a target gene(s), a recognition RNA sequence, and optionally a terminal minihelix sequence, an RNA binding domain sequence, one or more transport peptide (i.e., sequences selected from a cell penetrating peptide sequence, non-classical secretory domain, endosomal release domain, receptor binding domain, and fusogenic peptide).

The subject can be a mammalian subject, including, for example, a human, rodent, murine, bovine, canine, feline, sheep, equine, and simian subject. The biologically active RNA sequence can be a ribozyme, antisense nucleic acid, allozyme, aptamer, short interfering RNA (siRNA), double-stranded RNA (dsRNA), micro-RNA (miRNA), short hairpin RNA (shRNA), and a transcript encoding one or more biologically active peptides; the recognition RNA sequence can be a U1 loop, Group II intron, NRE stem loop, S1A stem loop, Bacteriophage Box BR, HIV Rev response element, AMVCP recognition sequence, and ARE sequence; the RNA binding domain can be a U1A, CRS1, CRM1, Nucleolin RBD12, hRBMY, Bacteriophage Protein N, HIV Rev, AMVCP, and tristetrapolin sequence; the cell penetrating peptide can be a penetratin, transportan, MAP, HIV TAT, Antp, Rev, FHV coat protein, TP10, and pVEC sequence; and the non-classical secretory domain can be a Galcetin-1 peptide, Galectin-3 peptide, IL-1α, IL-1β, HASPB, HMGB1, FGF-1, FGF-2, IL-2 signal, secretory transglutaminase, annexin-1, HIV TAT, Herpes VP22, thioredoxin, Rhodanese, and plasminogen activator signal nucleotide sequence. The bioreactor cell can be any of the bioreactor cells described herein.

The methods can be used to prevent, ameliorate, and/or treat a disease or condition associated with defective gene expression and/or activity in a subject. Suitable gene targets include, for example, Mmp2, Vascular Endothelial Growth Factor (VEGF), Vascular Endothelial Growth Factor Receptor (VEGFR), Cav-1, Epidermal Growth Factor Receptor (EGFR), H-Ras, Bcl-2, Survivin, FAK, STAT-3, HER-3, Beta-Catenin, and Src. The disorders associated with the defective expression of these genes are listed in Table V.

The invention also provides methods for modulating the expression of a target gene in a target cell ex vivo. In one embodiment, the invention provides a method for modulating the expression of a target gene in a target cell ex vivo comprising administering to the target cell ex vivo one or more expression vectors of the invention or a composition(s) thereof. In one specific embodiment, the method comprises the steps of: (a) obtaining target cells from a subject; (b) administering a composition comprising one or more expression vector(s) of the invention and a pharmaceutically acceptable carrier to the target cells of step (a), wherein the expression vector(s) encodes an RNA-protein complex of the invention; and (c) administering the cells in step (b) to said subject. In another embodiment, the invention provides a method for modulating the expression of a target gene in a target cell ex vivo comprising administering to the target cell ex vivo one or more bioreactor cells of the invention, or a composition thereof, wherein the method comprises the steps of: (a) obtaining target cells from a subject; (b) administering a one or more bioreactor cell(s) of the invention to the target cells of step (a), wherein the bioreactor cell(s) produces and secretes an RNA-protein complex of the invention; and (c) administering the cells in step (b) to said subject.

The invention also provides methods for modulating gene expression in a cell in culture comprising administering to the cell one or more expression vectors of the invention or a composition(s) thereof. Additionally, the invention provides a method for modulating the expression of one or more target gene(s) in a cell in culture comprising administering to the cell one or more bioreactor cells of the invention or a composition thereof.

Mechanism of Action for Viral Based Delivery Systems

The viral based RNA delivery system utilizes an engineered, replication competent or replication defective virus to deliver biologically active RNAs from transformed packaging cells to target cells. This system takes advantage of the capacity virus particles have to effectively deliver nucleic acids to the interior of target cells in vitro (Lund P E, et al., Pharm Res. 2009 Dec. 9; Koerber J T, et al., Mol. Ther. 2008 October; 16(10):1703-9; Cascante A, Gene Ther. 2007 October; 14(20):1471-80; Ring C J. J Gen Virol. 2002 March; 83(Pt 3):491-502; Parada C, et al., Cancer Gene Ther. 2003 February; 10(2):152-60; Tiede A, et al., Gene Ther. 2003 October; 10(22):1917-25; Lee Y J, Cancer Gene Ther. 2001 June; 8(6):397-404; Nestler U, et al., Gene Ther. 1997 November; 4(11):1270-7) and in vivo (Tseng J C, et al. Gene Ther. 2009 February; 16(2):291-6; Kikuchi E, et al., Clin Cancer Res. 2007 Aug. 1; 13(15 Pt 1):4511-8; Bourbeau D, et al., Cancer Res. 2007 Apr. 1; 67(7):3387-95; Hiraoka K, et al., Cancer Res. 2007 Jun. 1; 67(11):5345-53; Hiraoka K, et al., Clin Cancer Res. 2006 Dec. 1; 12(23):7108-16; Varghese S, et al., Cancer Res. 2007 Oct. 1; 67(19):9371-9; Varghese S, et al., Clin Cancer Res. 2006 May 1; 12(9):2919-27; Qiao J, et al., Gene Ther. 2006 October; 13(20):1457-70; Heinkelein M, et al., Cancer Gene Ther. 2005 December; 12(12):947-53). Many studies have demonstrated that viral delivery systems of siRNAs results in effective RNAi responses in vitro and in vivo (Anesti A M, et al., Nucleic Acids Res. 2008 August; 36(14):e86; Gorbatyuk M, et al., Vision Res. 2007 April; 47(9):1202-8; Scherr M, et al., Nucleic Acids Res. 2007; 35(22):e149; Chen W, et al., J. Virol. 2006 April; 80(7):3559-66; Raoul C, et al., Nat. Med. 2005 April; 11(4):423-8; Bromberg-White J L, et al., J. Virol. 2004 May; 78(9):4914-6; Scherr M, et al., Cell Cycle. 2003 May-June; 2(3):251-7). The present invention provides construct plasmid vectors (pVir) that produce virus particles (or pseudovirions) upon transfection into mammalian cells. These viruses carry biologically active RNAs targeting genes of interest as part of a partial viral genome, allowing for expression of those inhibitory sequences by either viral or host expression machinery. When viral packaging cells are added to target cells or tissues, the delivered RNAs can then modulate gene expression within each infected target cell. For replication competent virus, a suicide gene is added to the viral sequence such that viral replication can be inhibited by the addition of a prodrug. This allows use of the prodrug to prevent uncontrolled viral replication. For replication defective virus, virus particles are produced exclusively in the packaging cells for distribution to surrounding tissues; packaged viral genomes include the biologically active RNAs but lack the structural genes required for viral particle formation. This arrangement prevents uncontrolled replication of the virus. This system takes advantage of the highly efficient viral infection efficiency and replication machinery to deliver and amplify the inhibitory signal. As such, this approach is a direct compliment to our plasmid based bioreactor delivery system.

In order for the viral packaging cell to function as a delivery system, the viral particles must package and distribute a biological signal, for example an inhibitory signal. This biological signal could take the form of the biological RNA itself or a DNA molecule encoding the biological RNA. Backbone vectors for construction of viral based delivery systems therefore include both DNA and RNA viruses, the former including appropriate promoters and terminators for expression, the latter providing efficient Dicer substrates. RNA viruses need only deliver the partial viral genome (including the biological RNA) to the cytoplasm of the target cell; DNA viruses require delivery of the DNA genome to the nucleus for transcription of the biological RNA from the DNA template. Whereas cytoplasmic delivery can be more efficient with the RNA viruses, nuclear delivery provides opportunity for additional amplification as multiple biologically active RNAs can be produced from a single template molecule.

Viral packaging cells are generated by transfection of recipient cells with plasmids encoding for the two independent viral RNAs, one encoding the virus structural genes, the other encoding the non-structural genes and the biologically active RNA molecule. Successful co-transfection of both plasmids yields packaging cells capable of producing replication defective viral particles. Packaging of the DNA or RNA viral genome is driven by the natural viral process, as is the secretion from the packaging cell and import into the target cell. Once inside the target cell, cellular mechanisms take over the specific biological process depending on the identity of the particular biological molecule. This delivery system is capable of accommodating any of the biologically active RNAs described herein that act to modulate gene expression of the target cell.

Viral based delivery can be combined with protein based delivery in DNA viruses such that the initial transfection with pVir plasmids results in production of viruses carrying both the expression cassette for the biologically activeRNA and the expression cassette for the fusion protein. In this aspect, the viruses released from the viral packaging cells infect primary target cells and transform them into protein based bioreactor cells. These bioreactor cells then produce both the fusion protein and the biologically active RNA for secretion and distribution to secondary target cells. The expression cassettes for the biologically active RNA and the fusion protein can be any of the expression cassettes described herein.

Viral Backbones

Both DNA and RNA viruses are utilized as potential carriers for inhibitory signals. A number of commonly used viral vectors are appropriate for this type of application and have been characterized in both in vitro and in vivo applications as described above. Application of a particular viral system depends on the desired target cells and can vary from tumor specific delivery of the Sindbis virus particle through specific interactions with the overexpressed laminin receptor (Tseng J C, et al., Gene Ther. 2009 February; 16(2):291-6; Tseng J C, et al., J Natl Cancer Inst. 2002; 94: 1790-1802) to non-specific delivery to a broad spectrum of tissues as with the Foamy virus particle (Heinkelein M, et al., Cancer Gene Ther. 2005 December; 12(12):947-53; Falcone V, et al., Curr Top Microbiol Immunol. 2003; 277: 161-180). Biological RNAs are intergrated into the expression cassette for the non-structural viral genes for eventual packaging into the replication defective viral particles.

In cases where gene knockdown is needed but lysis of the target cell is undesirable, the use of replication defective viruses is appropriate. These viruses efficiently deliver their nucleic acid cargo to the interior of the cell, including the biological RNA template or molecule. However, given that the delivered nucleic acid does not contain a complete genome capable of producing new virus particles, there is no viral replication or subsequent cell lysis. In cases where lysis of the target cells is desirable, such as cancer cells, the use of replication competent oncolytic viruses may be most appropriate. These viruses are selectively replicated in cancer target cells leading to their eventual lysis (Ring C J, J Gen Virol. 2002 March; 83(Pt 3):491-502, Varghese S, et al., Cancer Res. 2007 Oct. 1; 67(19):9371-9; Varghese S, et al., Clin Cancer Res. 2006 May 1; 12(9):2919-27; Reinblatt M. et al., Surgery 2004; 136: 579-584). The use of viruses that are capable of infecting human cells but do not normally do so, such as viruses from other primates (Lund P E, et al., Pharm Res. 2009 Dec. 9; Lund P E, et al., Pharm Res. 2009 Dec. 9; Heinkelein M, et al., Cancer Gene Ther. 2005 December; 12(12):947-53; Falcone V, et al., Curr Top Microbiol Immunol. 2003; 277: 161-180), can be useful in avoiding neutralizing antibodies that can exist for viruses to which humans are natural hosts.

Application of Viral Packaging Cells In Vitro

Viral particles produced in viral packaging cells grown in vitro are ultimately released from the packaging cells into the culture media. These particles are routinely collected from growth media, concentrated and used as transfection reagents for biologically active RNAs (Heinkelein M, et al., Cancer Gene Ther. 2005 December; 12(12):947-53; Anesti A M, et al., Nucleic Acids Res. 2008 August; 36(14):e86; Gorbatyuk M, et al., Vision Res. 2007 April; 47(9):1202-8; Scherr M, et al., Nucleic Acids Res. 2007; 35(22):e149; Chen W, et al., J. Virol. 2006 April; 80(7):3559-66; Raoul C, et al., Nat. Med. 2005 April; 11(4):423-8; Bromberg-White J L, et al., J. Virol. 2004 May; 78(9):4914-6; Scherr M, et al., Cell Cycle. 2003 May-June; 2(3):251-7). It may be possible to infect target cells growing in culture without any processing of the media from the viral packaging cells, by physically separating the viral production and target cells yet allowing the two cultures to share a common media. This is achieved using inserts designed to fit in cell culture plates or by manual transfer of media from production to target cells. In this case, the identity of the packaging cells is optimized for virus production only. The viral backbone is chosen to optimize particle stability in the cell culture media and the highest possible titer without concentration.

Viral packaging cells are also be used to transfect cells growing in vitro by direct addition of the packaging cells to the target cells. In one aspect, the viral delivered biological RNAs (without intermediate concentration steps) are directly transferred using the described type of co-culturing of viral production cells and target cells transfected with reporter plasmids. The presence of a specific reporter requires no distinction of viral production and target cells and instead provides a direct readout of viral based delivery of the biologically active RNAs. When using viral systems to target endogenous genes, the readout for modulation of gene expression by the biologocally active RNA must be unique to the target cell and not shared by the viral production cell, similar to the experiments with the protein based bioreactor cells. Recipient cells for the viral delivery system are dictated by the identity of the target cells, so that species specific readout simplifies analysis of the mRNA and protein knockdown. The optimal ratio of viral packaging cells to target cells is determined empirically for each combination of target cells and target genes.

Modulation of Gene Expression In Vivo

Application of the viral packaging cells to in vivo systems follow methods of transkaryotic implantation developed for the overexpression of protein molecules in mouse model systems. As with the protein based bioreactor cells, an in vivo test system utilizing co-implantation of mouse tumor cell lines (SCCVII or Renka) with viral packaging cells of mouse origin (see Examples 29 and 30) is used. A mixture of these cell types is implanted into mice by subcutaneous injection into the rear flanks of the animal. Viral particles deliver shRNAs targeting VEGF or Mmp2. Activity is assayed by successful knockdown of the target gene in the region of implantation or by physiological effects on tumor growth and metastasis.

Viral packaging cells of mouse origin (NIH3T3 fibroblasts or mESCs) is also implanted into mice to assay viral secretion and delivery to surrounding mouse tissues. In this case, viral particles containing biologically active RNA molecules target the endogenous tissues of mouse models for human disease (see Examples 31-32). Relevant disease tissues are collected from each animal and target gene expression is assessed at the transcript level using RT-PCR or at the protein level using ELISA assays. Physiological assays of disease progression is also measured and compared among treated and non-treated control mice in order to assess both the function of the viral based delivery system and the efficacy of the gene target to treatment of the disease.

Kits

The invention further provides kits that can be used in the methods described herein. For example, the invention provides kits for constructing an expression vector, wherein the expression vector expresses an RNA-protein complex of the invention. In one embodiment, the kit comprises a first polynucleotide that encodes a nucleic acid molecule comprising a recognition RNA sequence and optionally a terminal minihelix sequence (hereinafter referred to as the "RNA sequence") and a second polynucleotide that encodes a polypeptide comprising an RNA binding domain and optionally one or more transport peptide sequences (selected from a non-classical secretory domain, a cell penetrating peptide, a receptor binding domain, and an endosomal release domain (hereinafter referred to as the "protein sequence"). In another embodiment, the kit additionally comprises a third polynucleotide that encodes a nucleic acid molecule comprising one or more biologically active RNA sequences targeted to Dicer and/or Drosha (hereinafter referred to as "Dicer/Drosha sequence").

Thus, in one embodiment, the kit further comprises one or more primer sequences for amplifying the polynucleotide encoding the RNA sequence (including the RNA binding sequence(s)). In one embodiment, the primer sequence(s) comprises one or more sequences complementary to the polynucleotide encoding the RNA sequence (including the RNA binding sequence(s)), one or more restriction enzyme site sequences, and optionally one or more sequences comprising at least four GC base pairs. In another embodiment, the kit additionally comprises a promoter sequence suitable for expressing the polynucleotide encoding the RNA sequence (including the RNA binding sequence(s)). In another embodiment, the kit additionally comprises a termination sequence suitable for expressing the polynucleotide encoding the RNA sequence (including the RNA binding sequence(s)). In another embodiment, the kit additionally comprises one or more primer sequences for amplifying the polynucleotide encoding the protein sequence. In one embodiment, the primer sequence(s) comprises one or more sequences complementary to the polynucleotide encoding the protein sequence, one or more restriction enzyme site sequences, and optionally one or more sequences comprising at least four GC base pairs. In another embodiment, the primer sequence(s) further comprises one or more initiation codon sequences and one or more translational start site sequences. In another embodiment, the kit additionally comprises a promoter sequence suitable for expressing the polynucleotide encoding the protein sequence. In another embodiment, the kit additionally comprises a termination sequence suitable for expressing the polynucleotide encoding the protein sequence.

In alternate embodiments, the kit comprises a polynucleotide comprising a recognition RNA sequence, optionally a terminal minihelix sequence, optionally one or more biologically active RNA sequences, one or more primer sequences, one or more promoter sequences and one or more termination sequences. In one embodiment, the polynucleotide comprises one or more biologically active RNA sequences, wherein the biologically active RNA is selected from a ribozyme, antisense nucleic acid, allozyme, aptamer, short interfering RNA (siRNA), double-stranded RNA (dsRNA), micro-RNA (miRNA), short hairpin RNA (shRNA), and a transcript encoding one or more biologically active peptides. The biologically active RNA can be targeted to any gene target of interest, including, for example, VEGF, VEGFR, MMP2, Cav-1, EGFR, H-RAs, Bc1-2, Survivin, FAK, STAT3, Her-3, Beta-catenin, hRET Receptor Tyrosine Kinase. In another embodiment, polynucleotide does not include a biologically active RNA sequence, which sequence is supplied by the individual user of the kit. In one embodiment, the primer sequence(s) comprises one or more sequences complementary to the polynucleotide encoding the RNA sequence (including the biologically active RNA), one or more restriction enzyme site sequences, and optionally one or more sequences comprising at least four GC base pairs. In another of the alternate embodiments, the kit further comprises a polynucleotide comprising an RNA binding domain, one or more sequences selected from a non-classical secretory domain, a cell penetrating peptide, a receptor binding domain, an endosomal release domain, one or more primer sequences, one or more promoter sequences, and one or more termination sequences. In one embodiment, the primer sequence(s) comprises one or more sequences complementary to the polynucleotide encoding the protein sequence, one or more restriction enzyme site sequences, optionally one or more sequences comprising at least four GC base pairs, one or more initiation codon sequences, and one or more translational start site sequences. In another alternate embodiment, the kit also comprises a polynucleotide comprising one or more biologically active RNA sequences targeted to Dicer and/or Drosha, one or more primer sequences, one or more promoter sequences and one or more termination sequences.

In any of the described kit embodiments, the polynucleotide encoding the RNA sequence (including the biologically active RNA) can comprise a sequence wherein the recognition RNA sequence, the individual biologically active RNA sequences, the optional terminal minihelix sequence, and any other included sequences are joined directly or are joined with the addition of one or more intervening or additional sequences. In any of the described kit embodiments, the polynucleotide encoding the protein sequence can comprise a sequence wherein the RNA binding domain and the non-classical secretory domain, cell penetrating peptide, receptor binding domain, and endosomal release domain sequences and any other included sequences are joined directly or are joined with the addition of one or more intervening or additional sequences. Thus, in certain embodiments, the kit additionally comprises linker sequences for joining the various sequences and domains of the polynucleotide encoding the RNA sequence and the polynucleotide encoding the protein sequence.

In any of the described kit embodiments, the recognition RNA sequence can be selected from a U1 loop, Group II intron, NRE stem loop, S1A stem loop, bacteriophage BoxBR, HIV Rev response element, AMVCP recognition sequence, and ARE sequence. In any of the described kit embodiments, the RNA binding domain can be selected from a U1A, CRS1, CRM1, Nucleolin RBD12, hRBMY, Bacteriophage Protein N, HIV Rev, AMVCP, and tristetrapolin sequence. In any of the described kit embodiments, the cell penetrating peptide can be selected from a penetratin, transportan, MAP, HIV TAT, Antp, Rev, FHV coat protein, TP10 and pVEC sequence. In any of the described kit embodiments, the non-classical secretory domain can be selected from Galcetin-1 peptide, Galectin-3 peptide, IL-1α, IL-1β, HASPB, HMGB1, FGF-1, FGF-2, IL-2 signal, secretory transglutaminase, annexin-1, HIV TAT, Herpes VP22, thioredoxin, Rhodanese, and plasminogen activator signal sequences. In any of the kit embodiments, the promoter is a Pol II promoter. Non-limiting examples of suitable Pol II promoters include, but are not limited to, Simian Virus 40 (SV40), Cytomegalovirs (CMV), β-actin, human albumin, human HIF-α, human gelsolin, human CA-125, ubiquitin, and PSA promoters. In another embodiment, the promoter is a Pol III promoter. Examples of suitable Pol III promoters include, but are not limited to, human H1 and human U6 promoters. Non-limiting examples of suitable termination sequences include, but are not limited to, the human growth hormone (hGH) polyadenylation sequence, the bovine growth hormone (BGH) polyadenylation sequence, the Simian Virus 40 (SV40) large T polyadenylation sequence, and the Herpes Simplex Virus Thymidine Kinase (HSV-tk) polyadenylation sequence.

In yet another embodiment, the kit further comprises one or more backbone vectors into which the polynucleotide encoding the RNA sequence (including the biologically active RNA) and/or the polynucleotide encoding the protein sequence and/or the polynucleotide encoding the Dicer/Drosha sequence can be inserted. In one embodiment, the polynucleotide encoding the RNA sequence is inserted into a first backbone vector and the polynucleotide encoding the protein sequence is inserted into a second backbone vector. In another embodiment, the polynucleotide encoding the RNA sequence and the polynucleotide encoding the protein sequence is inserted into a single backbone vector. In one embodiment, the polynucleotide encoding the Dicer/Drosha sequence can be inserted into a third backbone vector. In another embodiment, the polynucleotide encoding the Dicer/Drosha sequence can be inserted into the same vector as the polynucleotide encoding the RNA sequence. Non-limiting examples of suitable backbone vectors include pCI, pET, pSI, pcDNA, pCMV, etc. In any of the above embodiments, the backbone vector additionally comprises a pUC origin of replication. In one embodiment, the backbone vector additionally comprises one or more drug resistance genes selected from a kanamycin, ampicillin, puromycin, tetracycline, and chloramphenicol resistant genes, as well as any other drug resistant genes known and described in the art.

In other embodiments, the kit additionally comprises buffers, enzymes, and solutions useful for amplifying, cloning and/or expressing the polynucleotide encoding the RNA (including the biologically active RNA) sequence, the polynucleotide encoding the protein sequence, and the polynucleotide encoding the Dicer/Drosha sequence, including, for example, one or more restriction enzymes, phosphatases, kinases, ligases, and polymerases.

In another embodiment, the kit additionally comprises instructions for constructing the expression vectors, including, for example, polynucleotide sequence maps and plasmid maps.

In another embodiment, the kit additionally comprises materials for packaging the kits for commercial use.

In addition, the invention provides kits comprising expression vectors useful for modulating the expression of a target gene. The kit provides one or more expression vectors that produce an RNA-protein complex of the invention that can be used to modulate gene expression in vivo, ex vivo, and in vitro. In one embodiment, the kit comprises separate expression vectors for expressing the RNA portion of the RNA-protein complex and the fusion protein portion of the RNA-protein complex. One of the advantages of the kits comprising separate expression vectors for the RNA portion and the protein portion of the RNA-protein complex is that the activity of the biologically active RNA can be verified by transfecting the vector comprising the biologically active RNA into target cells. In the absence of the vector expressing the fusion protein, the gene-modulation of the vector expressing the biologically active RNA can be verified directly in the target cell. In another embodiment, the kit comprises a single expression vector for expressing the RNA-protein complex.

In one embodiment, the kit provides an expression vector comprising one or more biologically active RNA sequences directed to a target gene, a recognition RNA sequence, optionally a terminal minihelix sequence, one or more promoter sequences, one or more termination sequences, restriction enzyme sites, primer sequences, and optionally GC base pair sequences, wherein the biologically active RNA sequence(s), the recognition RNA sequence, and the optional terminal minihelix sequence are downstream of a promoter sequence. The biologically active RNA can be any biologically active RNA described herein or otherwise known in the art. The biologically active RNA sequence can be selected from a ribozyme, antisense nucleic acid, allozyme, aptamer, short interfering RNA (siRNA), double-stranded RNA (dsRNA), micro-RNA (miRNA), short hairpin RNA (shRNA), and a transcript encoding one or more biologically active peptides. The biologically active RNA can be targeted to any gene target of interest, including, for example, VEGF, VEGFR, MMP2, Cav-1, EGFR, H-RAs, Bcl-2, Survivin, FAK, STAT3, Her-3, Beta-catenin, hRET Receptor Tyrosine Kinase. In another embodiment, the expression vector does not include a biologically active RNA sequence, which sequence is supplied by the individual user of the kit. Thus, in one embodiment, the kit provides an expression vector comprising a recognition RNA sequence, optionally a terminal minihelix sequence, one or more promoter sequences, one or more termination sequences, restriction enzyme sites, primer sequences, and optionally GC base pair sequences, wherein the recognition RNA sequence and the optional terminal minihelix sequence are downstream of a promoter sequence. The restriction enzymes sites are located so as to provide convenient cloning sites for insertion of the user's biologically active RNA sequence. In another alternate embodiment, the kit also comprises a polynucleotide comprising one or more biologically active RNA sequences targeted to Dicer and/or Drosha, one or more primer sequences, one or more promoter sequences and one or more termination sequences.

In any of the above embodiments, the recognition RNA sequence can be selected from a U1 loop, Group II intron, NRE stem loop, S1A stem loop, Bacetriophage BoxB, HIV Rev response element, AMVCP recognition sequence, and ARE sequence. In one embodiment, the promoter sequence is a polIII promoter. Non-limiting examples of suitable polIII promoters include human U6 polIII promoter and human H1 polIII promoter. In one embodiment, the promoter sequence is a polII promoter. Non-limiting examples of suitable polII promoters include SV40, β-actin, human albumin, human HIF-α, human gelsolin, human CA-125, human ubiquitin, PSA, and cytomegalovirus (CMV) promoters. In one embodiment, the biologically active RNA sequence and the recognition RNA sequence are operably linked to the promoter sequence. In one embodiment, the termination sequence is a Pol-III polyT termination sequence.

In any of the above embodiments, the expression vector additionally comprises a pUC origin of replication. In any of the above embodiments, the expression vector additionally comprises one or more drug resistance genes. Examples of suitable drug resistant genes include, but are not limited to, kanamycin, ampicillin, puromycin, tetracycline, and chloramphenicol resistant genes, as well as any other drug resistant genes known and described in the art.

In one embodiment, the kit additionally comprises an expression vector comprising an RNA binding domain, and one or more sequences selected from a cell penetrating peptide, a non-classical secretory domain, a receptor binding domain, an endosomal release domain, and a fusogenic peptide, and additionally comprises one or more promoter sequences, one or more termination sequences, restriction enzyme sites, primer sequences, optionally GC base pair sequences, an initiation codon, and a translational start site, wherein the RNA binding domain and the cell penetrating peptide, non-classical secretory domain, receptor binding domain, endosomal release domain, and fusogenic peptide are downstream of the promoter sequence. In one embodiment, the promoter sequence is a Pol II promoter. Non-limiting examples of suitable polII promoters include SV40, β-actin, human albumin, human HIF-α, human gelsolin, human CA-125, human ubiquitin, PSA, and cytomegalovirus (CMV) promoters. The termination sequence can be a polyadenylation sequence, for example, a poly adenylation sequence derived from hGH. In certain embodiments, the RNA binding domain comprises an amino acid sequence selected from a U1A, CRS1, CRM1, Nucleolin RBD12, hRBMY, Bacteriophage Protein N, HIV Rev, AMVCP, and tristetrapolin amino acid sequence. In certain embodiments, the cell penetrating peptide comprises an amino acid sequence selected from a penetratin, transportan, MAP, HIV TAT, Antp, Rev, FHV coat protein, TP10, and pVEC amino acid sequence. In certain embodiments, the non-classical secretory domain comprises an amino acid sequence selected from Galcetin-1 peptide, Galectin-3 peptide, IL-1α, IL-1β, HASPB, HMGB1, FGF-1, FGF-2, IL-2 signal, secretory transglutaminase, annexin-1, HIV TAT, Herpes VP22, thioredoxin, Rhodanese, and plasminogen activator signal amino acid sequences.

In any of the above embodiments, the expression vector additionally comprises a pUC origin of replication. In one embodiment, the expression vector additionally comprises one or more drug resistance genes selected from a kanamycin, ampicillin, puromycin, tetracycline, and chloramphenicol resistant genes, as well as any other drug resistant genes known and described in the art.

In one embodiment, the kit can optionally further comprise an expression vector comprising one or more biologically active RNA sequences, optionally a terminal minihelix sequence, one or more promoter sequences, one or more termination sequences, restriction enzyme sites, primer sequences, and optionally GC base pair sequences, wherein the biologically active RNA sequence(s) and the optional terminal minihelix sequence are downstream of a promoter sequence and wherein the biologically active RNA sequence(s) are targeted to Dicer and/or Drosha. In certain embodiments, the biologically active RNA sequence is selected from a ribozyme, antisense nucleic acid, allozyme, aptamer, short interfering RNA (siRNA), double-stranded RNA (dsRNA), micro-RNA (miRNA), short hairpin RNA (shRNA), and a transcript encoding one or more biologically active peptides. In one embodiment, the promoter sequence(s) is a polIII promoter, including for example, a human U6 polIII promoter and human H1 polIII promoter. In one embodiment, the promoter sequence is a polII promoter, including, for example, SV40, β-actin, human albumin, human HIF-α, human gelsolin, human CA-125, human ubiquitin, PSA, and cytomegalovirus (CMV) promoters. In one embodiment, the termination sequence(s) is a Pol-III polyT termination sequence. In any of the above embodiments, the expression vector additionally comprises a pUC origin of replication. In one embodiment, the expression vector additionally comprises one or more drug resistance genes selected from a kanamycin, ampicillin, puromycin, tetracycline, and chloramphenicol resistant genes, as well as any other drug resistant genes known and described in the art.

In another embodiment, the kit additionally comprises instructions and materials for packaging the kits for commercial use.

Alternatively, the kit comprises a single expression vector encoding an RNA-protein complex of the invention. In one embodiment, the kit comprises an expression vector comprising a first expression cassette, a second expression cassette, and optionally a third expression cassette. The first expression cassette comprises one or more biologically active RNA sequences directed to a target gene(s), a recognition RNA sequence, optionally a terminal minihelix sequence, one or more promoter sequences, one or more termination sequences, restriction enzyme sites, primer sequences, and optionally GC base pair sequences, wherein the biologically active RNA sequence(s), the recognition RNA sequence, and the optional terminal minihelix sequence are downstream of a promoter sequence. In certain embodiments, the biologically active RNA sequence is selected from a ribozyme, antisense nucleic acid, allozyme, aptamer, short interfering RNA (siRNA), double-stranded RNA (dsRNA), micro-RNA (miRNA), short hairpin RNA (shRNA), and a transcript encoding one or more biologically active peptides. The target gene can be any target gene, including, for example, Mmp2, Vascular Endothelial Growth Factor (VEGF), Vascular Endothelial Growth Factor Receptor (VEGFR), Cav-1, Epidermal Growth Factor Receptor (EGFR), H-Ras, Bc1-2, Survivin, FAK, STAT-3, HER-3, Beta-Catenin, and Src gene targets. In certain embodiments, the recognition RNA sequence is selected from a U1 loop, Group II intron, NRE stem loop, S1A stem loop, Bacetriophage BoxBR, HIV Rev response element, AMVCP recognition sequence, and ARE sequence. In one embodiment, the promoter sequence is a polIII promoter, including, for example, a promoter selected from a human U6 polIII promoter and human H1 polIII promoter. In one embodiment, the promoter sequence is a polII promoter, including, for example, a promoter selected from an SV40, β-actin, human albumin, human HIF-α, human gelsolin, human CA-125, human ubiquitin, PSA, and cytomegalovirus (CMV) promoters. In one embodiment, the termination sequence is a Pol-III polyT termination sequence.

The expression vector of the kit further comprises a second expression cassette, wherein the second expression cassette comprises an RNA binding domain sequence, one or more sequences selected from a cell penetrating peptide, a non-classical secretory domain, a receptor binding domain, an endosomal release domain, and a fusogenic peptide, one or more promoter sequences, one or more termination sequences, restriction enzyme sites, primer sequences, GC base pair sequences, an initiation codon, and translational start site, wherein the RNA binding domain and the cell penetrating peptide, non-classical secretory domain, receptor binding domain, endosomal release domain, and fusogenic peptide are downstream of a promoter sequence. In certain embodiments, the RNA binding domain is selected from a U1A, CRS1, CRM1, Nucleolin RBD12, hRBMY, Bacteriophage Protein N, HIV Rev, AMVCP, and tristetrapolin sequence. In certain embodiments, the cell penetrating peptide is selected from a penetratin, transportan, MAP, HIV TAT, Antp, Rev, FHV coat protein, TP10, and pVEC amino acid sequence. In certain embodiments, the non-classical secretory domain is selected from a Galectin-1 peptide, Galectin-3 peptide, IL-1α, IL-1β, HASPB, HMGB1, FGF-1, FGF-2, IL-2 signal, secretory transglutaminase, annexin-1, HIV TAT, Herpes VP22, thioredoxin, Rhodanese, and plasminogen activator signal sequence. In one embodiment, the promoter sequence is a Pol II promoter, including, for example, a promoter selected from an SV40, β-actin, human albumin, human HIF-α, human gelsolin, human CA-125, human ubiquitin, PSA, and cytomegalovirus (CMV) promoters. In one embodiment, the termination sequence is a polyadenylation sequence. In one embodiment, the poly adenylation sequence is derived from hGH.

The expression vector of the kit optionally further comprises a third expression cassette, wherein the third expression cassette comprises one or more biologically active RNA sequences and optionally a terminal minihelix sequence, one or more promoter sequences, one or more termination sequences, restriction enzyme sites, primer sequences, and optionally GC base pair sequences, wherein the biologically active RNA sequence(s) and the optional terminal minihelix sequence are downstream of the promoter sequence. In certain embodiments of the above-described expression vectors, the biologically active RNA sequence is selected from a ribozyme, antisense nucleic acid, allozyme, aptamer, short interfering RNA (siRNA), double-stranded RNA (dsRNA), micro-RNA (miRNA), short hairpin RNA (shRNA), and a transcript encoding one or more biologically active peptides. In one embodiment, one or more of the biologically active RNA sequences is directed to Dicer and/or Drosha. In one embodiment, the promoter sequence is a polIII promoter. Non-limiting examples of suitable polIII promoters include human U6 polIII promoter and human H1 polIII promoter. In one embodiment, the promoter sequence is a polII promoter. Non-limiting examples of suitable polII promoters include SV40, β-actin, human albumin, human HIF-α, human gelsolin, human CA-125, human ubiquitin, PSA, and cytomegalovirus (CMV) promoters. In one embodiment, the biologically active RNA sequence is operably linked to the promoter sequence. In one embodiment, the termination sequence is a Pol-III polyT termination sequence.

The expression vector additionally comprises a pUC origin of replication. In one embodiment, the expression vector additionally comprises one or more drug resistance genes selected from a kanamycin, ampicillin, puromycin, tetracycline, and chloramphenicol resistant gene, as well as any other drug resistant genes known and described in the art.

In an alternate embodiment, the kit comprises an expression vector comprising a first expression cassette, a second expression cassette, and optionally a third expression cassette, wherein the first expression cassette comprises a recognition RNA sequence, optionally a terminal minihelix sequence, one or more promoter sequences, one or more termination sequences, restriction enzyme sites, primer sequences, and optionally GC base pair sequences, and wherein the recognition RNA sequence and the optional terminal minihelix sequence are downstream of a promoter sequence. The kit does not include a biologically active RNA sequence, which sequence is supplied by the individual user of the kit. The kit optionally comprises one or more primer sequences comprising restriction enzymes sites which can be ligated to the biologically active RNA sequence for convenient cloning into the expression vector. The second expression cassette and optional third expression cassette can be any of the second and third expression cassettes described above.

In an alternate embodiment, the kit comprises an expression vector comprising the second expression cassette and optionally the third expression cassette. The kit additionally comprises an isolated polynucleotide comprising a first expression cassette that can be ligated into the expression vector, wherein the first expression cassette comprises a recognition RNA sequence, optionally a terminal minihelix sequence, one or more promoter sequences, one or more termination sequences, restriction enzyme sites, primer sequences, and optionally GC base pair sequences, and wherein the recognition RNA sequence, and the optional terminal minihelix sequence are downstream of a promoter sequence. The kit does not include a biologically active RNA sequence, which sequence is supplied by the individual user of the kit. The kit optionally comprises one or more primer sequences which can be ligated to the biologically active RNA sequence for convenient insertion into the first expression cassette. The first expression cassette can then be cloned into the expression vector comprising the second expression cassette and the third expression cassette. The kit optionally comprises one or more primer sequences comprising restriction sites compatible with the expression vector which can be ligated to the first expression cassette for convenient cloning into the expression vector. The second expression cassette and third expression cassette can be any of the second and third expression cassettes described above. In embodiments wherein the expression vector comprises only the second expression cassette, the kit can additionally comprise an isolated polynucleotide comprising a third expression cassette that can be ligated into the expression vector. The third expression cassette can be any of the third expression cassettes described above. The kit optionally comprises one or more primer sequences comprising restriction sites compatible with the expression vector which can be ligated to the third expression cassette for convenient cloning into the expression vector.

In any of these embodiments, the expression vector additionally comprises a pUC origin of replication. In one embodiment, the expression vector additionally comprises one or more drug resistance genes selected from a kanamycin, ampicillin, puromycin, tetracycline, and chloramphenicol resistant gene, as well as any other drug resistant genes known and described in the art.

The invention also provides a kit comprising one or more bioreactor cells that produce an RNA-protein complex of the invention that can be used to modulate gene expression in vivo, ex vivo, and in vitro. The invention provides a solution of bioreactor cells that produce and secrete an RNA-protein complex comprising one or more biologically active RNA sequences, a recognition RNA sequence, optionally a terminal minihelix, an RNA binding domain sequence, and one or more sequences selected from a cell-penetrating peptide, non-classical secretory domain, endosomal release domain, receptor binding domain, and fusogenic peptide sequence. In one embodiment, the bioreactor cell produces an RNA-protein complex comprising one or more biologically active RNA sequences, a recognition RNA sequence, an optional terminal minihelix sequence, an RNA binding domain sequence, and a cell-penetrating peptide sequence. In another embodiment, the bioreactor cell produces an RNA-protein complex comprising one or more biologically active RNA sequences, a recognition RNA sequence, an optional terminal minihelix sequence, an RNA binding domain sequence, and a non-classical secretory domain sequence. In yet another embodiment, the bioreactor cell produces an RNA-protein complex comprising one or more biologically active RNA sequences, a recognition RNA sequence, an optional terminal minihelix sequence, an RNA binding domain sequence, a cell-penetrating peptide sequence, and a non-classical secretory domain sequence.

In certain embodiments of the above-described kits comprising bioreactor cells, the biologically active RNA sequence(s) is selected from a ribozyme, antisense nucleic acid, allozyme, aptamer, short interfering RNA (siRNA), double-stranded RNA (dsRNA), micro-RNA (miRNA), short hairpin RNA (shRNA), and a transcript encoding one or more biologically active peptides. The biologically active RNA sequence(s) can be targeted to any gene, including but are not limited to, Mmp2, Vascular Endothelial Growth Factor (VEGF), Vascular Endothelial Growth Factor Receptor (VEGFR), Cav-1, Epidermal Growth Factor Receptor (EGFR), H-Ras, Bcl-2, Survivin, FAK, STAT-3, HER-3, Beta-Catenin, and Src gene targets. In certain embodiments of the above-described cells, the recognition RNA sequence is selected from a U1 loop, Group II intron, NRE stem loop, S1A stem loop, Bacteriophage BoxBR, HIV Rev response element, AMVCP recognition sequence, and ARE sequence. In certain embodiments of the above-described cells, the RNA binding domain is selected from a U1A, CRS1, CRM1, Nucleolin RBD12, hRBMY, Bacteriopage Protein N, HIV Rev, AMVCP, and tristetrapolin sequence. In certain embodiments of the above-described cells, the cell penetrating peptide comprises a sequence selected from a penetratin, transportan, MAP, HIV TAT, Antp, Rev, FHV coat protein, TP10, and pVEC amino acid sequence. In certain embodiments of the above-described cells, the non-classical secretory domain comprises a sequence selected from a Galcetin-1 peptide, Galectin-3 peptide, IL-1α, IL-1β, HASPB, HMGB1, FGF-1, FGF-2, IL-2 signal, secretory transglutaminase, annexin-1, HIV TAT, Herpes VP22, thioredoxin, Rhodanese, and plasminogen activator signal sequence.

Non-limiting examples of suitable cells include NIH 3T3, Cos-1, Cos-7, SCCVII, HEK293, PC-12, Renka, A549, CT26, CHO, HepG2, Jurkat, and HeLa cells, as well as any other cells known and described in the art.

It will be clear that the invention may be practiced otherwise than as particularly described in the foregoing description and the following examples. Numerous modifications and variations of the invention are possible in light of the teachings herein and, therefore, are within the scope of the appended claims.

EXAMPLES

Example 1

General Construction of a Bioreactor Plasmid of the Invention

Expression vectors are constructed from isolated plasmid backbones and PCR amplified expression cassettes for both the RNA (sec-RNA) and protein (fusion protein) components. Examples of suitable backbone vectors include those derived from pCI, pET, pSI, pcDNA, pCMV, etc. The expression vector should include at least the following components: an origin of replication for preparation in bacteria, an antibiotic selectable marker, a promoter for RNA expression (Pol-II or Pol-III), a terminator sequence appropriate to the promoter sequence, a promoter for fusion protein expression and a poly-A tail sequence. One example of a suitable backbone vector is selected from the various pEGEN backbone vectors described herein, which are derived from pSI (Promega, product #E1721), pCI (Promega, product #E1731), pVAX (Invitrogen, product #12727-010) and other in house constructs. The pEGEN vectors, e.g. pEGEN 1.1, pEGEN 2.1, pEGEN 3.1, and pEGEN 4.1, contain a pUC origin of replication and a kanamycin resistance gene allowing the vector to be replicated in bacteria and cultured in the presence of kanamycin. Other suitable backbone vectors are well-known and commercially available, for example, pCI, pSI, pcDNA, pCMV, etc. The pEGEN vector is transformed into XL1-Blue competent cells via standard heat shock methods. Transformed cells are selected by growth on LB-Kanamycin plates, individual colonies are used to seed 5 mL LB-Kanamycin liquid cultures and grown overnight at 37° C. Resulting cultures are used to prepare purified plasmid stocks using standard methods.

Expression cassettes for the protein components of the bioreactor plasmid are prepared by PCR amplification of the relevant sequences from cDNA clones using the appropriate forward and reverse primers. Primers typically include sequences complementary to the domain(s) of interest (e.g., RNA binding domain, cell penetrating peptide, non-classical secretory domain, endosomal release domain, receptor binding domain, fusogenic peptide, etc.), sites for restriction enzymes used in the subcloning, and at least four GC base pairs at the 5' end of each primer to facilitate digestion with restriction enzymes. Other useful primers can include sequences complementary to the domain(s) of interest (e.g., RNA binding domain, cell penetrating peptide, non-classical secretory domain, endosomal release domain, receptor binding domain, fusogenic peptide, etc.), sites for restriction enzymes used in the subcloning, and 15 bases of vector sequence flanking the restriction site for use in recombination cloning (In-fusion Advantage PCR cloning kit, Clontech, Catalog #639620). Other suitable primers include sequences complementary to the protein domain(s), sites for restriction enzymes used in subcloning and six GC base pairs at the 5' end of each primer. Initiation codons and optimized Kozak translational start sites are added to each primer corresponding to the 5' end of the transcript to promote translation of the N-terminal domains of each fusion protein. Restriction sites are added to the primer corresponding to the 3' end of the transcript to facilitate assembly of delivery domains with RNA binding domains. A typical PCR reaction contains 10 mM Tris-HCl pH 9.0, 50 mM KCl, 1.5 mM $MgCl_2$, 0.1% Triton X-100, 200 µM each dNTP, 1.0 µM sense primer, 1.0 µM antisense primer, 100 ng DNA template and 1.0 U of Taq polymerase per 50 µL reaction. Reactions are cycled through 3 temperature steps: a denaturing step at 95° C. for 30 seconds, an annealing step at 50° C. to 60° C. for 30 seconds and an elongation step at 72° C. for 1 minute. Typically, the total number of cycles ranges from 20 to 35 cycles depending on the specific amplification reaction.

Domains can be linked to one another directly or via sequences encoding alpha helical linker or other linker domains. These linkers provide separation between the two functional domains to avoid possible steric issues. In each case, restriction digestions of DNAs encoding each domain produce compatible ends for directional ligation. A typical restriction digestion contains 10 mM Tris (pH 8.0), 100 mM NaCl, 5 mM $MgCl_2$, 1 mM DTT, 0.1-1 unit of each restriction enzyme and 1 µg of DNA and is digested at 37° C. for 1 hour. Products are purified on 2% agarose gels run in 1×TAE and excised bands are recovered using Qiagen's Qiaex II gel purification system. These expression cassettes are cloned into the multiple cloning site of the pEGEN vector using restriction enzymes matching the insert of interest. A typical ligation reaction contains 30 mM Tris (pH 7.8), 10 mM $MgCl_2$, 10 mM DTT, 1 mM ATP, 100 ng DNA vector, 100 to 500 ng DNA insert, 1 unit T4 DNA ligase and is ligated overnight at 16° C. Another typical recombination reaction contains 1× In-fusion reaction buffer, 100 ng of linearized plasmid, 50-200 ng of insert, 1 unit of In-fusion enzyme, which is incubated first at 37° C. for 15 minutes and then at 50° C. for 15 minutes. This process places the expression cassette downstream of a strong Pol II promoter sequence and upstream of an hGH polyA signal sequence. As shown in FIGS. 5-7, the Pol II promoter for pEGEN 1.1 comprises an SV40 promoter, the Pol II promoter for pEGEN 2.1 comprises a chicken β-actin promoter, and the Pol II promoter for pEGEN 3.1 comprises a CMV promoter. Successful cloning of the PCR product into the plasmid vector can be confirmed with restriction mapping using enzymes with sites flanking the insertion point and with PCR using primers specific to the insert sequence (for example, see FIG. 15).

The vector comprising the fusion protein cassette can be can be used to transfect cells in combination with a vector comprising a Sec-RNA of the invention, described below.

Expression cassettes for the RNA components (e.g., recognition RNA sequence and biologically active RNA sequence, including, for example, ribozymes, antisense nucleic acids, allozymes, aptamers, short interfering RNA (siRNA), double-stranded RNA (dsRNA), micro-RNA (miRNA), short hairpin RNA (shRNA), and RNA transcript encoding a biologically active peptide) of the bioreactor plasmid are prepared by PCR amplification of the relevant sequences from RNA expressing plasmids using the appropriate forward and reverse primers. Primers include sequences complementary to the biologically active RNA sequence(s), sites for restriction enzymes used in subcloning and at least four GC base pairs at the 5' end of each primer to facilitate digestion with restriction enzymes. Other suitable primers can include sequences complementary to the domain(s) of interest (e.g., RNA binding domain, cell penetrating peptide, non-classical secretory domain, endosomal release domain, receptor binding domain, fusogenic peptide, etc.), sites for restriction enzymes used in the subcloning, and 15 bases of vector sequence flanking the restriction site for use in recombination cloning (In-fusion Advantage PCR cloning kit, Clontech, Catalog #639620). In one specific example, the primers include sequences complementary to the biologically active RNA sequence(s), sites for restriction enzymes used in subcloning and six GC base pairs at the 5' end of each primer. The recognition RNA sequence is added to the primer corresponding to the 5' end of the biologically active RNA sequence in order to generate the Sec-RNA expression construct. This expression construct is digested with appropriate restriction enzymes for subcloning into the pEGEN4.1 construct, which places the Sec-RNA expression cassette downstream from a strong Pol-III promoter sequence (the human U6 promoter for pEGEN4.1, and the human H1 promoter for pEGEN5.1) and upstream of a Pol III poly-T termination sequence. See FIG. 8. Alternatively, the expression construct is subcloned into the pEGEN5.1 construct, which places the Sec-RNA expression cassette downstream from the human H1 promoter sequence (Pol-III promoter) and upstream of a Pol III poly-T termination sequence. Alternatively, the Sec-RNA expression cassette can be subcloned into pEGEN1.1, 2.1, or 3.1, which places RNA expression under the control of the SV40, β-actin, and CMV Pol-II promoter, respectively, and terminates with a human GH polyadenylation signal. Alternatively, the Sec-RNA expression cassette can be subcloned into any of pEGEN 6.1-11.1.

The vector comprising the Sec-RNA expression cassette can be used to transfect cells in combination with a vector comprising a fusion protein of the invention, described above.

Successful cloning of the PCR product into the plasmid vector can be confirmed with restriction mapping using enzymes with sites flanking the insertion point and with PCR using primers specific to the insert sequence. For example, FIG. 15 shows restriction enzyme analysis (15 C and D) and PCR amplification analysis (15E) of a sec-RNA plasmid (15C) and fusion protein plasmids (15D and E). FIG. 15C shows the restriction enzyme analysis of the pE3.1 Sec-Reporter, in which a novel EcoNI restriction site is introduced with the RNA expressing insert. FIGS. 15D and 15E show the restriction enzyme and PCR analyses, respectfully, of two pE1 TAT-RBD plasmids. In FIG. 15C, Sec-Reporter (–) refers to the pE3.1 Sec-Reporter plasmid only and Sec-Reporter (+) refers to the pE3.1 Sec-Reporter plasmid with the sec-RNA expressing insert. In FIGS. 15D and 15E, p1.1 refers to the pE1.1 plasmid only, TAT(–) refers to the pE1.1 plasmid with the fusion protein insert comprising a TAT cell penetrating peptide fused to a Rev RNA binding domain, and TAT(+) refers to the pE1.1 plasmid with the fusion protein insert comprising a TAT cell penetrating peptide fused to a Protein N RNA binding domain. Restriction digestion of each plasmid with XcmI and AleI enzymes (which flank the site of insertion) allows agarose gel analyses which distinguishes between empty parent plasmid (a 99 by product) and successful subcloning of the insert (245 by product). PCR amplification of the insertion site using one primer annealing to the coding strand of the fusion protein insert and a second primer annealing to the non-coding strand of the polyA sequence produces a 416 by product for a properly oriented insert. Plasmid insert identity was confirmed through DNA sequencing.

In those embodiments of the invention wherein the Sec-RNA expressing cassette and the fusion protein cassette are in a single vector, the final subcloning step joins the fusion protein expressing cassette with the Sec-RNA expressing cassette into a single plasmid vector, the pBioR plasmid. In one embodiment, the Sec-RNA expression cassette (e.g., primers, promoter, recognition RNA sequence, biologically active RNA, and termination sequence) is ligated into the pEGEN plasmid comprising the fusion protein to generate the complete pBioR plasmid. Restriction sites flanking the expression cassette, as shown in for example, the Sec-RNA in pEGEN4.1 (FIG. 8) or pEGEN5.1 (not depicted) release the insert from the plasmid, which is then purified on 2% agarose gels run in 1×TAE and excised bands are recovered using, for example, Qiagen's Qiaex II gel purification system. The plasmid containing the expression cassette for the fusion protein is digested with the same restriction enzyme flanking the Sec-shRNA expression cassette. The Sec-RNA expression cassette is then ligated into the plasmid containing the fusion protein to generate the complete pBioR plasmid.

Example 2

Construction of a Bioreactor Plasmid pBioR(1) with a Sec-shRNA Delivered by a CPP-RBD Fusion Protein An expression vector capable of expressing a bioreactor fusion protein and a secreted shRNA (Sec-shRNA) is described here. Production and delivery of Sec-shRNAs targeting any of the gene targets listed in Table I and Table VII, as well as any other target mRNAs, is accomplished with the plasmid pBioR(1), which is constructed from two parent plasmids. The first parent plasmid, pEGENFP, expresses the fusion protein and is constructed by cloning a fusion protein cassette comprising an RNA binding domain sequence from Table III and a cell penetrating peptide sequence from Table IV into the multiple cloning site of a pEGEN vector from Table VIII using the plasmids and methods described in Example 1. In one embodiment, this process places the fusion protein cassette downstream of a strong Pol II promoter sequence (chicken β-actin promoter) and upstream of an hGH polyA signal sequence. The RNA binding domain and the cell penetrating peptide fusion protein can be assembled with or without alpha helical linker domains. This vector can be transfected into cells in combination with a pEGENSR vector.

The second parent plasmid, pEGENSR, expresses the secreted RNA and is constructed by cloning a secreted RNA cassette comprising an RNA recognition element from Table II and a biologically active RNA from Table I into the multiple cloning site of the pEGEN4.1 or pEGEN5.1 vector (see Table VIII) using the plasmids and methods described in Example 1. This process places the Sec-RNA cassette downstream from a Pol III promoter (a human U6 promoter for pEGEN4.1, a human H1 promoter for pEGEN5.1) and upstream of a Pol III poly-T termination sequence. This vector can be transfected into cells in combination with a pEGENFP vector. Alternatively, the expression cassette for this Sec-shRNA (e.g., primers, promoters, recognition RNA hairpin from Table II, shRNA, and Pol III poly-T termination sequence) is released from the pEGENSR plasmid with appropriate restriction enzymes and ligated into the pEGEN FP vector comprising the fusion protein to create the final plasmid pBioR(1).

Specific examples of various Sec-shRNAs delivered by various CPP-RBD fusion proteins are shown in Table I and further described in U.S. Ser. No. 61/160,287 and 61/160,288 (Examples 1-20), both of which are incorporated by reference herein in their entireties.

Also, a different biologically active RNA sequence, such as an antisense, ribozyme, aptamer, allozyme, siRNA, miRNA, or any of the other biologically active molecules described herein, can be used to substitute the shRNA sequence in the described pEGENSR vector.

Example 3

Construction of the Bioreactor Plasmid pBioR(2) with a Sec-shRNA Delivered by a CPP-NCS-RBD Fusion Protein Delivery of Sec-shRNAs targeting any of the gene targets from Table I and Table VII, as well as any other gene targets, is also accomplished with the plasmid pBioR(2), which is constructed using the same methods described in Examples 1 and 2. pBioR 2 encodes a fusion protein comprising a non-classical secretory domain from Table V fused to an RNA binding domain from Table III and a cell penetrating peptide from Table IV. This fusion protein is assembled with or without alpha helical linker or other linker domains. The expression cassettes for the fusion protein and the Sec-shRNA are ligated into the pEGEN plasmids from Table VIII using the methods described in Examples 1 and 2. Specific examples of various Sec-shRNAs delivered by various CPP-NCS-RBD fusion proteins are shown in Table I and further described in U.S. Ser. Nos. 61/160,287 and 61/160,288 (Examples 21-26), both of which are incorporated by reference herein in their entireties.

Example 4

Construction of the Bioreactor Plasmid pBioR(3) with a Sec-shRNA Delivered by a CPP-NCS-RBD Fusion Protein Delivery of Sec-shRNAs targeting any of the gene targets from Table I and Table VII, as well as any other gene targets, is also accomplished with the plasmid pBioR(3). The plasmid pBioR(3) is constructed using the same methods described in Example 1 for the construction of pBioR(1) and is similar to pBioR(2) except that it contains an additional expression cassette encoding an shRNA molecule targeting the Dicer protein of the bioreactor cell. The shRNA targeting Dicer has the following sequence: TTGGCTTCCTCCTGGTTATGT-TCAAGAGACATAACCAGGAGGAAGCCAA. The expression cassettes for the fusion protein and the Sec-shRNA are ligated into the pEGEN plasmids from Table VIII using the methods described in Examples 1 and 2. The shRNA targeting Dicer is expressed from the human H1 promoter and ends with a Pol-III poly-T terminator. An example of a plasmid having an additional cassette encoding an shRNA molecule targeting the Dicer protein is shown in FIGS. 13.

Example 5

Construction of the Bioreactor Plasmid pBioR(14) with a Sec-shRNA Delivered by a NCS-RBD-CPP Fusion Protein Delivery of Sec-shRNAs targeting any of the gene targets from Table I and Table VII, as well as any other gene targets, is accomplished with the plasmid pBioR(14). The plasmid pBioR(14) is constructed using the same methods described in Examples 1 and 2 for the construction of pBioR(1) and is similar to pBioR(2) except for the location of the expression cassette for the Sec-shRNA. The Sec-shRNA accompanies a fusion protein comprising a non-classical secretory domain from Table V fused to an RNA binding domain from Table III and a cell penetrating peptide from Table IV. In this plasmid, the Sec-shRNA is encoded within an artificial intron placed in either the 5' untranslated region (UTR) or within the coding sequence for the fusion protein. The Sec-shRNA sequence is subcloned between the splice donor and splice acceptor sites of the artificial intron using appropriate restriction sites. This multifunctional transcript is expressed from the chicken β-actin promoter and terminates with a human growth hormone polyadenylation signal. Examples of plasmids having this type of construction are shown in FIGS. 11 and 12.

Example 6

Construction of the Bioreactor Plasmid pBioR(15) with a Sec-Ribozyme Delivered by a NCS—RBD-CPP Fusion Protein Delivery of Sec-ribozymes targeting any of the gene targets listed in Table I and Table VII, as well as any other gene targets, is accomplished with the plasmid pBioR(15), constructed using the same methods described in Examples 1 and 2 for the construction of pBioR(1) encoding a fusion protein comprising a non-classical secretory domain from Table V fused to an RNA binding domain from Table III and a cell penetrating peptide from Table IV. The Sec-ribozyme that accompanies this particular fusion protein comprises an RNA recognition element from Table II and a RNA ribozyme that targets any of the mRNA transcripts of the gene targets listed in Table I and Table VII. The expression cassettes for the fusion protein and the Sec-ribozyme are ligated into the pEGEN2.1 plasmid. The fusion protein is expressed from the chicken β-actin promoter and terminates with a human growth hormone polyadenylation signal and the Sec-Ribozyme is expressed from the human U6 promoter and ends with a Pol-III poly-T terminator. Specific examples of expression vectors for Sec-ribozyme RNAs and CPP-NCS-RBD fusion proteins are described in U.S. Ser. Nos. 61/160,287 and 61/160,288 (Examples 39 and 40), both of which are incorporated by reference herein in their entireties.

Example 7

Construction of the Bioreactor Plasmid pBioR(16) with a Sec-Antisense RNA (Sec-asRNA) Delivered by an NCS-RBD-CPP Fusion Protein Delivery of Sec-asRNAs targeting any of the gene targets listed in Table I and Table VI, as well as any other gene targets, is accomplished with the plasmid pBioR(16), constructed using the same methods described in Examples 1 and 2 for the construction of pBioR(1) encoding a fusion protein comprising a non-classical secretory domain from Table V fused to an RNA binding domain from Table III and a cell penetrating peptide from Table IV. The Sec-asRNA that accompanies this particular fusion protein comprises an RNA recognition element from Table II and an antisense RNA complementary to any of the mRNA transcripts of gene targets listed in Table I and Table VII. The expression cassette for the fusion protein is ligated into the pEGEN2.1 plasmid and is expressed from the chicken β-actin promoter and terminates with a human growth hormone polyadenylation signal. The expression cassette for the Sec-asRNA is ligated into the pEGEN1.1 plasmid and is expressed from the SV40 promoter and terminates with a human growth hormone polyadenylation signal. The expression cassette for this Sec-asRNA (primers, U6 promoter, recognition RNA hairpin from Table II, asRNA, and Pol III poly-T termination sequence) is released from the pEGEN1.1 plasmid with appropriate restriction enzymes and ligated into the pEGEN 2.1/FP vector comprising the fusion protein to create the final plasmid pBioR(16) as described in Example 2. Specific examples of expression vectors for Sec-asRNAs and CPP-NCS-RBD fusion proteins are described in U.S. Ser. Nos. 61/160,287 and 61/160,288 (Examples 41 and 42), both of which are incorporated by reference herein in their entireties.

Example 8

Construction of the Bioreactor Plasmid pBioR(17) with a Sec-Antisense RNA (Sec-asRNA) Delivered by an NCS-RBD-CPP Fusion Protein Delivery of Sec-asRNAs targeting any of the gene targets from Table I and Table VII, as well as any other gene targets, is accomplished with the plasmid pBioR(17), constructed using the same methods described in Examples 1 and 2 for the construction of pBioR(1) encoding a fusion protein comprising a non-classical secretory domain from Table V fused to an RNA binding domain from Table III and a cell penetrating peptide from Table IV. The Sec-asRNA that accompanies this particular fusion protein comprises an RNA recognition element from Table II and an antisense RNA complementary to any of the mRNA transcripts of the gene targets listed in Table I and Table VII. The expression cassette for the fusion protein and the Sec-asRNA are ligated into the pEGEN2.1 plasmid and is expressed from the chicken β-actin promoter and terminated with a human growth hormone polyadenylation signal. In this plasmid, the Sec-asRNA is encoded within an artificial intron placed either in the 5' untranslated region (UTR) or within the coding sequence for the fusion protein. This multifunctional transcript is expressed from the chicken β-actin promoter and terminates with a human growth hormone polyadenylation signal.

Example 9

Construction of the Bioreactor Plasmid pBioR(18) with a Sec-Aptamer Secreted by a NCS-RBD Fusion Protein Delivery of Sec-aptamer targeting extracellular receptor proteins listed in Table I and Table VII, as well as any other extracellular receptor proteins, is accomplished with the plasmid pBioR(18), constructed using the same methods described in Examples 1 and 2 for the construction of pBioR (1), encoding a fusion protein comprising a non-classical secretory domain from Table V fused to an RNA binding domain from Table III. The Sec-aptamer that accompanies this particular fusion protein comprises an RNA recognition element from Table II and an aptamer sequence that targets any of the extracellular receptor proteins listed in Table I and Table VII. The expression cassettes for the fusion protein and the Sec-aptamer are ligated into the pEGEN2.1 plasmid. The fusion protein is expressed from the chicken β-actin promoter and terminates with a human growth hormone polyadenylation signal and the Sec-aptamer is expressed from the human U6 promoter and ends with a Pol-III poly-T terminator.

Specific examples of expression vectors for Sec-Aptamers and NCS-RBD fusion proteins are described in U.S. Ser. Nos. 61/160,287 and 61/160,288 (Examples 43 and 44), both of which are incorporated by reference herein in their entireties.

Example 10

Construction of the Bioreactor Plasmid pBioR(19) with a Sec-Aptamer Secreted by a NCS-RBD-CPP Fusion Protein Delivery of Sec-aptamer targeting any of the cellular proteins listed in Table I and Table VII, as well as any other cellular proteins, is accomplished with the plasmid pBioR (19), constructed using the same methods described in Examples 1 and 2 for the construction of pBioR(1) encoding a fusion protein comprising a non-classical secretory domain from Table V fused to an RNA binding domain from Table III and a cell penetrating peptide from Table IV. The Sec-aptamer that accompanies this particular fusion protein comprises an RNA recognition element from Table II and an aptamer sequence that targets any of the intracellular proteins listed in Table I and Table VII. The fusion protein and Sec-aptamer are constructed the same way and are expressed from the same promoters as described in Examples 1 and 2 for pBioR(1).

Specific examples of expression vectors for Sec-Aptamers and CPP-NCS-RBD fusion proteins are described in U.S. Ser. Nos. 61/160,287 and 61/160,288 (Examples 45 and 46), both of which are incorporated by reference herein in their entireties.

Example 11

Administration of Bioreactor Plasmids to Hela Cells in Culture Using Polymer Mediated Transfection.

Bioreactor cells are generated by co-transfecting pEGENFP and pEGENSR (see Example 2) into a recipient cell line, for example HeLa cells, in vitro. HeLa cells are cultured in six-well plates in DMEM+10% fetal bovine serum (2 mL total volume) to a density of 80% confluence in preparation for transfection by a polymeric delivery agent. Growth media is removed from the cells and replaced with 1 mL of DMEM only (no serum) preheated to 37° C. Transfection complexes are formed between the delivery reagent and the pBioR plasmid by incubation in DMEM at room temperature for 20 minutes (DNA and reagent concentrations optimized for each application). Transfection complexes are added to the HeLa cells by dropwise addition to the each culture and returned to the 37° C. incubator. After a five hour incubation, DMEM+20% serum is added to the transfection media to produce a final concentration of 10% serum and a final volume of 2 mL. Transiently transfected cells are ready for use as BioReactors by addition to target cells.

Example 12

Administration of Bioreactor Plasmid to Cells in Culture Using Polymer Mediated Transfection BioReactor cells are generated by transfecting a pBioR plasmid (any plasmid described elsewherein the application and in the previous examples) into a recipient cell line in vitro. Transfection protocols for generation of transiently transfected BioReactor cells are similar to those described in Example 11 for the generation of BioReactors based on HeLa cells. Non-limiting examples of suitable recipient cells in culture include A549 cells, Jurkat cells, HepG2 cells, NIH3T3 cells, Renka cells, CT26 cells, PC-12 cells, Cos-1 cells, Cos-7 cells, and CHO cells. The methods described in Example 11 can be applied to these cells in culture, as well as to other known established cell lines.

Example 13

Administration of Bioreactor Plasmid to Hela Cells in Culture Using Electroporation Mediated Transfection BioReactor cells are produced from HeLa recipient cells by transfection with the pBioR plasmid by electroporation. HeLa cells are cultured in 100 mm culture dishes in DMEM+ 10% fetal calf serum (15 mL total volume) to a density of 80% confluence in preparation for electroporation. Cells are released from the wells with trypsin and collected by centrifugation (500×g for 5 minutes at 4° C.). The cell pellet is resuspended in growth medium and the cell density is measured using a hemocytometer; the final volume is adjusted with growth medium to yield $5 \times 10^6$ cells/mL. The cells are transferred to the electroporation cuvette along with 20 ug of the pBioR plasmid and placed in between the electrodes. The electroporator is discharged at 260V (Capacitance=1000 μF, infinite internal resistance) and the cuvette is allowed to rest for 2 minutes. Electroporated cells are then transferred to a culture dish along with two rinses of the cuvette with growth medium. Cells are grown at 37° C. under 5% $CO_2$ for 48 hours.

BioReactor cells are produced from other recipient cells by transfection with the pBioR plasmid as described above for the generation of BioReactors based on HeLa cells. Non-limiting examples of suitable recipient cells in culture include A549 cells, Jurkat cells, HepG2 cells, NIH3T3 cells, Renka cells, CT26 cells, PC-12 cells, Cos-1 cells, Cos-7 cells, and CHO cells. Assays that demonstrate function of the BioReactor cell are as described in Example 16.

Example 14

Administration of Bioreactor Plasmid to Hela Cells in Culture Using Viral Mediated Transfection Viral vectors are constructed from isolated plasmid backbones, expression cassettes for the structural and non-structural components of the virus and expression cassettes for the biologically active RNA. PCR amplification of expression cassettes, subcloning of expression cassettes into plasmid backbones, amplification and isolation of the resulting virus producing vectors and subsequent verification of plasmid sequences are all carried out as described in Example 1. Viral vectors are constructed from one of several DNA viral expression cassettes such as Adenovirus and Adeno-associated virus (2-3, 7, 11, 19, 21) and Herpes Simplex Virus (5, 14-15, 18) or RNA viral expression cassettes such as Lentivirus (6, 20, 22, 24), Sindbis Virus (9), Murine Leukemia Virus (10, 12-13, 16) or Foamy Virus (8, 17) and any of the biologically active RNA molecules described elsewhere in the application and in the previous examples. For each virus, the structural genes encoding viral coat proteins and fusogenic proteins are subcloned into any of the pEGEN backbone plasmids for expression from a Pol-II promoter sequence generating pVir1. Separately, the non-structural genes encoding the polymerases and accessory proteins are coupled with the biologically active RNA sequence and fusion protein sequence and subcloned into a second pEGEN plasmid for expression from a Pol-II promoter sequence generating pVir2. Plasmids pVir1 and pVir2 are co-transfected into recipient cells to generate virus producing cells. Virus particles can then be purified and concentrated for use in administration of the bioreactor expression cassettes to bioreactor cells.

Example 15

Administration of Bioreactor Plasmid to Hela Cells in Culture Using Polymer Mediated Transfection and Generation of Stable Cell Lines BioReactor cells are produced from HeLa recipient cells by transfection with the pBioR plasmid as described in Examples 11-14. Stable integration of the pBioR plasmid into the recipient cell genome is achieved by extended growth in selective media. pBioR plasmids for stable integration contain a puromycin resistance gene or a G418/Neomycin resistance gene in addition to the pUC origin and kanamycin resistance gene. Newly transfected cells are allowed to recover in complete, non-selective media for 48 hours. These cells are then transferred to selective media and grown at 37° C. under 5% CO2 with media changes every 3 days. Individual isolates of cells with stably integrated plasmids are moved to individual wells and expanded. These expanded cell lines are then assayed for optimal bioreactor activity. Assays that demonstrate function of the BioReactor cell are as described in Example 16.

Example 16

Assays for Confirming the Production and Secretion of the RNA-Protein Complex in Cell Culture Cells are transfected with a pBioR expression vector or a null vector using the methods described in Examples 11-14. Successful generation of BioReactor cells is confirmed by assays that verify one or more of the following: (1) production of the fusion protein, (2) production of the Sec-RNA, (3) binding of the Sec-RNA by the fusion protein and (4) successful secretion of the RNA-protein complex. Production of the fusion protein can be verified through RT-PCR based assays that detect the plasmid derived mRNA transcript encoding the fusion protein and antibody based assays that detect the fusion protein itself. For purposes of detecting the fusion protein, short "protein tags" which are recognized by commercially available antibodies, can be included in the sequence of the fusion protein. These protein tags are used to verify the function of the BioReactor cell and are not necessarily included in the functional BioReactor fusion proteins.

To detect the plasmid derived mRNA transcript, total RNA is prepared from pBioR-transfected, null vector-transfected, and non-transfected cells, i.e., HeLa cells or any of the other cells described herein and otherwise known in the art, using Tri-Reagent (Sigma-Aldrich, product #T9424) according to the manufacturer's protocols. A cDNA library is prepared from the total RNA using a poly-T primer and used as template for the PCR amplification. Primers for two separate amplification reactions, each producing a different size product, are included in the PCR reactions: (1) Primers amplifying sequences from an internal control gene, such as β-actin or GAPDH, and (2) Primers amplifying sequences specific to the mRNA encoding the fusion protein. Products are resolved on 2% agarose gels run in 1×TAE or on 10% acrylamide gels run in 1×TBE. Products are compared for the non-transfected cells (negative control), cells transfected with a null vector (backbone vector without the fusion protein), and the potential BioReactors (i.e., cells transfected with a pBioR) through staining with ethidium bromide and illumination with UV light at 302 nm. Non-transfected control cells have a single PCR product for the internal control gene while successful BioReactors have products for both the internal control gene and the transcript encoding the fusion protein.

Direct detection of the fusion protein is accomplished by collection of total protein from pBioR-transfected, null vector-transfected, and non-transfected cells, as well as the media in which those cells are growing. Total protein is concentrated from each sample by acetone precipitation and the concentrated proteins are resuspended in either a native buffer for ELISA analysis or denaturing buffer for western blot analysis. Each assay utilizes standard methods and antibodies specific for an internal control gene (β-actin or GAPDH) and a protein tag present in the fusion protein. As discussed, protein tags are included in the fusion proteins as a convenient means for verifying function of the BioReactor cell. Non-transfected and null vector-transfected control cells have a single protein detected for the internal control gene while successful BioReactors have both the internal control protein and the fusion protein.

Successful production of the Sec-RNA includes both transcription of the RNA and export of that transcript from the nucleus. RT-PCR assays are used to show production of the plasmid derived Sec-RNA molecule and cellular fractionation is used to demonstrate accumulation of the RNA in the cytoplasm. The cellular fractionation is accomplished with the PARIS RNA isolation kit (Ambion, Product #1921) according to the manufacturer's protocol. A cDNA library is prepared from the fractionated RNA using a random hexamer non-specific primer and is used as template for the PCR amplification. Primers for two separate amplification reactions, each producing a different size product, are included in the PCR reactions: (1) Primers amplifying sequences from an internal control gene, such as β-actin or GAPDH, and (2) Primers amplifying sequences specific to the Sec-RNA. Products are resolved on 2% agarose gels run in 1×TAE or on 10% acrylamide gels run in 1×TBE. Products are compared for the null vector-transfected and non-transfected cells (negative controls) and the potential BioReactors through staining with ethidium bromide and illumination with UV light at 302 nm. Null vector-transfected and non-transfected control cells have a single PCR product for the internal control gene while successful BioReactors have products for both the internal control gene and the Sec-RNA.

FIG. 16 shows the results of experiments to confirm the expression of Sec-RNA and the fusion protein. For the secreted RNA reporter transcript analyses shown in FIG. 16A, CT26 cells were transfected with pE3.1 Sec-Reporter (FIG. 15A). After 48 hours, total cellular RNA was collected from untransfected control cells and transfected bioreactor cells using Quigen's RNEasy kit according to the manufacturer's recommended protocol and purified RNA was amplified using RT-PCR and separated on 3% low melt agarose gels (1×TAE). RT-PCR reactions for the sec-RNA included probes and primers for amplifying both 18S rRNA (internal control, 196 by product) and the secreted RNA reporter (100 by product). Untransfected control cells ("U") show only the 18S rRNA internal control (18S) whereas the transfected cells show both the 18S rRNA product and the parent reporter RNA product ("R"), which corresponds to the plasmid only, or the secreted reporter RNA product ("SR"), which corresponds to the plasmid and the Sec-RNA sequence insert. FIG. 16B shows the fusion protein expression analyses, in which CT26 cells were transfected with plasmids expressing the bioreactor fusion protein. After 48 hours, the cells were harvested in TENT buffer, boiled for 5 minutes, spun at 16,000×G for 15 minutes to remove the cellular debris and allow for collection of the cell lysate (total protein). Aliquots of cell lysates from untransfected cells and cells transfected with pE3.1 Sec-Reporter and either pE1.1 TAT+(TAT fused to a Protein N RNA binding domain and 6× Histidine epitope tage) or pE2.1TAT+ (TAT fused to a Protein N RNA binding domain and 6× Histidine epitope tag) were spotted to PVDF membranes along with a positive control protein for the blotting antibody. The blots were developed with chromogenic substrates and recorded with an image documentation center.

Binding of the Sec-RNA molecule by the fusion protein is demonstrated by immunoprecipitation of the RNA-protein complex via the peptide tags described above. Antibodies specific for an internal control gene (β-actin or GAPDH) or the protein tag present in the fusion protein are coupled to protein-A sepharose (PAS) beads or protein-G sepharose (PGS) beads. Beads are rehydrated in cell lysis buffer and antibodies are coupled by incubation with beads at 4° C. overnight. A non-specific antibody, often a preimmune serum, is used as a negative control for the immunoprecipitation assay. The antibody coupled beads are spun out of solution (1500×g for 5 minutes), the supernatant is removed, and the antibody coupled beads are washed with cell lysis buffer. Proteins are prepared from pBioR-transfected, null vector-transfected, and non-transfected cells, as well as the media in which those cells are growing The proteins are collected in native cell lysis buffers in order to preserve the RNA-protein complexes, the precise composition of which is adjusted to the specific purification. A typical cell lysis buffer composition is 20 mM Tris (pH 7.5), 150 mM NaCl, 1 mM EDTA, and 0.05% Nonidet P-40. Protein extracts are added to the antibody coupled beads and the immunoprecipitation is carried out under conditions optimized for each reaction. Typical precipitations are incubated at room temperature for 2 to 4 hours. Isolated RNA-protein complexes are spun out of solution and the supernatant is collected as the precipitation input. The beads are washed repeatedly to remove non-specifically bound proteins; the total number of washes is empirically determined for each precipitation. Isolated complexes are eluted from the beads with a peptide matching that of the fusion protein tag which competes for the binding sites present on the antibody. Isolated RNAs are then detected by northern blotting or by RT-PCR as described above.

Successful secretion of the RNA-protein complex is verified by detection of the Sec-RNA in the extracellular matrix, or media in the case of cells in culture. Intact RNA-protein complexes may be isolated from the media via immunoprecipitation, as described above, or total RNA may be prepped using Tri-Reagent in accordance with the manufacturer's protocol (Sigma-Aldrich, product #T9424). The Sec-RNA is detected by northern blotting or by RT-PCR as described above.

FIG. 17 shows the results of an experiment to confirm the secretion of an RNA-protein complex from a bioreactor cell. Total cellular RNA from untransfected control CT26 cells and CT26 cells transfected with the pE3.1 Sec-Reporter and pE1TAT-RBD plasmids expressing the secreted RNAs and the bioreactor fusion proteins was collected after 48 hours transfection using Qiagen's RNEasy kit according to the manufacturer's recommended protocol. RNA was also collected from the cell culture media and purified using the RNAeasy kit. The purified RNA was used as template for RT-PCR amplification reactions and the amplified products were separated on 3% low melt agarose gels (1×TAE) along with DNA size standards. RT-PCR was carried out with probes and primers for both 18S rRNA (internal control) and the secreted RNA reporter. FIGS. 17A and 17B show the results of a transfection assay with pE3.1 Sec-Reporter and either pE1.1 TAT(+) (TAT fused to the proper RBD) or pE1.1 TAT(−) (TAT fused to a negative control RBD). The left hand panel of FIG. 17A shows RT-PCR products for cell lysates collected from cells transfected with the parent reporter plasmid ("R"), the reporter plasmid containing the sec-RNA sequence insert ("SR"), the sec-RNA reporter plasmid co-transfected with pE1.1 TAT(+) or with pE1.1 TAT(−). The right hand panel of FIG. 17A shows both cell lysates ("C") and extracellular media samples ("M") from cells cotransfected with the sec-RNA reporter plasmid and pE1.1 TAT(+) or pE1.1 TAT(−). As shown, in cells transfected with the pE3.1 Sec-Reporter and pE1 TAT(+) plasmids, the RNA-protein complex is secreted into the media, whereas in cells transfected with the pE3.1 Sec-Reporter and pE1 TAT(−) plasmids (TAT fused to a negative RBD control), the fusion protein (sec-RNA) was not present in the media.

Example 17

Assaying CPP-Mediated Secretion Activity of a Luciferase/Alkaline Phosphatase Reporter Gene FIG. 14A is a non-limiting schematic showing an exemplary transfection assay to generate and test the secretory activity of bioreactor cells using the CPP-Luciferase/CPP-Alkaline Phosphatase reporter system. Fusion protein cassettes fusing cell penetrating peptides to a luciferase reporter gene are generated via PCR. These PCR products include restriction sites at each end of the DNA to facilitate subcloning into the pEGEN1.1 plasmid, placing the fusion protein cassette between an SV40 promoter and an hGH poly-A tail sequence. The resulting plasmids are transfected into a number of different cell types in vitro to generate BioReactor reporter cells as described in Examples 11-14. Total protein is collected from the growth media and the cells and luciferase activity is measured in both to establish the distribution of tagged luciferase molecules inside and outside the cell. Requirements for secretion are established through comparison to control proteins including luciferase/alkaline phosphatase alone and luciferase/alkaline phosphatase fused to a scrambled CPP domain.

FIG. 14B shows CPP-mediated secretion of the luciferase reporter protein from cells transfected with reporter plasmids and cultured in vitro. CT26 cells were transfected with plasmids expressing luciferase or a TAT-luciferase fusion protein. After 48 hours, cell media was replaced with PBS and cells were incubated at 37° C. for an additional 3 hours. The PBS supernatant was collected and the cells were lysed in TENT buffer. Luciferase activity was measured for equivalent amounts of solubilized cellular protein and PBS supernatant using standard methods. The relative luciferase activity present in cellular and supernatant fractions is presented as a percentage of the total luciferase activity observed in both fractions. The addition of the TAT cell penetrating peptide to the luciferase reporter protein shifts the distribution of luciferase activity out of the transfected cell and into the supernatant.

Example 18

Assaying CPP-Mediated Delivery of a Split GFP Reporter Gene

FIG. 18 is a non-limiting schematic showing an exemplary transfection assay to generate and test the import activity of bioreactor cells using the GFP reporter system. Fusion protein cassettes fusing cell penetrating peptides to an isolated domain from a split GFP reporter system are generated by PCR. A separate PCR reaction generates a protein cassette encoding a GFP complementary fragment. These PCR products each include restriction sites at each end of the DNA to facilitate subcloning into the pEGEN1.1 plasmid, placing the fusion protein cassette and the GFP complimentary fragment cassette between an SV40 promoter and an hGH poly-A tail sequence. The resulting plasmids are transfected independently into cells in vitro to generate Bioreactor reporter cells expressing the CPP-GFP fusion protein and target cells expressing the GFP complimentary fragment. The experiment is initiated by mixing the bioreactor cells with the target cells. Secretion of the CPP fusion protein from the bioreactor cells and subsequent import into the target cells will be detected upon docking of the activating domain to the GFP complimentary fragment by the resulting GFP signal.

Example 19

Application of the Bioreactor Cell Transfection Reagent to Hela Cells for the Purpose of mRNA Transcript Knockdown in Culture Bioreactor cells, such as those produced from Examples 11-14 and confirmed using the methods described in Examples 16, are applied directly to target cells for the purpose of knocking down the gene product targeted by the Sec-RNA molecule. The particular pBioR plasmid and recipient cells used in the transfection are determined by the gene target of interest and the target cell identity. In this example, the HeLa target cells are transfected with NIH3T3 BioReactor cells secreting a Sec-shRNA—fusion protein complex with an shRNA targeting the VEGF transcript. In using mouse derived BioReactor cells to transfect human derived target cells, it is possible to observe knockdown of the VEGF transcript in the human target cells through the use of species specific primer sets. Depletion of VEGF protein in human cells and subsequent decreases in the amount of secreted protein can also be detected in the media using assays with VEGF antibodies specific for the human protein.

BioReactor cells are produced from NIH3T3 recipient cells by transfection of NIH3T3 cells with the pBioR plasmid as described in Examples 11-14. BioReactor function is also verified with assays described in Example 16. It is not necessary to separate or purify the BioReactor cells following transient transfection of the NIH3T3 cells. HeLa cells are cultured in 6 well plates in DMEM+10% fetal bovine serum (2 mL total volume) to a density of 50% confluence. BioReactor cells are collected by trypsinization and centrifugation (500×g for 5 minutes). The cell pellet is resuspended in the same growth medium used for the HeLa target cells and the cell density is measured using a hemocytometer. Bioreactor cells are added to the HeLa target cells and the combined culture is incubated at 37° C. under 5% $CO_2$. The optimal ratio of BioReactor cells to target cells is determined empirically for each system of cells and gene targets. RNA or protein samples are collected from each cell culture 48-96 hours after addition of the BioReactor cells in order to assay knockdown of the mRNA transcript or protein, respectively, as described in Example 16.

Example 20

Bioreactor Mediated Delivery of an RNA Aptamer to the Extracellular Matrix

This example describes an exemplary transfection assay to determine the secretion activity of bioreactor cells secreting an aptamer, for example, an aptamer targeted to Oncostatin M protein, which is an activator of the gp130 receptor mediated signaling pathway (see FIG. 19). The assay employs the use of a reporter system and a secreted RNA aptamer targeting the Oncostatin M protein. An expression plasmid for the fusion protein (pEGENFP, Example 2) and as expression plasmid for an RNA aptamer (pEGENSR, Example 2) targeting Oncostatin M are transfected into a number of different cell types in vitro to generate Bioreactor cells secreting the RNA aptamer as described in Examples 11-14. A reporter plasmid expressing the luciferase protein under the control of promoter elements responsive to the gp130 mediated STAT3 signaling pathway (SABiosciences, Cignal Reporter Assays, Catalog #CCS-9028) is transfected into HepG2 cells (gp130 expressing cells) in vitro to generate target (reporter) cells. After 48 hours, cell media is collected from the bioreactor cells secreting the aptamer for Oncostatin M and incubated with a recombinant Oncostatin M protein (0.2-20 ng/mL) for 3 hours at room temperature to allow for binding of the secreted aptamer to the target protein. The media is then transferred to the target (reporter) cells and cultures are incubated at 37° C. for 24 hours. Controls include addition of recombinant Oncostatin M protein directly to reporter cells, Oncostatin M incubated with media from untransfected cells, Oncostatin M incubated with media from bioreactor cells transfected with only the RNA aptamer expressing plasmid (pEGENSR), Oncostatin M incubated with media from cells expressing mismatched RNA binding domains and Oncostatin M treated with RNA aptamers purified from pEGENSR transfected cells. Luciferase assays are carried out as described in Example 17. Reporter cells incubated with the media containing the aptamer targeting Oncostatin M will have less luciferase activity than reporter cells incubated with Oncostatin M alone or incubated with Oncostatin M and control media. The secretion of other aptamers from bioreactor cells can be assayed using similar methods with the appropriate luciferase or other reporter vector system.

Example 21

Bioreactor Mediated Delivery of an RNA Aptamer to the Extracellular Matrix

This example describes an exemplary transfection assay to determine the secretion activity of bioreactor cells secreting an aptamer, for example, an aptamer targeted to HER3 (see FIG. 20). The assay employs the use of a reporter system and a secreted RNA aptamer targeting the HER3 protein. An expression plasmid for the fusion protein (pEGENFP, Example 2) and as expression plasmid for an RNA aptamer (pEGENSR, Example 2) targeting HER3 are transfected into a number of different cell types in vitro to generate Bioreactor cells secreting the RNA aptamer as described in Examples 11-14. Reporter cells expressing the HER3 receptor protein (MCF7 for example) are cultured separately. After 48 hours, cell media is collected from the bioreactor cells secreting the aptamer for HER3 and transferred to the HER3 expressing reporter cells and cultures are incubated at 37° C. for 24-72 hours. Controls include addition of media from untransfected cells, media from bioreactor cells transfected with only the RNA aptamer expressing plasmid (pEGENSR), media from cells expressing mismatched RNA binding domains and with RNA aptamers purified from pEGENSR transfected cells. Cell growth is monitored using Promega's CellTiter 96 Aqueous Non-Radioactive Cell Proliferation Assay (Catalog #G5421) according to the manufacturer's protocol. Reporter cells incubated with the media containing the aptamer targeting HER3 will show less cell growth than reporter cells incubated with control media. The secretion of other aptamers from bioreactor cells can be assayed using similar methods with the appropriate reporter vector system.

Example 22

Bioreactor Mediated Delivery of an shRNA to the Cytoplasm of a Target Cell

This example describes an exemplary transfection assay to determine the secretion activity of bioreactor cells and subsequent delivery of an inhibitory shRNA to the cytoplasm of a target cell (see FIG. 21). An expression plasmid for the fusion protein (pEGENFP, example 2) and an expression plasmid for the shRNA (pEGENSR, example 2) are transfected into a number of different cell types in vitro to generate Bioreactor cells as described in Examples 11-14. Target cells expressing the mRNA transcript targeted by the shRNA are cultured separately. After 48 hours, cell media is collected from the bioreactor cells and transferred to the target cells and cultures are incubated at 37° C. for 24-72 hours. Controls include addition of media from untransfected cells, media from bioreactor cells transfected with only the shRNA expressing plasmid (pEGENSR), media from cells expressing mismatched RNA binding domains and with shRNAs purified from pEGENSR transfected cells. Total RNA is prepared from the target cells and RT-PCR analysis is carried out as described in Example 11. Knockdown of the target gene is assessed by comparison to a non-targeted internal control gene. Alternatively, bioreactor cells and target cells can be cultured together during the experiment if the primers and probes used in the RT-PCR assays do not recognize the corresponding transcripts in the bioreactor cells. This is most easily achieved by using cell lines derived from one species for bioreactor cells and cell lines derived from a different species for the target cells. In this case, bioreactor cells can be collected 24 hours after transfection and mixed with target cells for direct assays of bioreactor activity as assayed by RT-PCR analysis. Target cells expressing the mRNA transcript targeted by the shRNA are cultured separately. The secretion of other shRNAs from bioreactor cells can be assayed using similar methods with the appropriate target cells.

Example 23

Ex Vivo Administration of the pBioR Expression Vectors to Cells

BioReactor cells are produced from NIH3T3 recipient cells by transfection with the pBioR plasmid as described in Examples 11-14. BioReactor function is verified with assays described in Example 16. In this example, the NIH3T3 BioReactor cells secrete an Sec-shRNA—fusion protein complex with an shRNA targeting the VEGF transcript. The BioReactor cells are mixed with SCCVII target cells (a mouse squamous cell carcinoma line) and the mixture is transplanted into nude mice (immune-compromised) by subcutaneous injection into the rear flanks of each animal. BioReactor activity is monitored by assessment of VEGF transcript and protein levels in tissues surrounding the transplantation site compared with controls. Bioreactor function are also be assessed in vivo by comparing tumor growth in the BioReactor/SCCVII transplants to control mice receiving SCCVII cells alone or SCCVII cells with non-functional BioReactor cells (non-specific shRNAs or delivery compromised fusion proteins).

Example 24

In Vivo Administration of Bioreactor Cells to Mouse Muscle Tissue

BioReactor cells are produced from primary mouse myoblast recipient cells by transfection with the pBioR plasmid as described in Examples 11-14. BioReactor function is verified using assays described in Examples 16. In this example, BioReactors cells secrete an Sec-shRNA—fusion protein complex with an shRNAs targeting the mRNA transcript for myostatin, a negative regulator of skeletal muscle growth. The BioReactor cells are transplanted into the tibialis muscle of mdx mice, a model system for Duchenne muscular dystrophy (Li S, Kimura E, Ng R, Fall B M, Meuse L, Reyes M, Faulkner J A, Chamberlain J S., A highly functional mini-dystrophin/GFP fusion gene for cell and gene therapy studies of Duchenne muscular dystrophy., Hum Mol. Genet. 2006 May 15; 15(10):1610-22). BioReactor activity is monitored by assessment of myostatin transcript and protein levels in tissues surrounding the transplantation site. RNA and protein samples are prepared from tibialis muscles collected from untreated mice, mice transplanted with BioReactor cells secreting non-specific Sec-shRNAs and mice transplanted with BioReactor cells secreting shRNAs targeting the myostatin transcript using Tri-Reagent (Sigma-Aldrich, product #T9424). Relative levels of myostatin transcript and protein can then be assessed by RT-PCR or ELISA, respectively, as described in Example 16. BioReactor function is also assessed in vivo by comparing body mass, muscle mass, muscle size and muscle strength in the BioReactor transplants relative to control mice receiving no BioReactor cells or non-functional BioReactor cells (Bogdanovich S, Krag T O, Barton E R, Morris L D, Whittemore L A, Ahima R S, Khurana T S., Functional improvement of dystrophic muscle by myostatin blockade., Nature. 2002 Nov. 28; 420(6914): 418-21).

Example 25

In Vivo Administration of Bioreactor Cells to Mouse Neural Tissue

BioReactor cells are produced from mouse neural stem cells (mNSC) by transfection with the pBioR plasmid as described in Examples 11-14. BioReactor function is verified with assays described in Examples 16. In this example, the mNSC BioReactor cells secrete an Sec-shRNA—fusion protein complex with an shRNA targeting the mRNA transcript for the CAG repeat expansion of the mutant huntingtin (htt) protein. The BioReactor cells are transplanted into the brain of mouse models for Huntington's disease to evaluate the efficacy of BioReactor mediated knockdown of the mRNA transcript for the mutant form of the htt protein. RNA samples are prepared from mouse brain tissue collected from untreated mice, mice transplanted with BioReactor cells secreting non-specific Sec-shRNAs and mice transplanted with BioReactor cells secreting shRNAs targeting the mutant huntingtin transcript using Tri-Reagent (Sigma-Aldrich, product #T9424). Relative levels of huntingtin transcript can then be assessed by RT-PCR as described in Example 16. Mouse models for Huntington's disease also display abnormal protein build-up in striatal tissues and abnormal gaits, both of which may provide physiological readouts of BioReactor activity. See Yang C R, Yu R K., Intracerebral transplantation of neural stem cells combined with trehalose ingestion alleviates pathology in a mouse model of Huntington's disease., J Neurosci Res. 2008 Aug. 5; 87(1):26-33.; DiFiglia M, Sena-Esteves M, Chase K, Sapp E, Pfister E, Sass M, Yoder J, Reeves P, Pandey R K, Rajeev K G, Manoharan M, Sah D W, Zamore P D, Aronin N., Therapeutic silencing of mutant huntingtin with siRNA attenuates striatal and cortical neuropathology and behavioral deficits., Proc Natl Acad Sci USA. 2007 Oct. 23; 104(43):17204-9.

Example 26

Administration of Bioreactor Cells to Human Synovial Fluid

BioReactor cells are produced from human synovial fibroblasts by transfection with the pBioR plasmid as described in Examples 11-14. BioReactor function is verified with assays described in Examples 16. In this example, the fibroblast BioReactor cells secrete an Sec-shRNA—fusion protein complex with an shRNA targeting the mRNA transcript for either the IL-1β, the IL-6 or the IL-18 proinflammatory cytokines. The transfected cells are expanded for injection of transciently transfected cells or generation of stable cells via selective growth with antibiotics. The BioReactor cells are resuspended in 1×PBS (without $Ca^{2+}$ or $Mg^{2+}$) and injected into the joints of arthritis patients (Evans C H, Robbins PD, Ghivizzani SC, Wasko MC, Tomaino MM, Kang R, Muzzonigro TA, Vogt M, Elder EM, Whiteside TL, Watkins SC, Herndon JH., Gene transfer to human joints: progress toward a gene therapy of arthritis., Proc Natl Acad Sci USA. 2005 Jun. 14; 102(24):8698-703). Sec-shRNA—fusion protein complexes produced by the fibroblast BioReactor cells will be delivered to the interleukin producing monocytes to reduce the amount of cytokine present in the synovial fluid. BioReactor function is assessed by monitoring the amount of IL-1α, IL-6, IL-18 and TNFα protein present in the synovial fluid, as well as physiological indications of the disease. (Khoury M, Escriou V, Courties G, Galy A, Yao R, Largeau C, Scherman D, Jorgensen C, Apparailly F., Efficient suppression of murine arthritis by combined anticytokine small interfering RNA lipoplexes., Arthritis Rheum. 2008 August; 58(8):2356-67).

Example 27

Construction of the Viral Vector

Viral vectors are constructed from isolated plasmid backbones, expression cassettes for the structural and non-structural components of the virus and expression cassettes for the biologically active RNA. PCR amplification of expression cassettes, subcloning of expression cassettes into plasmid backbones, amplification and isolation of the resulting virus producing vectors and subsequent verification of plasmid sequences are all carried out as described in Example 1. Viral vectors are constructed from one of several DNA viral expression cassettes such as Adenovirus and Adeno-associated virus (2-3, 7, 11, 19, 21) and Herpes Simplex Virus (5, 14-15, 18) or RNA viral expression cassettes such as Lentivirus (6, 20, 22, 24), Sindbis Virus (9), Murine Leukemia Virus (10, 12-13, 16) or Foamy Virus (8, 17) and any of the biologically active RNA molecules described elsewhere in the application and in the previous examples. For each virus, the structural genes encoding viral coat proteins and fusogenic proteins are subcloned into any of the pEGEN backbone plasmids for expression from a Pol-II promoter sequence generating pVir1. Separately, the non-structural genes encoding the polymerases and accessory proteins are coupled with the biologically active RNA sequence and subcloned into a second pEGEN plasmid for expression from a Pol-II promoter sequence generating pVir2. The arrangement of promoter sequences within pVir2 can vary for the different viral backbones. Viral non-structural genes and templates for biologically active RNA molecules can be expressed from either common or independent promoter sequences endogenous to the native virus or from within Table VIII. Plasmids pVir1 and pVir2 are co-transfected into recipient cells to generate virus producing cells.

Successful generation of virus producing cells can be verified via a number of different experimental assays. Expression of viral structural genes can be assessed using RT-PCR with primers specific to the virus transcript and ELISAs with antibodies specific to the viral proteins. Expression of the viral non-structural genes can also be assessed by RT-PCR with primers specific to the virus transcript and also with primers that bridge the non-structural genes and the biologically active RNA. Secretion of viral particles can be assessed by collecting the media in which the virus producing cells are growing, isolating the protein, DNA, or RNA from that media and then assaying for viral proteins or nucleic acids using ELISAs, PCR, or RT-PCR. Functional viral particles can be detected via plaque assays utilizing cell lines carrying helper viruses.

Example 28

Administration of Viral Packaging Cells to Target Cells in Culture

Viral packaging cells are produced from MDCK recipient cells by transfection with pVir plasmids as described in Examples 11-14. Virus packaging function is verified with assays described in Example 29. In this example, the viral packaging cells produce a replication defective virus carrying an shRNA targeting the VEGF protein. These virus producing cells are used to knockdown the VEGF protein in HeLa cells, providing a mechanism for distinguishing the virus producing mouse cells from the human target cells. Depletion of VEGF mRNA transcript in human cells and subsequent decreases in the amount of secreted protein can be detected using species specific primer sets in RT-PCR and species specific antibodies in ELISAs, respectively. HeLa cells are cultured in 6 well plates in DMEM+10% fetal bovine serum (2 mL total volume) to a density of 50% confluence. Viral packaging cells are collected by trypsinization and centrifugation (500×g for 5 minutes). The cell pellet is resuspended in the same growth medium used for the HeLa target cells and the cell density is measured using a hemocytometer. Viral packaging cells are added to the HeLa target cells and the combined culture is incubated at 37° C. under 5% $CO_2$. The optimal ratio of viral packaging cells to target cells is determined empirically for each system of cells and gene targets. RNA or protein samples are collected from each cell culture 48-96 hours after addition of the viral packaging cells in order to assay knockdown of the mRNA transcript or protein, respectively.

Example 29

Assays for Confirming the Production and Secretion of the Recombinant Virus in Cell Culture Cells are transfected with a pVir expression vectors or a null vector using the methods described in Examples 11-14. Successful generation of virus producing cells is confirmed by assays that verify one or more of the following: (1) production of the viral protein components, (2) production of the partial viral genome containing the biologically active RNA template or molecule, (3) encapsulation of the Sec-RNA into the viral particle and (4) successful release of the viral particle from the viral production cell. Production of the viral protein components can be verified through RT-PCR based assays that detect the plasmid derived mRNA transcript encoding those proteins and antibody based assays that detect the proteins themselves. For purposes of detecting the viral proteins, short "protein tags" which are recognized by commercially available antibodies, can be included in the sequence of the viral proteins. These protein tags are used to verify the function of the viral production cell and are not necessarily included in the functional viral particles.

To detect the plasmid derived mRNA transcript, total RNA is prepared from pVir-transfected, null vector-transfected, and non-transfected cells, i.e., HeLa cells or any of the other cells described herein and otherwise known in the art, using Tri-Reagent (Sigma-Aldrich, product #T9424) according to the manufacturer's protocols. A cDNA library is prepared from the total RNA using a poly-T primer and used as template for the PCR amplification. Primers for two separate amplification reactions, each producing a different size product, are included in the PCR reactions: (1) Primers amplifying sequences from an internal control gene, such as β-actin or GAPDH, and (2) Primers amplifying sequences specific to the mRNA encoding the fusion protein. Products are resolved on 2% agarose gels run in 1×TAE or on 10% acrylamide gels run in 1×TBE. Products are compared for the non-transfected cells (negative control), cells transfected with a null vector (backbone vector without the fusion protein), and the potential viral production cells (i.e., cells transfected with a pVir) through staining with ethidium bromide and illumination with UV light at 302 nm. Non-transfected control cells have a single PCR product for the internal control gene while successful BioReactors have products for both the internal control gene and the transcript encoding the fusion protein.

Direct detection of the viral proteins is accomplished by collection of total protein from pVir-transfected, null vector-transfected, and non-transfected cells, as well as the media in which those cells are growing. Total protein is concentrated from each sample by acetone precipitation and the concentrated proteins are resuspended in either a native buffer for ELISA analysis or denaturing buffer for western blot analysis. Each assay utilizes standard methods and antibodies specific for an internal control gene (β-actin or GAPDH) and a protein tag present in the viral protein. As discussed, protein tags are included in the viral proteins as a convenient means for verifying function of the viral production cell. Non-transfected and null vector-transfected control cells have a single protein detected for the internal control gene while successful viral production cells have both the internal control protein and the viral proteins.

Successful production of the partial viral genome with the inhibitory RNA template or molecule can be verified through amplification of the DNA or RNA product. RT-PCR assays are used to show production of the plasmid derived partial viral genome and cellular fractionation is used to demonstrate accumulation of this nucleic acid in the cytoplasm. The cellular fractionation is accomplished with the PARIS RNA isolation kit (Ambion, Product #1921) according to the manufacturer's protocol. A cDNA library is prepared from the fractionated RNA using a random hexamer non-specific primer and is used as template for the PCR amplification. Primers for two separate amplification reactions, each producing a different size product, are included in the PCR reactions: (1) Primers amplifying sequences from an internal control gene, such as β-actin or GAPDH, and (2) Primers amplifying sequences specific to the partial viral genome. Products are resolved on 2% agarose gels run in 1×TAE or on 10% acrylamide gels run in 1×TBE. Products are compared for the null vector-transfected and non-transfected cells (negative controls) and the potential viral production cells through staining with ethidium bromide and illumination with UV light at 302 nm. Null vector-transfected and non-transfected control cells have a single PCR product for the internal control gene while successful viral production cells have products for both the internal control gene and the partial viral genome.

Encapsulation of the partial viral genome and inhibitory RNA template or molecule is demonstrated through isolation of viral particles by ultracentrifugation through CsCl gradients. Virus particles are harvested from pVir-transfected, null vector-transfected, and non-transfected cells and subjected to CsCl gradient purification. Nucleic acids are prepared from the isolated viral particles and used as template for either PCR analysis (DNA virus backbones) or RT-PCR (RNA virus backbones) as described above. Successful release of the viral particle is verified by detection of the viral proteins or partial viral genome in the extracellular matrix, or media in the case of cells in culture. Intact viral particles can be purified and concentrated from the media, and nucleic acids purified and used as templates for PCR or RT-PCR analysis as described above.

Example 30

Construction of Viral Vectors Producing Recombinant Virus Carrying Complete Bioreactor Cassettes in Cell Culture Viral vectors are constructed from isolated plasmid backbones, expression cassettes for the structural and non-structural components of the virus and expression cassettes for both the biologically active RNA and the fusion protein. PCR amplification of expression cassettes, subcloning of expression cassettes into plasmid backbones, amplification and isolation of the resulting virus producing vectors and subsequent verification of plasmid sequences are all carried out as described in Example 1. These viral vectors utilize DNA viruses (any listed in Example 28) such that the viral particles carry the bioreactor expression cassettes. For each virus, the structural genes encoding viral coat proteins and fusogenic proteins are subcloned into any of the pEGEN backbone plasmids for expression from a Pol-II promoter sequence generating pVir1. Separately, the non-structural genes encoding the polymerases and accessory proteins are coupled with the expression cassettes for the biologically active RNA(s) and the fusion protein and subcloned into a second pEGEN plasmid for expression from a Pol-II promoter sequence generating pVir3. Plasmids pVir1 and pVir3 are co-transfected into recipient cells to generate virus producing cells. Cells are transfected with the pVir expression vectors or a null vector using the methods described in Examples 11-14.

Example 31

Assays for Confirming the Production and Secretion of the Recombinant Virus Carrying Complete Bioreactor Cassettes in Cell Culture Cells transfected with the pVir plasmids become viral production cells and produce viral particles which, upon infection of a target cell, convert that target cell into a bioreactor cell. Successful generation of virus producing cells is confirmed by assays that verify one or more of the following: (1) production of the viral protein components, (2) production of the partial viral genome containing the biologically active RNA template or molecule as well as the template for the fusion protein, (3) encapsulation of the biologically active RNA template and the fusion protein template into the viral particle, (4) successful release of the viral particle from the viral production cell and (5) successful generation of bioreactor activity within the infected target cell. Production of the viral protein components are verified using assays described in Example 27. Production of the viral genomes and bioreactor expression components are verified using assays described in Example 16. Encapsulation of the required nucleic acids are verified using assays described in Example 29. Successful release of virus particles and generation of bioreactor activity in infected target cells are verified using assays described in Example 16.

Example 32

Administration of the Viral Production Cells to Hela Cells for the Purpose of mRNA Transcript Knockdown in Cell Culture Viral production cells, such as those produced from Examples 30-31 and confirmed using the methods described in Example 31, are applied directly to target cells for the purpose of knocking down the gene product targeted by the biologically active RNA molecule. The particular pVir plasmids and recipient cells used in the transfection are determined by the gene target of interest and the target cell identity. In this example, the HeLa target cells are co-cultured with MDCK viral production cells which generate viral particles carrying expression cassettes for a bioreactor fusion protein and an a secreted shRNA targeting VEGF (or any of the transcripts listed in Table VII). The infected HeLa cells then become bioreactor cells capable of producing the fusion protein—Sec-shRNA complex and secreting that complex into the growth media. This media can then be transferred to secondary target cells (HeLa or other cell lines) for transfection and subsequent VEGF knockdown. Alternatively, fusion protein—Sec-shRNA complexes can be purified through precipitation with the 6× Histidine epitope tags prior to application to the target cells. It is possible to observe knockdown of the VEGF transcript in the human target cells through the use of species specific primer sets and RT-PCR. Depletion of the VEGF protein in human cells and subsequent decreases in the amount of secreted protein can also be detected in the media using assays with VEGF antibodies specific for the human protein.

Example 33

Administration of Viral Packaging Cells In Vivo

Viral packaging cells are produced from NIH3T3 recipient cells by transfection with the pVir plasmids as described in Examples 11-14. Virus packaging function is verified with assays described in Example 29. In this example, the NIH3T3 virus packaging cells produce a replication defective virus carrying an shRNA targeting the VEGF protein. The viral packaging cells are mixed with SCCVII target cells (a mouse squamous cell carcinoma line) and the mixture is transplanted into nude mice (immune-compromised) by subcutaneous injection into the rear flanks of each animal. Activity is monitored by assessment of VEGF transcript and protein levels in tissues surrounding the transplantation site. RNA samples are prepared from tissue collected from the rear flanks of untreated mice, mice transplanted with BioReactor cells secreting non-specific Sec-shRNAs and mice transplanted with BioReactor cells secreting shRNAs targeting the VEGF transcript using Tri-Reagent (Sigma-Aldrich, product #T9424). Relative levels of VEGF transcript can then be assessed by RT-PCR as described in Example 11. Viral packaging function are also assessed in vivo by comparing tumor growth in the virus producing/SCCVII transplants to control mice receiving SCCVII cells alone or SCCVII cells with non-functional virus producing cells (non-specific shRNAs or delivery compromised viruses).

Example 34

In Vivo Administration of Viral Packaging Cells to Mouse Muscle Tissue

Viral packaging cells are produced from primary mouse myoblast recipient cells by transfection with the pVir plasmids as described in Examples 11-14. Virus function is verified using assays described in Example 29. In this example, viral packaging cells produce a replication incompetent viral particle with an shRNAs targeting the mRNA transcript for myostatin, a negative regulator of skeletal muscle growth. The viral packaging cells are transplanted into the tibialis muscle of mdx mice, a model system for Duchenne muscular dystrophy (Li S, Kimura E, Ng R, Fall B M, Meuse L, Reyes M, Faulkner J A, Chamberlain J S., A highly functional mini-dystrophin/GFP fusion gene for cell and gene therapy studies of Duchenne muscular dystrophy., Hum Mol. Genet. 2006 May 15; 15(10):1610-22). Virus activity is monitored by assessment of myostatin transcript and protein levels in tissues surrounding the transplantation site. RNA and protein samples are prepared from tibialis muscles collected from untreated mice, mice transplanted with viral production cells producing viral particles with non-specific shRNAs and mice transplanted with viral packaging cells with shRNAs targeting the myostatin transcript using Tri-Reagent (Sigma-Aldrich, product #T9424). Relative levels of myostatin transcript and protein can then be assessed by RT-PCR or ELISA, respectively, as described in Example 16. Virus function is also assessed in vivo by comparing body mass, muscle mass, muscle size and muscle strength in the viral packaging cell transplants relative to control mice receiving no viral packaging cells or non-functional viral packaging cells (Bogdanovich S, Krag T O, Barton E R, Morris L D, Whittemore L A, Ahima R S, Khurana T S., Functional improvement of dystrophic muscle by myostatin blockade., Nature. 2002 Nov. 28; 420(6914):418-21.).

Example 35

Administration of Viral Packaging Cells to Mouse Neural Tissue

Viral packaging cells are produced from mouse neural stem cells (mNSC) by transfection with the pVir plasmid as described in Examples 11-14. Virus function is verified with assays described in Example 29. In this example, the mNSC viral packaging cells produce a replication defective virus carrying an shRNA targeting the mRNA transcript with the CAG repeat expansion of the mutant huntingtin (htt) protein. The virus producing cells are transplanted into the brain of mouse models for Huntington's disease to evaluate the efficacy of virus mediated knockdown of the mRNA transcript for the mutant form of the htt protein. RNA samples are prepared from mouse brain tissue collected from untreated mice, mice transplanted with viral production cells producing viral particles containing non-specific shRNAs and mice transplanted with viral production cells with shRNAs targeting the mutant huntingtin transcript using Tri-Reagent (Sigma-Aldrich, product #T9424). Relative levels of huntingtin transcript can then be assessed by RT-PCR as described in Example 11.

REFERENCES

Lund PE, Hunt RC, Gottesman MM, Kimchi-Sarfaty C. Pseudovirions as Vehicles for the Delivery of siRNA. Pharm Res. 2009 Dec. 9.

Koerber JT, Jang JH, Schaffer DV. DNA shuffling of adeno-associated virus yields functionally diverse viral progeny. Mol. Ther. 2008 October; 16(10):1703-9.

Cascante A, Abate-Daga D, Garcia-Rodríguez L, González JR, Alemany R, Fillat C. GCV modulates the antitumoural efficacy of a replicative adenovirus expressing the Tat8-TK as a late gene in a pancreatic tumour model. Gene Ther. 2007 October; 14(20):1471-80.

Ring CJ. Cytolytic viruses as potential anti-cancer agents. J Gen Virol. 2002 March; 83(Pt 3):491-502.

Parada C, Hernández Losa J, Guinea J, Sánchez-Arévalo V, Fernández Soria V, Alvarez-Vallina L, Sánchez-Prieto R, Ramón y Cajal S. Adenovirus E1a protein enhances the cytotoxic effects of the herpes thymidine kinase-ganciclovir system. Cancer Gene Ther. 2003 February; 10(2):152-60.

Tiede A, Eder M, von Depka M, Battmer K, Luther S, Kiem HP, Ganser A, Scherr M. Recombinant factor VIII expression in hematopoietic cells following lentiviral transduction. Gene Ther. 2003 October; 10(22):1917-25.

Lee YJ, Galoforo SS, Battle P, Lee H, Corry PM, Jessup JM. Replicating adenoviral vector-mediated transfer of a heat-inducible double suicide gene for gene therapy. Cancer Gene Ther. 2001 June; 8(6):397-404.

Nestler U, Heinkelein M, Lücke M, Meixensberger J, Scheurlen W, Kretschmer A, Rethwilm A. Foamy virus vectors for suicide gene therapy. Gene Ther. 1997 November; 4(11):1270-7.

Tseng JC, Daniels G, Meruelo D. Controlled propagation of replication-competent Sindbis viral vector using suicide gene strategy. Gene Ther. 2009 February; 16(2):291-6.

Kikuchi E, Menendez S, Ozu C, Ohori M, Cordon-Cardo C, Logg CR, Kasahara N, Bochner B H. Highly efficient gene delivery for bladder cancers by intravesically administered replication-competent retroviral vectors. Clin Cancer Res. 2007 Aug. 1; 13(15 Pt 1):4511-8.

Bourbeau D, Lau CJ, Jaime J, Koty Z, Zehntner SP, Lavoie G, Mes-Masson AM, Nalbantoglu J, Massie B. Improvement of antitumor activity by gene amplification with a replicating but nondisseminating adenovirus. Cancer Res. 2007 Apr. 1; 67(7):3387-95.

Hiraoka K, Kimura T, Logg CR, Tai CK, Haga K, Lawson GW, Kasahara N. Therapeutic efficacy of replication-competent retrovirus vector-mediated suicide gene therapy in a multifocal colorectal cancer metastasis model. Cancer Res. 2007 Jun. 1; 67(11):5345-53.

Hiraoka K, Kimura T, Logg CR, Kasahara N. Tumor-selective gene expression in a hepatic metastasis model after locoregional delivery of a replication-competent retrovirus vector. Clin Cancer Res. 2006 Dec. 1; 12(23):7108-16.

Varghese S, Rabkin SD, Nielsen GP, MacGarvey U, Liu R, Martuza RL. Systemic therapy of spontaneous prostate cancer in transgenic mice with oncolytic herpes simplex viruses. Cancer Res. 2007 Oct. 1; 67(19):9371-9.

Varghese S, Rabkin SD, Nielsen PG, Wang W, Martuza RL. Systemic oncolytic herpes virus therapy of poorly immunogenic prostate cancer metastatic to lung. Clin Cancer Res. 2006 May 1; 12(9):2919-27.

Qiao J, Moreno J, Sanchez-Perez L, Kottke T, Thompson J, Caruso M, Diaz RM, Vile R. VSV-G pseudotyped, MuLV-based, semi-replication-competent retrovirus for cancer treatment. Gene Ther. 2006 October; 13(20):1457-70.

Heinkelein M, Hoffmann U, Lücke M, Imrich H, Müller JG, Meixensberger J, Westphahl M, Kretschmer A, Rethwilm A. Experimental therapy of allogeneic solid tumors induced in athymic mice with suicide gene-transducing replication-competent foamy virus vectors. *Cancer Gene Ther.* 2005 December; 12(12):947-53.

Anesti AM, Peeters PJ, Royaux I, Coffin RS. Efficient delivery of RNA Interference to peripheral neurons in vivo using herpes simplex virus. *Nucleic Acids Res.* 2008 August; 36(14):e86.

Gorbatvuk M, Justilien V, Liu J, Hauswirth WW, Lewin AS. Suppression of mouse rhodopsin expression in vivo by AAV mediated siRNA delivery. *Vision Res.* 2007 April; 47(9): 1202-8.

Scherr M, Venturini L, Battmer K, Schaller-Schoenitz M, Schaefer D, Dallmann I, Ganser A, Eder M. Lentivirus-mediated antagomir expression for specific inhibition of miRNA function. *Nucleic Acids Res.* 2007; 35(22):e149.

Chen W, Liu M, Jiao Y, Yan W, Wei X, Chen J, Fei L, Liu Y, Zuo X, Yang F, Lu Y, Zheng Z. Adenovirus-mediated RNA interference against foot-and-mouth disease virus infection both in vitro and in vivo. *J. Virol.* 2006 April; 80(7): 3559-66.

Raoul C, Abbas-Terki T, Bensadoun JC, Guillot S, Haase G, Szulc J, Henderson CE, Aebischer P. Lentiviral-mediated silencing of SOD1 through RNA interference retards disease onset and progression in a mouse model of ALS. *Nat. Med.* 2005 April; 11(4):423-8.

Bromberg-White JL, Webb CP, Patacsil VS, Miranti CK, Williams BO, Holmen SL. Delivery of short hairpin RNA sequences by using a replication-competent avian retroviral vector. *J. Virol.* 2004 May; 78(9):4914-6.

Scherr M, Battmer K, Ganser A, Eder M. Modulation of gene expression by lentiviral-mediated delivery of small interfering RNA. *Cell Cycle.* 2003 May-June; 2(3):251-7.

Tseng JC, Levin B, Hirano T, Yee H, Panpeno C, Meruelo D. In vivo antitumor activity of sindbis viral vectors. J Natl Cancer Inst. 2002; 94: 1790-1802.

Falcone V, Schweizer M, Neumann-Haefelin C. Replication of primate foamy viruses in natural and experimental hosts. Curr Top Microbiol Immunol. 2003; 277: 161-180.

Reinblatt M. Pin RH, Federoff HJ, Fong Y. Carcinoembryonic antigen directed herpes viral oncolysis improves selectivity and activity in colorectal cancer. Surgery 2004; 136: 579-584.

The entire disclosure of each document cited (including patents, patent applications, journal articles, abstracts, laboratory manuals, books, or other disclosures) is hereby incorporated herein by reference in its entirety. Further, the Sequence Listing submitted herewith is incorporated herein by reference in its entirety.

While this invention has been particularly shown and described with references to preferred embodiments thereof, it will be understood by those skilled in the art that various changes in form and details may be made therein without departing from the scope of the invention encompassed by the appended claims.

It will be clear that the invention may be practiced otherwise than as particularly described in the foregoing description and examples. Numerous modifications and variations of the invention are possible in light of the above teachings and, therefore, are within the scope of the appended claims.

TABLE I

Non-limiting examples of Bilogically Active RNA Sequences

| | Name | Nucleotide Sequence | SEQ ID NO |
|---|---|---|---|
| 1 | Mmp2 | GCAAUACCUGAAUACUUUCUACUCGA GUAGAAAGUAUUCAGGUAUUGC | 1 |
| 2 | VEGF (shRNA) | GCGGAUCAAACCUCACCAAACUCGAG UUUGGUGAGGUUUGAUCCGCA | 2 |
| 3 | VEGF (ribozyme) | CCAUGUACCAGCCUGGCUGAUGAGUC CGUGAGGACGAAAACCACUUG | 3 |
| 4 | Cav-1 | GACCCACUCUUUGAAGCUGUUCUCGA GAACAGCUUCAAAGAGUGGGU | 4 |
| 5 | EGFR | CUCCAUAAAUGCUACGAAUACUCGAG UAUUCGUAGCAUUUAUGGAGA | 5 |
| 6 | H-Ras | CCAGGAGGAGUACAGCGCCAUCUCGA GAUGGCGCUGUACUCCUCCUGG | 6 |
| 7 | Bcl-2 | GGAUGACUGAGUACCUGAACCUCGAG GUUCAGGUACUCAGUCAUCCA | 7 |
| 8 | Survivin | GGCUGGCUUCAUCCACUGCUUCAAGA GAGCAGUGGAUGAAGCCAGCC | 8 |
| 9 | FAK | AACCACCUGGGCCAGUAUUAUCUCGA GAUAAUACUGGCCCAGGUGGUU | 9 |
| 10 | STAT3 | GCCGAUCUAGGCAGAUGCCACAC-CCAU CUGCCUAGAUCGGC | 10 |
| 11 | HER3 | CGCGUGUGCCAGCGAAAGUUGCGUAU GGGUCACAUCGCAGGCACAUGUCAUC UGGGCGGUCCGUUCG | 11 |
| 12 | β-catenin | GGACGCGUGGUACCAGGCCGAUCUAC GGACGCUAUAGGCACACCGGAUACUU UAACGAUUGGCUAAGCUUCCGCGGGG AUC | 12 |
| 13 | Src | UCAGAGCGGUUACUGCUCAAUCUCGA GAUUGAGCAGUAACCGCUCUGA | 13 |
| 14 | RET | GCGCGGGAAUAGUAUGGAAGGAUACG UAUACCGUGCAAUCCAGGGCAACG | 14 |
| 15 | NF-κB | GAUCUUGAAACUGUUUUAAGGUUGGC CGAUCUU | 15 |

TABLE II

Non-limiting Examples of RNA Recognition Sequences

| | Name | Nucleotide Sequence | SEQ ID NO |
|---|---|---|---|
| 1 | U1 loop sequence | GGGUAUCCAUUGCACUCCGGAUGCC | 16 |
| 2 | Group II intron | UUUGAAGAAAAAUAAAAGGAAUUCU AUCAAUUUUAUUUUCCAUUUAUUUA GUUAGUUUUUCUUAAUGAAAUUGAAA UUAUUAACUAACAGAGCAAACACAAA | 17 |
| 3 | NRE stem loop | GGCCGAAAUCCCGAAGUAGGCC | 18 |
| 4 | S1A stem loop | GGACUGUCCACAAGACAGUCC | 19 |
| 5 | ARE sequence | AUUUAUUUAUUUA | 20 |
| 6 | Box B sequence | GGCCCUGAAAAGGGC | 21 |

TABLE II-continued

Non-limiting Examples of RNA Recognition Sequences

| | Name | Nucleotide Sequence | SEQ ID NO |
|---|---|---|---|
| 7 | Rev sequence | GGUCUGGGCGCAGCGCAAGCUGCGGU ACAGGCC | 22 |
| 8 | AMV sequence | GGCAUGCUCAUGCAAAACUGCAUGAA UGCCCCUAAGGGAUGC | 23 |

TABLE III

Non-limiting Examples of RNA Binding Domains

| | Name | Amino Acid Sequence | SEQ ID NO |
|---|---|---|---|
| 1 | U1A | MAVPETRPNHTIYINNLNEKIKKDELKKS LYAIFSQFGQILDILVSRSLKMRGQAFV IFKEVSSARNALRSMQGFPFYDKPMRI QYAKTDSDIIAKMK | 24 |
| 2 | CRS1 CRM1 | LETHELRRLRRLARGIGRWARAKKAGVT DEVVKEVRREWASGEELAAVRIVEPLRR SMDRAREILEIKTGGLVVWTKGDMHFV YRG | 25 |
| 3 | Nucleolin RBD | MGSHMVEGSESTTPFNLFIGNLNPNKS VAELKVAISELFAKNDLAVVDVRTGTNR KFGYVDFESAEDLEKALELTGLKVFGNE IKLEKPKGRDSKKVRAARTLLAKNLSFNI TEDELKEVFEDALEIRLVSQDGKSKCIA YIEFKSEADAEKNLEEKQGAEIDGRSV SLYYTGEKG | 26 |
| 4 | hRBMY | MVEADHPGKLTIGGLNRETNEKMLKAVF GKHGPISEVLLIKDRTSKSRGFAFITF ENPADAKNAAKDMNGKSLHGKAIKVEQA KKPSFQSGGRRRPPA | 27 |
| 5 | Tristetrapolin TTP73 | MSRYKTELCRTFSESGRCRYGAKCQFAH GLGELRQANRHPKYKTELCHKFYLQGRC PYGSRCHFIHNPSEDLAA | 28 |
| 6 | Bacteriophage Protein N | MDAQTRRRERRAEKQAQWKAAN | 29 |
| 7 | Rev | DTRQARRNRRRRWRERQRAAAAR | 30 |
| 8 | AMV coat | SSSQKKAGGKAGKPTKRSQNYAALRK | 31 |

TABLE IV

Non-limiting examples of Cell Penetrating Peptide Sequences

| | Name | Amino Acid Sequence | SEQ ID NO |
|---|---|---|---|
| 1 | Penetratin | RQIKIWFQNRRMKWKK | 32 |
| 2 | Transportan | GWTLNSAGYLLKINLKALAALAKKIL | 33 |
| 3 | MAP | KLALKLALKALKAALKLA | 34 |
| 4 | TAT | GRKKRRQRRRPPQ | 35 |
| 5 | Antp | RQIKIYFQNRRMKWKK | 36 |
| 6 | Rev | TRQARRNRRRRWRERQR | 37 |
| 7 | FHV | RRRNRTRRNRRRVR | 38 |

TABLE IV-continued

Non-limiting examples of Cell Penetrating Peptide Sequences

| | Name | Amino Acid Sequence | SEQ ID NO |
|---|---|---|---|
| 8 | TP10 | AGYLLGKINLKALAALAKKIL | 39 |
| 9 | pVEC | LLIILRRRIRKQAHAHSK | 40 |

TABLE V

Non-limiting examples of Non-classical Secretory Domain Sequences

| | Name | Amino Acid Sequence | SEQ ID NO |
|---|---|---|---|
| 1 | FGF1 | MAEGEITTFAALTERFNLPLGNYKKPKLL YCSNGGHFLRILPDGTVDGTRDRSDQHIQ LQLSAESAGEVYIKGTETGQYLAMDTEG LLYGSQTPNEECLFLERLEENHYNTYTSK KHAEKNWFVGLKKNGSCKRGPRTHYGQ KAILFLPLPVSSD | 41 |
| 2 | FGF2 | MAAGSITTLPALPEDGGSGAFPPGHFKDP KRLYCKNGGFFLRIHPDGRVDGVREKSD PHIKLQLQAEERGVVSIKGVCANRYLAM KEDGRLLASRCVTDECFFFERLESNNYNT YRSRKYTSWYVALKRTGQYKLGSKTGP GQKAILFLAMSAKS | 42 |
| 3 | Thioredoxin | MVKQIESKTAFQEALDAAGDKLVVVDFS ATWCGPCKMIKPFFHSLSEKYSNVIFLEV DVDDCQDVASECEVKCMPTFQFFKKGQ KVGEFSGANKEKLEATINELV | 43 |
| 4 | Galectin-1 | MACGLVASNLNLKPGECLRVRGEVAPD AKSFVLNLGKDSNNLCLHFNPRFNAHGD ANTIVCNSKDGGAWGTEQREAVFPFQPG SVAEVCITFDQANLTVKLPDGYEFKFPNR LNLEAINYMAADGDFKIKCVAFD | 44 |
| 5 | Galectin-3 | MADNFSLHDALSGSGNPNPQGWPGAWG NQPAGAGGYPGASYPGAYPGQAPPGAYP GQAPPGAYPGAPGAYPGAPAPGVYPGPP SGPGAYPSSGQPSATGAYPATGPYGAPA GPLIVPYNLPLPGGVVPRMLITILGTVKPN ANRIALDFQRGNDVAFHFNPRFNENNRR VIVCNTKLDNNWGREERQSVFPPFESGKPF KIQVLVEPDHFKVAVNDAHLLQYNHRV KKLNEISKLGISGDIDLTSASYTMI | 45 |
| 6 | IL-1α | MAKVPDMFEDLKNCYSENEEDSSSIDHL SLNQKSFYHVSYGPLHEGCMDQSVSLSIS ETSKTSKLTFKESMVVVATNGKVLKKRR LSLSQSITDDDLEAIANDSEEEIIKPRSAPF SFLSNVKYNFMRIIKYEFILNDALNQSIIR ANDQYLTAAALHNLDEAVKFDMGAYKS SKDDAKITVILRISKTQLYVTAQDEDQPV LLKEMPEIPKTITGSETNLLFFWETHGTK NYFTSVAHPNLFIATKQDYWVCLAGGPP SITDFQILENQA | 46 |
| 7 | IL-1β | MAEVPELASEMMAYYSGNEDDLFFEAD GPKQMKCSFQDLDLCPLDGGIQLRISDHH YSKGFRQAASVVVAMDKLRKMLVPCPQ TFQENDLSTFFPFIFEEEPIFFDTWDNEAY VHDAPVRSLNCTLRDSQQKSLVMSGPYE LKALHLQGQDMEQQVVFSMSFVQGEES NDKIPVALGLKEKNLYLSCVLKDDKPTL QLESVDPKNYPKKKMEKRFVFNKIEINN KLEFESAQFPNWYISTSQAENMPVFLGGT KGGQDITDFTMQFVSS | 47 |

TABLE V-continued

Non-limiting examples of Non-classical Secretory Domain Sequences

| | Name | Amino Acid Sequence | SEQ ID NO |
|---|---|---|---|
| 8 | Rhodanese | MVHQVLYRALVSTKWLAESVRAGKVGP GLRVLDASWYSPGTREARKEYLERHVPG ASFFDIEECRDKASPYEVMLPSEAGFADY VGSLGISNDTHVVVYDGDDLGSFYAPRV WWMFRVFGHRTVSVLNGGFRNWLKEG HPVTSEPSRPEPAIFKATLNRSLLKTYEQV LENLESKRFQLVDSRAQGRYLGTQPEPD AVGLDSGHIRGSVNMPFMNFLTEDGFEK SPEELRAMFEAKKVDLTKPLIATCRKGVT ACHIALAAYLCGKPDVAIYDGSWFEWFH RAPPETWVSQGKGGKA | 48 |

TABLE VI

Non-limiting examples of Fusogenic Peptide Sequences

| | Name | Amino Acid Sequence | SEQ ID NO |
|---|---|---|---|
| 1 | HA from influenza | GLFGAIAGFIEGGWTGLIDG | 50 |
| 2 | Gp41 from HIV | AVGIGALFLGFLGAAG | 51 |
| 3 | Melittin | GIGAVLKVLTTGLPA LISWIKRKRQQ | 52 |
| 4 | GALA | WEAALAEALAEALAEHLAEA LAEALEALAA | 53 |
| 5 | KALA | WEAKLAKALAKALAKHLAK ALAKALKACEA | 54 |

TABLE VII

Non-limiting examples of Targeted Sequences and Associated Human diseases

| | Name | Disease System - Cellular Function |
|---|---|---|
| 1 | Mmp2 | Cancer Metastasis Arthritis |
| 2 | VEGF | Cancer Cell Growth/Angiogenesis Macular Degeneration |
| 3 | Cav-1 | Cancer Metastasis |
| 4 | EGFR | Cancer Cell Growth |
| 5 | H-Ras | Cancer |
| 6 | Bcl-2 | Cancer Cell Apoptosis/Drug Resistance |
| 7 | Survivin | Cancer Cell Apoptosis |
| 8 | FAK | Cancer Cell Apoptosis |
| 9 | STAT3 | Cancer Cell Apoptosis |
| 10 | HER3 | Cancer Cell Growth/Differentiation |
| 11 | β-catenin | Cancer Cell Growth/Oncogene Activation |
| 12 | Src | Cancer Cell Metastasis/Growth |
| 13 | RET | Cancer Cell Growth/Survival |
| 14 | NF-κB | Cancer Cell Drug Resistance |
| 15 | Myostatin | Duchennes Muscular Dystrophy |
| 16 | Huntingtin | Huntington's Disease |
| 17 | KSP | Cancer Cell Division |
| 18 | MDR | Cancer Cell Drug Resistance |
| 19 | ApoB | Coronary Heart Disease |

TABLE VIII

Non-limiting examples of suitable promoters for Plasmids of the invention

| | Name | Corresponding plasmid |
|---|---|---|
| 1 | SV40 | pEGEN1.1 |
| 2 | Chicken β-actin | pEGEN2.1 |
| 3 | CMV | pEGEN3.1 |
| 4 | Human U6 | pEGEN4.1 |
| 5 | Human H1 | pEGEN5.1 |
| 6 | Human Albumin | pEGEN6.1 |
| 7 | Human HIF-a | pEGEN7.1 |
| 8 | Human Gelsolin | pEGEN8.1 |
| 9 | Human CA-125 | pEGEN9.1 |
| 10 | Human PSA | pEGEN10.1 |
| 11 | Human Ubiquitin | pEGEN11.1 |

---

What we claim is:

1. An expression vector comprising a first polynucleotide and a second polynucleotide, wherein
the first polynucleotide encodes a biologically active RNA sequence and a recognition RNA sequence; and
the second polynucleotide encodes a polypeptide comprising (i) an RNA binding domain sequence that binds the recognition RNA sequence and (ii) a non-classical secretory domain sequence that facilitates secretion of a RNA-polypeptide complex from a cell via an ER-Golgi independent pathway, the RNA-polypeptide complex comprising the biologically active RNA sequence, the recognition RNA sequence, and the polypeptide.

2. A cell comprising the expression vector of claim 1.

3. A method for secreting a biologically active RNA molecule from a cell comprising transfecting the cell with the expression vector of claim 1, transcribing the first polynucleotide, expressing the polypeptide, forming the complex, and secreting the complex from the cell, thereby secreting the biologically active RNA molecule from the cell.

4. The expression vector of claim 1, wherein the first polynucleotide further encodes a terminal minihelix sequence.

5. The expression vector of claim 1, wherein the second polynucleotide further encodes a cell penetrating peptide.

6. The expression vector of claim 1, wherein the biologically active RNA sequence of the first polynucleotide is selected from the group consisting of an RNA ribozyme, an antisense RNA, an RNA aptamer, a small interfering RNA (siRNA), a double stranded RNA (dsRNA), a micro RNA (miRNA), and a small hairpin RNA (shRNA).

7. The expression vector of claim 1, wherein the non-classical secretory domain sequence is selected from the group consisting of Galectin-1, Galectin-3, interleukin 1α(IL-1α), interleukin 1β(IL-1β), hydrophilic acylated surface protein B (HASPB), high mobility group box protein 1 (HMGB1), fibroblast growth factor 1 (FGF-1), fibroblast growth factor 2 (FGF-2), interleukin 2 (IL-2), Thioredoxin, and Rhodanese.

8. The expression vector of claim 1, wherein the recognition RNA sequence of the first polynucleotide is a U1 loop sequence and the RNA binding domain sequence is a U1A domain.

9. The expression vector of claim 1, wherein the recognition RNA sequence of the first polynucleotide is a nucleon recognition element (NRE) stem loop sequence and the RNA binding domain sequence is a Nucleolin RNA binding domain.

10. The expression vector of claim 1, wherein the recognition RNA sequence of the first polynucleotide is a S1A stem loop sequence and the RNA binding domain sequence is a hRBMY domain.

11. The expression vector of claim 1, wherein the recognition RNA sequence of the first polynucleotide is an AU rich element (ARE) sequence and the RNA binding domain sequence is a Tristetrapolin TTP73 domain.

12. The expression vector of claim 1, wherein the recognition RNA sequence of the first polynucleotide is a Box B sequence and the RNA binding domain sequence is a Bacteriophage Protein N domain.

13. The expression vector of claim 1, wherein the recognition RNA sequence of the first polynucleotide is a Rev sequence and the RNA binding domain sequence is a Rev protein domain.

14. The expression vector of claim 1, wherein the recognition RNA sequence of the first polynucleotide is an alpha mosaic virus (AMV) sequence and the RNA binding domain sequence is a AMV coat domain.

15. The cell of claim 2, wherein the biologically active RNA sequence of the first polynucleotide is selected from the group consisting of an RNA ribozyme, an antisense RNA, an RNA aptamer, a siRNA, a dsRNA, a miRNA, and an shRNA.

16. The cell of claim 15, wherein the first polynucleotide further encodes a terminal minihelix sequence.

17. The expression vector of claim 5, wherein the biologically active RNA sequence of the first polynucleotide is selected from the group consisting of an RNA ribozyme, an antisense RNA, an RNA aptamer, a siRNA, a dsRNA, a miRNA, and an shRNA.

18. The expression vector of claim 5, wherein the cell penetrating peptide sequence is selected from the group consisting of penetratin, transportin, model amphiphatic peptide (MAP), trans-activator of transcription (TAT), homeodomain of antennepedia (AntP), feline herpes virus (FHV) coat protein, and transportin 10 (TP10).

19. An expression vector comprising a first polynucleotide and a second polynucleotide, wherein
   the first polynucleotide encodes a biologically active RNA sequence and a recognition sequence, operably linked to a first promoter sequence and a first polyA addition sequence; and
   the second polynucleotide encodes a polypeptide comprising (i) an RNA binding domain sequence that binds the recognition RNA sequence, and (ii) a non-classical secretory domain sequence that facilitates secretion of a RNA-protein complex from a cell via an ER-Golgi independent pathway, operably linked to a second promoter sequence and a second polyA addition sequence, wherein the RNA-polypeptide complex comprises the biologically active RNA sequence, the recognition RNA sequence, and the polypeptide.

20. The expression vector of claim 19, wherein the first polynucleotide further encodes a terminal minihelix sequence.

21. The expression vector of claim 19, wherein the second polynucleotide further encodes a cell penetrating peptide.

22. The expression vector of claim 19, wherein the biologically active RNA sequence of the first polynucleotide is selected from the group consisting of an RNA ribozyme, an antisense RNA, an RNA aptamer, a siRNA, a dsRNA, a miRNA, and an shRNA.

23. A cell comprising the expression vector of claim 19.

24. A method for secreting a biologically active RNA molecule from a cell transfecting the cell with the expression vector of claim 19, transcribing the first polynucleotide, expressing the polypeptide, forming the complex, and secreting the complex from the cell, thereby secreting the biologically active RNA molecule from the cell.

25. The cell of claim 23, wherein the biologically active RNA sequence of the first polynucleotide is selected from the group consisting of an RNA ribozyme, an antisense RNA, an RNA aptamer, a siRNA, a dsRNA, a miRNA, and an shRNA.

26. The cell of claim 25, wherein the first polynucleotide further encodes a terminal minihelix sequence.

27. A pharmaceutical composition comprising:
   a first expression vector comprising a first polynucleotide encoding a biologically active RNA sequence and a recognition RNA sequence;
   a second expression vector comprising a second polynucleotide encoding a polypeptide comprising (i) an RNA binding domain sequence that binds the recognition RNA sequence and (ii) a non-classical secretory domain sequence that facilitates secretion of a RNA-polypeptide complex from a cell via an ER-Golgi independent pathway, the RNA-polypeptide complex comprising the biologically active RNA sequence, the recognition RNA sequence, and the polypeptide, and
   a pharmaceutically acceptable carrier.

28. The pharmaceutical composition of claim 27, wherein the first polynucleotide further encodes a terminal minihelix sequence.

29. The pharmaceutical composition of claim 27, wherein the second polynucleotide further encodes a cell penetrating peptide.

30. The pharmaceutical composition of claim 27, wherein the biologically active RNA sequence of the first polynucleotide is selected from the group consisting of an RNA ribozyme, an antisense RNA, an RNA aptamer, a siRNA, a dsRNA, a miRNA, and an shRNA.

* * * * *